United States Patent
Kim et al.

(10) Patent No.: US 10,062,852 B2
(45) Date of Patent: Aug. 28, 2018

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Hyunjung Kim, Suwon-si (KR); Miyoung Chae, Suwon-si (KR); Sangmo Kim, Hwaseong-si (KR); Soonok Jeon, Seoul (KR); Yeonsook Chung, Seoul (KR); Yongsik Jung, Yongin-si (KR); Dalho Huh, Suwon-si (KR); Youngmok Son, Hwaseong-si (KR); Namheon Lee, Suwon-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 73 days.

(21) Appl. No.: 15/145,158

(22) Filed: May 3, 2016

(65) Prior Publication Data

US 2016/0380210 A1    Dec. 29, 2016

(30) Foreign Application Priority Data

Jun. 23, 2015 (KR) .................. 10-2015-0089088
Mar. 31, 2016 (KR) .................. 10-2016-0039619

(51) Int. Cl.

| | | |
|---|---|---|
| H01L 51/00 | (2006.01) | |
| C07D 403/10 | (2006.01) | |
| C07D 209/86 | (2006.01) | |
| C09K 11/02 | (2006.01) | |
| C09K 11/06 | (2006.01) | |
| H01L 51/50 | (2006.01) | |
| H01L 51/52 | (2006.01) | |

(52) U.S. Cl.
CPC ........ *H01L 51/0072* (2013.01); *C07D 209/86* (2013.01); *C07D 403/10* (2013.01); *C09K 11/02* (2013.01); *C09K 11/06* (2013.01); *H01L 51/008* (2013.01); *H01L 51/009* (2013.01); *H01L 51/0085* (2013.01); *C09K 2211/1007* (2013.01); *C09K 2211/1022* (2013.01); *C09K 2211/1029* (2013.01); *C09K 2211/1044* (2013.01); *C09K 2211/185* (2013.01); *H01L 51/0061* (2013.01); *H01L 51/5004* (2013.01); *H01L 51/5012* (2013.01); *H01L 51/5016* (2013.01); *H01L 51/5028* (2013.01); *H01L 51/5056* (2013.01); *H01L 51/5072* (2013.01); *H01L 51/5088* (2013.01); *H01L 51/5092* (2013.01); *H01L 51/5096* (2013.01); *H01L 51/5206* (2013.01); *H01L 51/5221* (2013.01); *H01L 2251/552* (2013.01)

(58) Field of Classification Search
CPC ..................................................... C09K 11/06
See application file for complete search history.

(56) References Cited

U.S. PATENT DOCUMENTS

| | | | |
|---|---|---|---|
| 2013/0234119 A1 | 9/2013 | Mizuki et al. | |
| 2013/0264548 A1 | 10/2013 | Mizuki et al. | |
| 2014/0183467 A1 | 7/2014 | Choi et al. | |
| 2016/0301015 A1* | 10/2016 | Zheng | C09K 11/06 |

FOREIGN PATENT DOCUMENTS

| | | | |
|---|---|---|---|
| EP | 3015457 A1 | 5/2016 | |
| EP | 3015465 A1 | 5/2016 | |
| KR | 2011-0105664 A | 9/2011 | |
| KR | 2012-0116282 A | 10/2012 | |
| WO | 2013-112557 A1 | 8/2013 | |
| WO | 2013-165192 A1 | 11/2013 | |
| WO | 2014-208698 A1 | 12/2014 | |
| WO | 2015-016498 A1 | 2/2015 | |
| WO | WO-2015066354 A1 * | 5/2015 | C09K 11/06 |

OTHER PUBLICATIONS

Yang (Chem. Commun. (2008) 453-455).*
Extended European Search Report dated Nov. 2, 2016, issued by the European Patent Office for European Patent Application No. 16168952.6-1501.
Woo Jae Park et al. "Effective thermally activated delayed fluorescence emitter and its performance in OLED device", Synthetic Metals 209 (2015) pp. 99-104.

* cited by examiner

*Primary Examiner* — Kuo Liang Peng
(74) *Attorney, Agent, or Firm* — Cantor Colburn LLP

(57) ABSTRACT

A condensed cyclic compound represented by Formula 1:

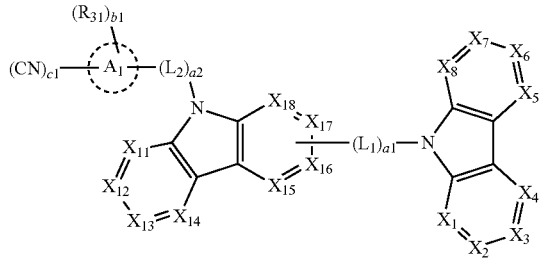

wherein, in Formula 1, groups and variables are the same as described in the specification.

20 Claims, 1 Drawing Sheet

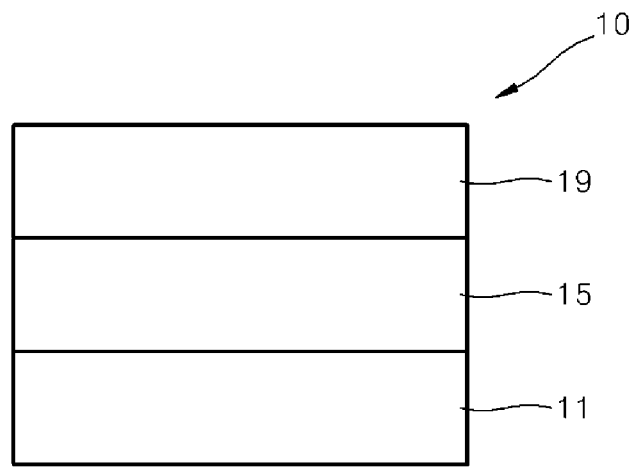

CONDENSED CYCLIC COMPOUND AND ORGANIC LIGHT-EMITTING DEVICE INCLUDING THE SAME

CROSS-REFERENCE TO RELATED APPLICATIONS

This application claims priority to Korean Patent Application No. 10-2015-0089088, filed on Jun. 23, 2015 in the Korean Intellectual Property Office and Korean Patent Application No. 10-2016-0039619, filed on Mar. 31, 2016 in the Korean Intellectual Property Office, and all the benefits accruing therefrom under 35 U.S.C. § 119, the contents of which are incorporated herein in their entirety by reference.

BACKGROUND

1. Field

The present disclosure relates to a condensed cyclic compound and an organic light-emitting device including the same.

2. Description of the Related Art

Organic light-emitting devices (OLEDs) are self-emission devices that have wide viewing angles, high contrast ratios, and short response times. In addition, OLEDs exhibit high brightness, low driving voltage, and high response speed characteristics, and produce full-color images, compared to conventional organic light-emitting devices.

A typical organic light-emitting device includes an anode, a cathode, and an organic layer that is disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, are recombined in the emission layer to produce excitons. These excitons change from an excited state to a ground state, thereby generating light.

Different types of organic light emitting devices are known. However, there still remains a need in OLEDs having low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented exemplary embodiments.

According to an aspect of an exemplary embodiment, a condensed cyclic compound is represented by Formula 1:

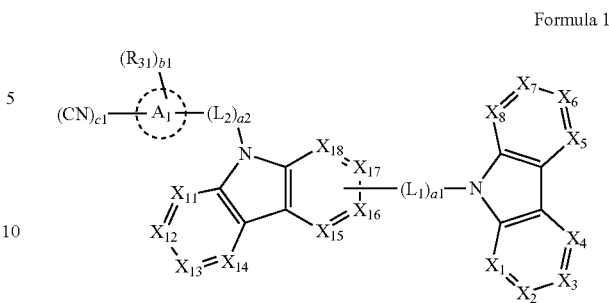

Formula 1 wherein, in Formula 1, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N, $C(R_{15})$, or a carbon atom connected to *-$(L_1)_{a1}$-*', $X_{16}$ is N, $C(R_{16})$, or a carbon atom connected to *-$(L_1)_{a1}$-*', $X_{17}$ is N, $C(R_{17})$, or a carbon atom connected to *-$(L_1)_{a1}$-*', and $X_{18}$ is N, $C(R_{18})$, or a carbon atom connected to *-$(L_1)_{a1}$-*', wherein one of $X_{15}$ to $X_{18}$ is connected to *-$(L_1)_{a1}$-*', ring $A_1$ is selected from a $C_5$-$C_{60}$ carbocyclic group and a $C_3$-$C_{60}$ heterocyclic group including at least one heteroatom selected from O, S, and Si, $L_1$ is selected from a phenylene group, a pyridinylene group, a pyrimidinylene group, a pyrazinylene group, a pyridazinylene group, a triazinylene group, a fluorenylene group, a dibenzofuranylene group, and a dibenzothiophenylene group; and a phenylene group, a pyridinylene group, a pyrimidinylene group, a pyrazinylene group, a pyridazinylene group, a triazinylene group, a fluorenylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —$Si(Q_{11})(Q_{12})(Q_{13})$, $L_2$ is selected from a phenylene group, a fluorenylene group, a dibenzofuranylene group, and a dibenzothiophenylene group; and a phenylene group, a fluorenylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a dibenzofuranyl group, a dibenzothiophenyl group, and —$Si(Q_{11})(Q_{12})(Q_{13})$, a1 and a2 are each independently an integer selected from 0 to 5, wherein when a1 is 2 or greater, two or more groups $L_1$ are identical to or different from each other, and when a2 is 2 or greater, two or more groups $L_2$ are identical to or different from each other, $R_1$ to $R_8$, $R_{11}$ to $R_{18}$, and $R_{31}$ are each independently selected from a hydrogen, a deuterium, —F, —Cl, —Br, —I, a hydroxyl group, a cyano group (—CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$), b1 is an integer selected from 0 to 4, c1 is an integer selected from 1 to 4, at least one substituent of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$), wherein $Q_1$ to $Q_3$, $Q_{11}$ to $Q_{13}$, and $Q_{21}$ to $Q_{23}$ are each independently selected from a hydrogen, a deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group in *-($L_1$)$_{a1}$-*', * and *' are each a binding site to a neighboring atom.

According to an aspect of another exemplary embodiment, an organic light-emitting device includes:

a first electrode;

a second electrode; and an organic layer disposed between the first electrode and the second electrode, wherein the organic layer includes an emission layer and at least one condensed cyclic compound represented by Formula 1.

BRIEF DESCRIPTION OF THE DRAWINGS

These and/or other aspects will become apparent and more readily appreciated from the following description of the exemplary embodiments, taken in conjunction with the accompanying drawing in which:

FIG. 1 is a schematic cross-sectional view of an organic light-emitting device according to an embodiment.

DETAILED DESCRIPTION

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

According to one or more exemplary embodiments, a condensed cyclic compound represented by Formula 1 is provided:

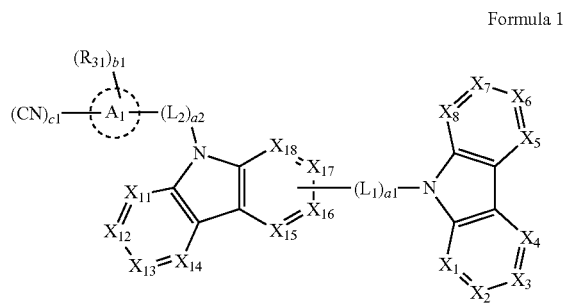

Formula 1

In Formula 1, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N, $C(R_{15})$, or a carbon atom connected to $*-(L_1)_{a1}-*'$, $X_{16}$ may be N, $C(R_{16})$, or a carbon atom connected to $*-(L_1)_{a1}-*'$, $X_{17}$ may be N, $C(R_{17})$, or a carbon atom connected to $*-(L_1)_{a1}-*'$, and $X_{18}$ may be N, $C(R_{18})$, or a carbon atom connected to $*-(L_1)_{a1}-*'$, wherein one of $X_{15}$ to $X_{18}$ may be connected to $*-(L_1)_{a1}-*'$. In $*-(L_1)_{a1}-*'$, $*$ and $*'$ may be each a binding site to a neighboring atom.

For example, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be N or $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$ or a carbon atom connected to $*-(L_1)_{a1}-*'$, $X_{16}$ may be $C(R_{16})$ or a carbon atom connected to $*-(L_1)_{a1}-*'$, $X_{17}$ may be $C(R_{17})$ or a carbon atom connected to $*-(L_1)_{a1}-*'$, and $X_{18}$ may be $C(R_{18})$ or a carbon atom connected to $*-(L_1)_{a1}-*'$, wherein one of $X_{15}$ to $X_{18}$ may be connected to $*-(L_1)_{a1}-*'$.

In Formula 1, ring $A_1$ may be selected from a $C_5$-$C_{60}$ carbocyclic group and a $C_3$-$C_{60}$ heterocyclic group that includes at least one heteroatom selected from O, S, and Si. When ring $A_1$ is a $C_3$-$C_{60}$ heterocyclic group, the $C_3$-$C_{60}$ heterocyclic group includes at least one heteroatom selected from O, S, and Si as a ring-forming atom. That is, for example, ring $A_1$ may not be a $C_3$-$C_{60}$ heterocyclic group that includes N as a ring-forming atom. For example, ring $A_1$ may not be a pyridine ring, a pyrimidine ring, a triazine ring, or a carbazole ring.

For example, in Formula 1, ring $A_1$ may be selected from a cyclopentane ring, a cyclohexane ring, a cyclopentene ring, a cyclohexene ring, a cycloheptene ring, a benzene ring, a pentalene ring, an indene ring, a naphthene ring, an azulene ring, a heptalene ring, an indacene ring, an acenaphthene ring, a fluorene ring, a spirobifluorene ring, a phenalene ring, a phenanthrene ring, an anthracene ring, a fluoranthene ring, a triphenylene ring, a pyrene ring, a chrysene ring, a naphthacene ring, a picene ring, a perylene ring, a pentaphene ring, a hexacene ring, a furane ring, a thiophene ring, a benzofurane ring, a benzothiophene ring, a dibenzofurane ring, and a dibenzothiophene ring.

According to an embodiment, in Formula 1, ring $A_1$ may be each independently selected from a benzene ring, a dibenzofurane ring, and a dibenzothiophene ring, but embodiments are not limited thereto.

In Formula 1, $L_1$ may be selected from
a phenylene group, a pyridinylene group, a pyrimidinylene group, a pyrazinylene group, a pyridazinylene group, a triazinylene group, a fluorenylene group, a dibenzofuranylene group, and a dibenzothiophenylene group; and
a phenylene group, a pyridinylene group, a pyrimidinylene group, a pyrazinylene group, a pyridazinylene group, a triazinylene group, a fluorenylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —$Si(Q_{11})(Q_{12})(Q_{13})$, and $L_2$ may be selected from
a phenylene group, a fluorenylene group, a dibenzofuranylene group, and a dibenzothiophenylene group; and
a phenylene group, a fluorenylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a dibenzofuranyl group, a dibenzothiophenyl group, and —$Si(Q_{11})(Q_{12})(Q_{13})$.

For example, in Formula 1, $L_1$ may be selected from
a phenylene group, a pyridinylene group, a pyrimidinylene group, a pyrazinylene group, a pyridazinylene group, a triazinylene group, a fluorenylene group, a dibenzofuranylene group, and a dibenzothiophenylene group; and
a phenylene group, a pyridinylene group, a pyrimidinylene group, a pyrazinylene group, a pyridazinylene group, a triazinylene group, a fluorenylene group, a dibenzofuranylene group, and a dibenzothiophenylene group, each substituted with at least one selected from a deuterium, a cyano group, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si(Q$_{11}$)(Q$_{12}$)(Q$_{13}$), and L$_2$ may be selected from a phenylene group, a fluorenylene group, a dibenzofuranylene group, and a dibenzothiophenylene group; and a phenylene group, a fluorenylene group, a dibenzofuranylene group, and a dibenzothiophenylene group, each substituted with at least one selected from a deuterium, a cyano group, a C$_1$-C$_{10}$ alkyl group, a C$_1$-C$_{10}$ alkoxy group, a phenyl group, a naphthyl group, a fluorenyl group, a dibenzofuranyl group, a dibenzothiophenyl group, and —Si(Q$_{ii}$)(Q$_{12}$)(Q$_{13}$), wherein Q$_{11}$ to Q$_{13}$ may be each independently selected from a hydrogen, a C$_1$-C$_{10}$ alkyl group, a C$_1$-C$_{10}$ alkoxy group, a phenyl group, a pyridinyl group, a pyrimidinyl group, and a triazinyl group.

According to an embodiment, in Formula 1, L$_1$ may be selected from groups represented by Formulae 3-1 to 3-56, and L$_2$ may be selected from groups represented by Formulae 3-1, 3-15, 3-28, and 3-41 to 3-56:

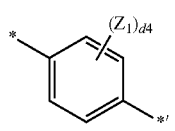

Formula 3-1

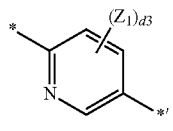

Formula 3-2

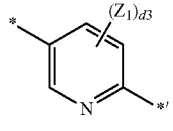

Formula 3-3

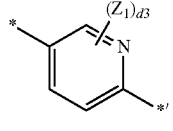

Formula 3-4

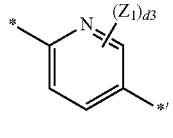

Formula 3-5

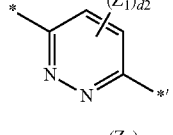

Formula 3-6

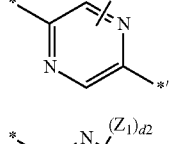

Formula 3-7

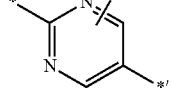

Formula 3-8

-continued

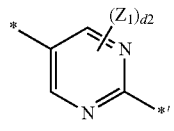

Formula 3-9

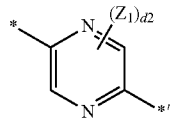

Formula 3-10

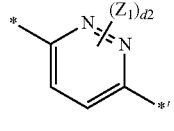

Formula 3-11

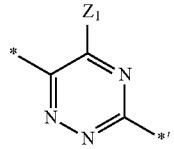

Formula 3-12

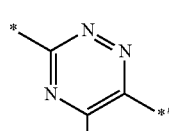

Formula 3-13

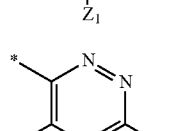

Formula 3-14

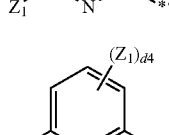

Formula 3-15

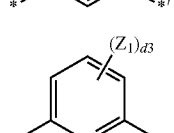

Formula 3-16

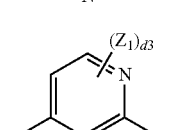

Formula 3-17

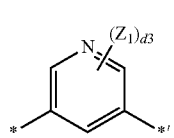

Formula 3-18

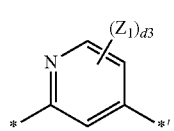

Formula 3-19

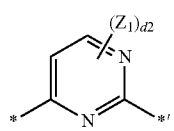

Formula 3-20

-continued
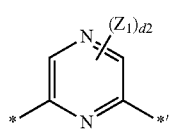
Formula 3-21
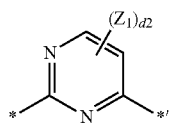
Formula 3-22
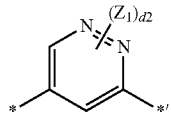
Formula 3-23
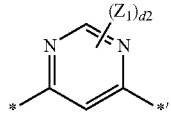
Formula 3-24
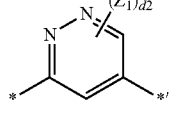
Formula 3-25
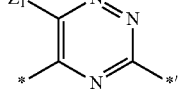
Formula 3-26
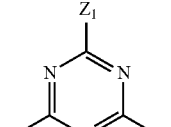
Formula 3-27
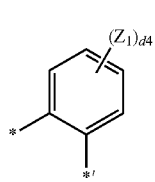
Formula 3-28
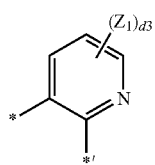
Formula 3-29
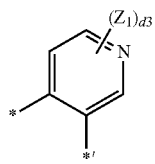
Formula 3-30
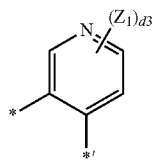
Formula 3-31
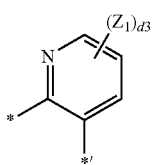
Formula 3-32
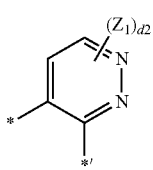
Formula 3-33
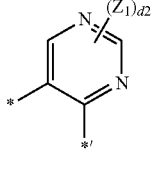
Formula 3-34
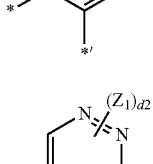
Formula 3-35
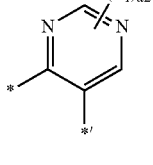
Formula 3-36
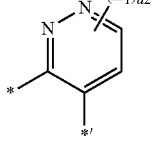
Formula 3-37
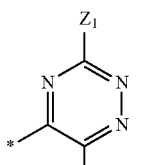
Formula 3-38
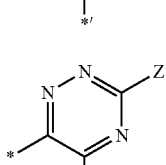
Formula 3-39
Formula 3-40

-continued

Formula 3-41
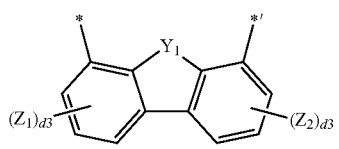

Formula 3-42
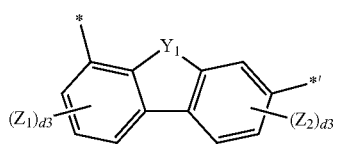

Formula 3-43
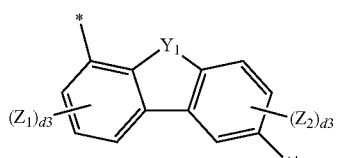

Formula 3-44
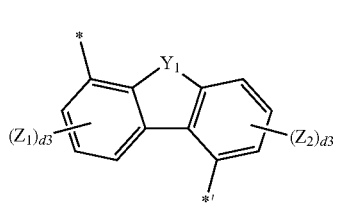

Formula 3-45
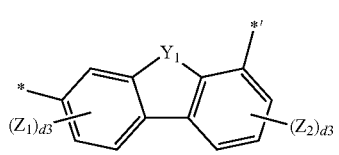

Formula 3-46
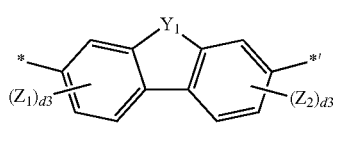

Formula 3-47
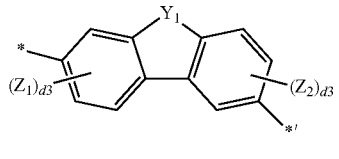

Formula 3-48
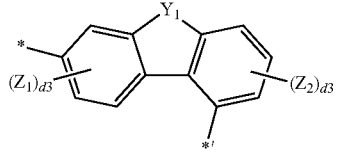

Formula 3-49
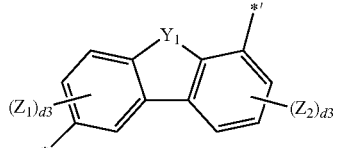

Formula 3-50
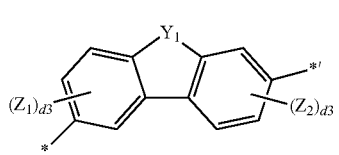

-continued

Formula 3-51
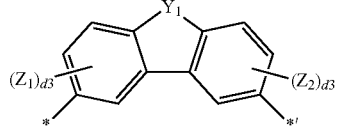

Formula 3-52
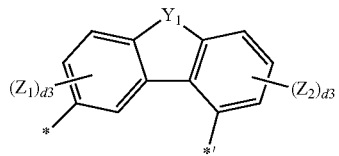

Formula 3-53
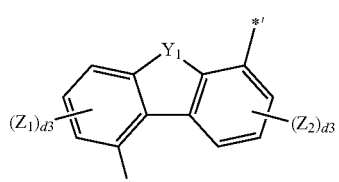

Formula 3-54
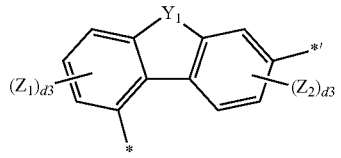

Formula 3-55
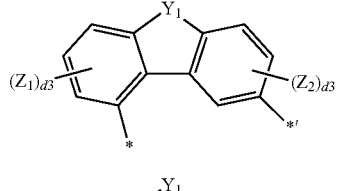

Formula 3-56
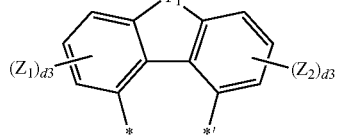

In Formulae 3-1 to 3-56, $Y_1$ may be selected from O, S, and $C(Z_3)(Z_4)$, $Z_1$ to $Z_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si$(Q_{11})(Q_{12})(Q_{13})$, wherein $Q_{11}$ to $Q_{13}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, d4 may be an integer selected from 0 to 4, d3 may be an integer selected from 0 to 3, d2 may be an integer selected from 0 to 2, and

* and *' may be each independently a binding site to a neighboring atom.

In Formula 1, a1 denotes the number of groups $L_1$, and is an integer selected from 0 to 5. When a1 is 0, *-$(L_1)_{a1}$-*' is a single bond, and when a1 is 2 or greater, two or more groups $L_1$ may be identical to or different from each other. Descriptions of a2 may be the same as defined in reference to a1 in Formula 1.

In Formula 1, a1 and a2 may be each independently an integer selected from 0 to 5.

For example, in Formula 1, a1 and a2 may be each independently 0, 1, or 2, but embodiments are not limited thereto.

According to an embodiment, in Formula 1, a1 may be 0.

According to another embodiment, in Formula 1, when a1 is not 0, at least one of groups $L_1$ may be selected from groups represented by Formulae 3-15 to 3-56.

In some embodiments, in Formula 1, when a1 is not 0, all of groups $L_1$ may be each independently selected from groups represented by Formulae 3-15 to 3-56.

In some embodiments, in Formula 1,
$L_1$ may be selected from groups represented by Formulae 3-15, 3-28, 3-41, and 3-51,
$L_2$ may be selected from groups represented by Formulae 3-1, 3-15, 3-28, 3-41, and 3-51, and
a1 and a2 may be each independently 0, 1, or 2,
but embodiments are not limited thereto.

In Formula 1, a group represented by *-$(L_1)_{a1}$-*' may be selected from groups represented by Formulae 3-41 to 3-56.

In some embodiments, in Formula 1, a group represented by *-$(L_1)_{a1}$-*' may be selected from groups represented by Formulae 4-1 to 4-39:

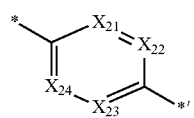

Formula 4-1

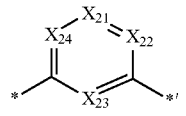

Formula 4-2

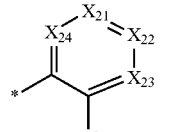

Formula 4-3

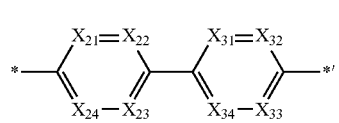

Formula 4-4

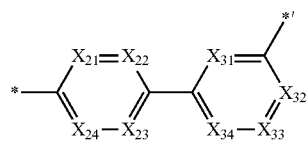

Formula 4-5

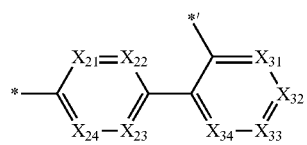

Formula 4-6

-continued

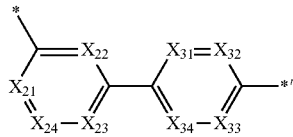

Formula 4-7

Formula 4-8

Formula 4-9

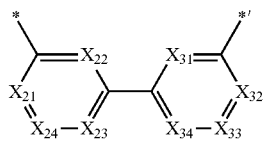

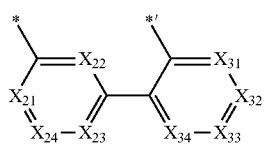

Formula 4-10

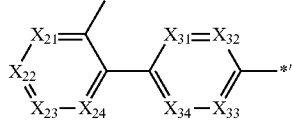

Formula 4-11

Formula 4-12

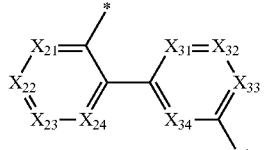

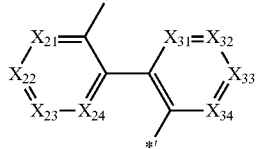

Formula 4-13

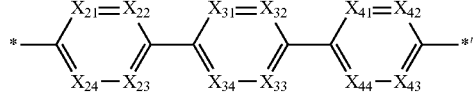

Formula 4-14

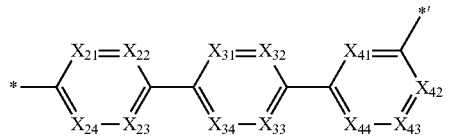

Formula 4-15

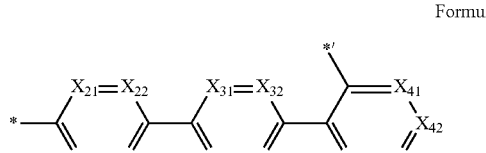

Formula 4-16
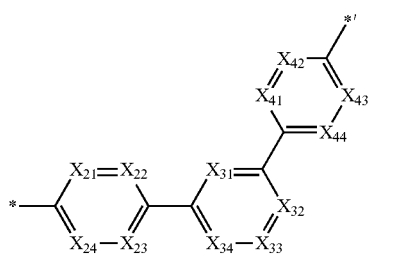
Formula 4-17
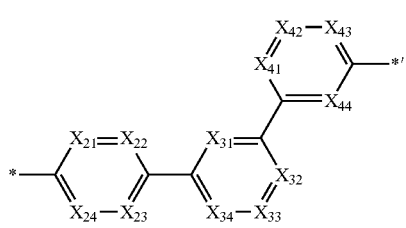
Formula 4-18
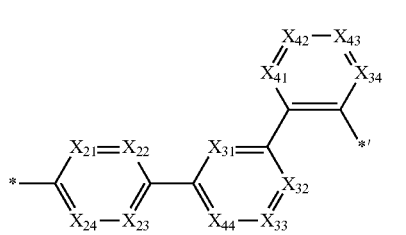
Formula 4-19
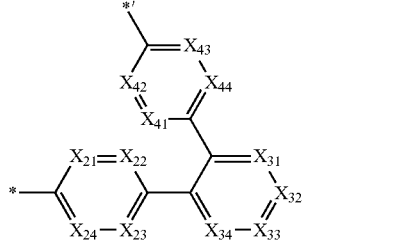
Formula 4-20
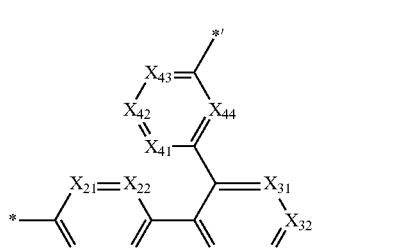
Formula 4-21
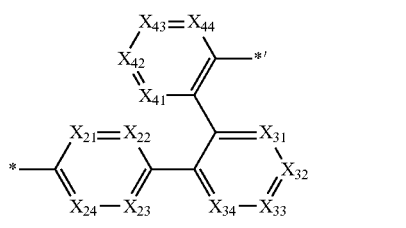
Formula 4-22
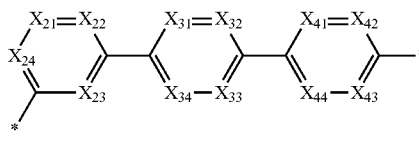
Formula 4-23
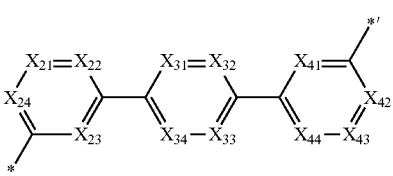
Formula 4-24
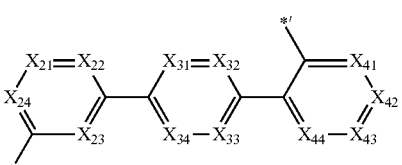
Formula 4-25
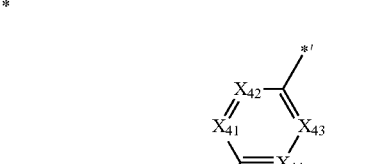
Formula 4-26
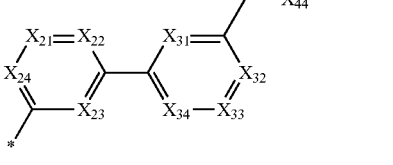
Formula 4-27
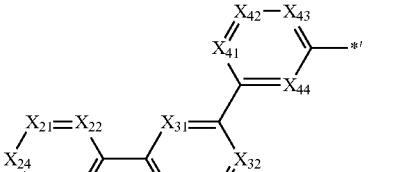
Formula 4-28
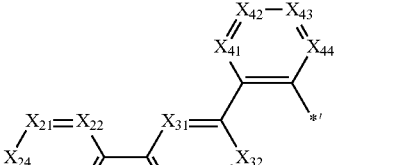
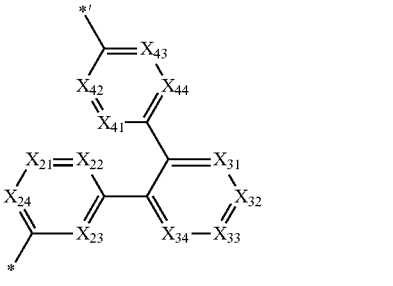

Formula 4-29
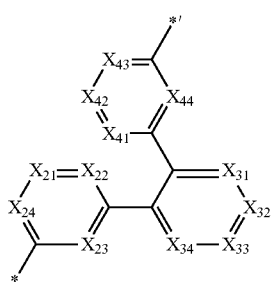

Formula 4-30
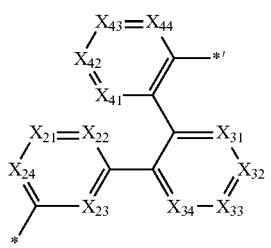

Formula 4-31
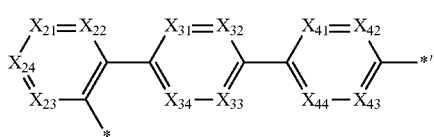

Formula 4-32
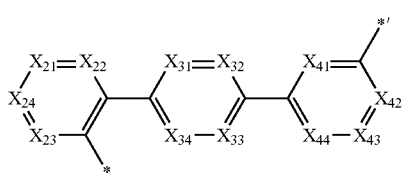

Formula 4-34
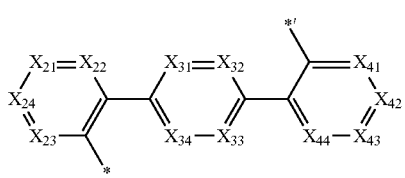

Formula 4-35
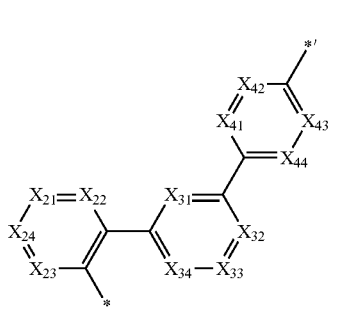

Formula 4-36
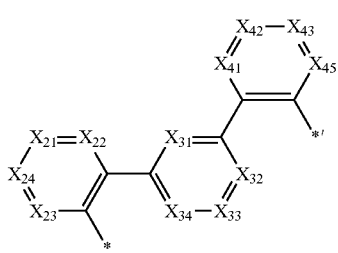

Formula 4-37
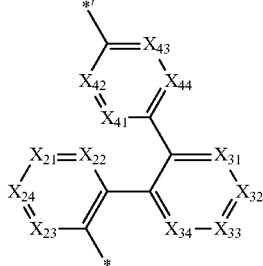

Formula 4-38
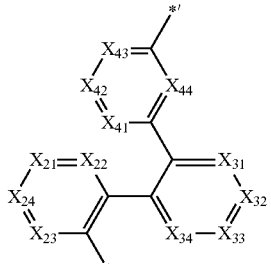

Formula 4-39
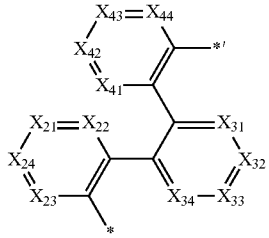

In Formulae 4-1 to 4-39, $X_{21}$ may be N or $C(Z_{21})$, $X_{22}$ may be N or $C(Z_{22})$, $X_{23}$ may be N or $C(Z_{23})$, $X_{24}$ may be N or $C(Z_{24})$, $X_{31}$ may be N or $C(Z_{31})$, $X_{32}$ may be N or $C(Z_{32})$, $X_{33}$ may be N or $C(Z_{33})$, $X_{34}$ may be N or $C(Z_{34})$, $X_{41}$ may be N or $C(Z_{41})$, $X_{42}$ may be N or $C(Z_{42})$, $X_{43}$ may be N or $C(Z_{43})$, and $X_{44}$ may be N or $C(Z_{44})$, but at least one of $X_{21}$ to $X_{24}$ may not be N, at least one of $X_{31}$ to $X_{34}$ may not be N, and at least one of $X_{41}$ to $X_{44}$ may not be N, $Z_{21}$ to $Z_{24}$, $Z_{31}$ to $Z_{34}$, and $Z_{41}$ to $Z_{44}$ may be each independently selected from a hydrogen, a deuterium, a cyano group, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si$(Q_{11})(Q_{12})(Q_{13})$, wherein $Q_{11}$ to $Q_{13}$ may be each independently a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group,

* and *' may be each independently a binding site to a neighboring atom.

According to an embodiment, none, one, two, or three atoms among all ring-forming atoms in each of Formulae 4-1 to 4-39 may be nitrogen.

According to another embodiment, none, one, or two atoms among all ring-forming atoms in each of Formulae 4-1 to 4-39 may be nitrogen.

In some embodiments, none or one atom among all ring-forming atoms in each of Formulae 4-1 to 4-39 may be nitrogen.

In some embodiments, in each of Formulae 4-1 to 4-39, $X_{21}$ may be $C(Z_{21})$, $X_{22}$ may be $C(Z_{22})$, $X_{23}$ may be $C(Z_{23})$, $X_{24}$ may be $C(Z_{24})$, $X_{31}$ may be $C(Z_{31})$, $X_{32}$ may be $C(Z_{32})$, $X_{33}$ may be $C(Z_{33})$, $X_{34}$ may be $C(Z_{34})$, $X_{41}$ may be $C(Z_{41})$, $X_{42}$ may be $C(Z_{42})$, $X_{43}$ may be $C(Z_{43})$, and $X_{44}$ may be $C(Z_{44})$ (That is, none of the ring-forming atoms in each of Formulae 4-1 to 4-30 may be nitrogen).

In Formula 1, $R_1$ to $R_8$, $R_{11}$ to $R_{18}$, and $R_{31}$ may be each independently selected from a hydrogen, a deuterium, —F, —Cl, —Br, —I, a hydroxyl group, a cyano group (—CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

For example, in Formula 1, $R_1$ to $R_8$, $R_{11}$ to $R_{18}$, and $R_{31}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, a pyrazinyl group, a pyridazinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, an imidazopyrimidinyl group, and an imidazopyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group and —Si($Q_{21}$)($Q_{22}$)($Q_{23}$); and —Si($Q_1$)($Q_2$)($Q_3$), wherein $Q_1$ to $Q_3$ and $Q_{21}$ to $Q_{23}$ may be each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group.

According to an embodiment, in Formula 1, $R_1$ to $R_8$, $R_{11}$ to $R_{18}$, and $R_{31}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group;

a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si($Q_{21}$)($Q_{22}$)($Q_{23}$); and —Si($Q_1$)($Q_2$)($Q_3$), $Q_1$ to $Q_3$ and $Q_{21}$ to $Q_{23}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group.

According to another embodiment, in Formula 1, $R_1$ to $R_8$, $R_{11}$ to $R_{18}$, and $R_{31}$ may be each independently selected from a hydrogen, a deuterium, —F, a cyano group, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, and a cyano group;

a phenyl group, a pyridinyl group, a pyrimidinyl group, a triazinyl group, a dibenzofuranyl group, and a dibenzothiophenyl group;

a phenyl group, a pyridinyl group, a pyrimidinyl group, a triazinyl group, a dibenzofuranyl group, and a dibenzothiophenyl group, each substituted with at least one selected from a deuterium, —F, a cyano group, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, a dibenzothiophenyl group, and —Si($Q_{21}$)($Q_{22}$)($Q_{23}$); and —Si($Q_1$)($Q_2$)($Q_3$), wherein $Q_1$ to $Q_3$ and $Q_{21}$ to $Q_{23}$ may be each independently selected from a hydrogen, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, and a dibenzothiophenyl group.

According to an embodiment, in Formula 1, at least one of $X_3$, $X_6$, $X_{13}$, and $X_{16}$ may be C(CN).

In Formula 1, b1 may denote the number of groups $R_{31}$ which may be an integer selected from 0 to 4. When b1 is 2 or greater, two or more groups $R_{31}$ may be identical to or different from each other.

For example, in Formula 1, b1 and b2 may be 0, 1, or 2.

In Formula 1, c1 may be an integer selected from 1 to 4. That is, ring $A_1$ may essentially include at least one cyano group. For example, in Formula 1, c1 may be 1 or 2.

According to an embodiment, in Formula 1, a group represented by

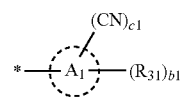

may be selected from groups represented by Formulae 5-1 to 5-60:

Formula 5-1

Formula 5-2

Formula 5-3

Formula 5-4

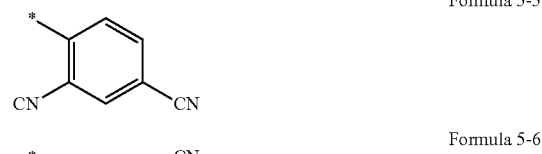
Formula 5-5

Formula 5-6

Formula 5-7

Formula 5-8

-continued
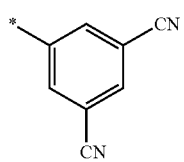
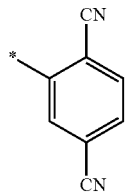
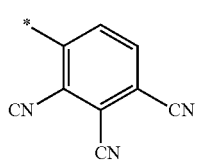
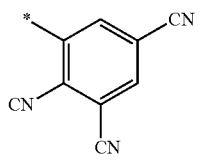
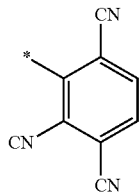
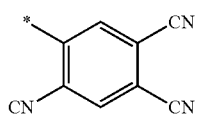
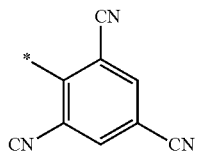
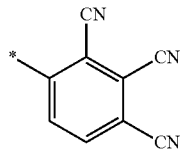
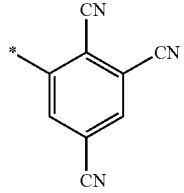
-continued
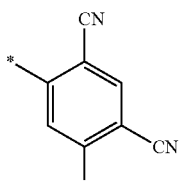  Formula 5-9
  Formula 5-10
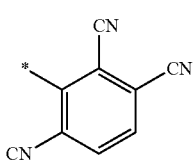  Formula 5-11
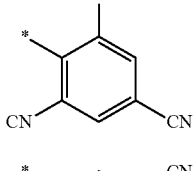  Formula 5-12
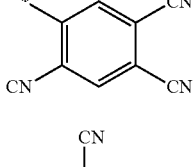  Formula 5-13
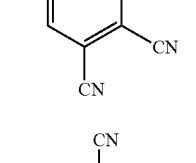  Formula 5-14
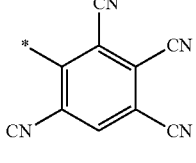  Formula 5-15
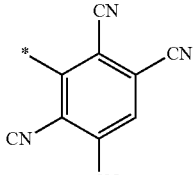  Formula 5-16
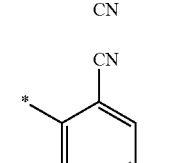  Formula 5-17
Formula 5-18
Formula 5-19
Formula 5-20
Formula 5-21
Formula 5-22
Formula 5-23
Formula 5-24
Formula 5-25
Formula 5-26
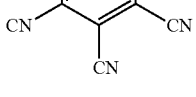

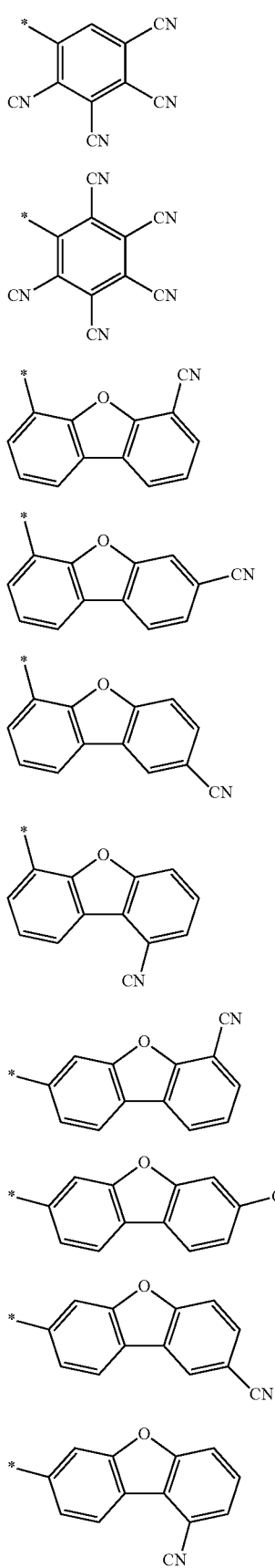
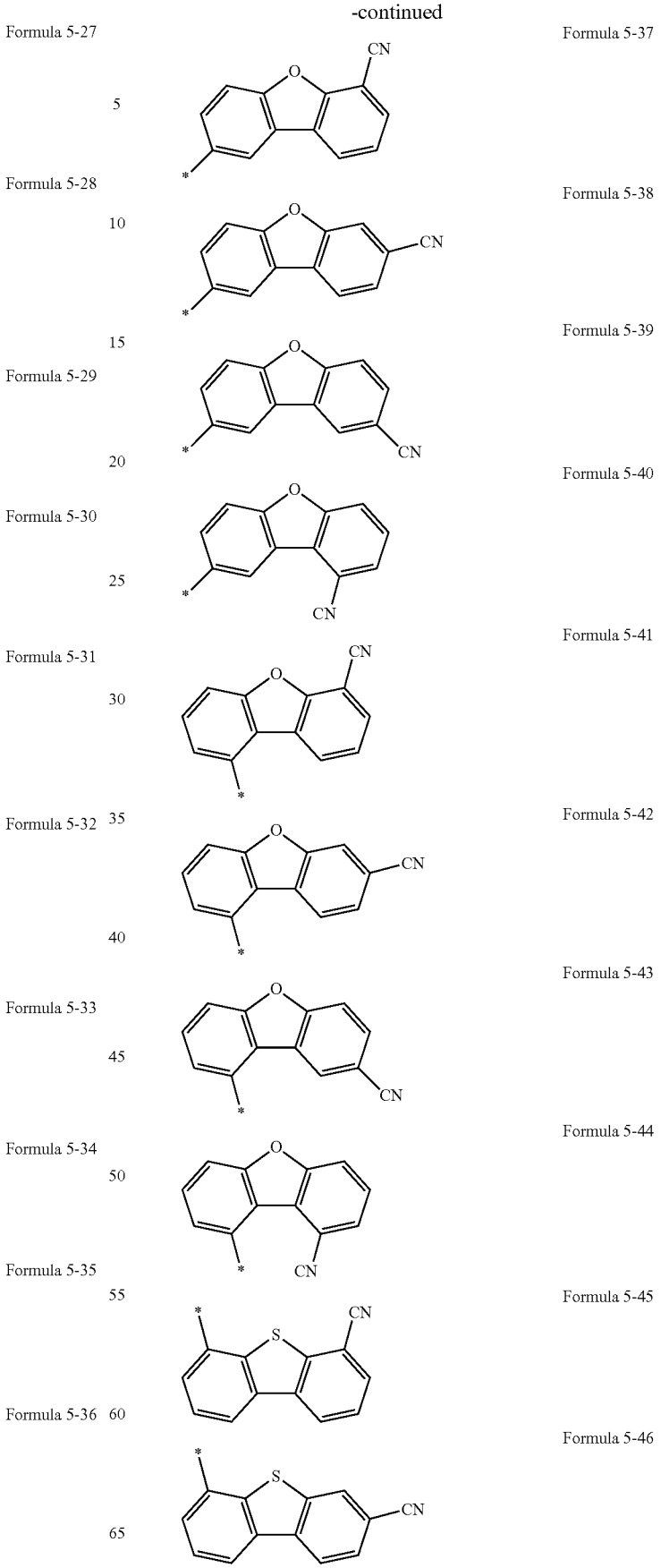

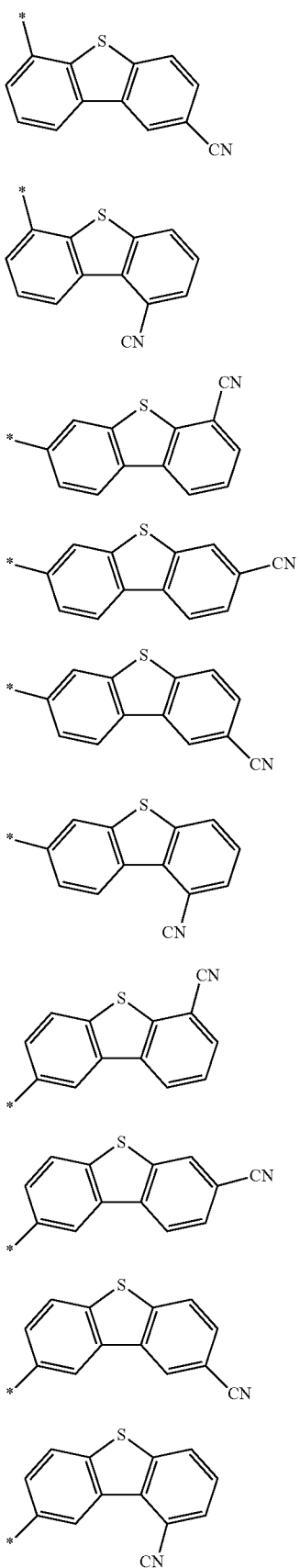
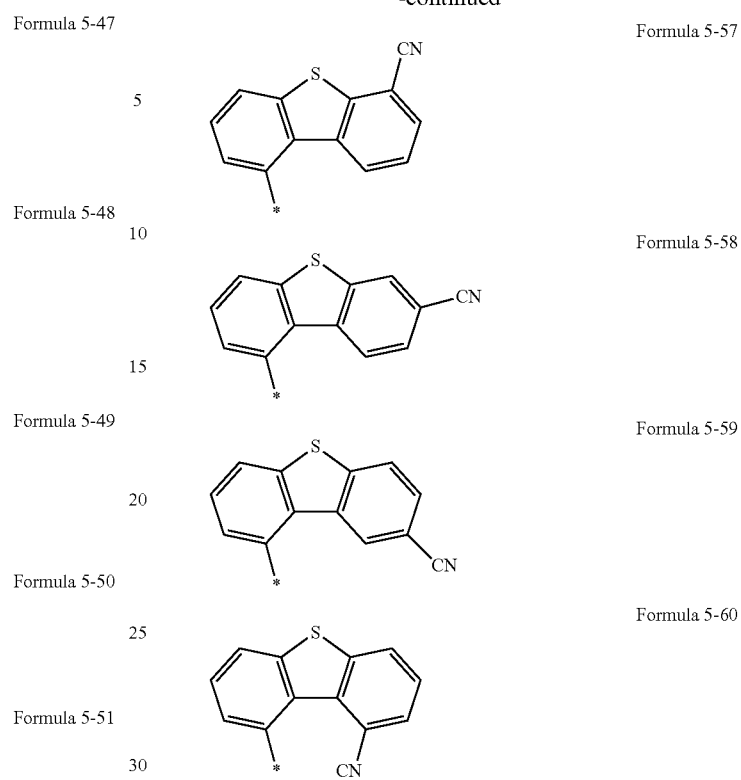
In Formulae 5-1 to 5-60, * may denote a binding site to a neighboring atom.
According to an embodiment, in Formula 1, a group represented by
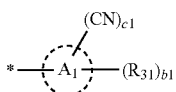
may be selected from groups represented by Formulae 5-1 to 5-3, 5-31, 5-39, 5-47, and 5-55, but embodiments are not limited thereto.
A condensed cyclic compound represented by Formula 1 may be represented by one of Formulae 1A to 1D:
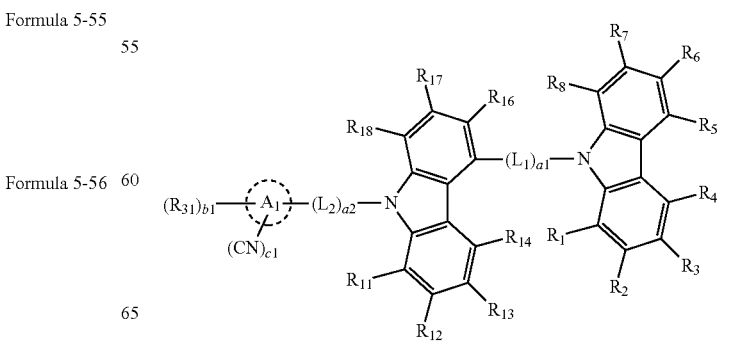
Formula 1A -continued Formula 1B Formula 1C Formula 1D

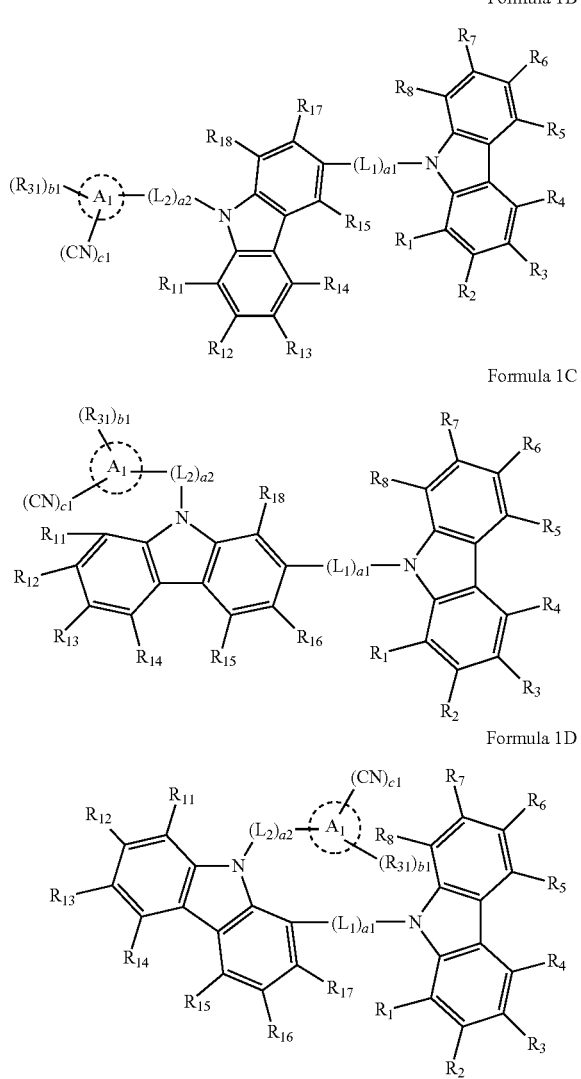

In Formulae 1A to 1D, ring $A_1$, $L_1$, $L_2$, a1 and a2, $R_1$ to $R_8$, $R_{11}$ to $R_{18}$, $R_{31}$, b1, and c1 may be understood by referring to the description provided herein.

For example, in Formulae 1A to 1D, ring $A_1$ may be selected from a benzene ring, a dibenzofurane ring, and a dibenzothiophene ring, $L_1$ may be selected from groups represented by Formulae 3-15, 3-28, 3-41, and 3-51, $L_2$ may be selected from groups represented by Formulae 3-1, 3-15, 3-28, 3-41, and 3-51, a1 and a2 may be each independently selected from 0, 1, and 2, $R_1$ to $R_8$, $R_{11}$ to $R_{18}$, and $R_{31}$ may be each independently selected from a hydrogen, a deuterium, —F, a cyano group, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, and a cyano group;

a phenyl group, a pyridinyl group, a pyrimidinyl group, a triazinyl group, a dibenzofuranyl group, and a dibenzothiophenyl group;

a phenyl group, a pyridinyl group, a pyrimidinyl group, a triazinyl group, a dibenzofuranyl group, and a dibenzothiophenyl group, each substituted with at least one selected from a deuterium, —F, a cyano group, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, a dibenzothiophenyl group, and —Si($Q_{21}$)($Q_{22}$)($Q_{23}$); and —Si($Q_1$)($Q_2$)($Q_3$), wherein $Q_1$ to $Q_3$ and $Q_{21}$ to $Q_{23}$ may be each independently selected from a hydrogen, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, and a dibenzothiophenyl group, b1 may be 0 or 1, and c1 may be 1 or 2.

According to another embodiment, in Formulae 1A to 1D, a group represented by

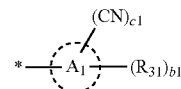

may be selected from groups represented by Formulae 5-1 to 5-3, 5-31, 5-39, 5-47, and 5-55, but embodiments are not limited thereto.

In some embodiments, in Formulae 1A to 1D, at least one of $R_3$, $R_6$, $R_{13}$, and $R_{16}$ may be a cyano group.

In some embodiments, the number of cyano groups in Formula 1 may be 1, 2, 3, or 4.

A compound represented by Formula 1 may be one of Compounds 1 to 336, but embodiments are not limited thereto:

1

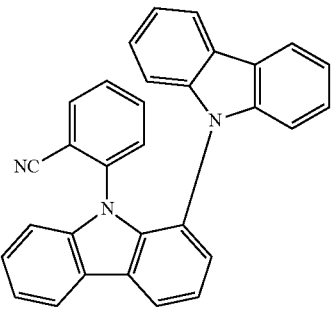

2

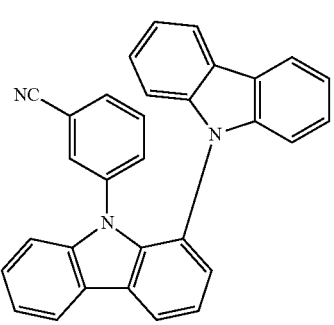

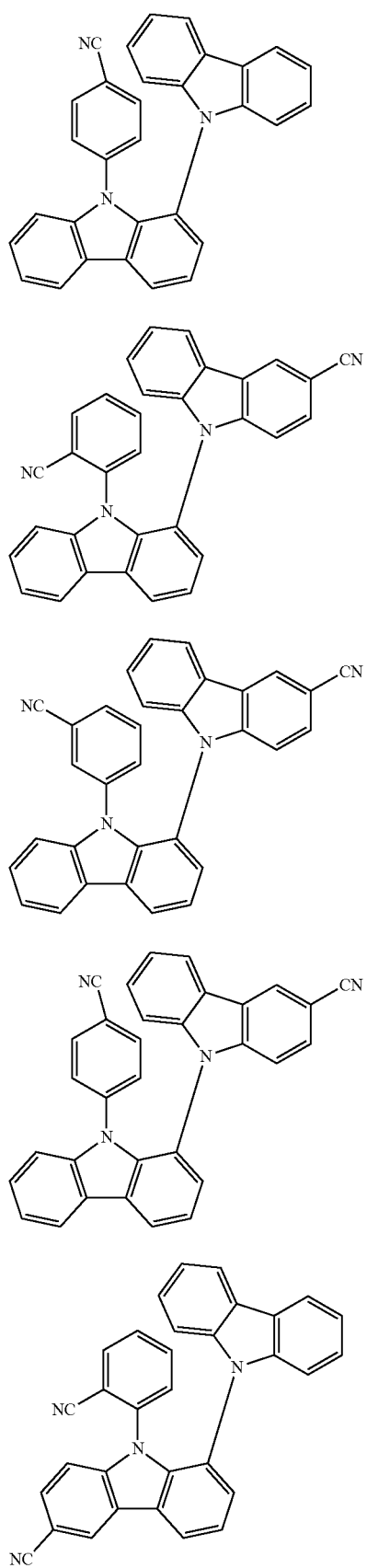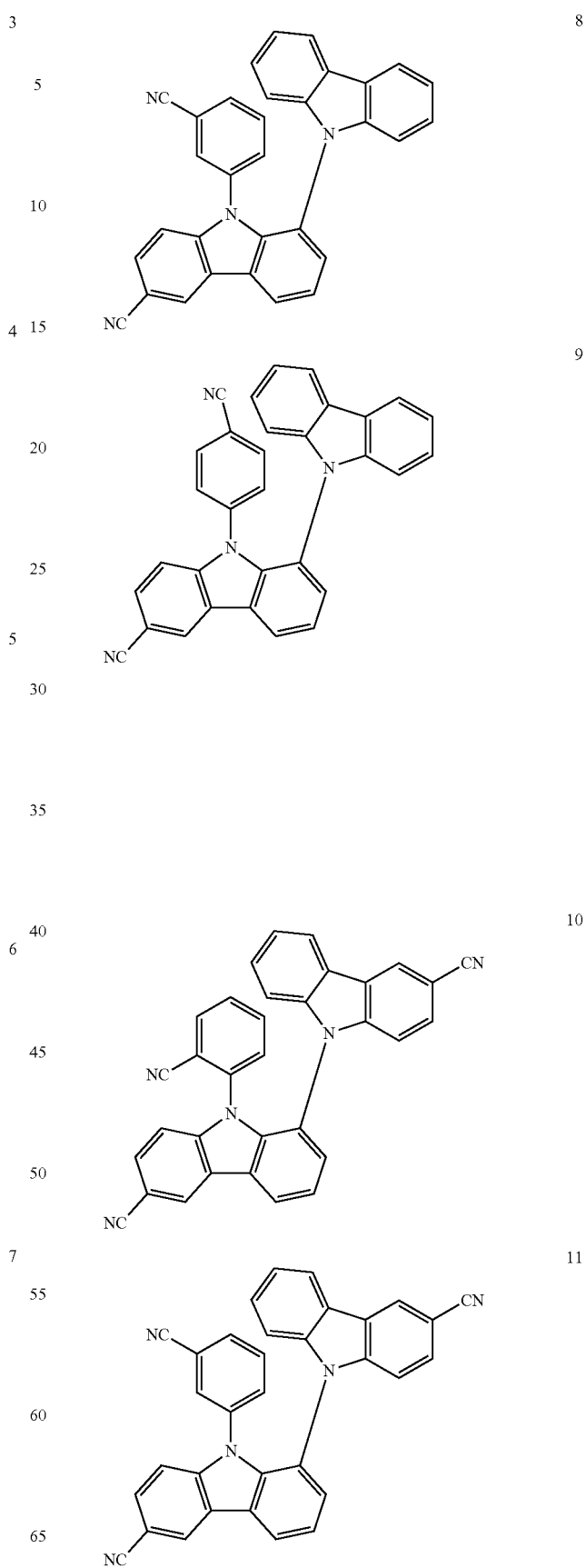

12
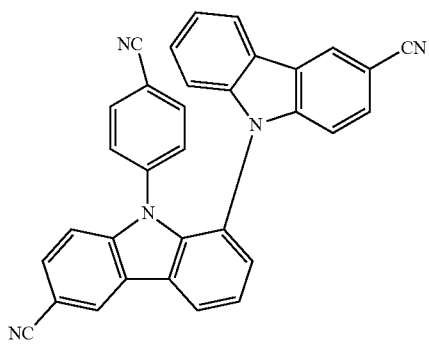
13
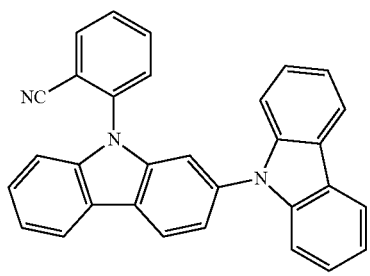
14
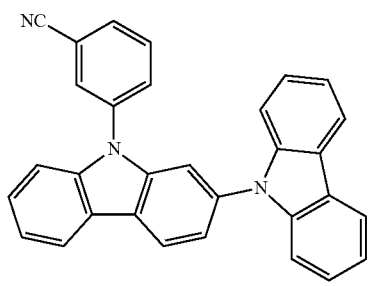
15
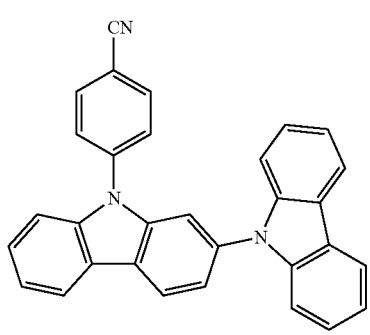
16
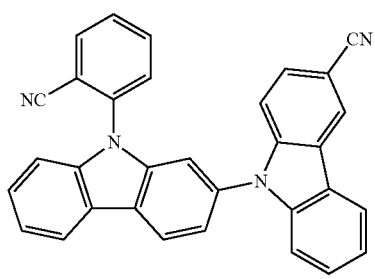
17
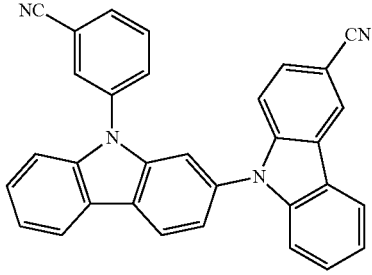
18
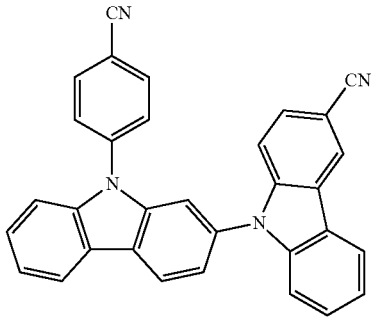
19
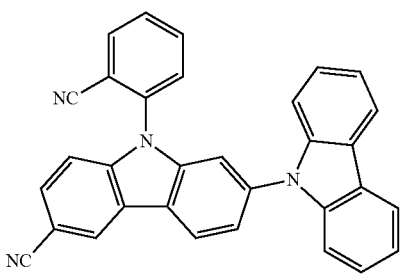
20
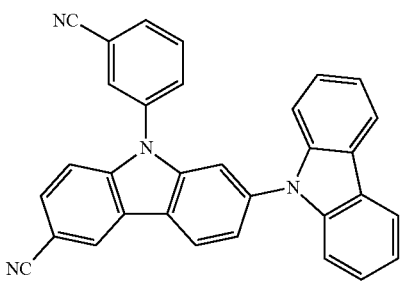
21
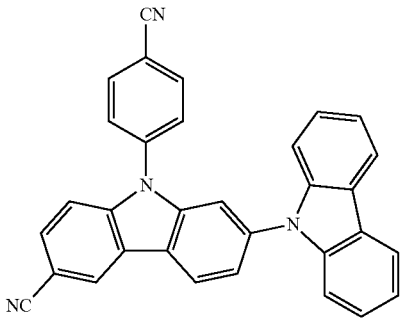

22
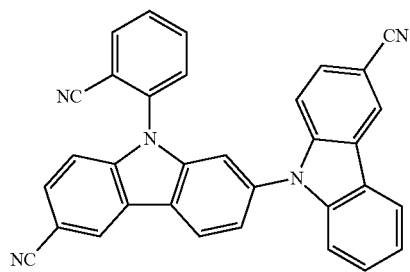
23
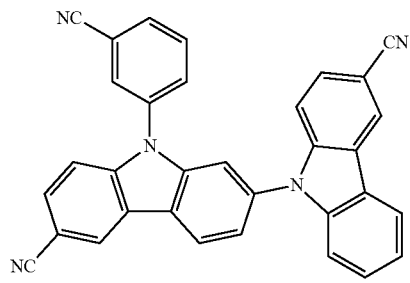
24
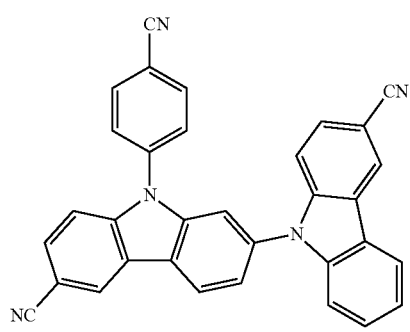
25
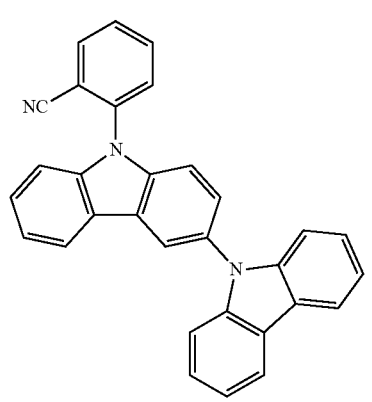
26
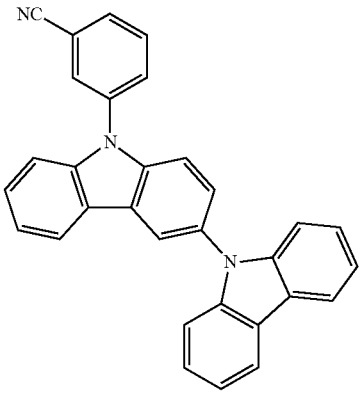
27
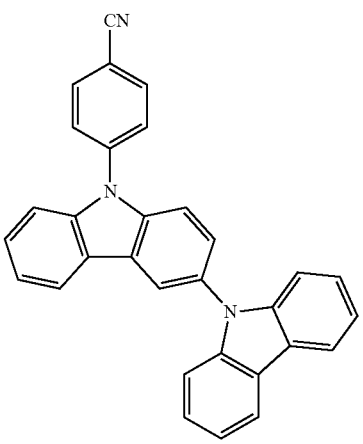
28
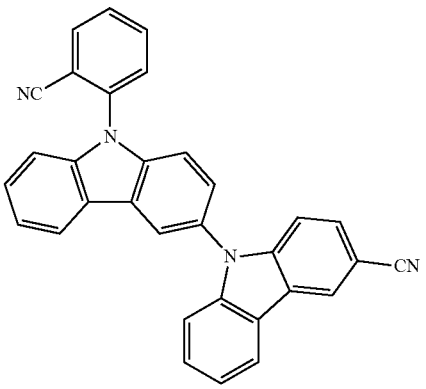
29
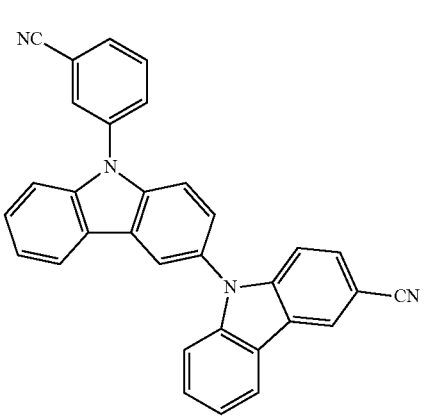

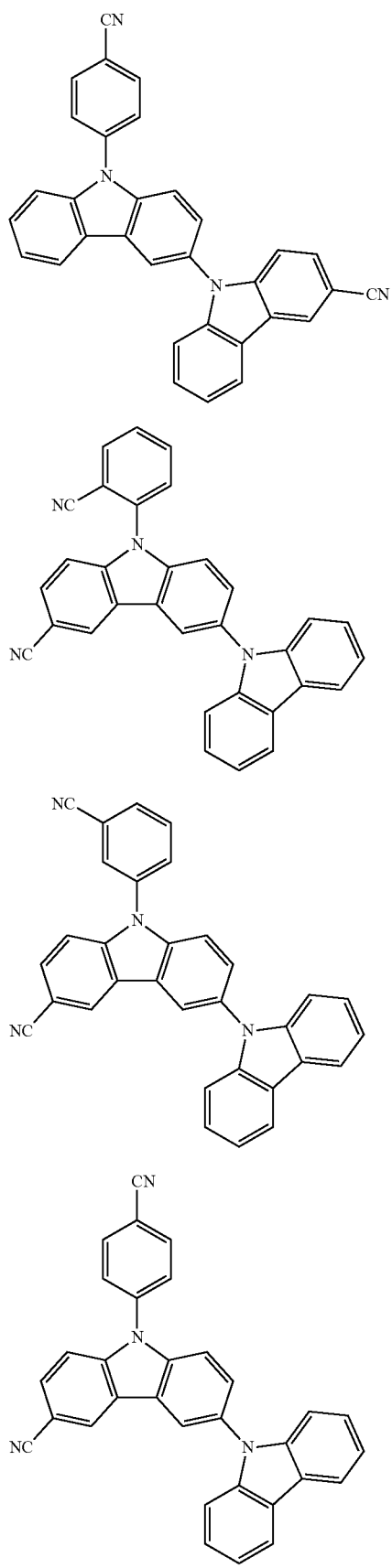
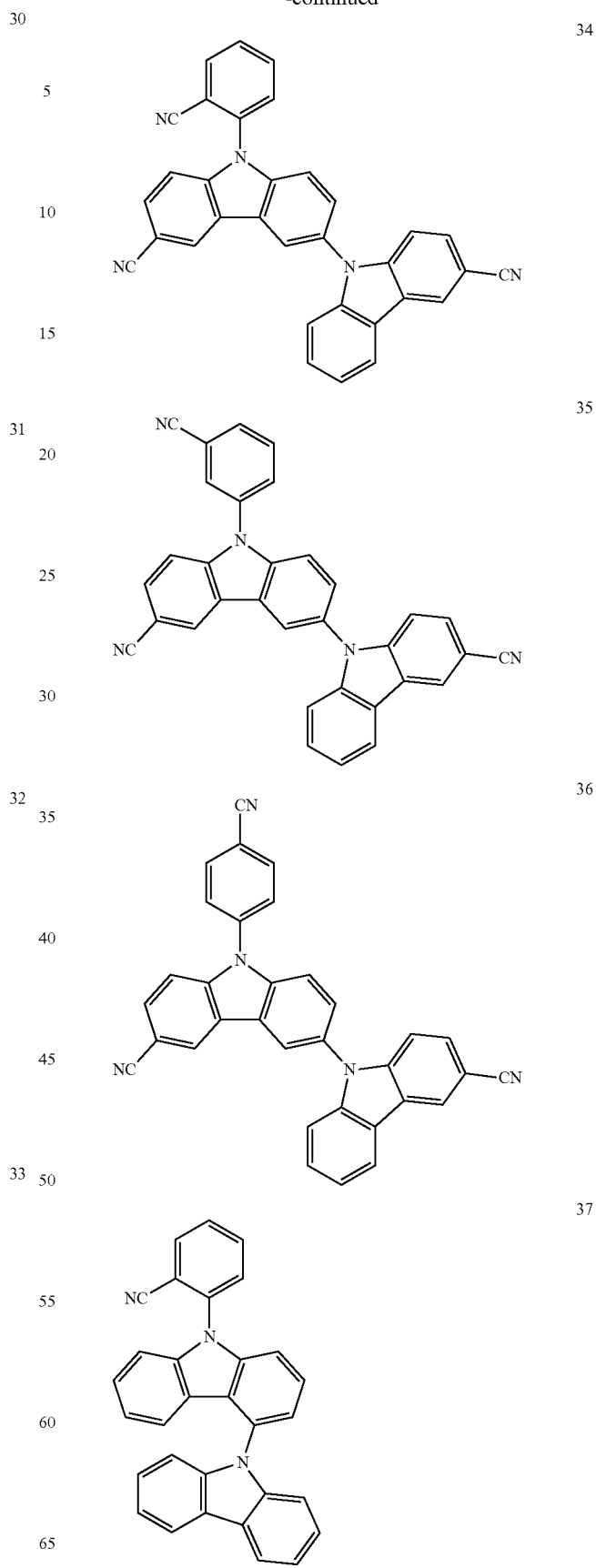

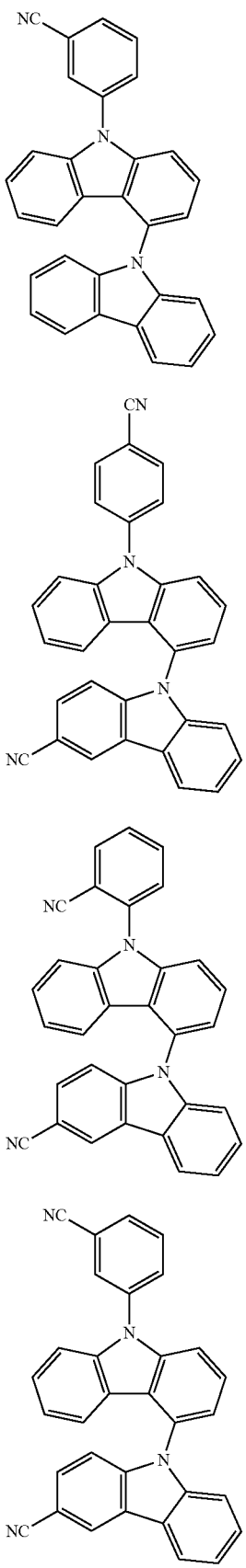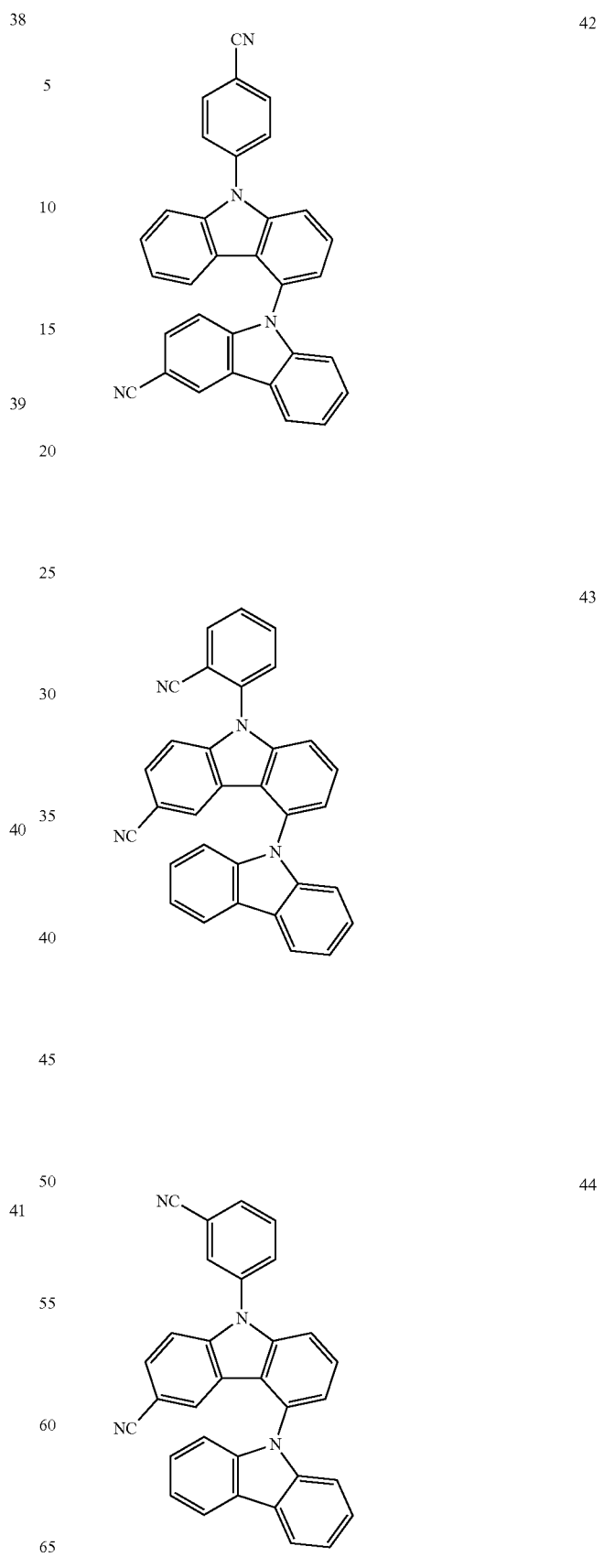

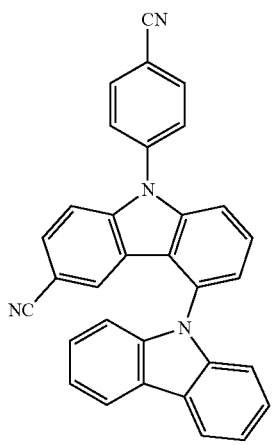
45
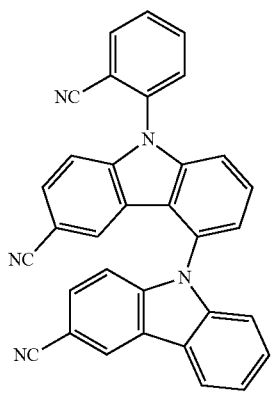
46
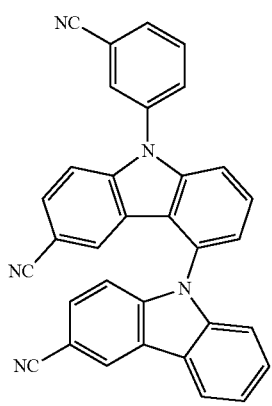
47
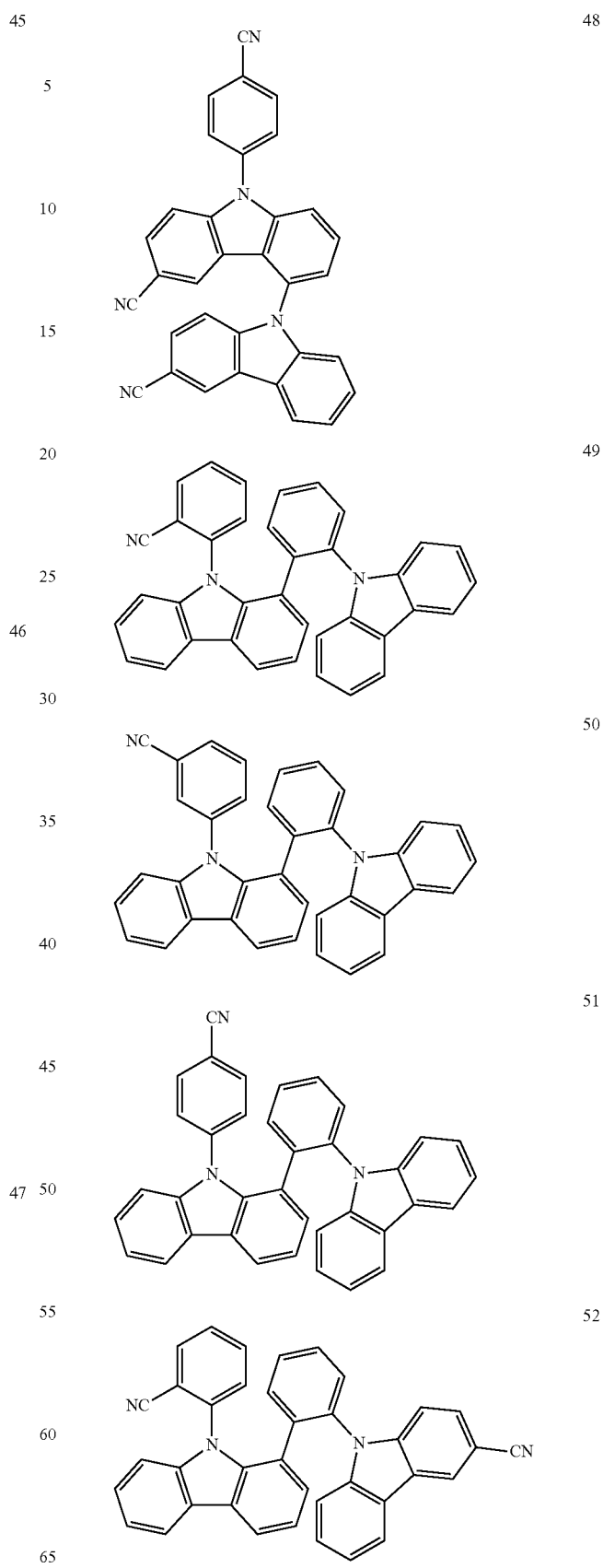

-continued
53
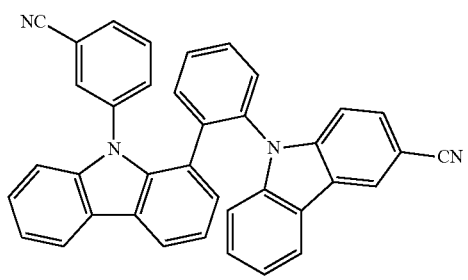
54
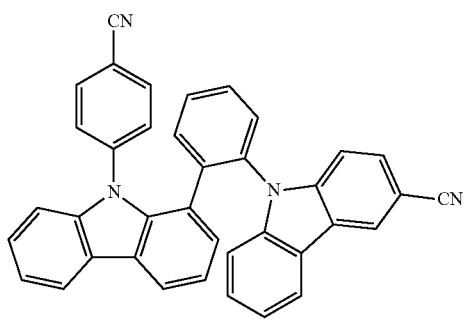
55
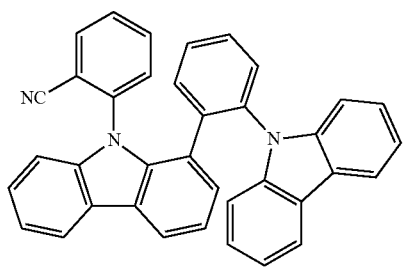
56
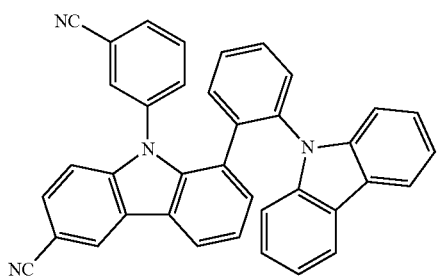
57
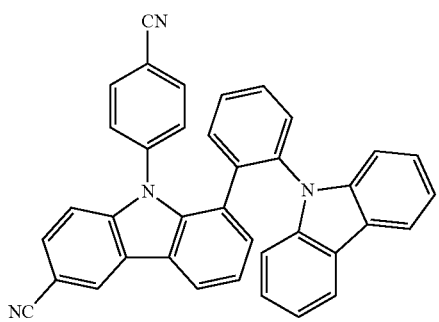
-continued
58
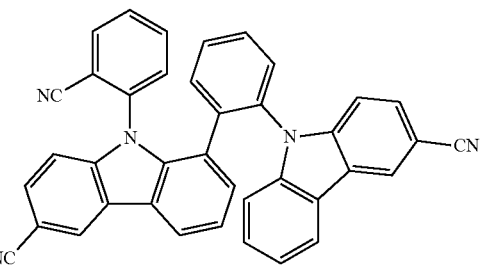
59
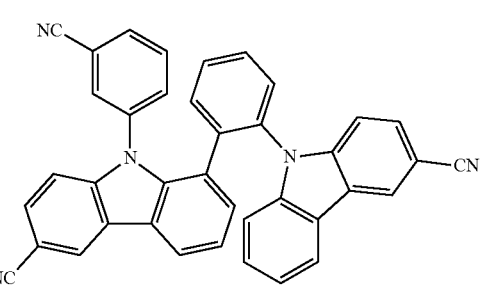
60
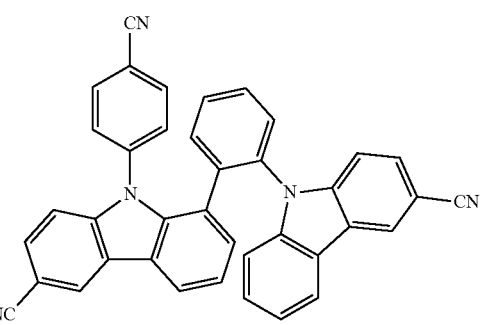
61
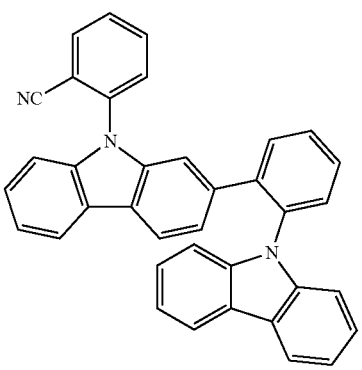
62
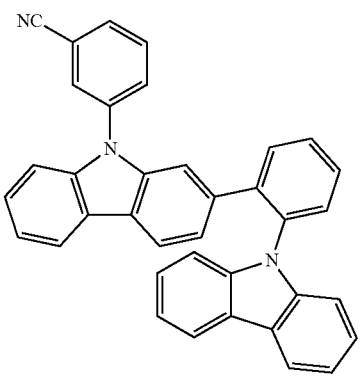

63
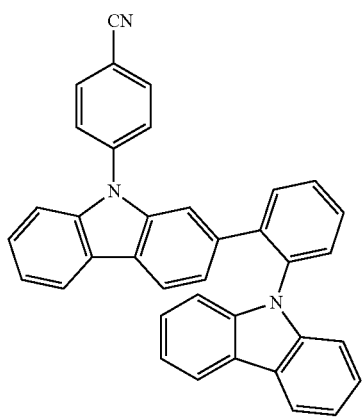
64
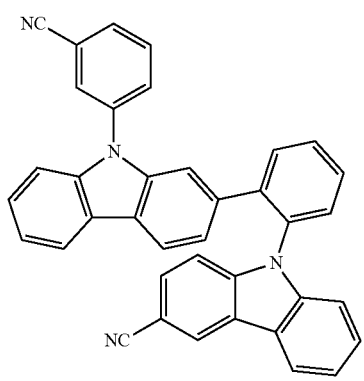
65
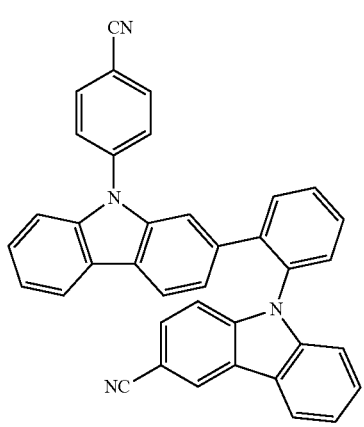
66
67
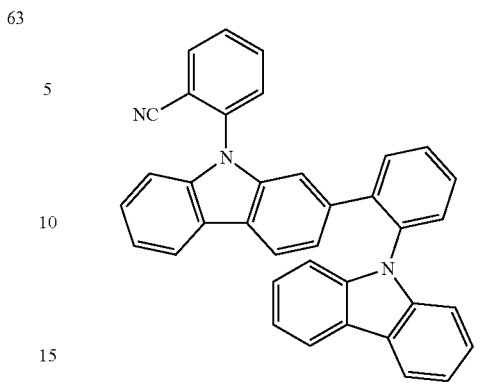
68
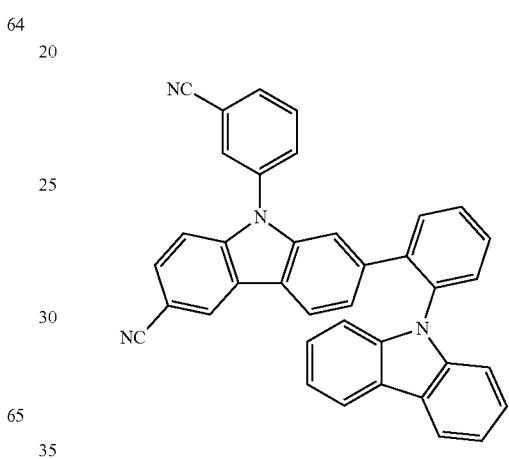
69
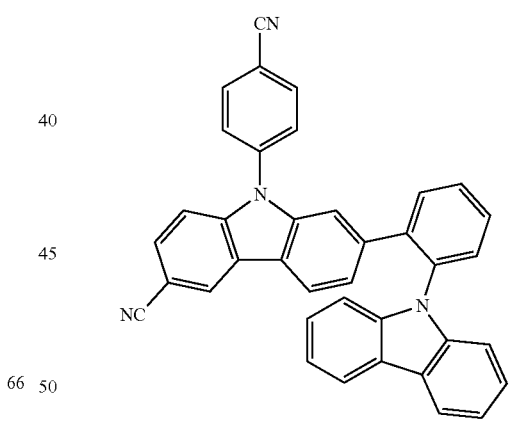
70
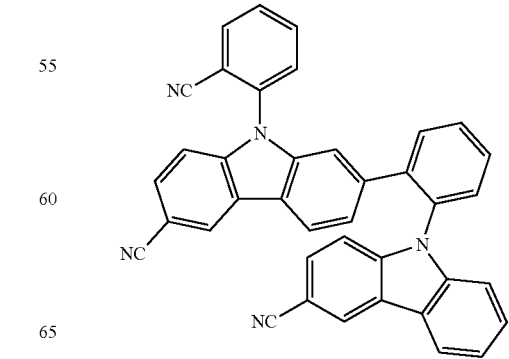

47
-continued
71
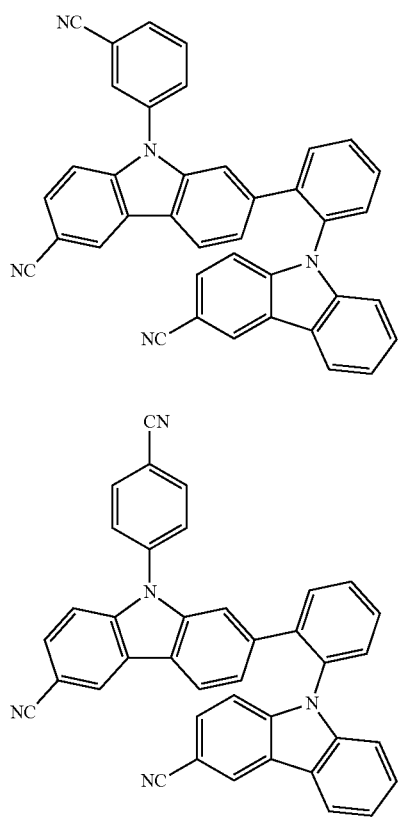
72
73
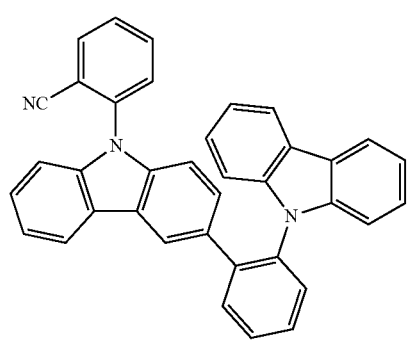
74
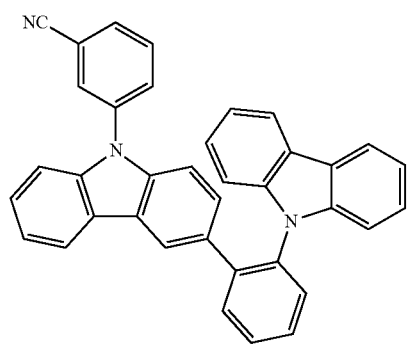
48
-continued
75
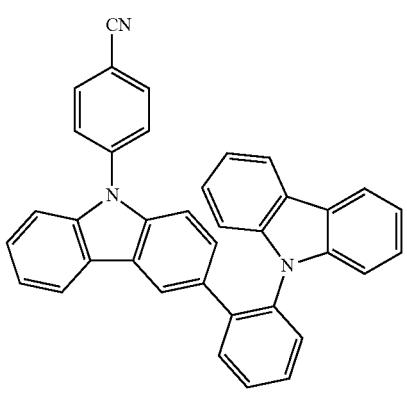
76
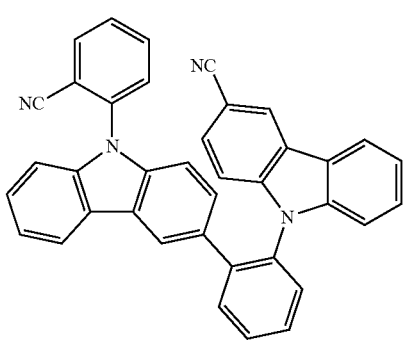
77
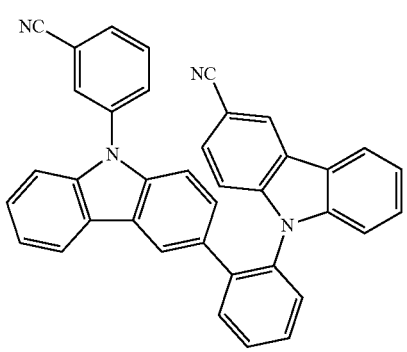
78
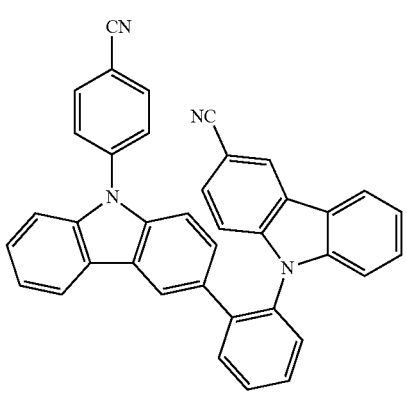

79
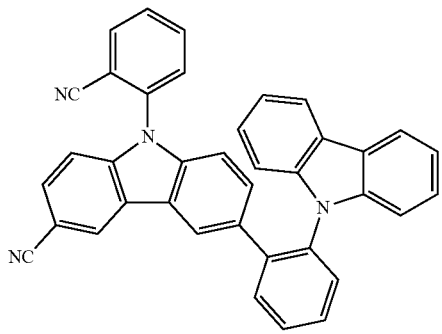
80
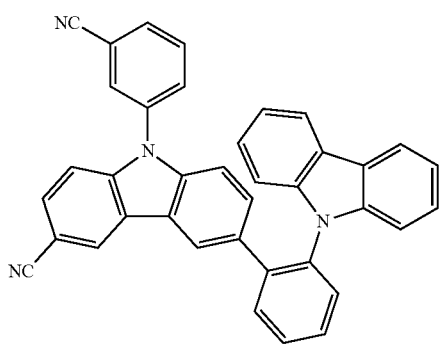
81
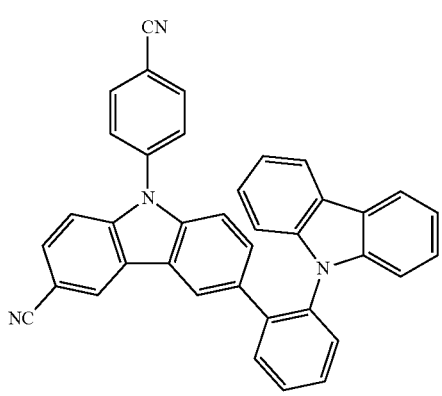
82
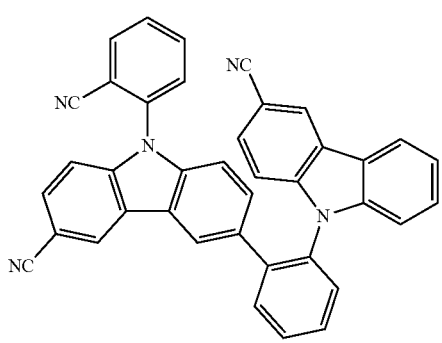
83
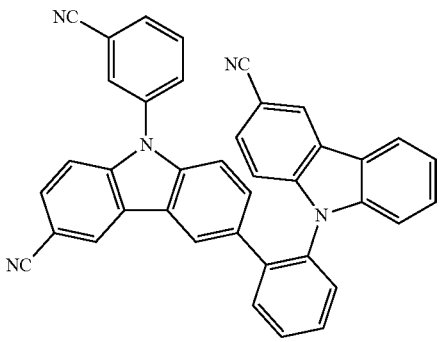
84
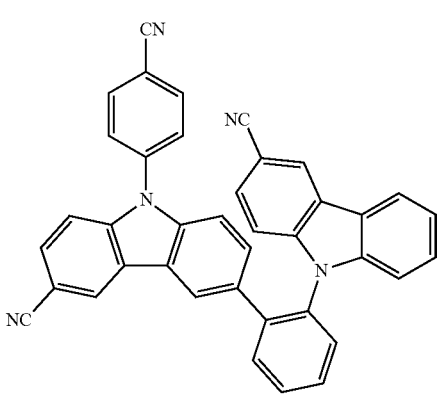
85
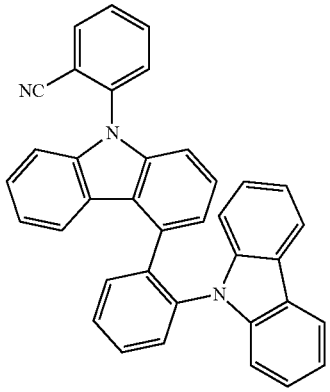
86
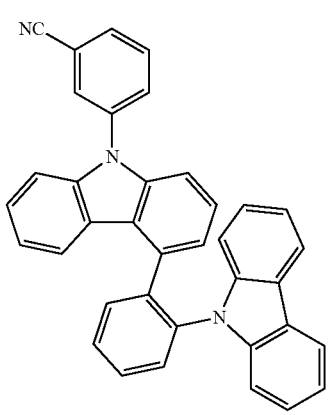

87
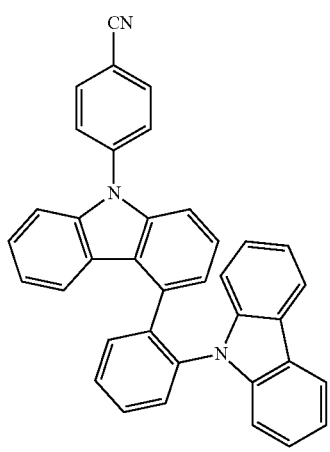
88
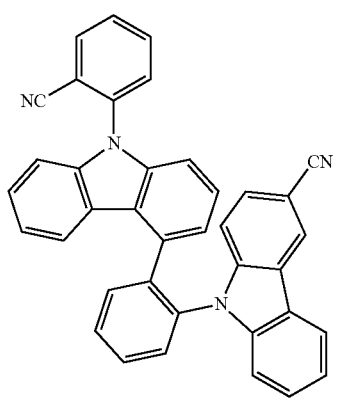
89
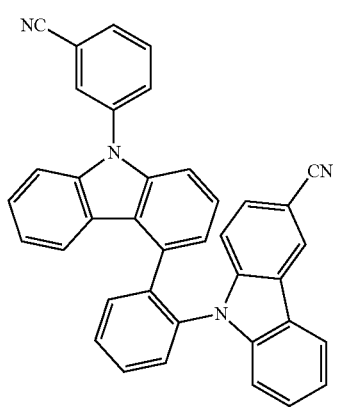
90
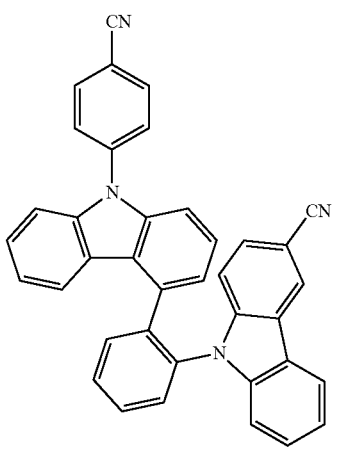
91
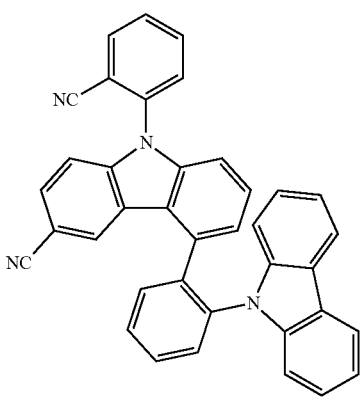
92
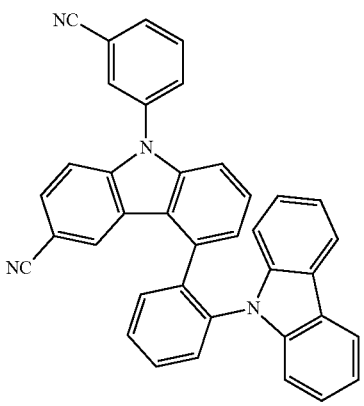

93
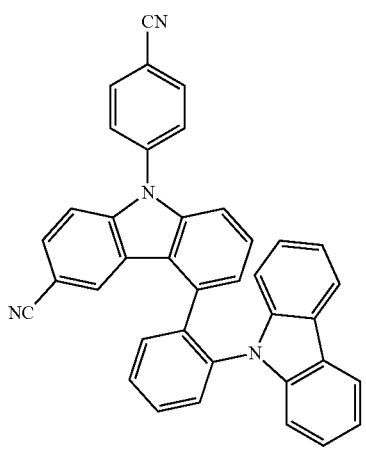
94
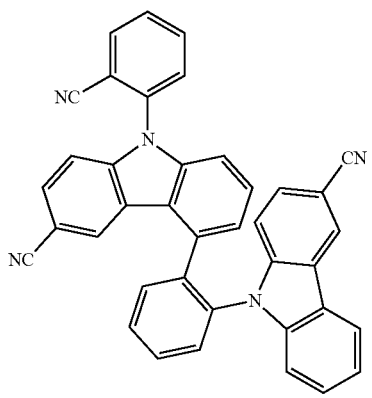
95
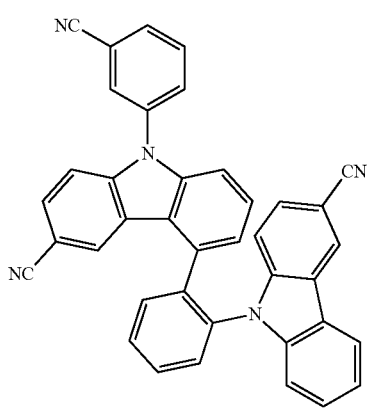
96
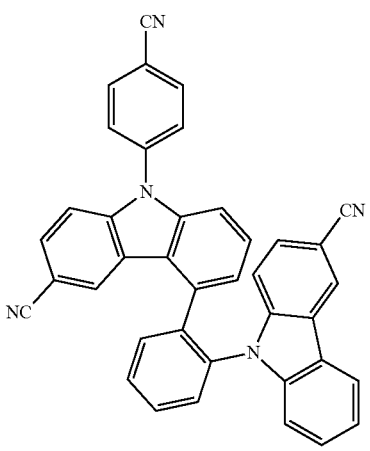
97
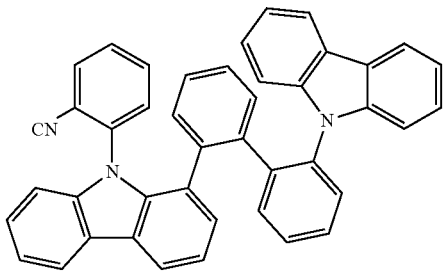
98
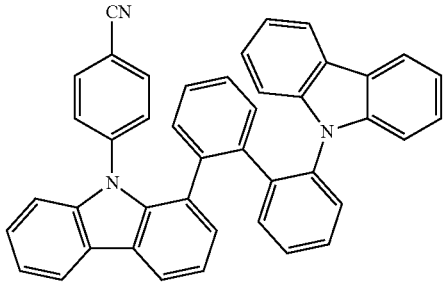
99
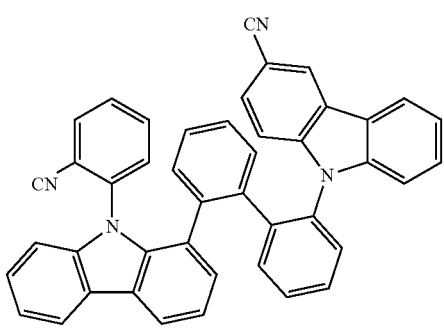
100

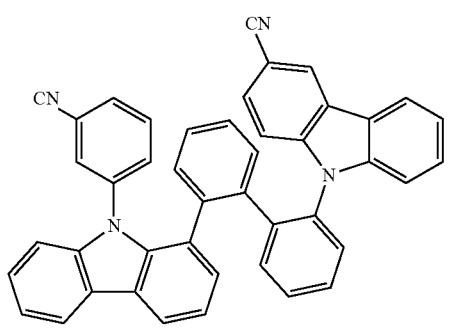
101
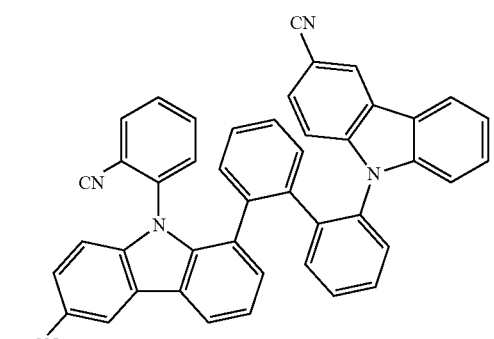
106

102
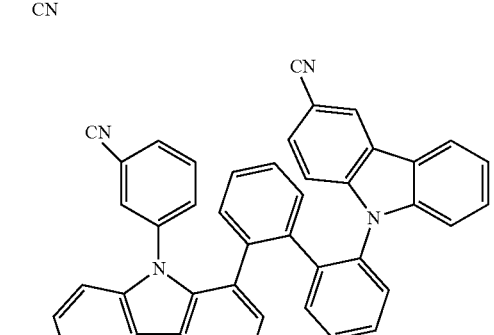
107
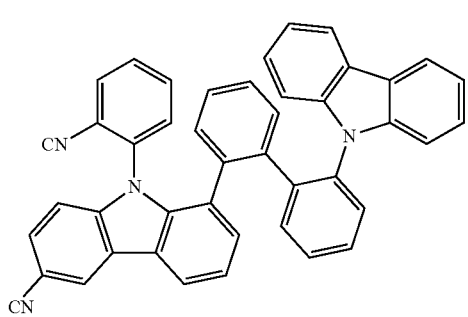
103
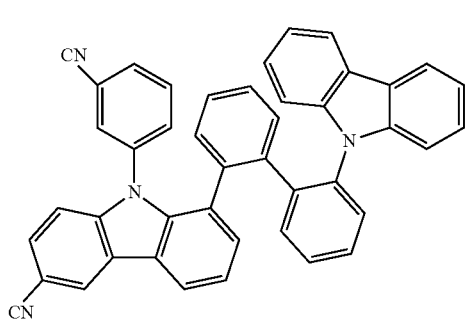
104
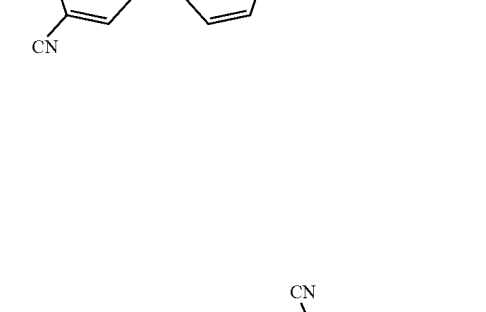
108
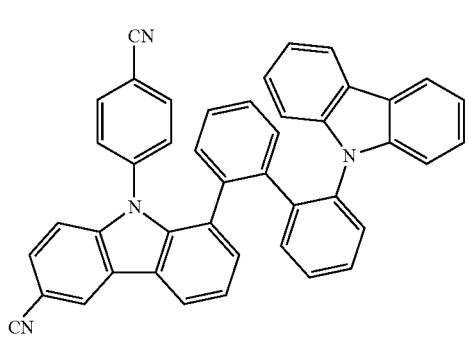
105
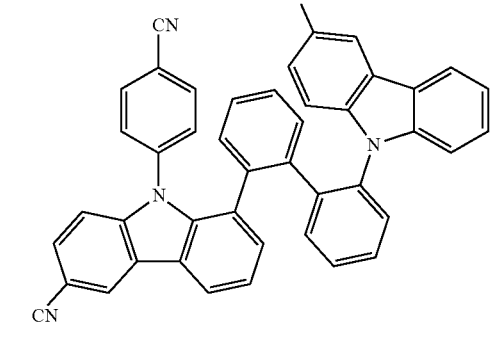
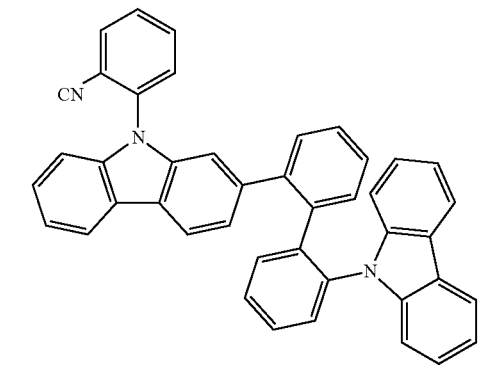
109

-continued
110
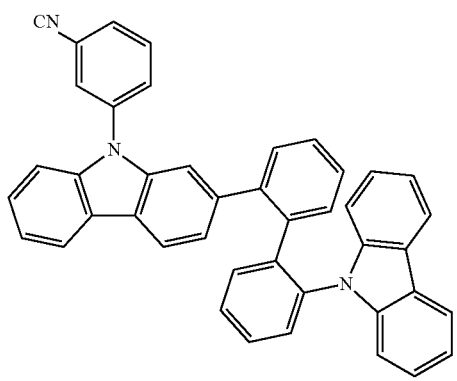
111
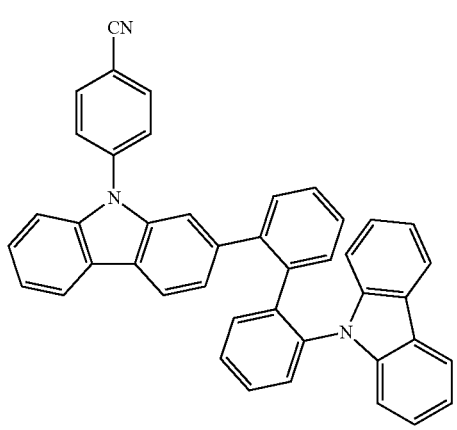
112
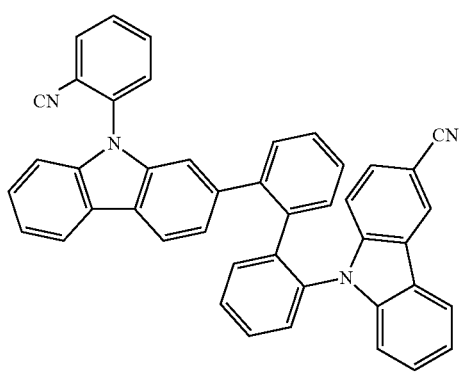
113
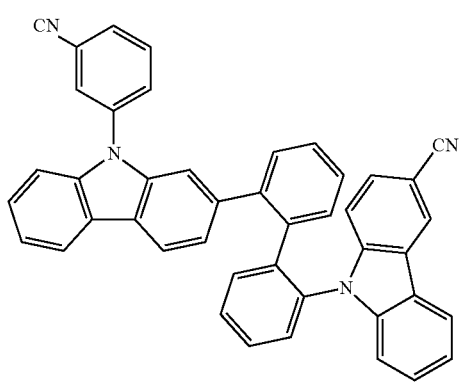
-continued
114
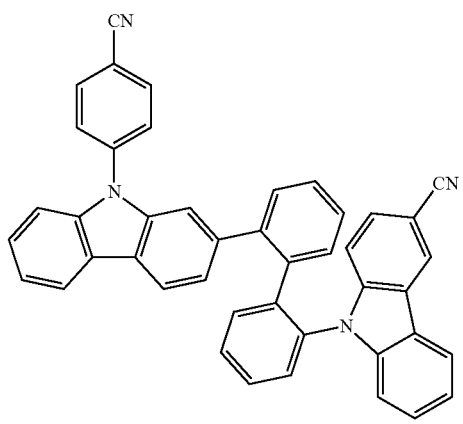
115
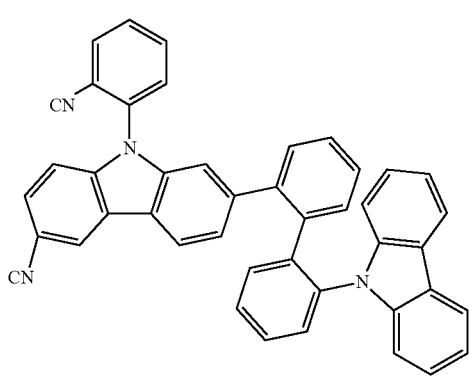
116
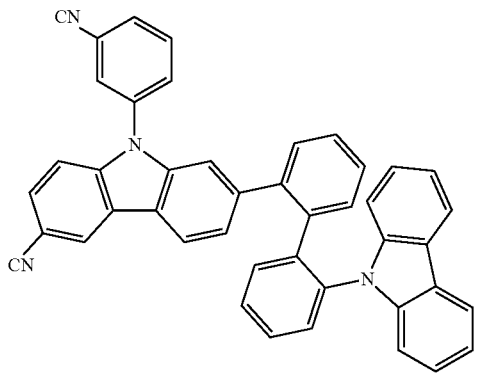
117
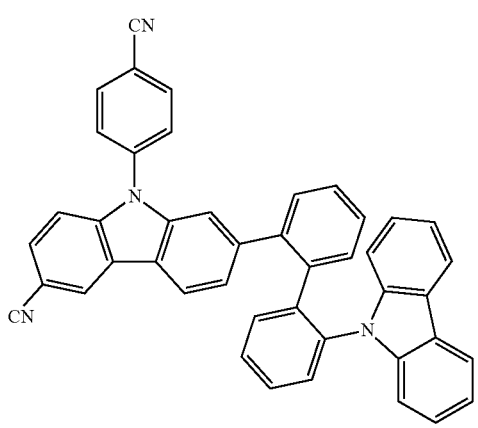

118
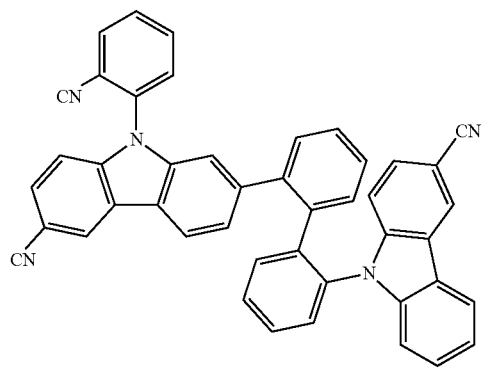
119
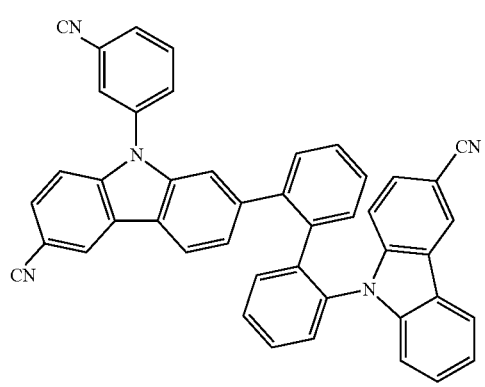
120
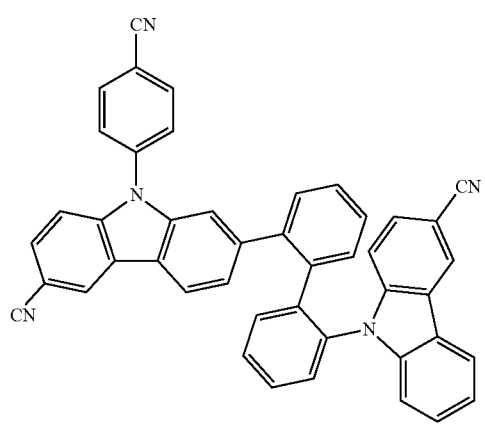
121
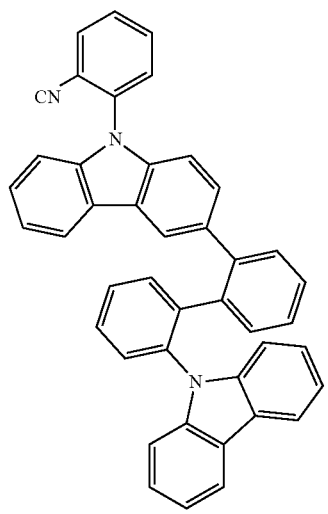
122
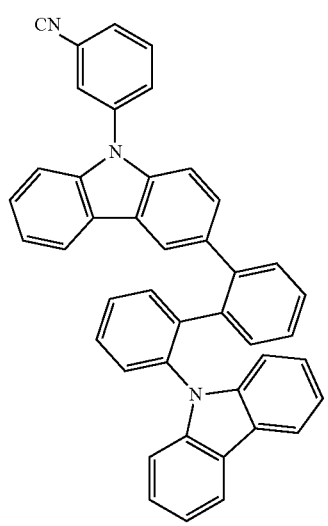
123
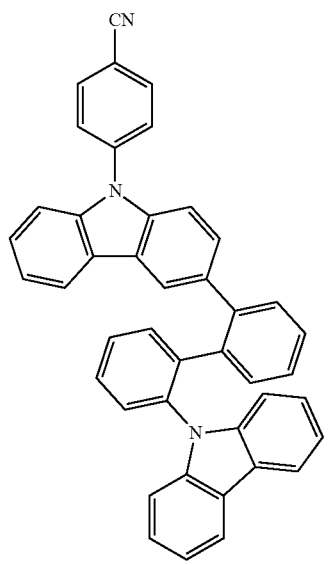

124
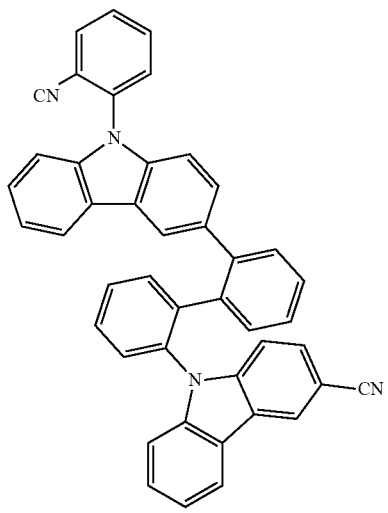
125
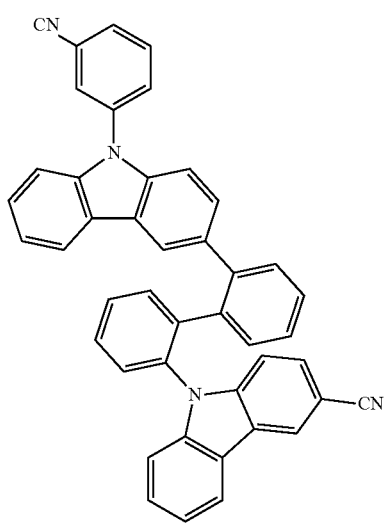
126
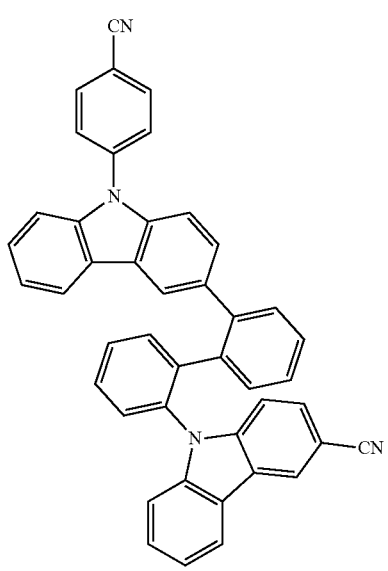
127
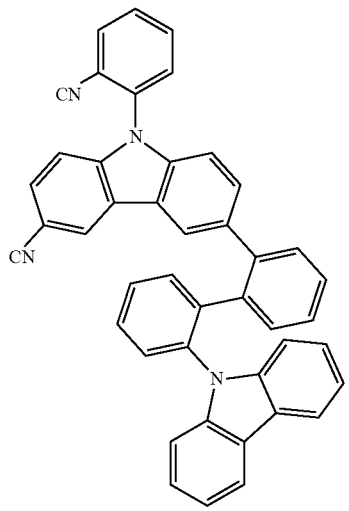
128
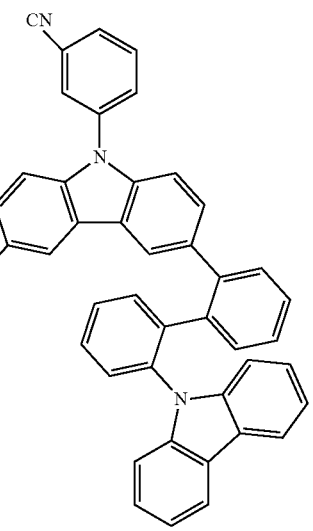
129
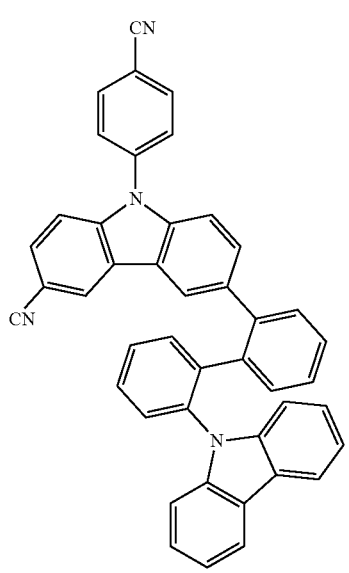

130
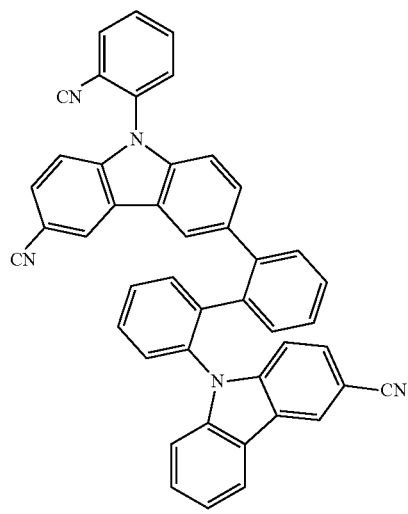
131
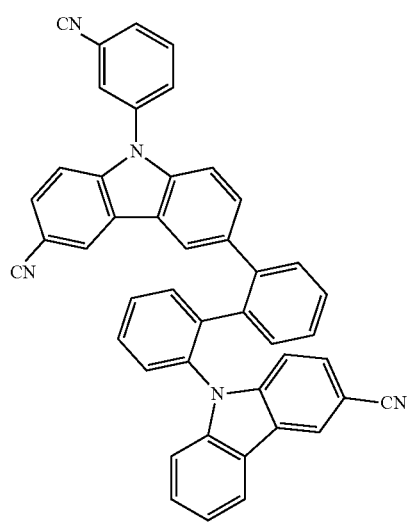
132
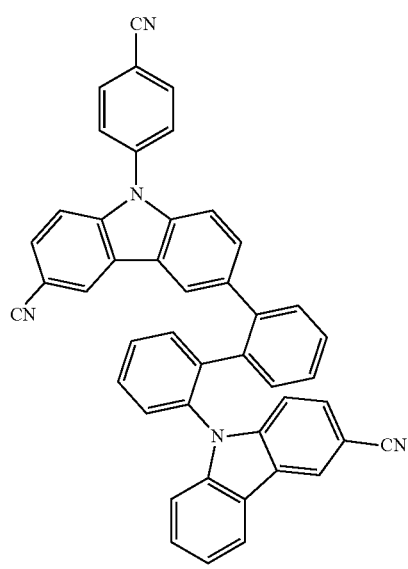
133
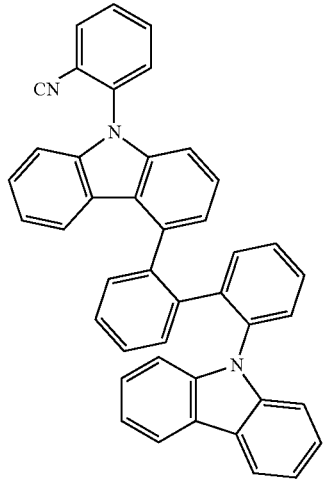
134
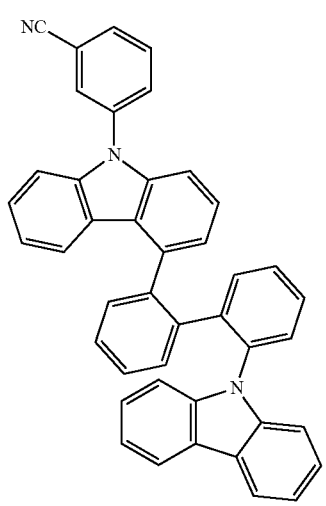
135
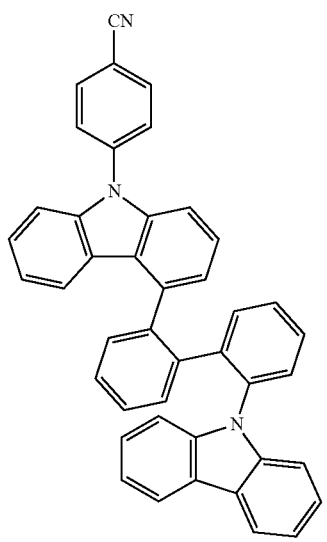

136
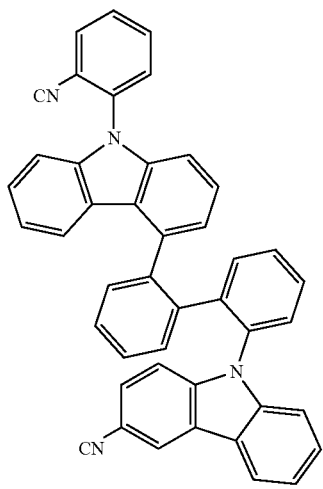
137
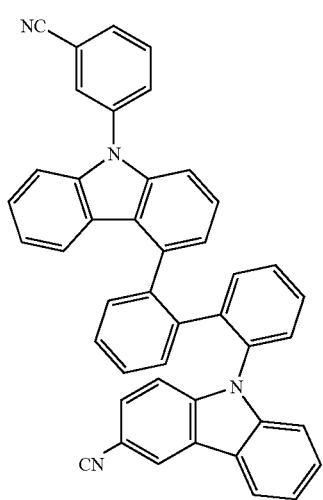
138
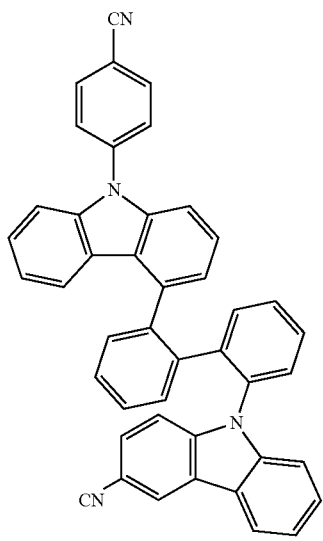
139
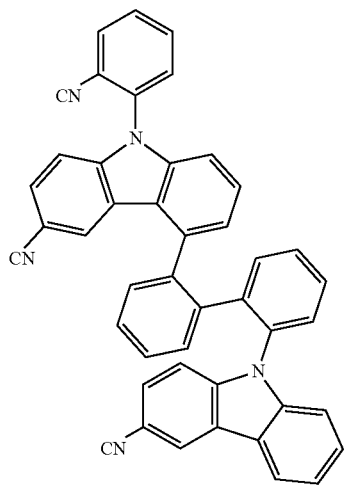
140
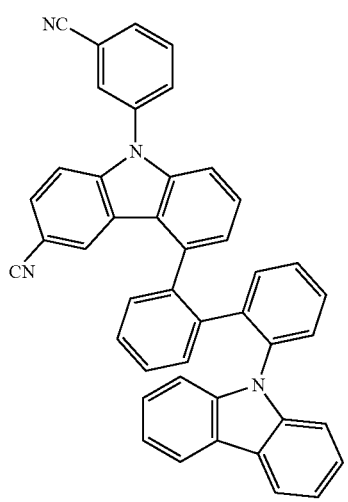
141
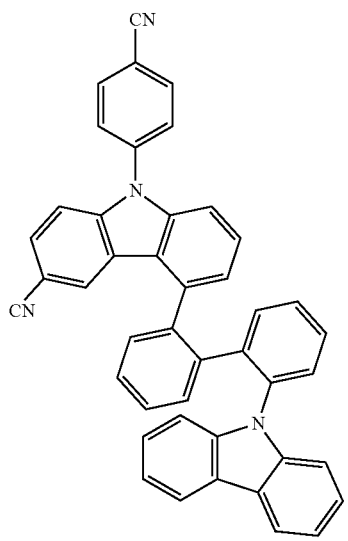

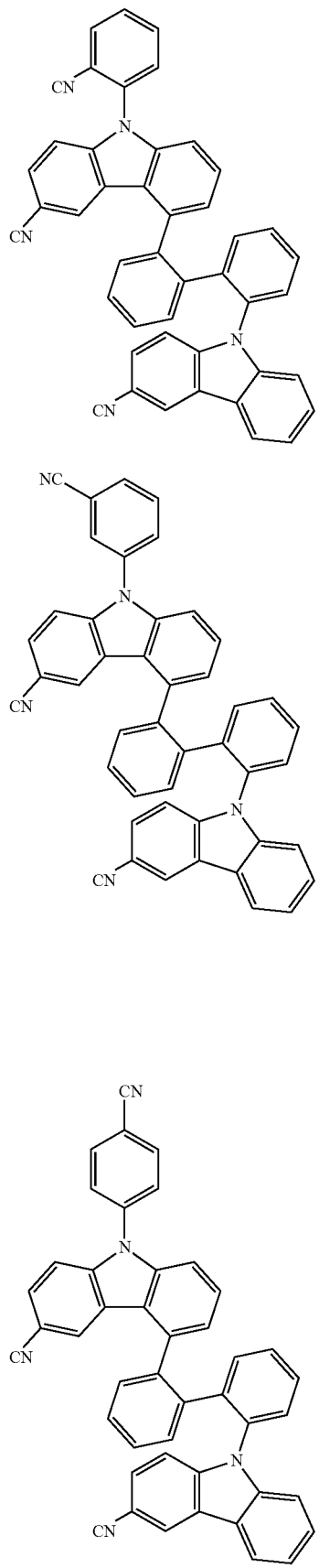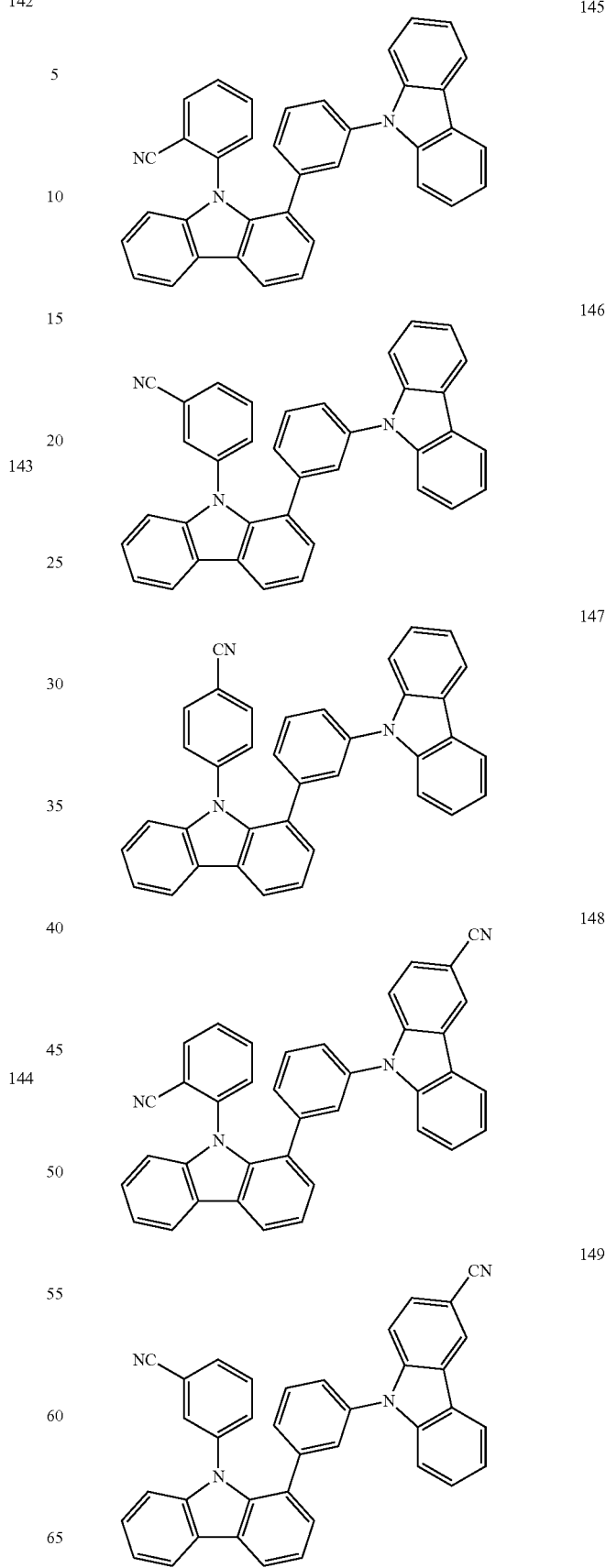

150 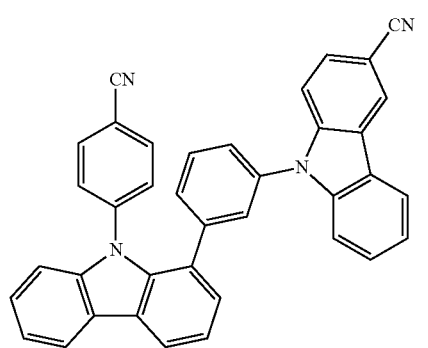
151 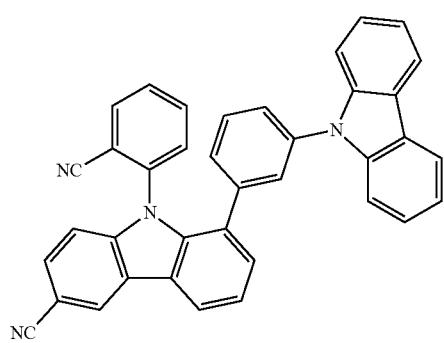
152 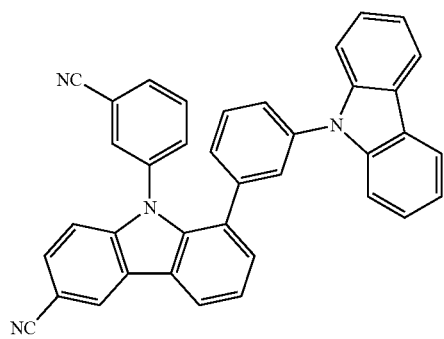
153 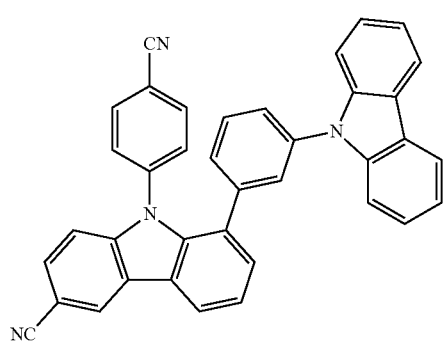
154 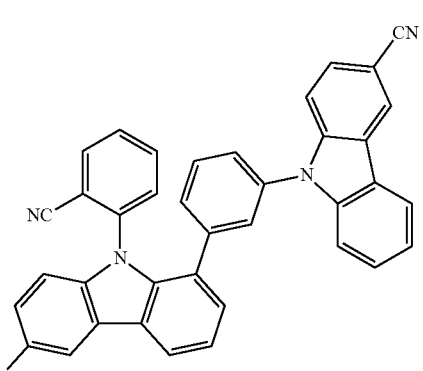
155 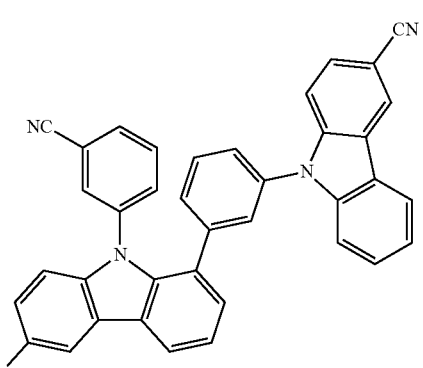
156 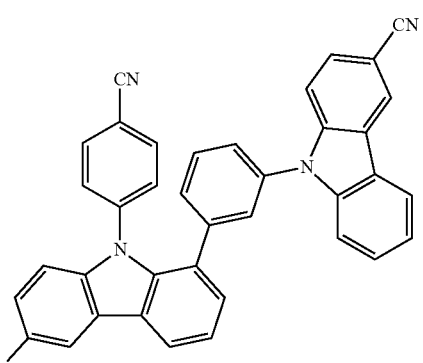
157 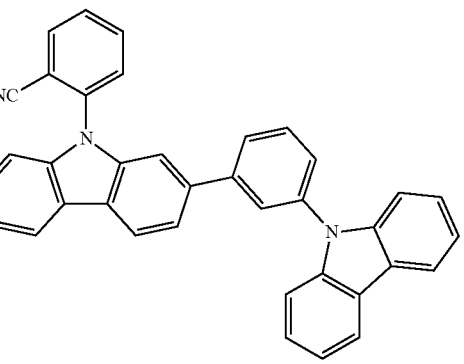

158
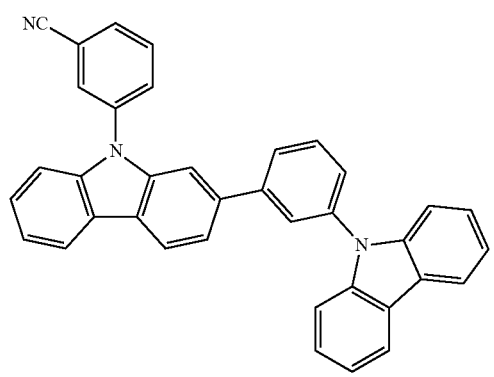
159
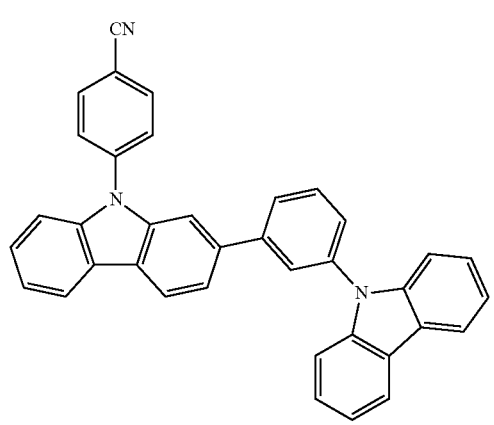
160
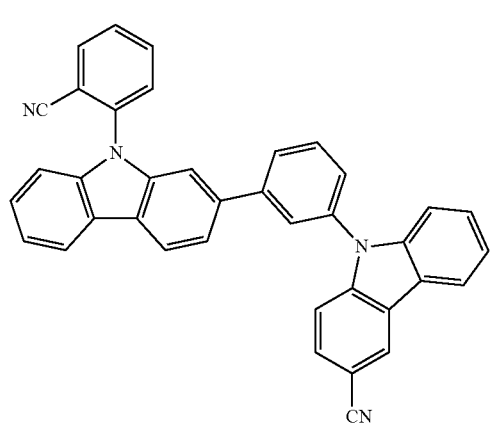
161
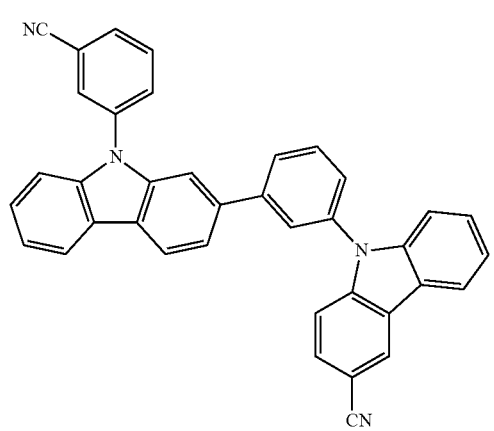
162
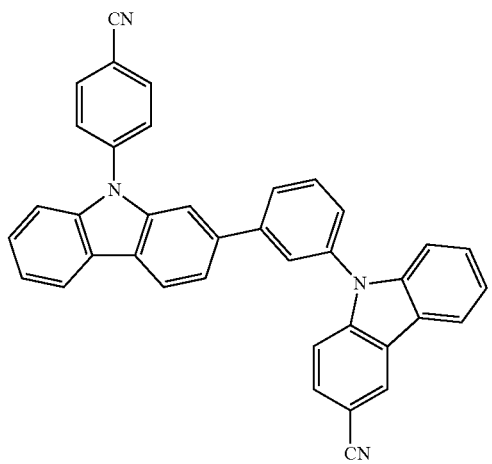
163
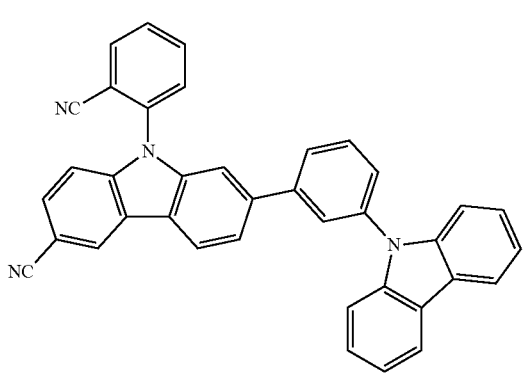
164
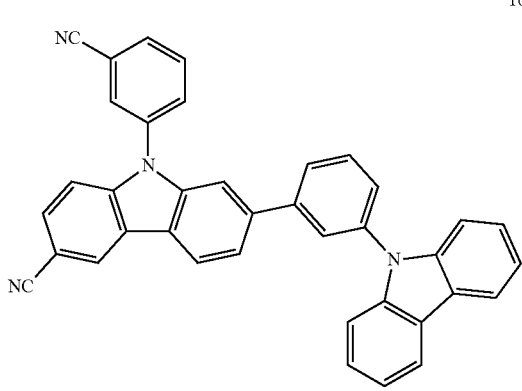
165
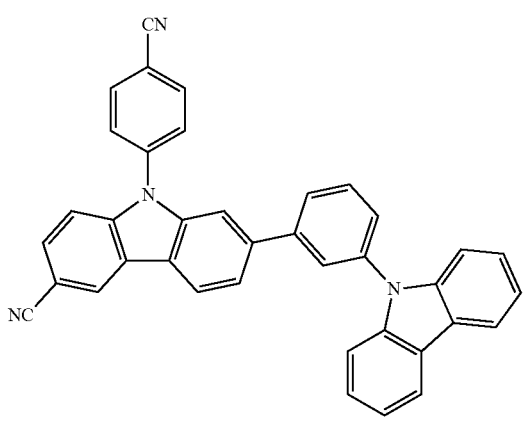

166
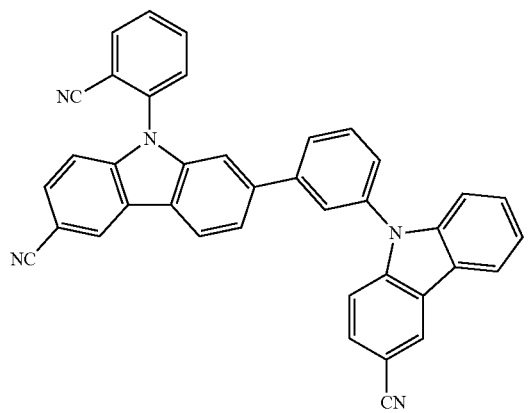
167
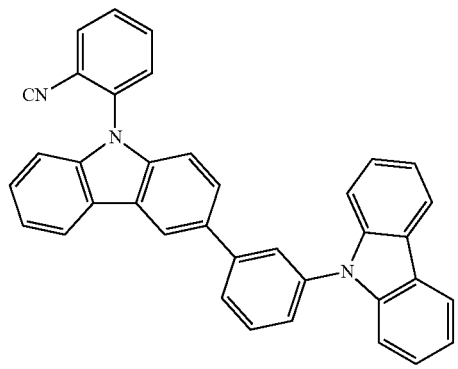
168
169
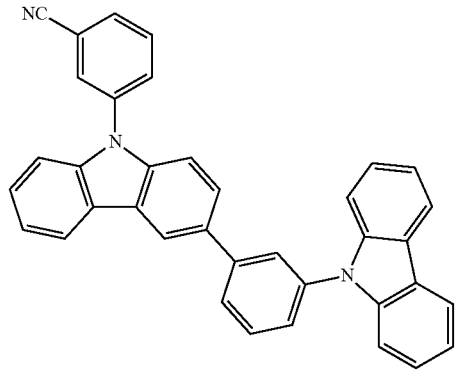
170
171
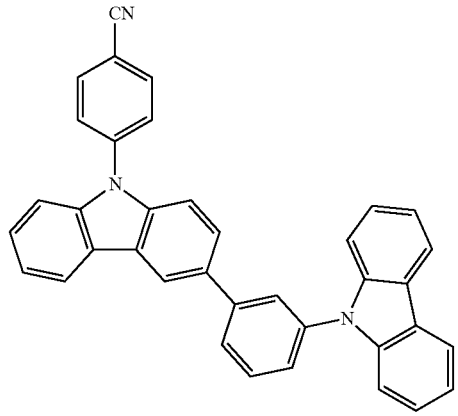
172
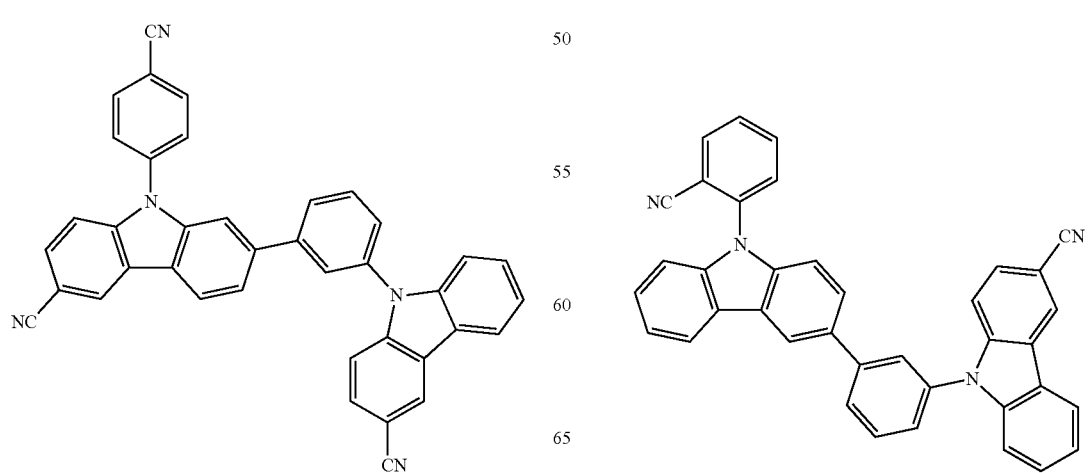

173
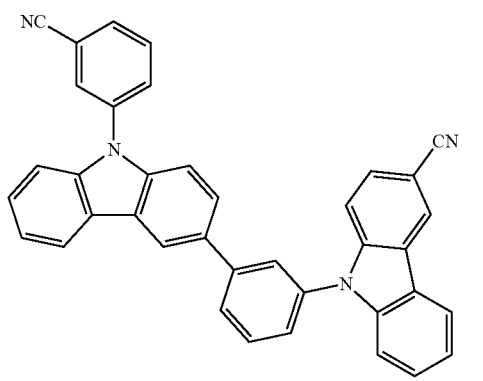
174
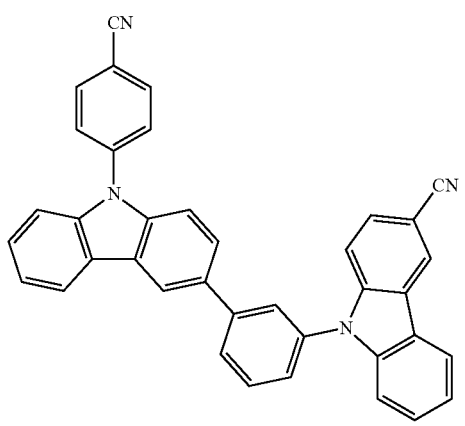
175
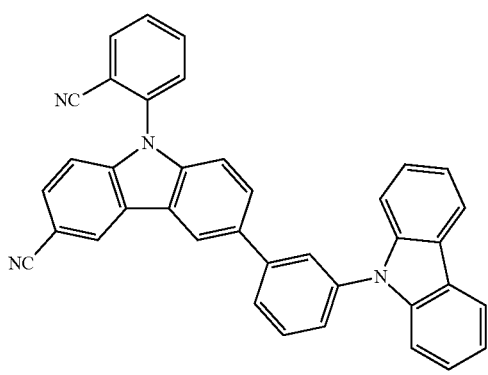
176
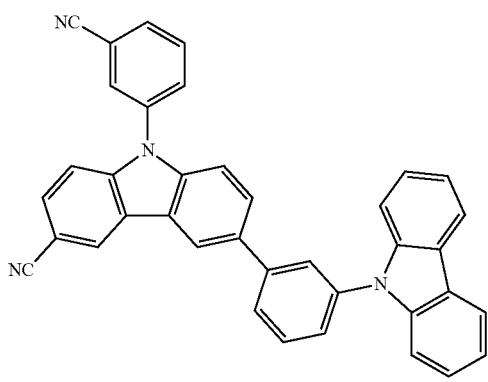
177
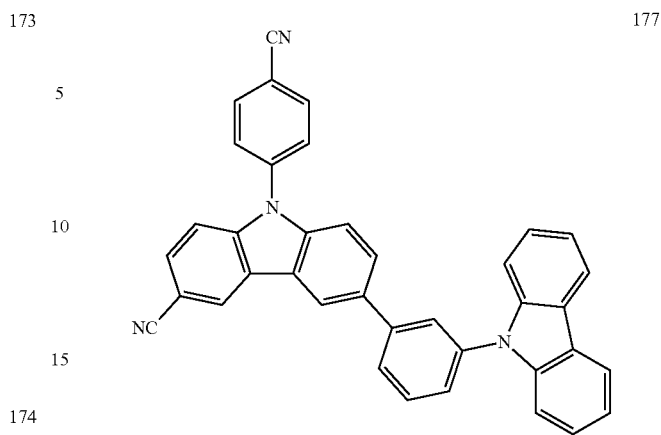
178
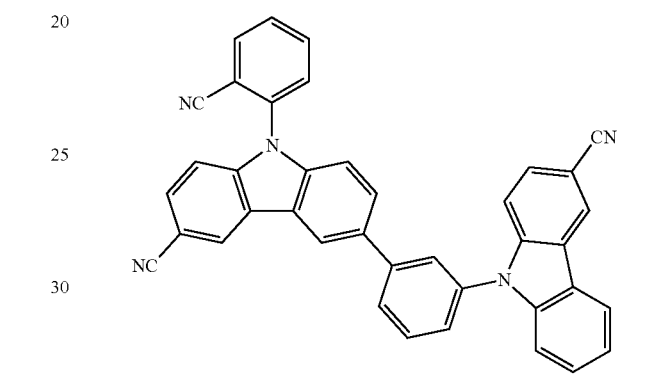
179
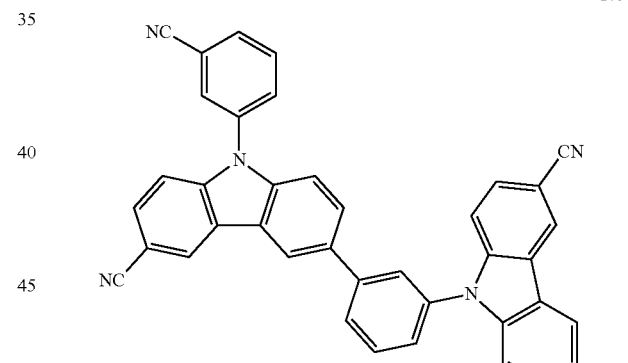
180
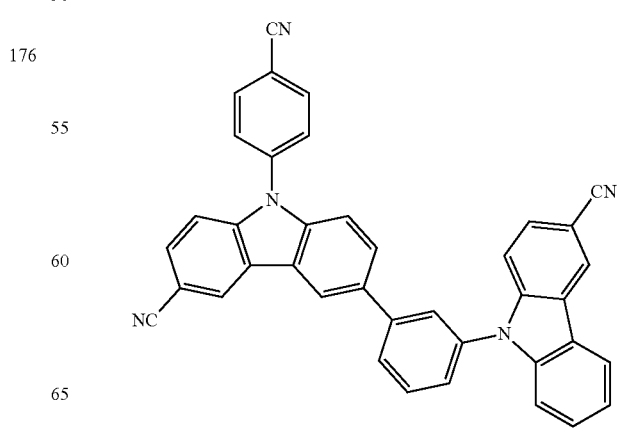

181
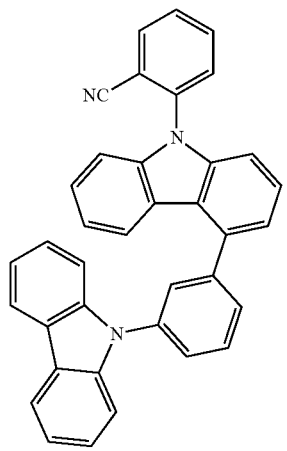
182
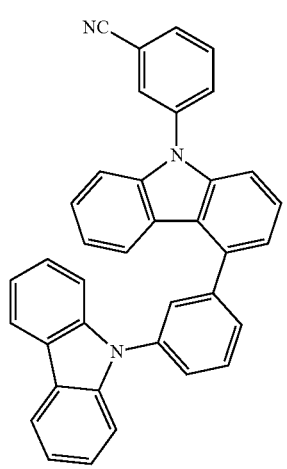
183
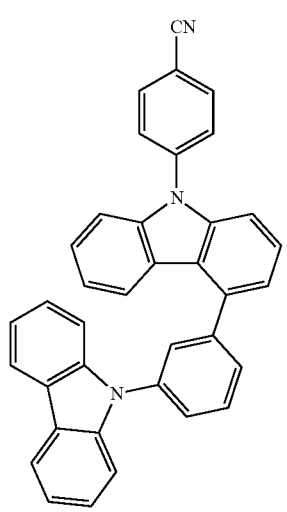
184
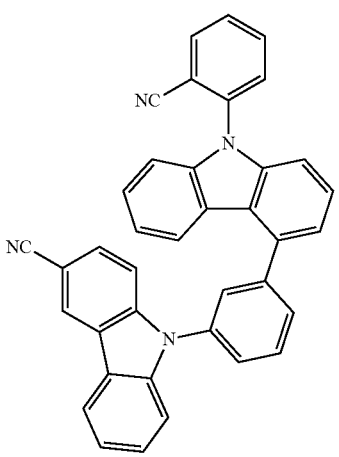
185
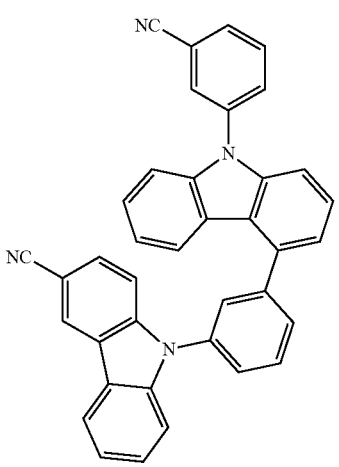
186
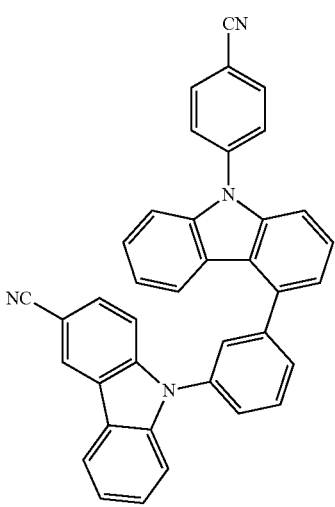

187
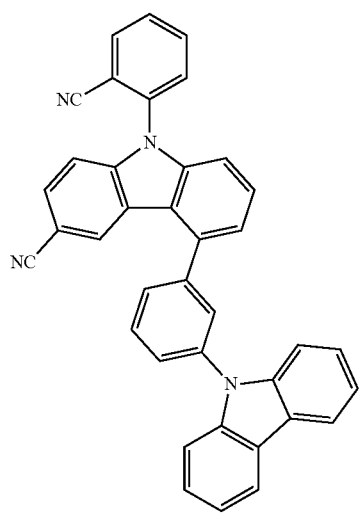
188
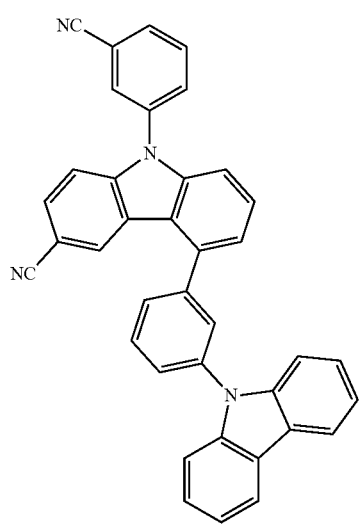
189
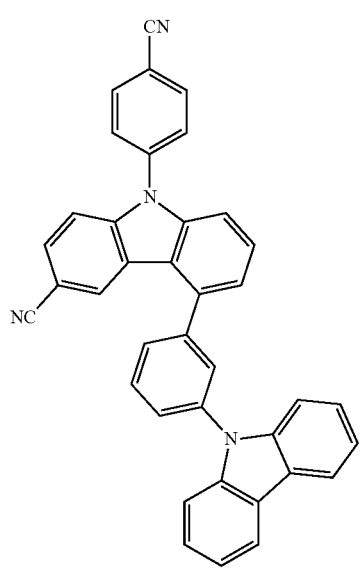
190
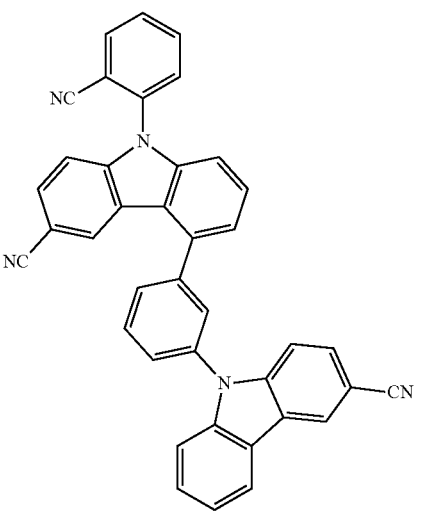
191
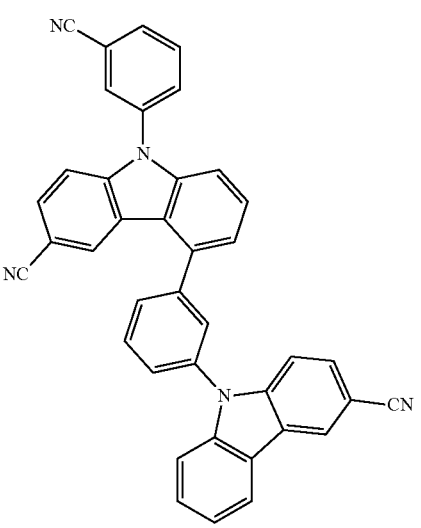
192
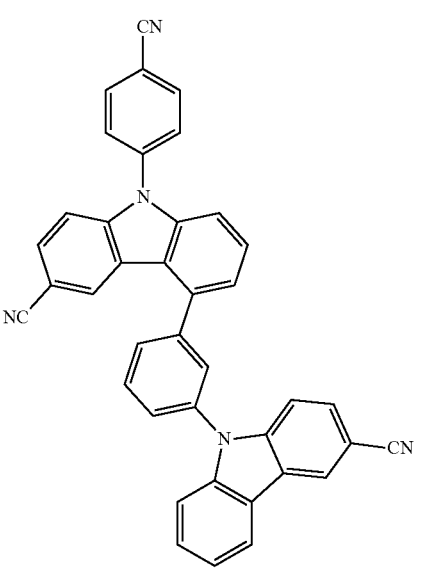

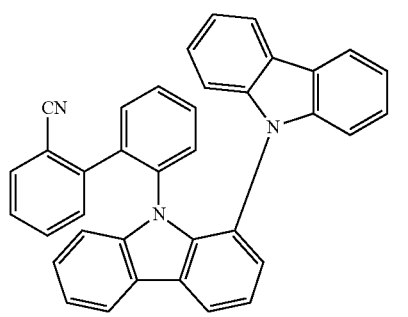
193

194
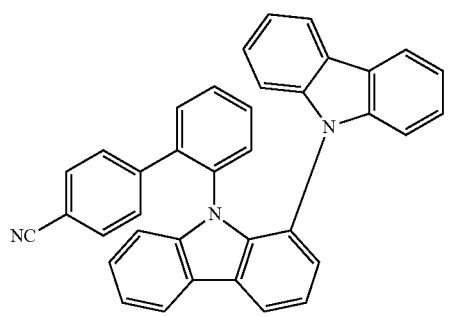
195
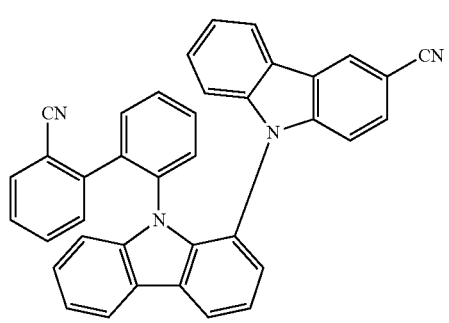
196
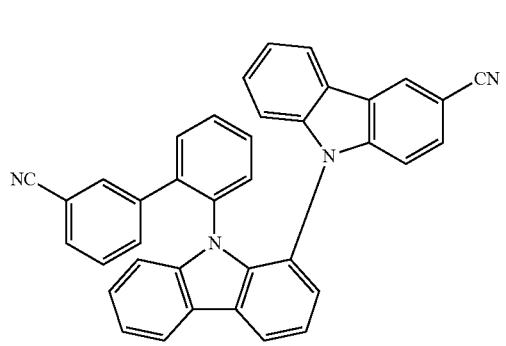
197
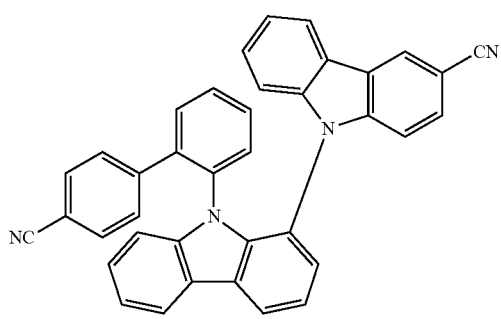
198
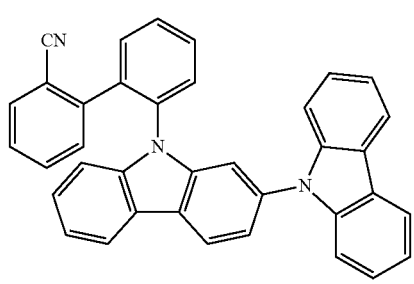
199
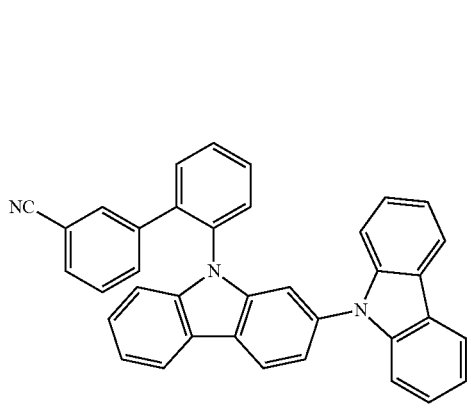
200
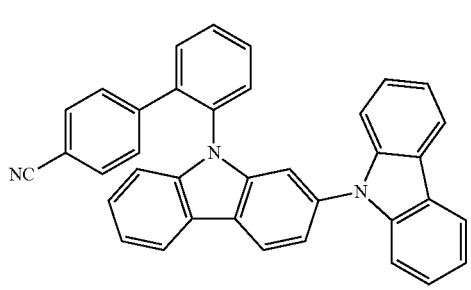
201
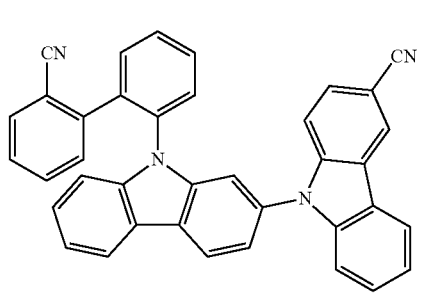
202

203
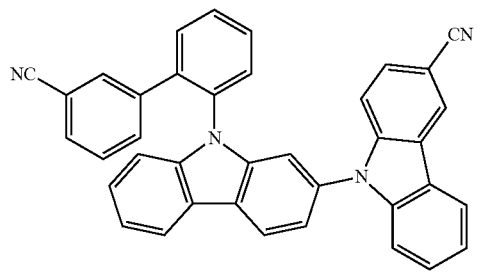
204
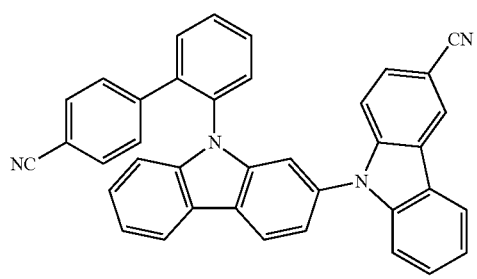
205
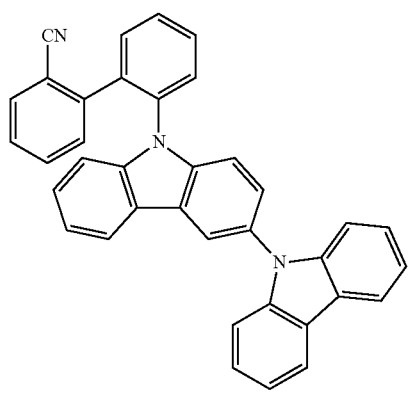
206
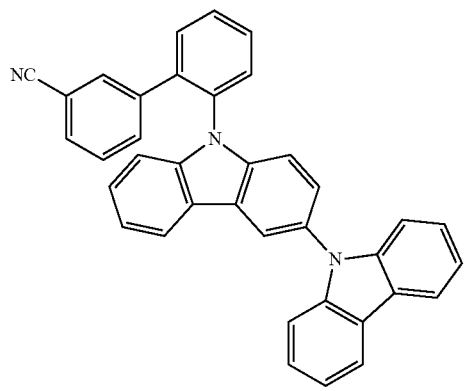
207
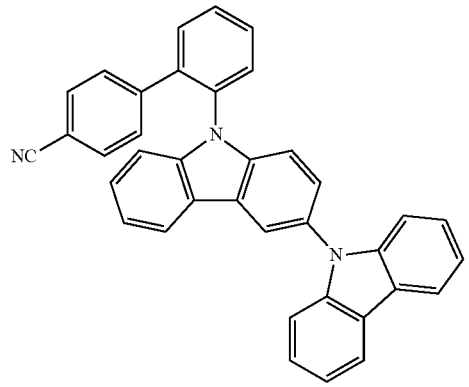
208
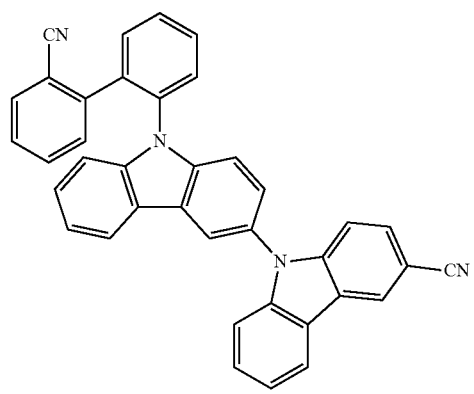
209
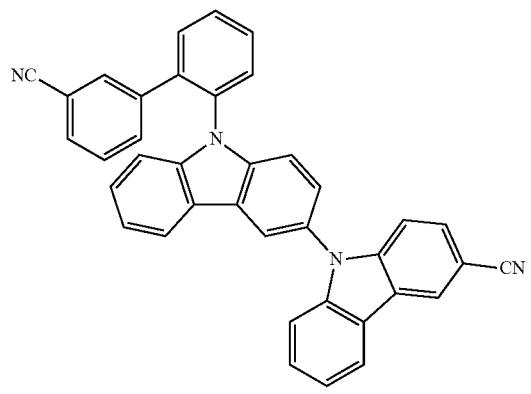
210
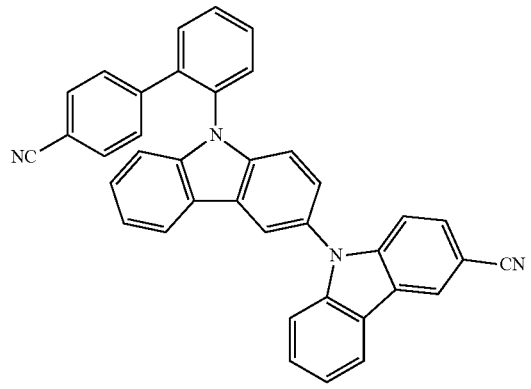

211 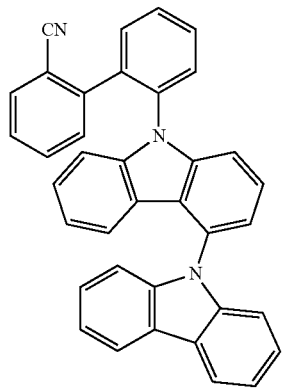
212 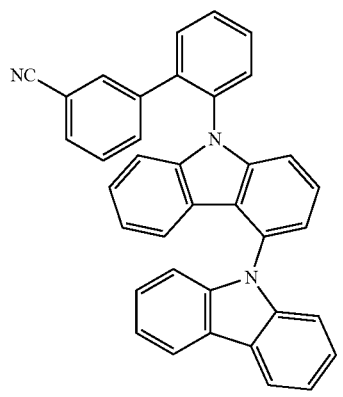
213 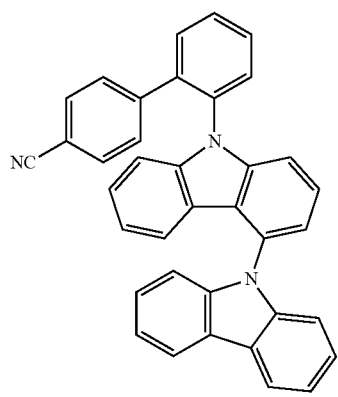
214 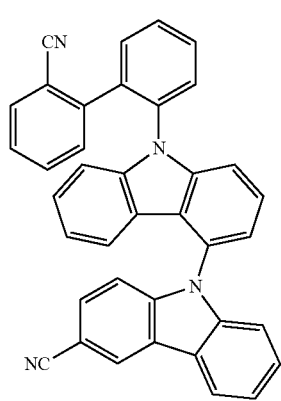
215 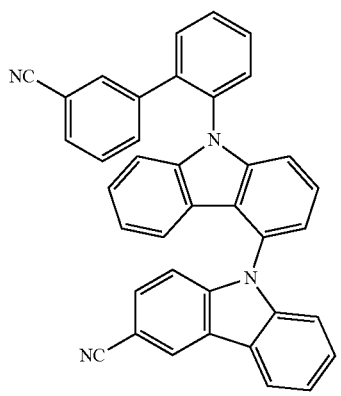
216 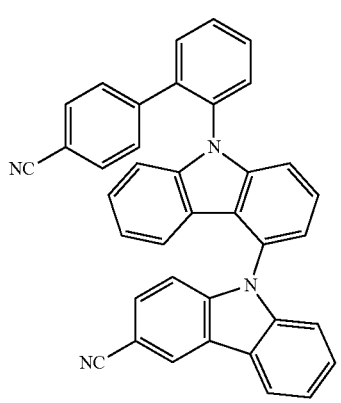
217 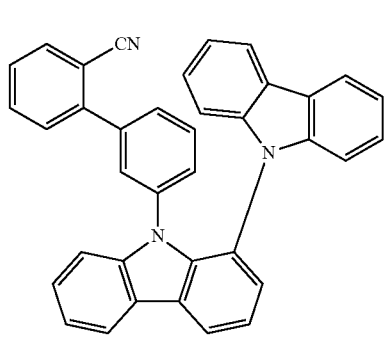
218 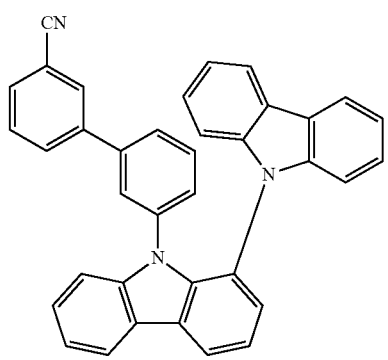

219
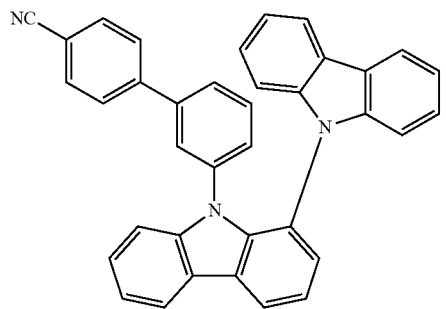
220
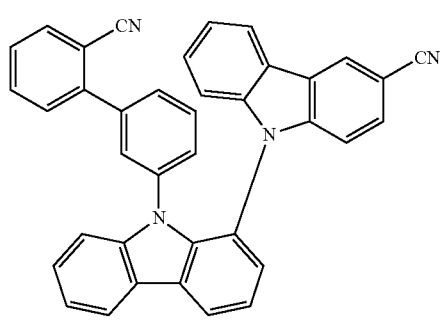
221
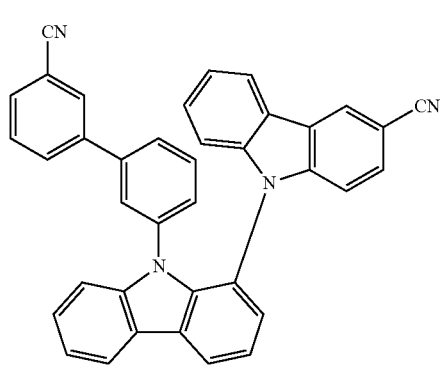
222
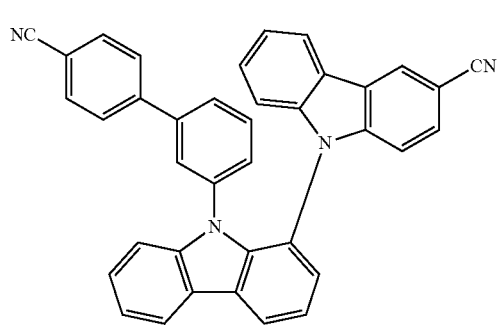
223
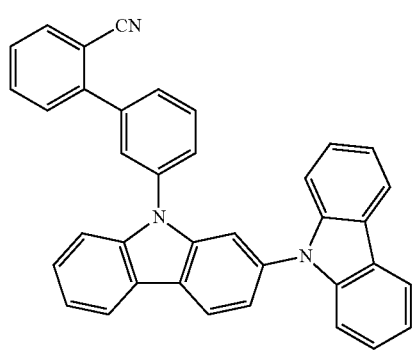
224
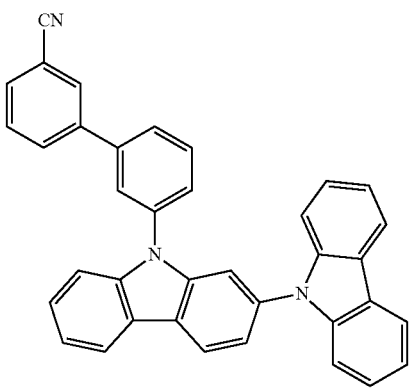
225
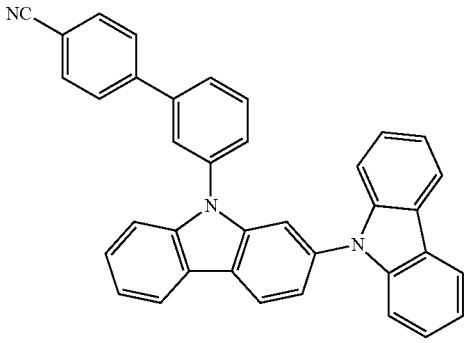
226
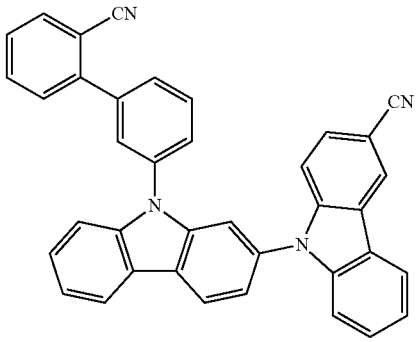
227
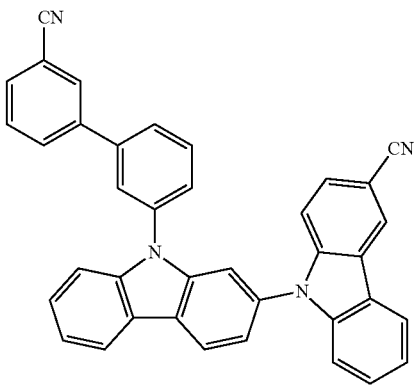

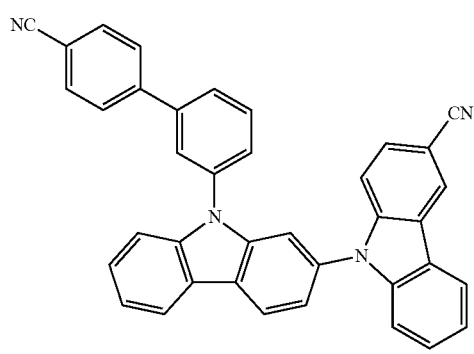
228
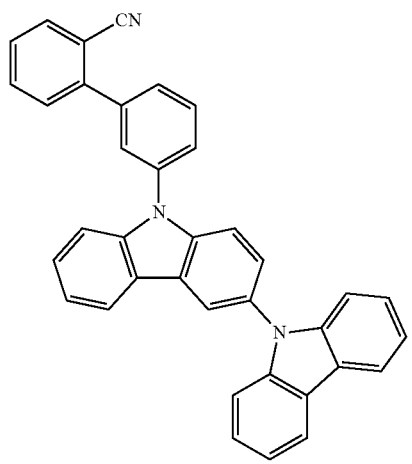
229
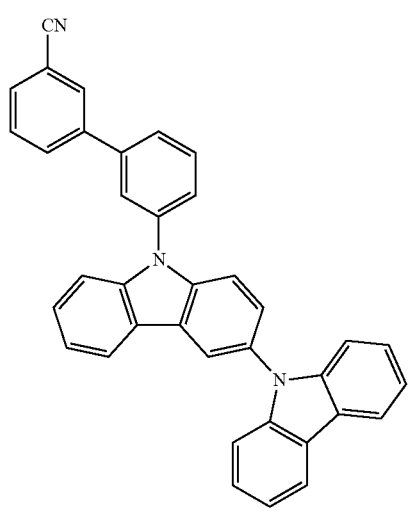
230
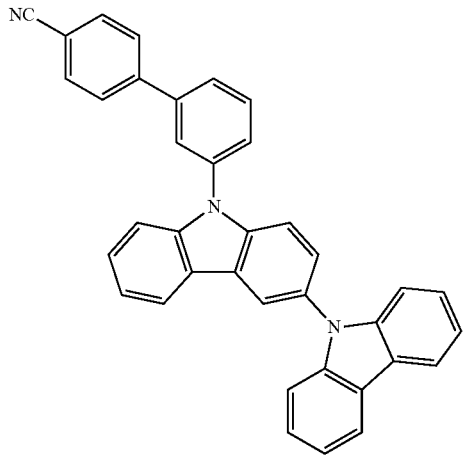
231
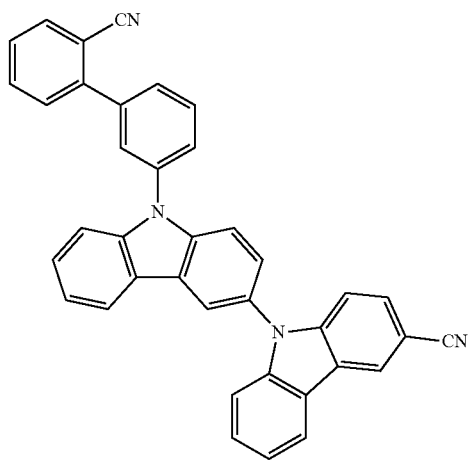
232
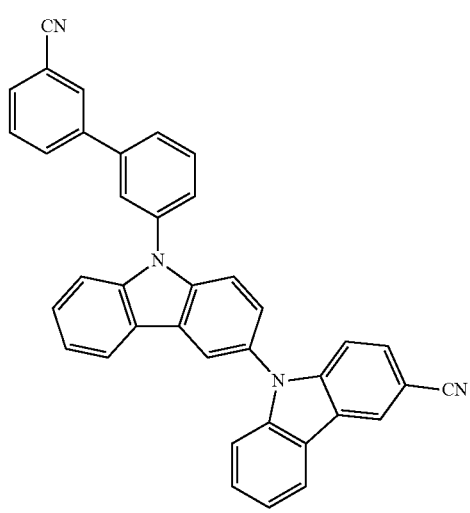
233

-continued
234
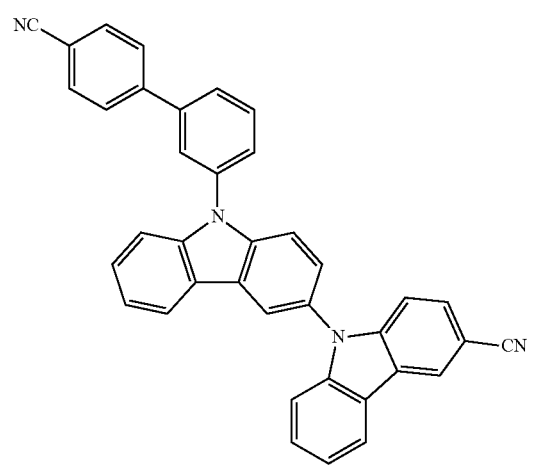
235
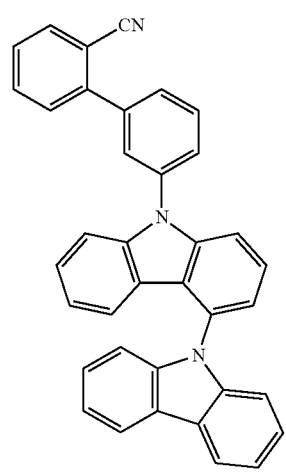
236
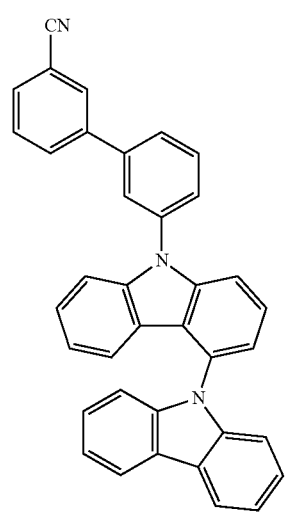
-continued
237
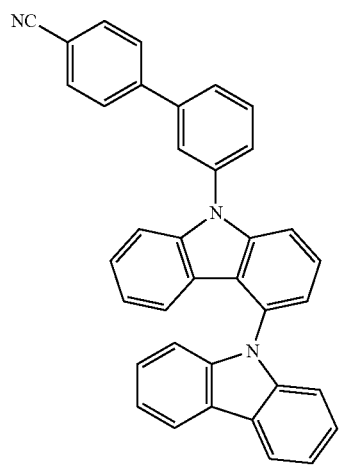
238
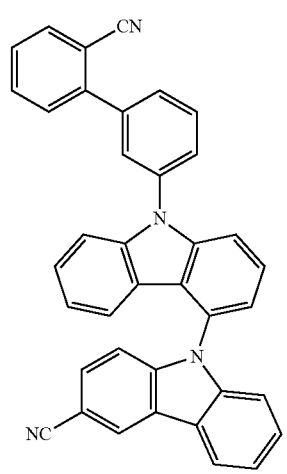
239
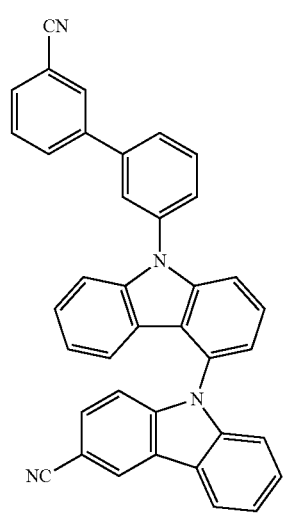

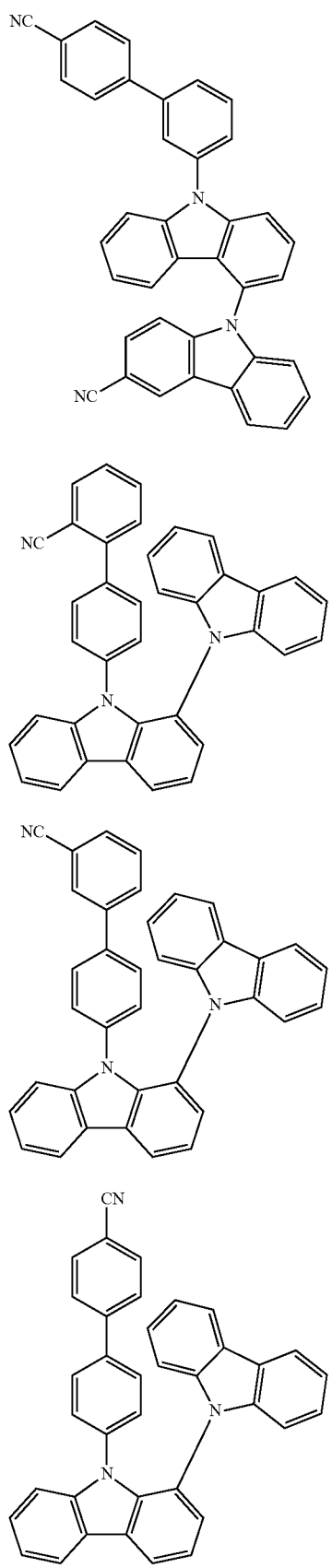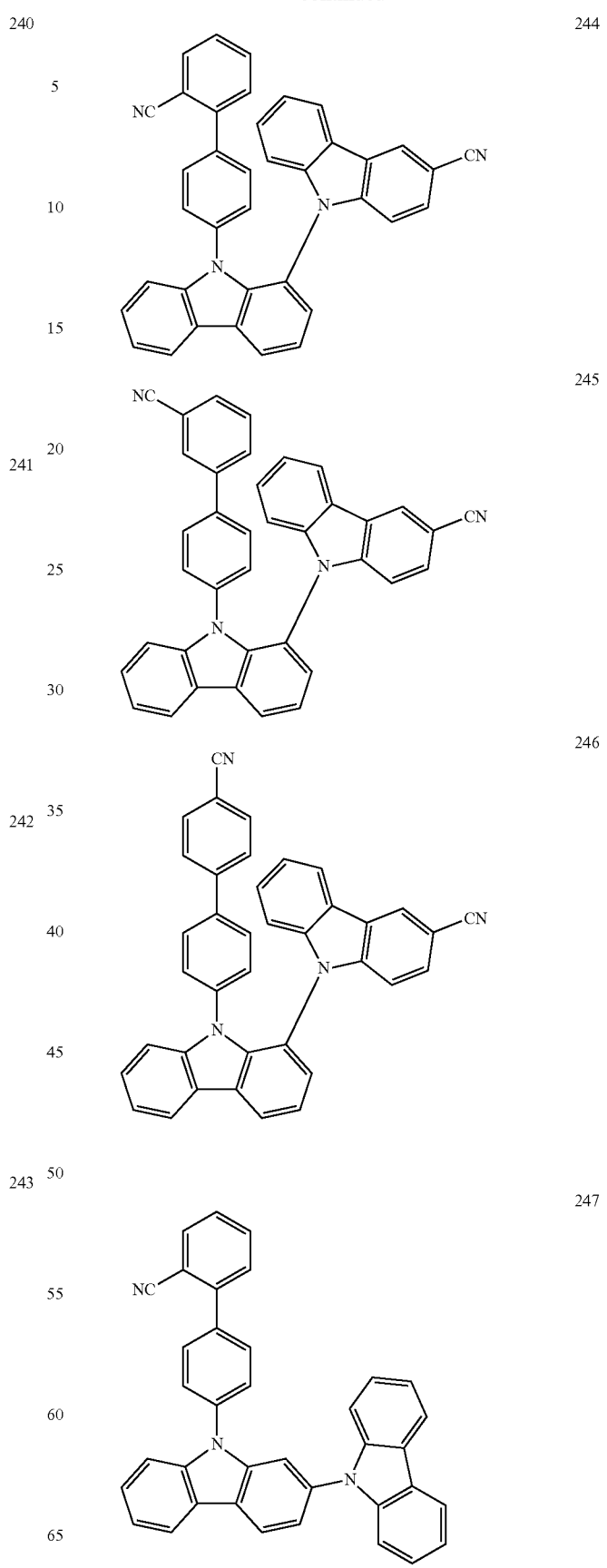

248 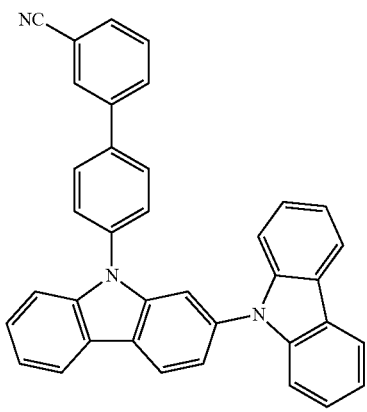
251 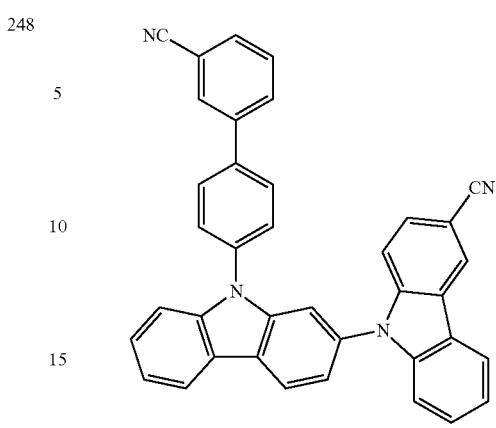
249 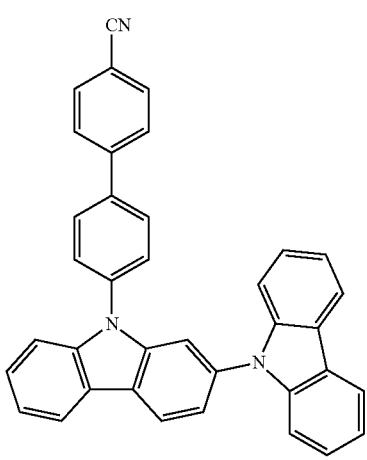
252 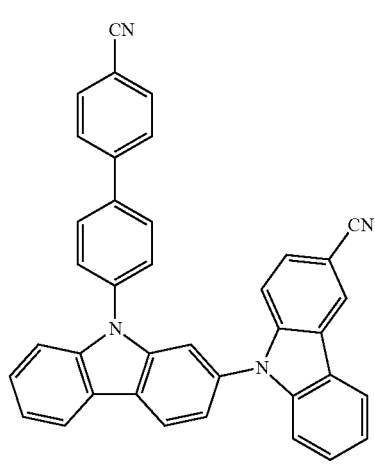
250 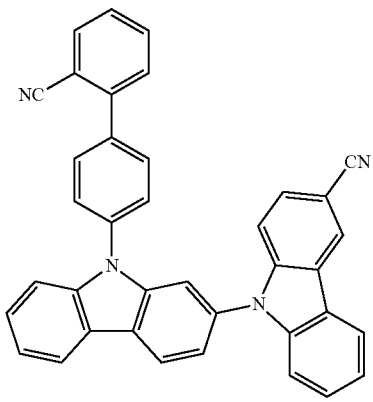
253 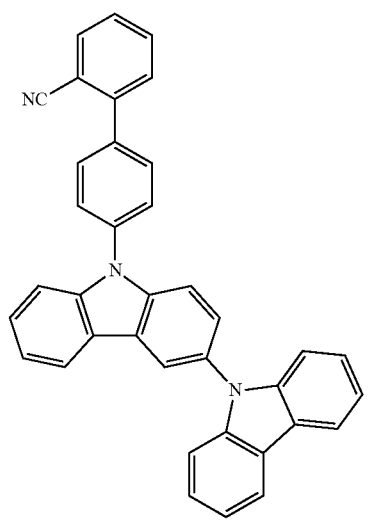

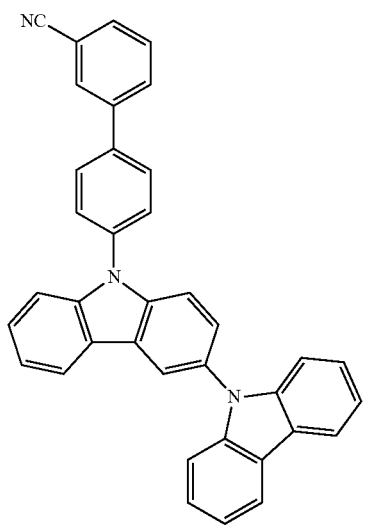
254
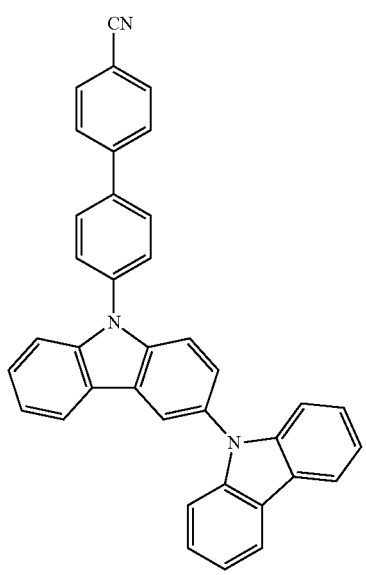
255
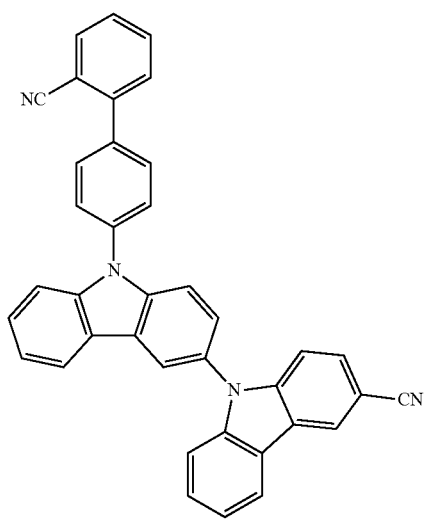
256
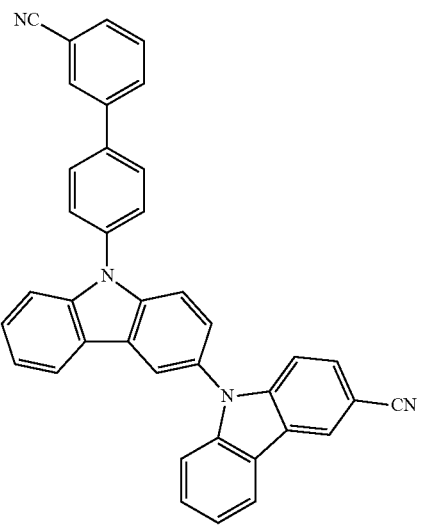
257
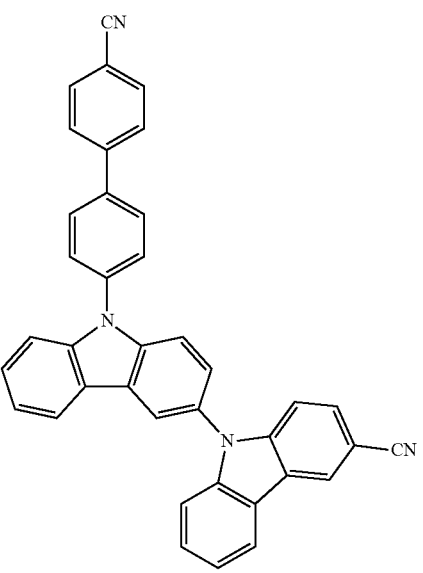
258
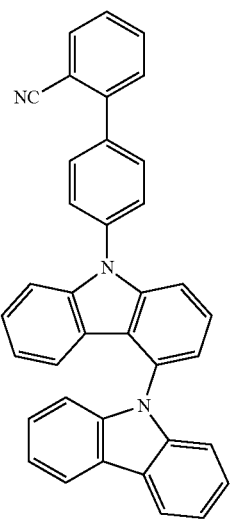
259

260
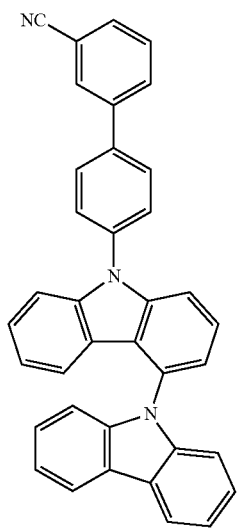
261
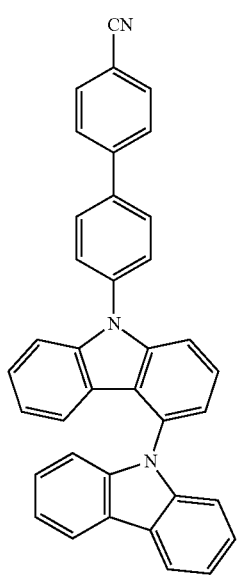
262
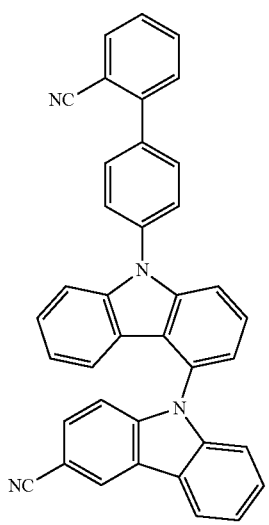
263
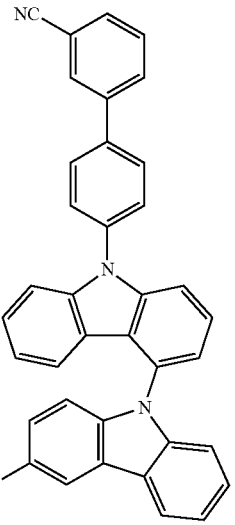
264
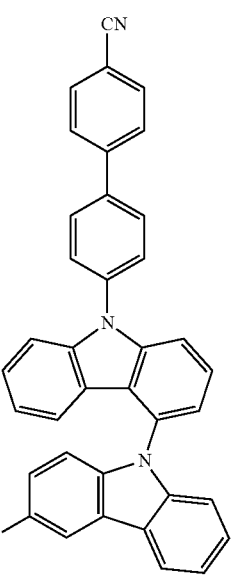
265
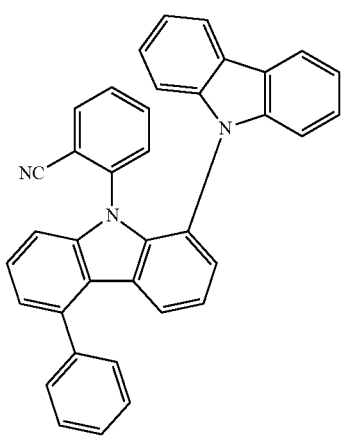

-continued
266
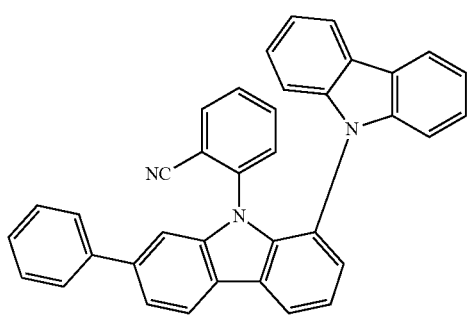
267
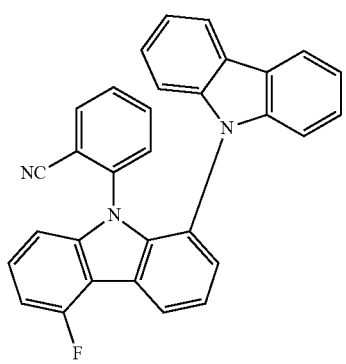
268
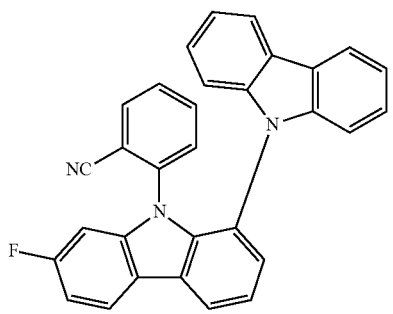
269
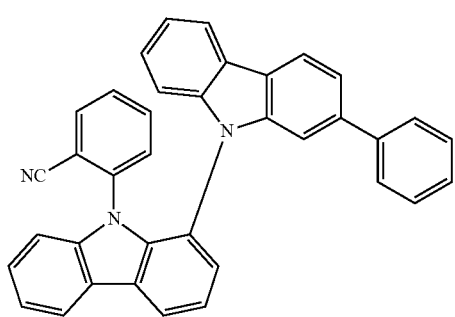
-continued
270
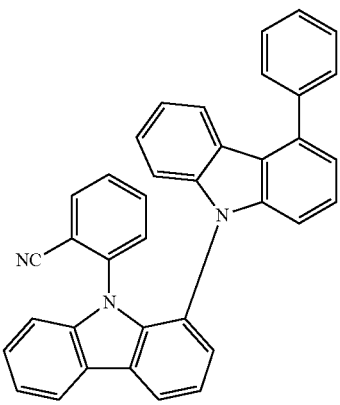
271
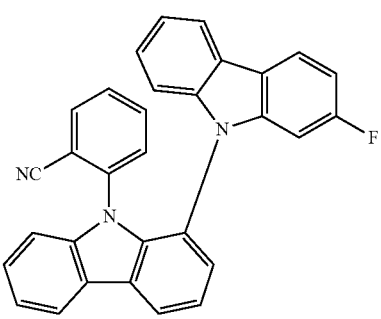
272
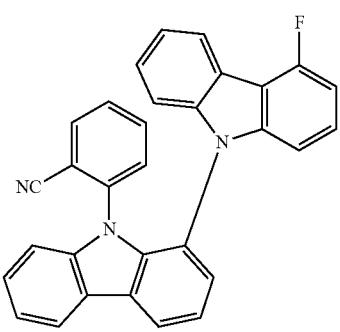
273
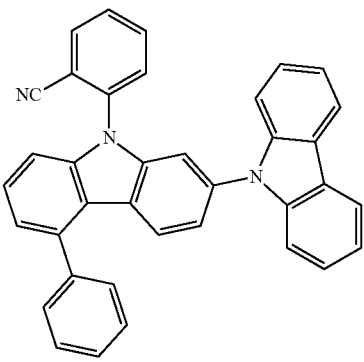

274
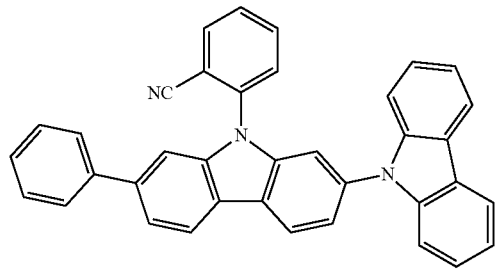
275
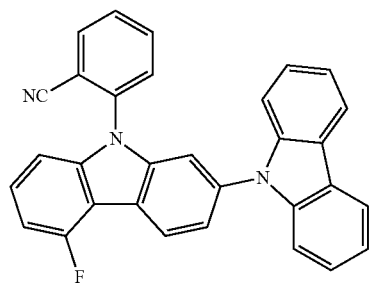
276
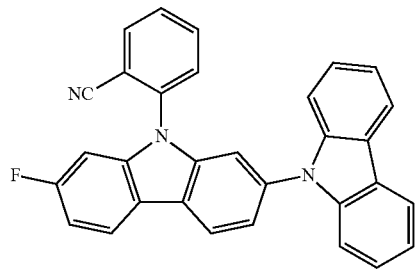
277
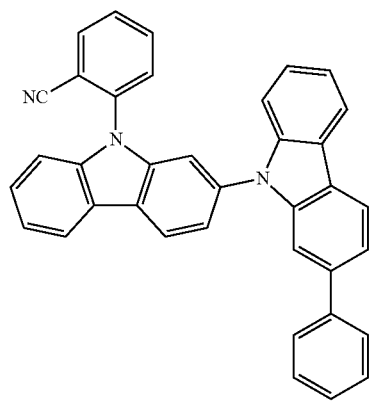
278
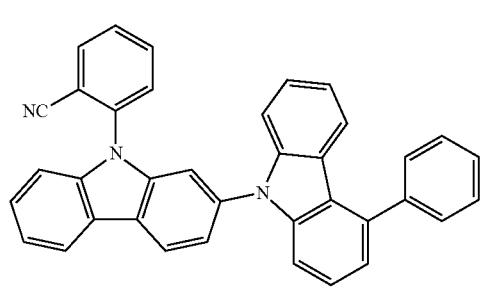
279
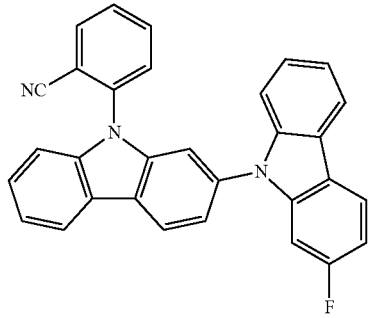
280
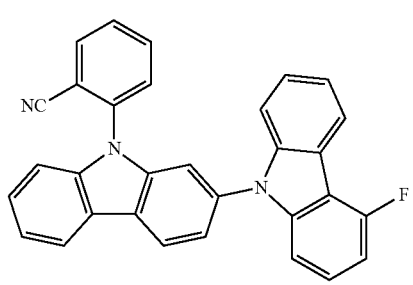
281
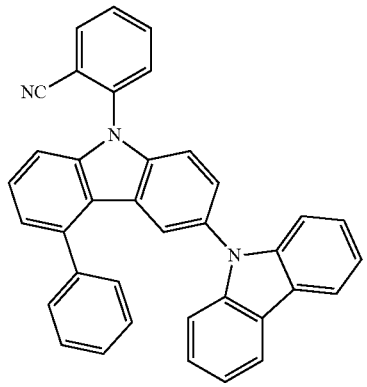
282
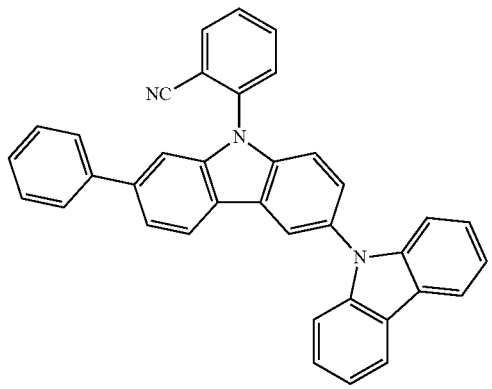

105
-continued
283
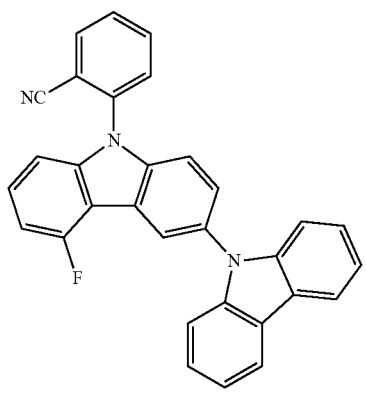
284
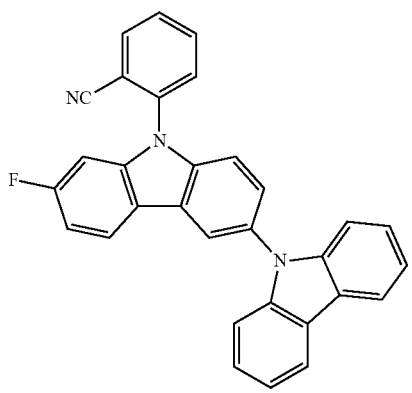
285
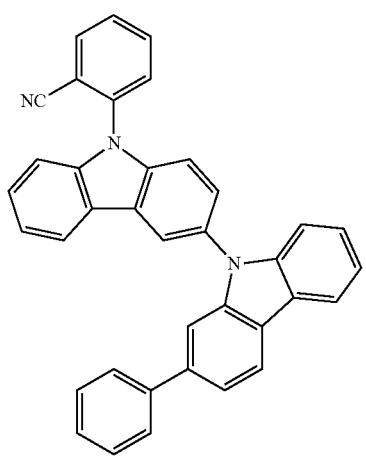
106
-continued
286
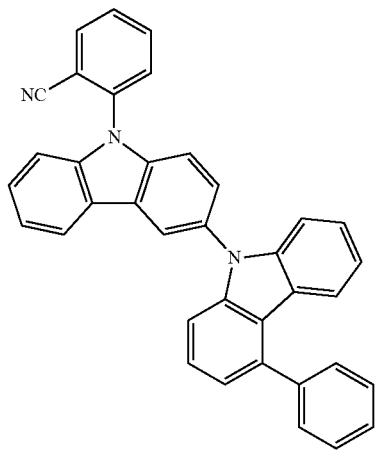
287
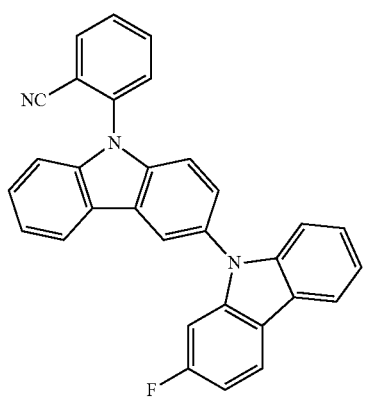
288
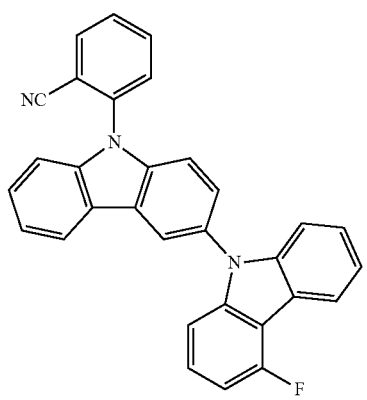

289
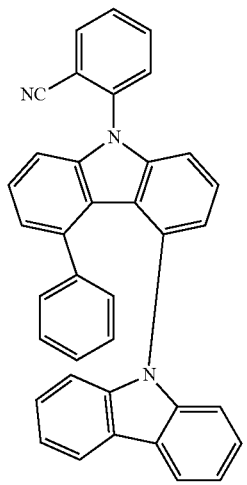
290
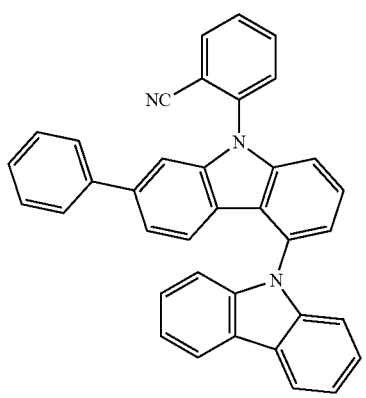
291
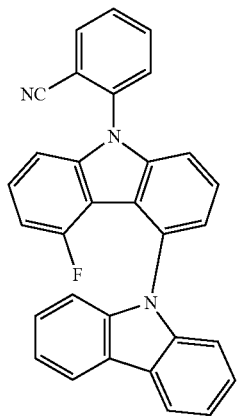
292
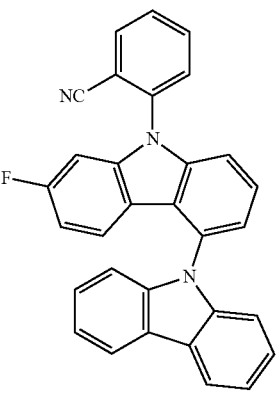
293
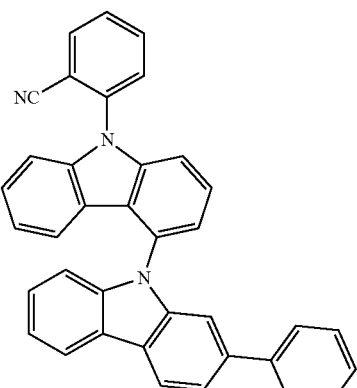
294
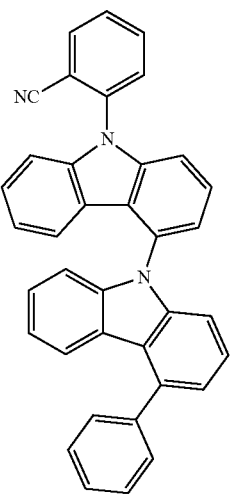

295 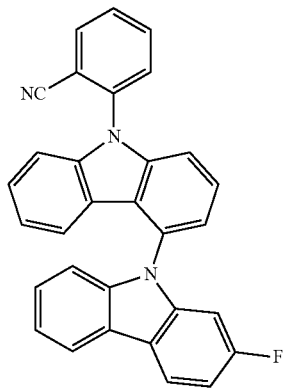
296 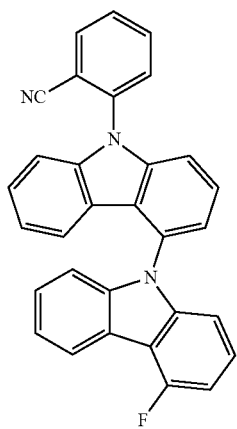
297 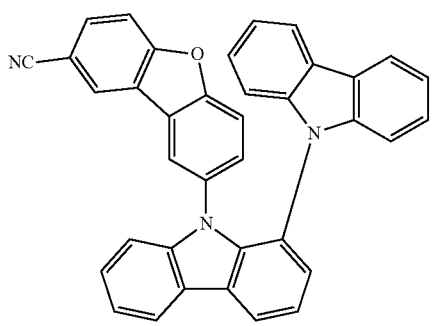
298 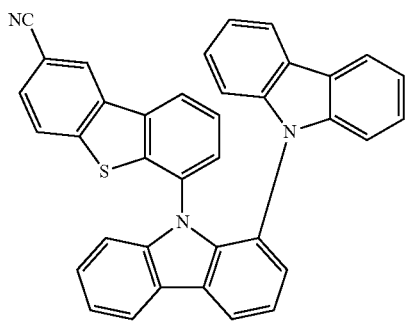
299 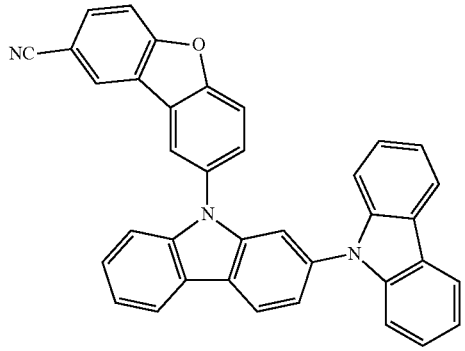
300 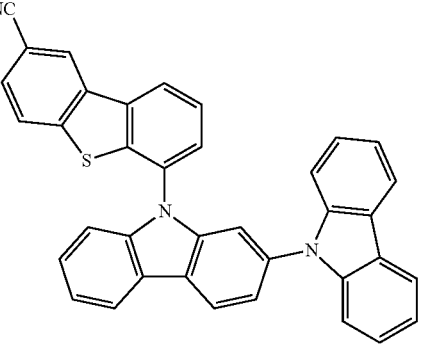
301 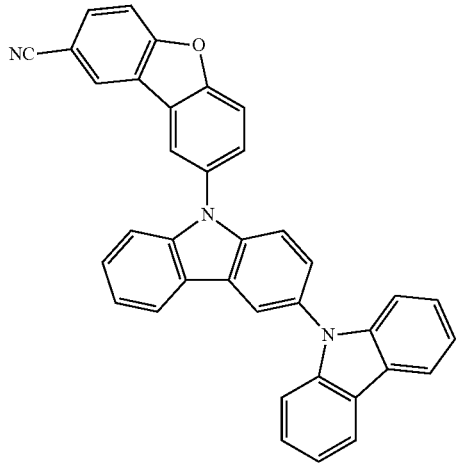
302 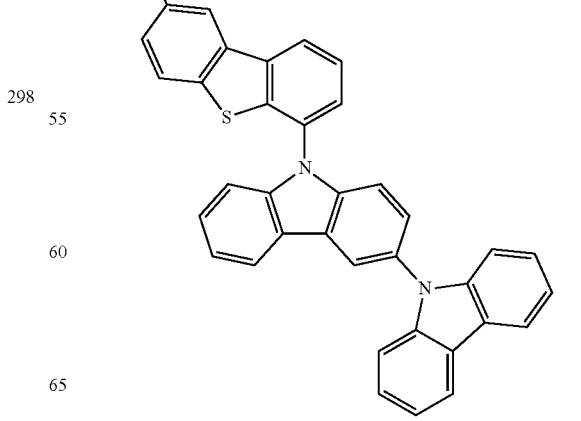

-continued
303
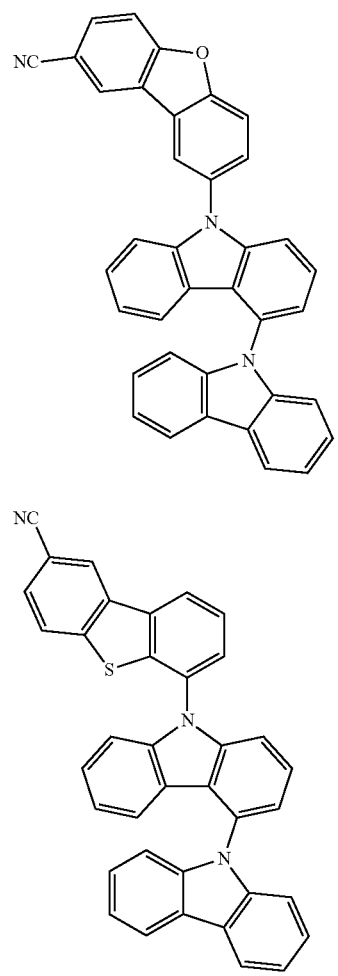
304
305
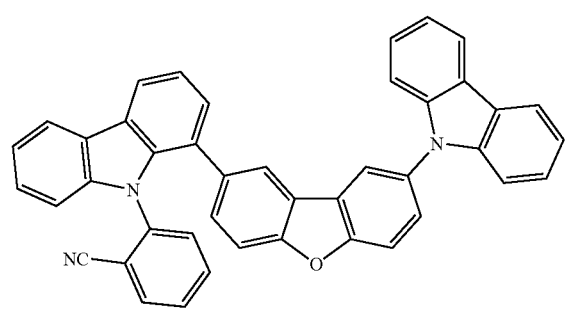
306
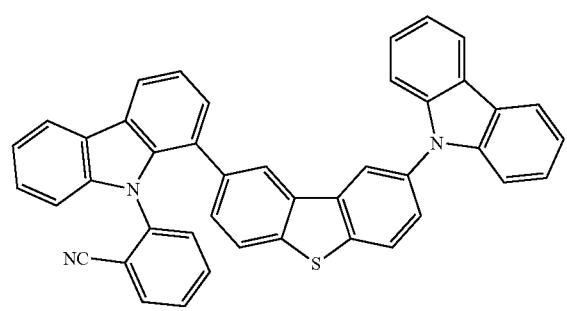
-continued
307
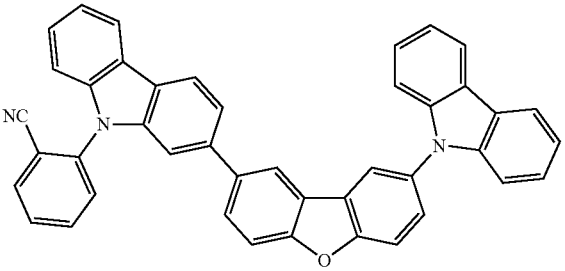
308
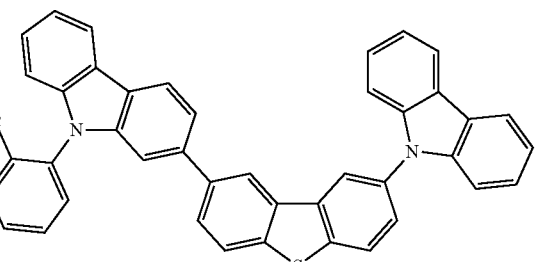
309
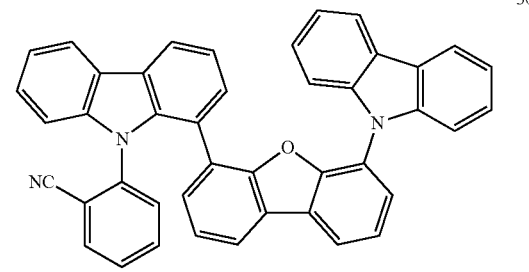
310
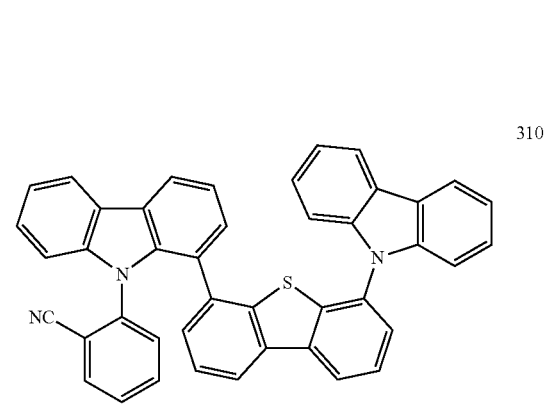
311
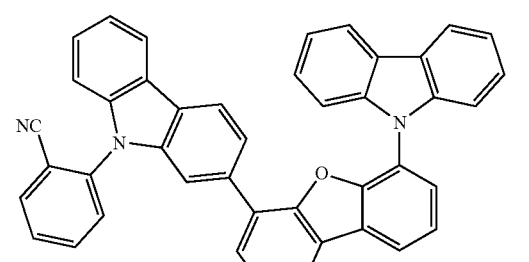

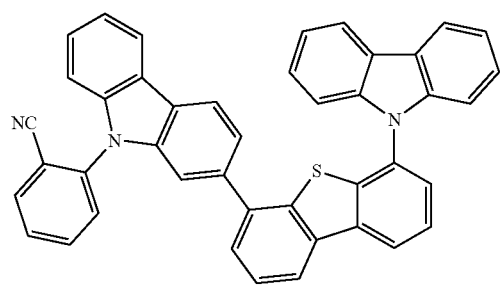
312
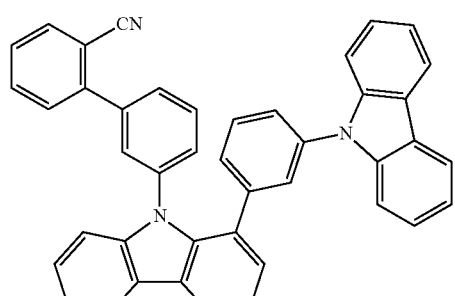
313
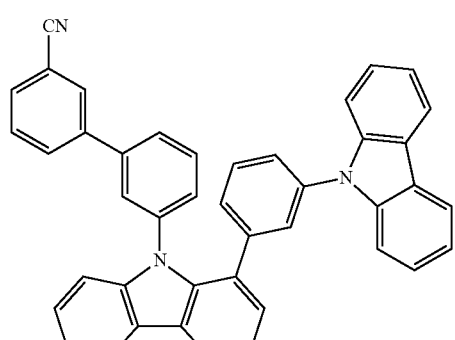
314
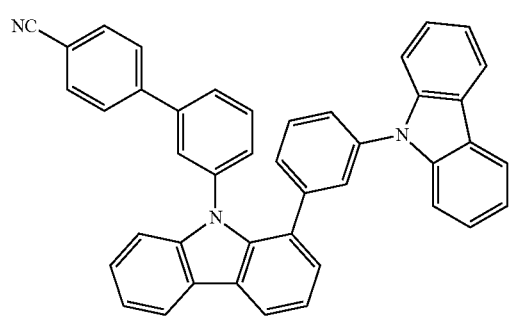
315
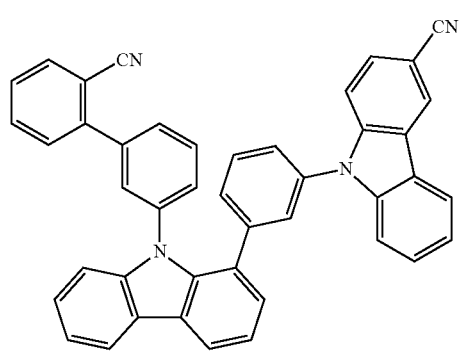
316
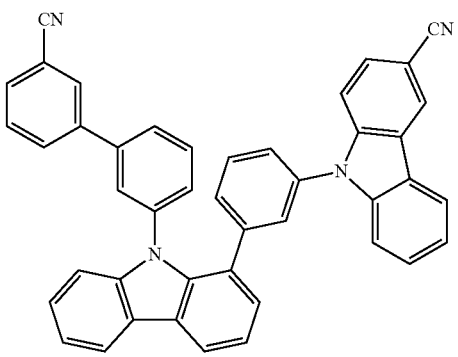
317
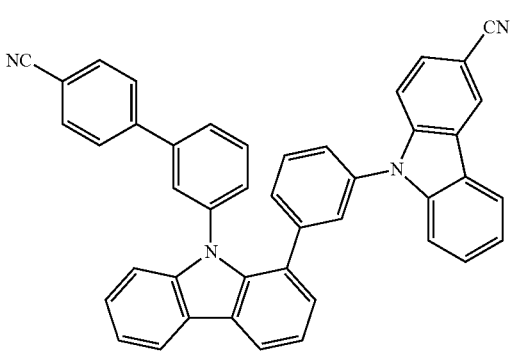
318
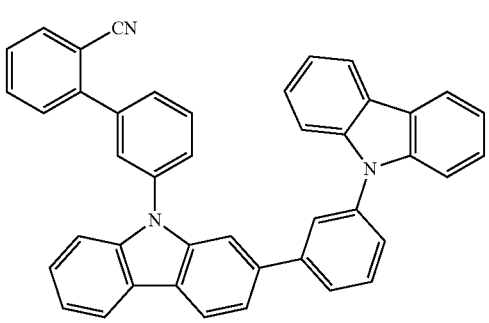
319
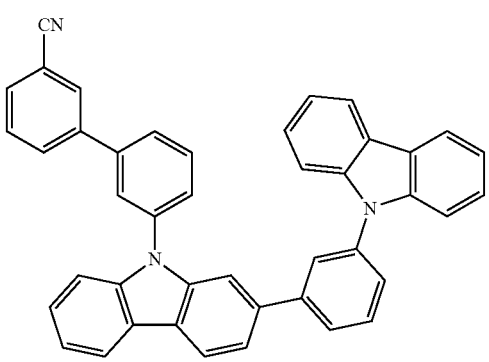
320

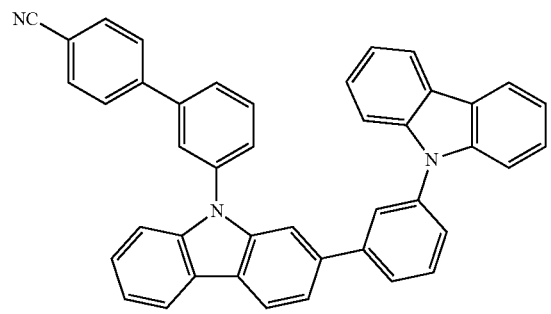
321
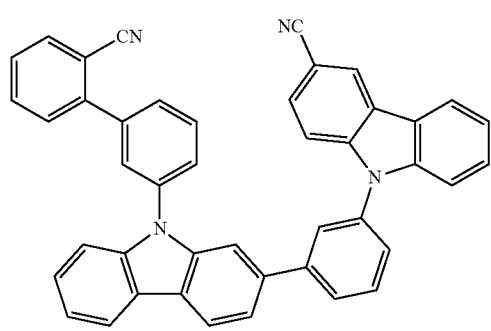
322
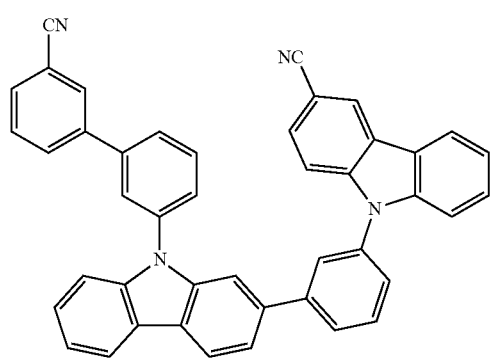
323
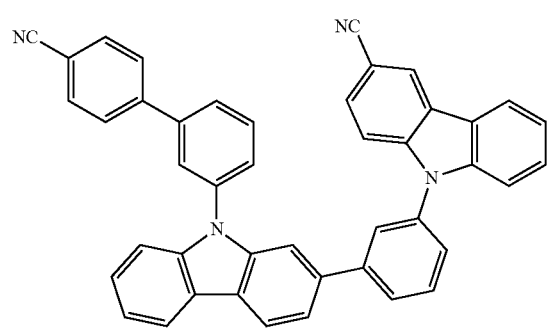
324
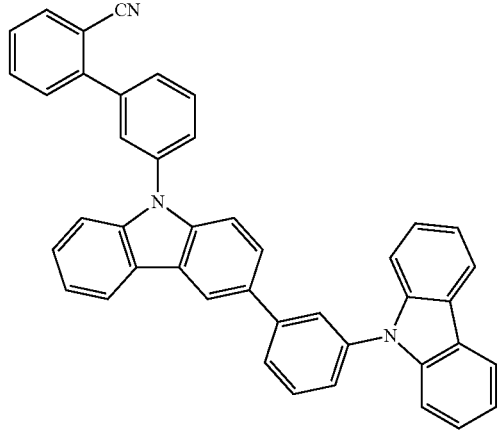
325
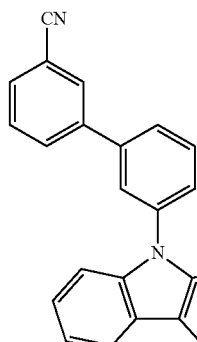
326
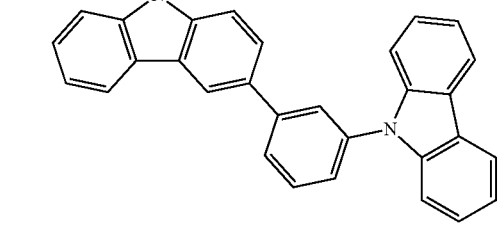
327

-continued
328
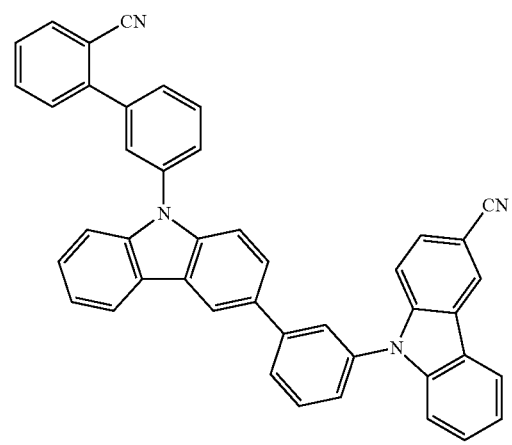
329
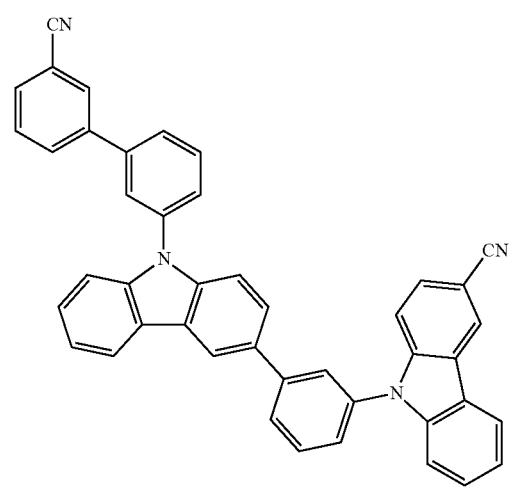
330
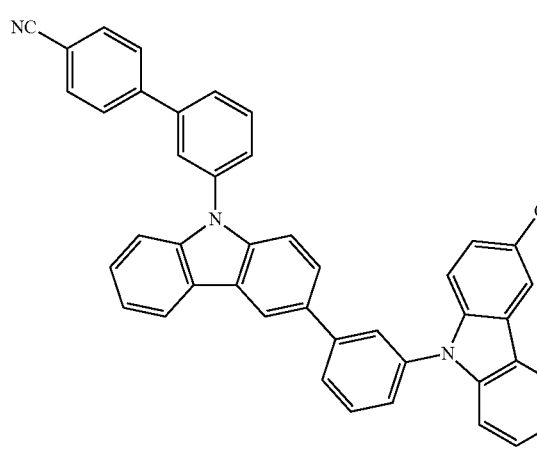
-continued
331
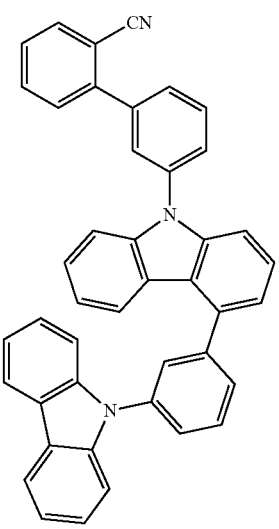
332
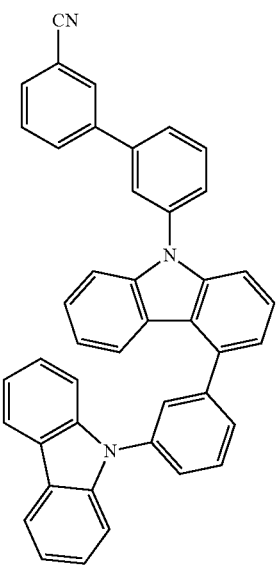
333
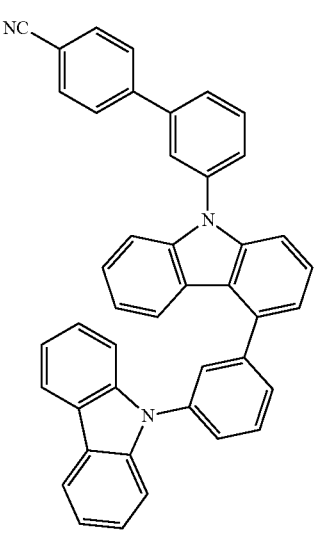

334

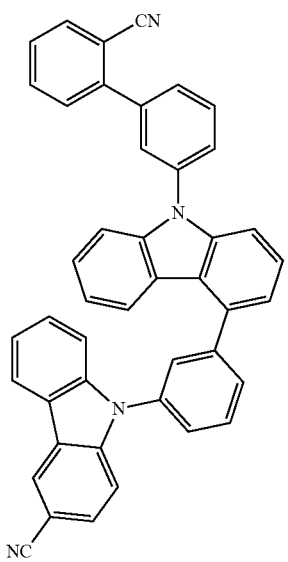

336

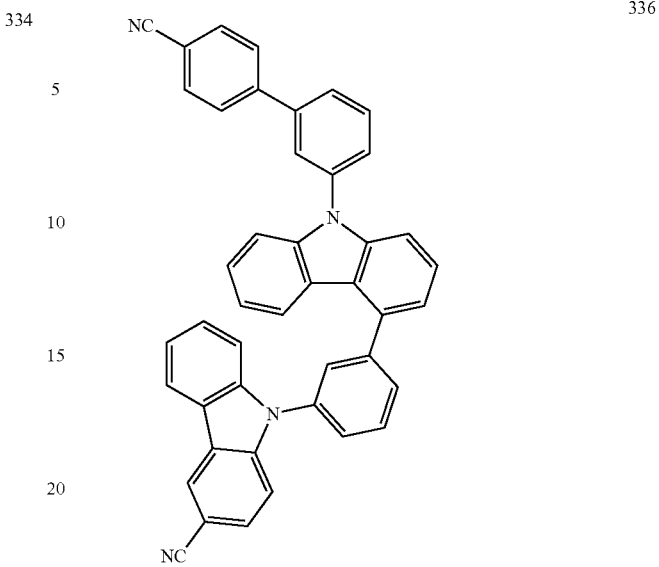

In Formula 1, "ring B" is bonded to "N" of "ring A" via *-(L₁)_{a1}-*' (see Formula 1').

In this regard, the condensed cyclic compound represented by Formula 1 may have a high triplet (T₁) energy level. Accordingly, although not limited to a particular theory, an electronic device, such as an organic light-emitting device including the condensed cyclic compound represented by Formula 1 (e.g., an organic light-emitting device including an emission layer that includes the condensed cyclic compound represented by Formula 1) may emit deep blue light at a high color purity.

335

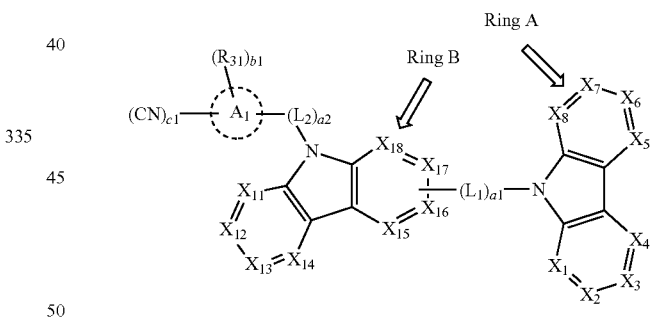

Formula 1'

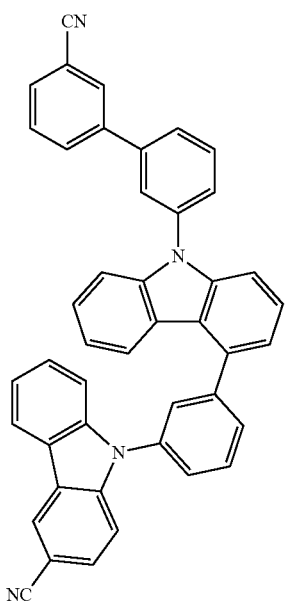

Also, in Formula 1, L₂ may be selected from a phenylene group, a fluorenylene group, a dibenzofuranylene group, and a dibenzothiophenylene group; and a phenylene group, a fluorenylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a fluorenyl group, a dibenzofuranyl group, a dibenzothiophenyl group, and —Si(Q₁₁)(Q₁₂)(Q₁₃).

In this regard, for example, the condensed cyclic compound represented by Formula 1 may have a higher triplet energy level than that of a virtual compound that has the same structure as Formula 1 except that $L_2$ is a nitrogen-containing ring. Therefore, although not limited to a particular theory, an electronic device, for example, an organic light-emitting device including the condensed cyclic compound represented by Formula 1 (e.g., an organic light-emitting device including an emission layer that includes the condensed cyclic compound represented by Formula 1), may emit deep blue light at a high color purity.

Also, a difference between $S_1$ (singlet) energy level and $T_1$ (triplet) energy level of the condensed cyclic compound represented by Formula 1 may be relatively small. In this regard, the condensed cyclic compound represented by Formula 1 may be used as a thermally activated delayed fluorescence (TADF) emitter.

For example, the results of HOMO, LUMO, $T_1$, and $S_1$ energy levels of Compounds 1, 13, 37, 97, 109, 169, 223, and 325 and Compounds B and C simulated and measured by using a density functional theory ("DFT") method of Gaussian program (structurally optimized at a level of B3LYP, 6-31 G(d,p)) are shown in Table 1.

TABLE 1

| Compound No. | HOMO (eV) | LUMO (eV) | $T_1$ (eV) | $S_1$ (eV) |
|---|---|---|---|---|
| 1 | −5.475 | −1.541 | 3.145 | 3.313 |
| 13 | −5.29 | −1.768 | 3.011 | 3.087 |
| 37 | −5.307 | −1.78 | 3.043 | 3.135 |
| 97 | −5.398 | −1.683 | 3.133 | 3.194 |
| 109 | −5.386 | −1.739 | 3.02 | 3.17 |
| 169 | −5.316 | −1.750 | 3.000 | 3.190 |
| 223 | −5.167 | −1.694 | 3.030 | 3.140 |
| 325 | −5.231 | −1.691 | 3.044 | 3.222 |
| Compound B | −5.194 | −1.65 | 2.8 | 3.212 |
| Compound C | −5.233 | −2.536 | 2.413 | 2.451 |

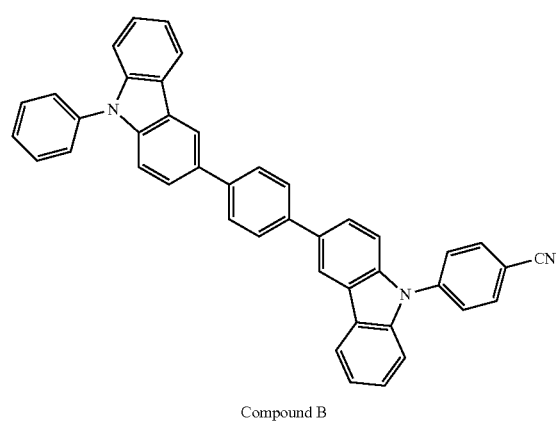 [SMILES: N#Cc1ccc(-n2c3ccccc3c3cc(-c4ccc(-c5ccc6c(c5)c5ccccc5n6-c5ccccc5)cc4)ccc32)cc1]

Compound B

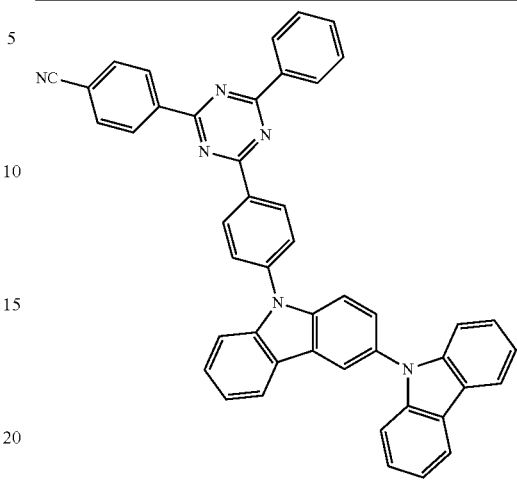

Compound C

A method of synthesizing the condensed cyclic compound represented by Formula 1 may be understood by one of ordinary skill in the art by referring to Synthesis Examples described below.

Therefore, the condensed cyclic compound represented by Formula 1 may be appropriate for use as an organic layer of an organic light-emitting device, for example, as a host or an emitter (e.g., a TADF emitter) of an emission layer in the organic layer. According to another aspect of an embodiment, an organic light-emitting device includes:
a first electrode;
a second electrode; and
an organic layer that is disposed between the first electrode and the second electrode,
wherein the organic layer includes an emission layer and at least one condensed cyclic compound represented by Formula 1.

When the organic light-emitting device includes the organic layer including the condensed cyclic compound represented by Formula 1, the organic light-emitting device may have low driving voltage, high efficiency, high luminance, high quantum efficiency, and long lifespan.

The condensed cyclic compound represented by Formula 1 may be included between a pair of electrodes of the organic light-emitting device. In some embodiments, the condensed cyclic compound may be included in at least one selected from the emission layer, a hole transport region (for example, including at least one selected from a hole injection layer, a hole transport layer, and an electron blocking layer) disposed between the first electrode and the emission layer, and an electron transport region (for example, including at least one selected from a hole blocking layer, an electron transport layer, and an electron injection layer) disposed between the emission layer and the second electrode.

In some embodiments, the condensed cyclic compound represented by Formula 1 may be included in the emission layer. Here, the condensed cyclic compound included in the emission layer may be a host, and the emission layer may further include a dopant (a fluorescent dopant or a phosphorescent dopant), wherein an amount of the condensed cyclic compound is larger than an amount of the dopant. The emission layer may be a green emission layer or a blue emission layer that emits green light or blue light. According to an embodiment, the condensed cyclic compound represented by Formula 1 may be included in the emission layer, the emission layer may further include a phosphorescent dopant, and the emission layer may emit blue light.

In some embodiments, the condensed cyclic compound represented by Formula 1 may be included in the emission layer, and the condensed cyclic compound may be a TADF emitter. Here, the emission layer may include the condensed cyclic compound represented by Formula 1 only or may further include a host and/or a dopant in addition to the condensed cyclic compound represented by Formula 1.

As used herein, the expression "(an organic layer) includes at least one condensed cyclic compound" may include an embodiment in which "(an organic layer) includes identical condensed cyclic compounds represented by Formula 1 and an embodiment in which (an organic layer) includes two or more different condensed cyclic compounds represented by Formula 1.

For example, the organic layer may include only Compound 1 as the condensed cyclic compound. In this regard, Compound 1 may be included in the emission layer of the organic light-emitting device. In some embodiments, the organic layer may include Compound 1 and Compound 2 as the condensed cyclic compounds. In this regard, Compound 1 and Compound 2 may be included in the same layer (for example, both Compound 1 and Compound 2 may be included in the emission layer) or in different layers, respectively.

The first electrode may be anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, the organic layer may include a hole transport region disposed between the first electrode and the emission layer and an electron transport region disposed between the emission layer and the second electrode, wherein the hole transport region includes at least one selected from a hole injection layer, a hole-transport layer, and an electron blocking layer, and wherein the electron transport region includes at least one selected from a hole blocking layer, an electron transport layer, and an electron injection layer.

As used herein, the term the "organic layer" refers to a single and/or a plurality of layers disposed between the first electrode and the second electrode in an organic light-emitting device. The "organic layer" may include not only organic compounds but also organometallic complexes including metals.

FIG. 1 is a schematic view of an organic light-emitting device 10 according to an embodiment. Hereinafter, a structure and a method of manufacturing the organic light-emitting device according to an embodiment will be described with reference to FIG. 1. The organic light-emitting device 10 includes a first electrode 11, an organic layer 15, and a second electrode 19, which are sequentially layered in the stated order.

A substrate may be additionally disposed under the first electrode 11 or on the second electrode 19. The substrate may be a conventional substrate that is used in an organic light-emitting device, such as glass substrate or a transparent plastic substrate, each having excellent mechanical strength, thermal stability, transparency, surface smoothness, ease of handling, and water repellency.

The first electrode 11 may be formed by depositing or sputtering a first electrode material on the substrate. The first electrode 11 may be an anode. The first electrode material may be selected from materials with a high work function for an easy hole injection. The first electrode 11 may be a reflective electrode, a semi-transmissive electrode, or a transmissive electrode. The first electrode material may be selected from an indium tin oxide (ITO), an indium zinc oxide (IZO), a tin oxide ($SnO_2$), and a zinc oxide (ZnO). In some embodiments, a metal such as magnesium (Mg), aluminum (Al), aluminum-lithium (Al—Li), calcium (Ca), magnesium-indium (Mg—In), or magnesium-silver (Mg—Ag) may be used as the first electrode material.

The first electrode 11 may have a single layer structure or a multi-layer structure including a plurality of layers. For example, the first electrode 11 may have a triple-layer structure of ITO/Ag/ITO, but embodiments are not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, hole transport layer, electron blocking layer, and buffer layer.

The hole transport region may only include a hole injection layer or a hole transport layer. Alternatively, the hole transport region may include a structure in which a hole injection layer/a hole transport layer or a hole injection layer/a hole transport layer/an electron blocking layer are sequentially layered on the first electrode 11.

When the hole transport region includes a hole injection layer, the hole injection layer HIL may be formed on the first electrode 11 by using various methods such as vacuum-deposition, spin coating, casting, and Langmuir-Blodgett (LB) method.

When a hole injection layer is formed by vacuum deposition, the deposition conditions may vary depending on a material that is used to form the hole injection layer and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0.01 Angstroms per second (Å/sec) to about 100 Å/sec. However, the deposition conditions are not limited thereto.

When the hole injection layer is formed by spin coating, the coating conditions may vary depending on a material used to form the hole injection layer and the structure and thermal characteristics of the hole injection layer. For example, a coating rate may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

The conditions for forming a hole transport layer and an electron blocking layer may be inferred based on the conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine (TCTA), polyaniline/dodecylbenzene sulfonic acid (Pani/DBSA), poly(3,4-ethylenedioxythiophene)/poly(4-styrene-sulfonate) (PEDOT/PSS), polyaniline/camphor sulfonic acid (Pani/CSA), (polyaniline)/poly(4-styrenesulfonate)

(Pani/PSS), a compound represented by Formula 201 below, and a compound represented by Formula 202 below:
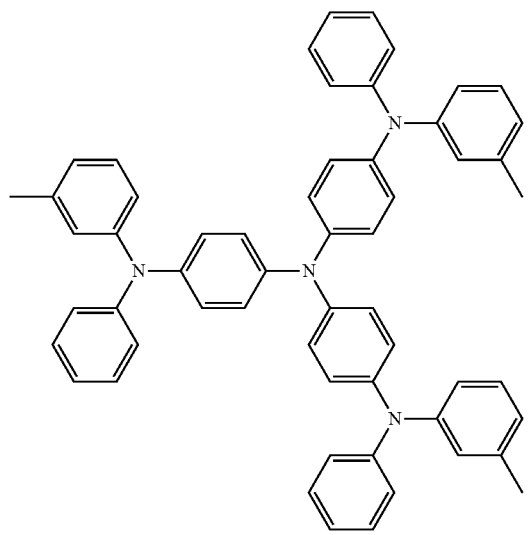
m-MTDATA
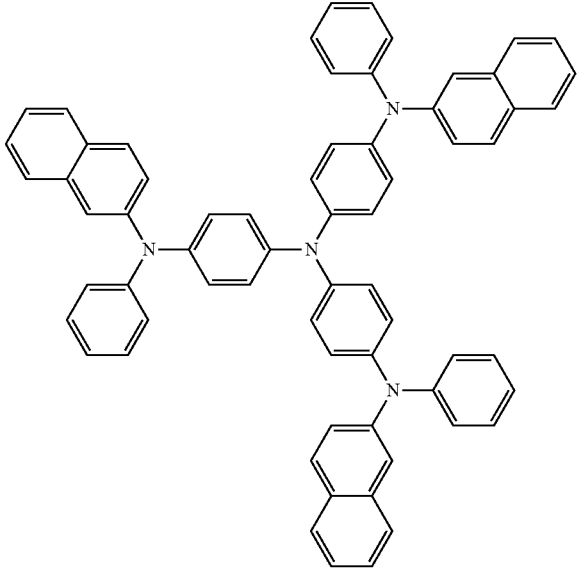
2-TNATA
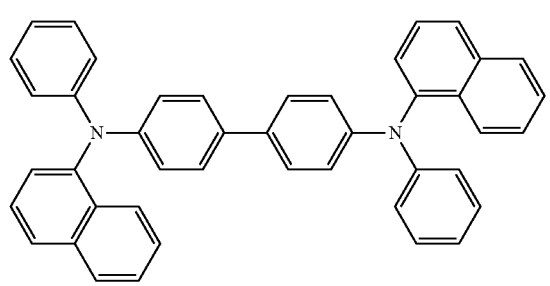
NPB
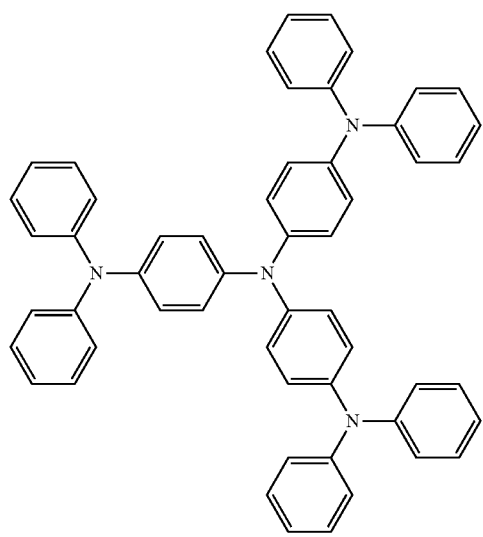
TDATA
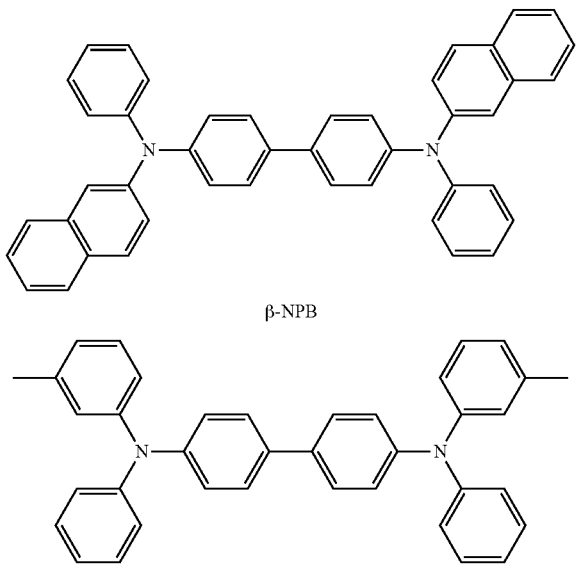
β-NPB
TPD -continued

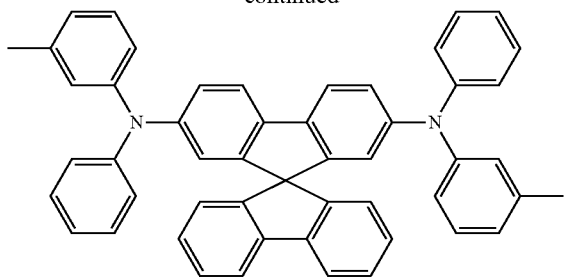
Spiro-TPD

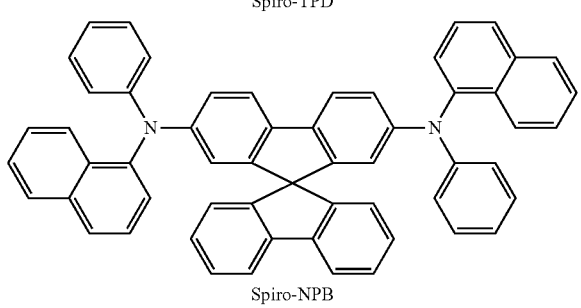
Spiro-NPB

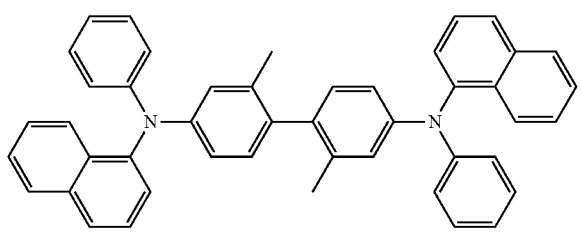
methylated NPB

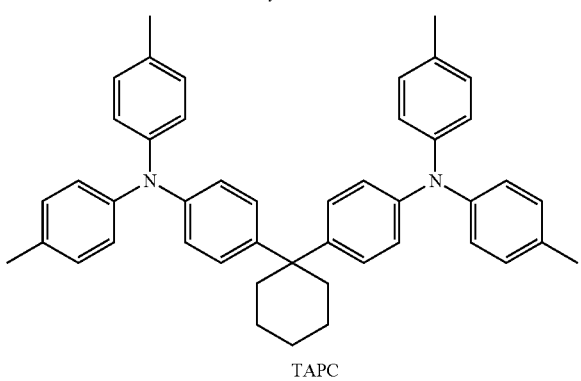
TAPC

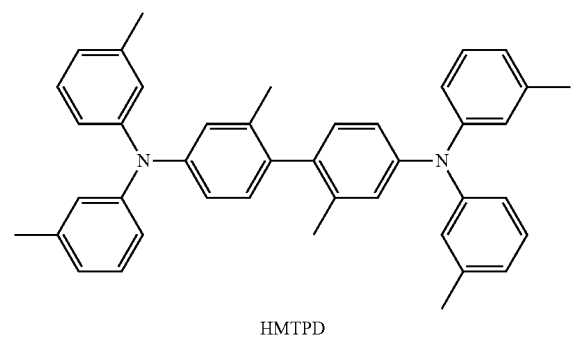
HMTPD

-continued

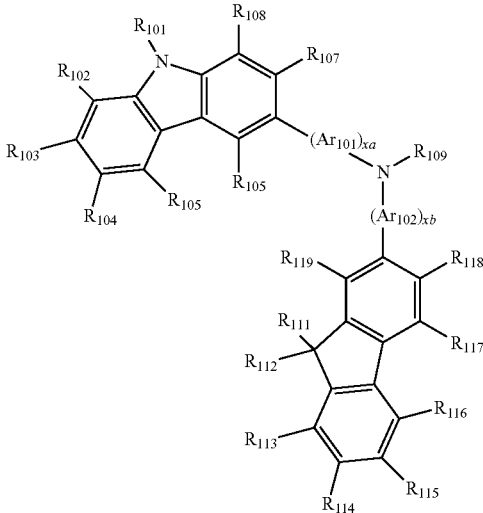

Formula 201 / Formula 202

In Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be each independently an integer selected from 0 to 5 or may be 0, 1, or 2. For example, xa may be 1 and xb may be 0, but embodiments are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, pentyl group, or a hexyl group), and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, a compound represented by Formula 201 may be represented by Formula 201A, but embodiments are not limited thereto:

Formula 201A

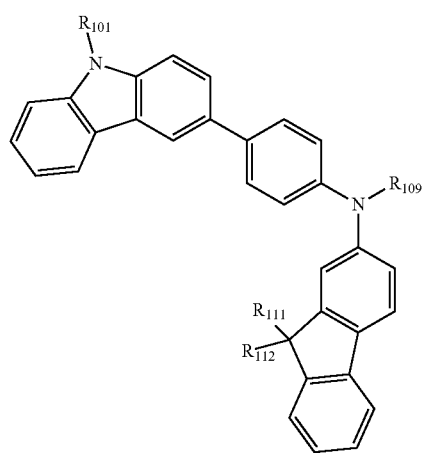

In Formula 201A, $R_{101}$, $R_{111}$, $R_{112}$, and $R_{109}$ may be understood by referring to the description provided herein.

For example, the compound represented by Formula 201 and the compound represented by Formula 202 may include Compounds HT1 to HT20, but embodiments are not limited thereto:

HT1

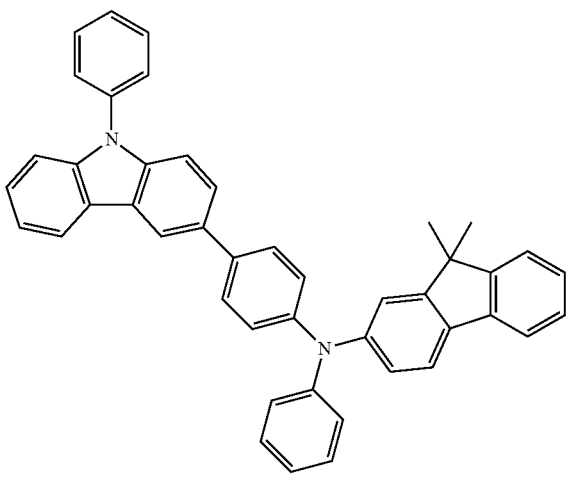

HT2

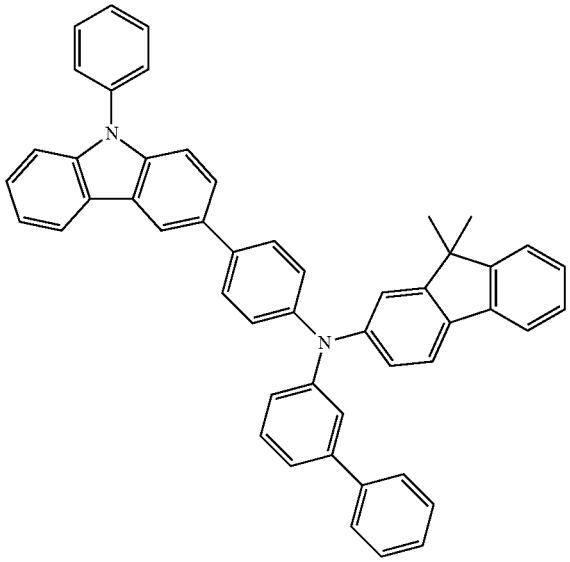

HT3
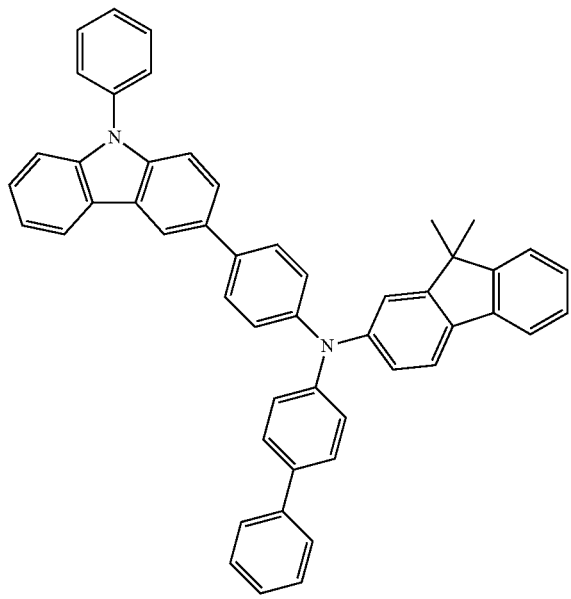
HT5
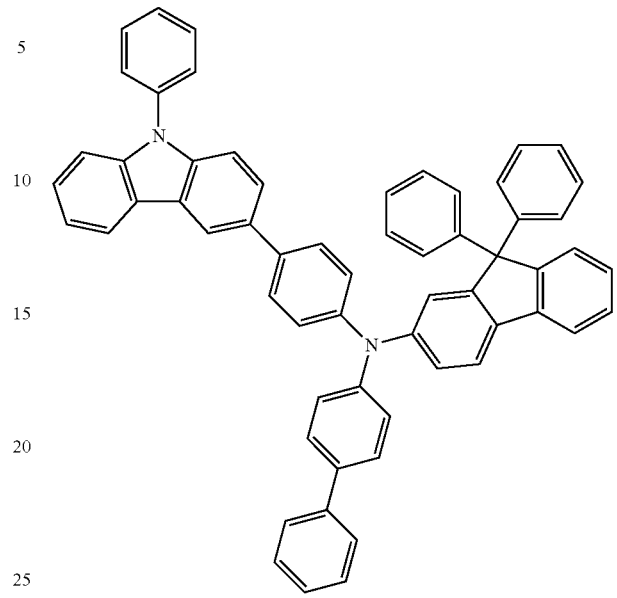
HT4
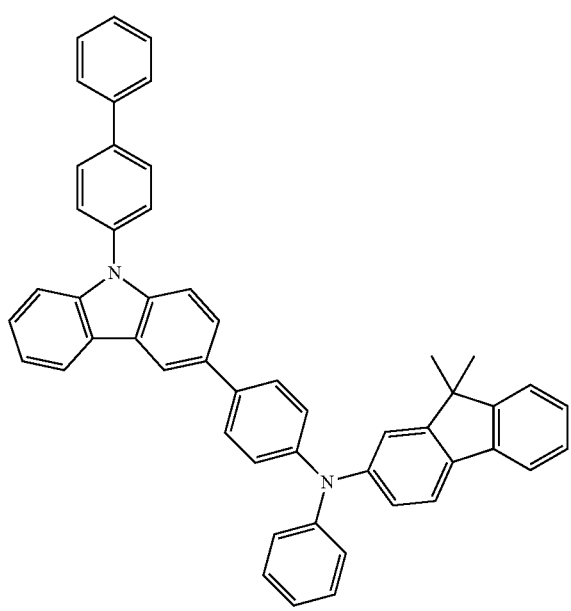
HT6
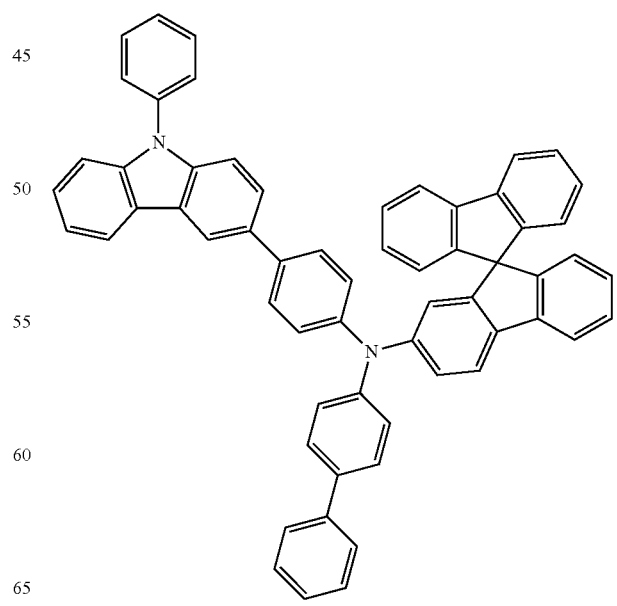

HT7
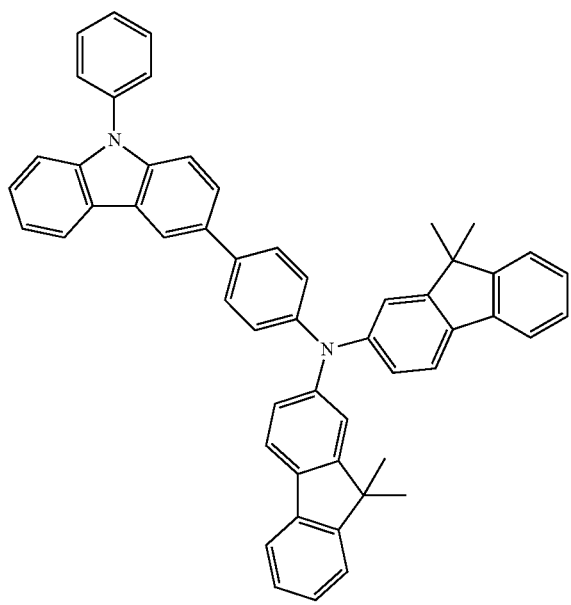
HT8
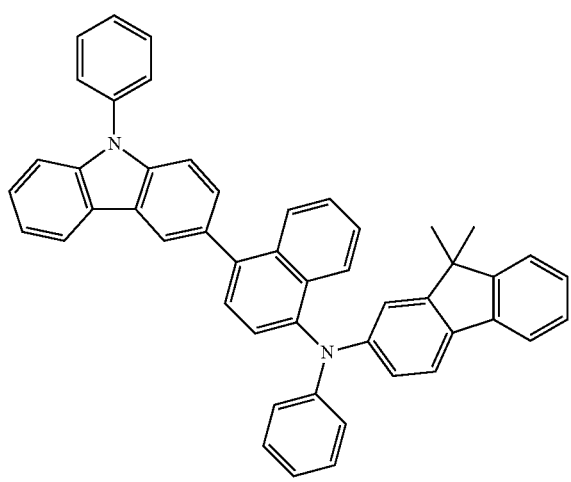
HT9
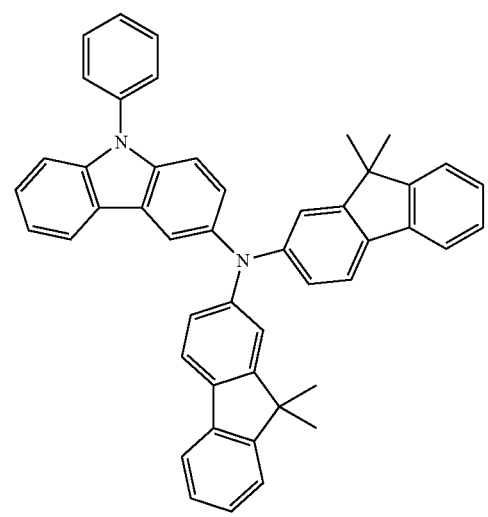
HT10
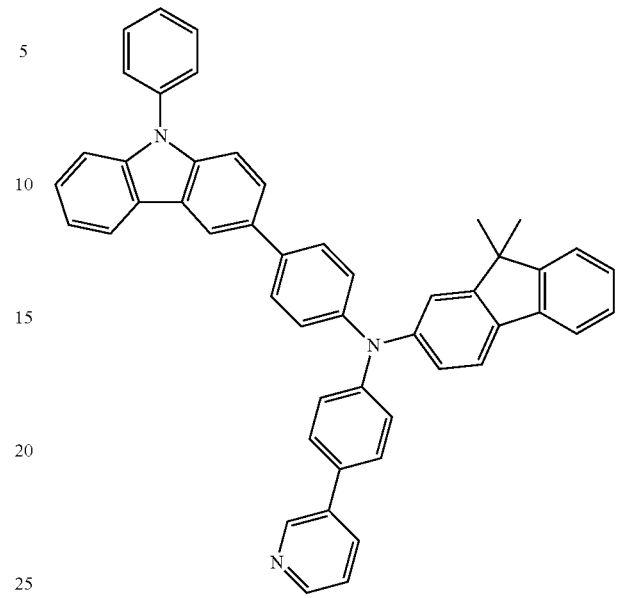
HT11
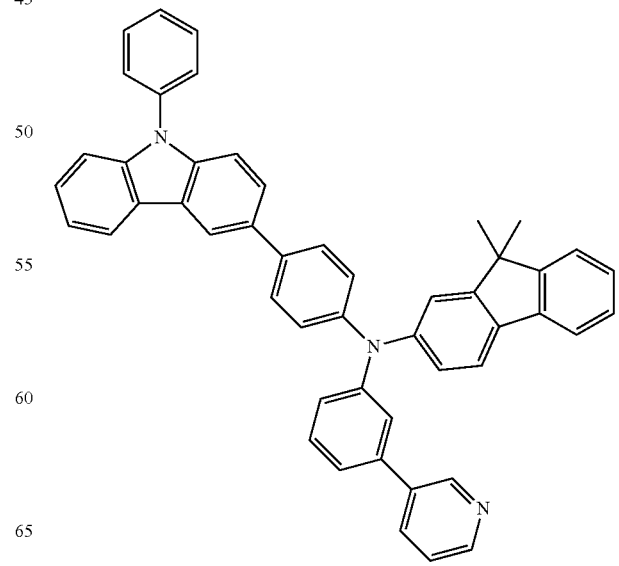

-continued
HT12
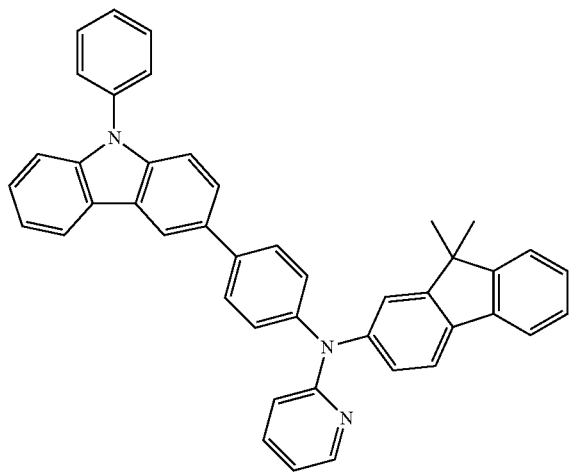
HT13
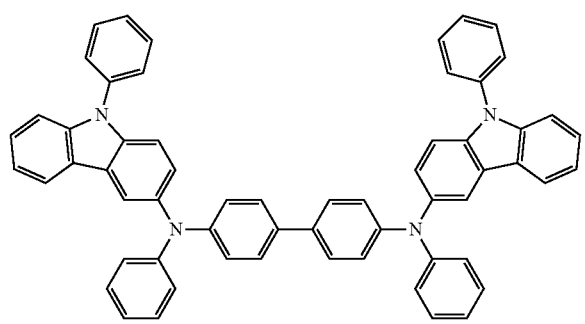
HT14
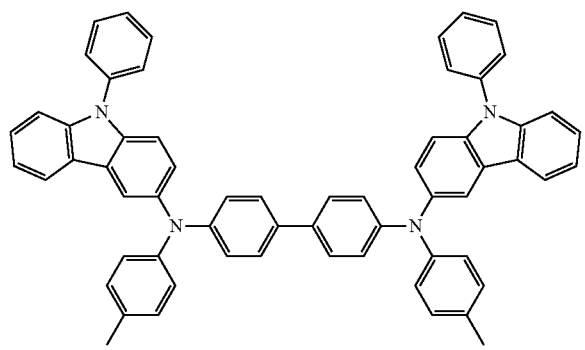
HT15
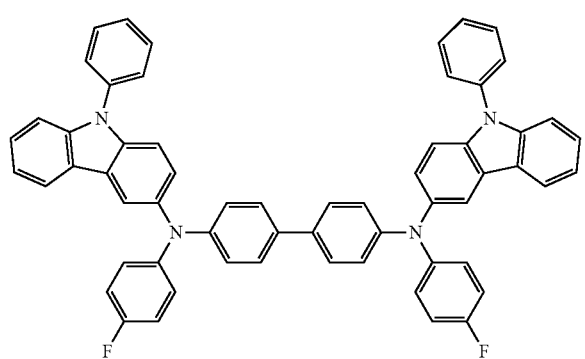
HT16
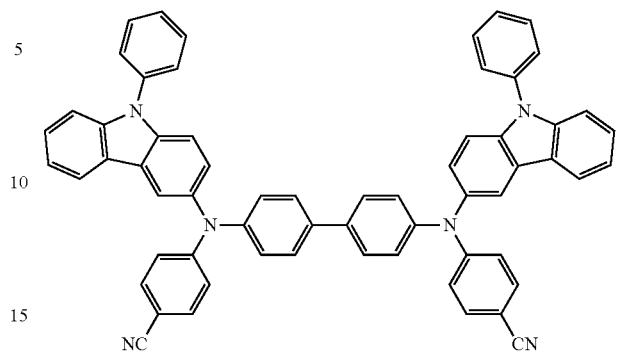
HT17
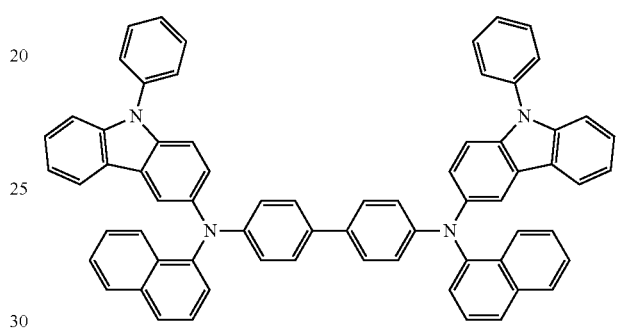
HT18
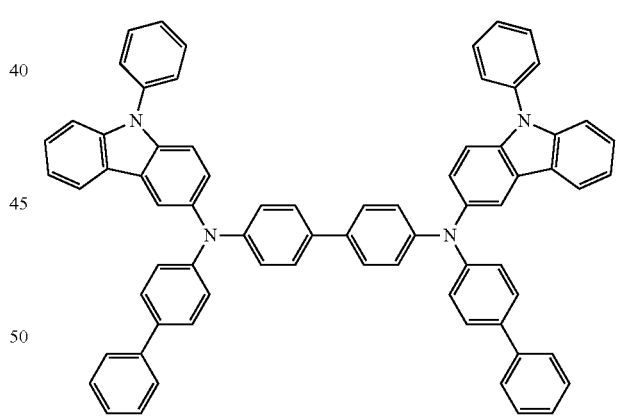
HT19
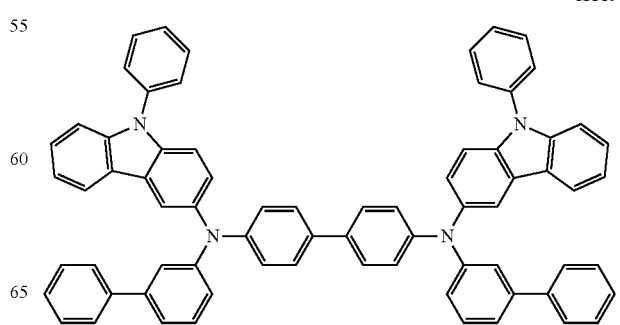

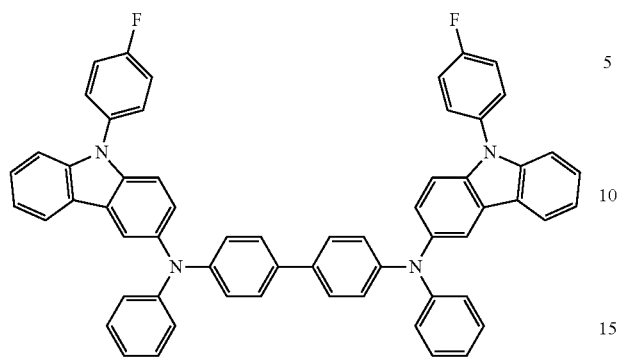
HT20

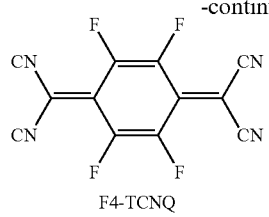
F4-TCNQ

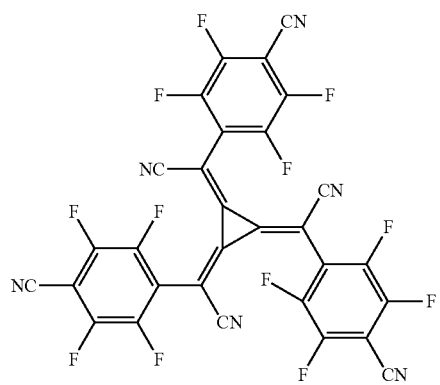
HP-1

A thickness of the hole transport region may be in a range of about 100 Å to about 10,000 Angstroms (Å), for example, about 100 Å to about 1,000 Å. While not wishing to be bound by a theory, it is understood that when the hole transport region includes at least one of a hole injection layer and a hole transport layer, the thickness of the hole injection layer may be in a range of about 100 Å to about 10,000 Å, and for example, about 100 Å to about 1,000 Å, and the thickness of the hole transport layer may be in a range of about 50 Å to about 2,000 Å, and for example, about 100 Å to about 1.500 Å. While not wishing to be bound by a theory, it is understood that when the thicknesses of the hole transport region, the hole injection layer, and the hole transport layer are within these ranges, hole transporting characteristics may be satisfactory without a substantial increase in driving voltage.

The hole transport region may further include, in addition to the mentioned materials above, a charge-generating material to improve conductive properties. The charge-generating material may be homogeneously or non-homogeneously dispersed throughout the hole transport region.

The charge-generating material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but embodiments are not limited thereto.

Compound HT-D1

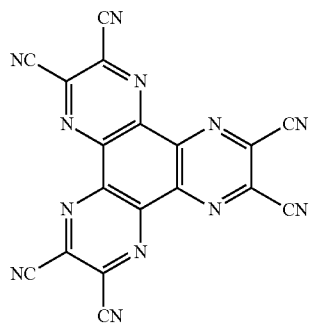

The hole transport region may further include a buffer layer.

The buffer layer may compensate for an optical resonance distance according to a wavelength of light emitted from the emission layer to improve the efficiency of an organic light-emitting device.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary depending on the material that is used to form the emission layer.

The hole transport region may further include an electron blocking layer. The electron blocking layer may include, for example, mCP, but embodiments are not limited thereto.

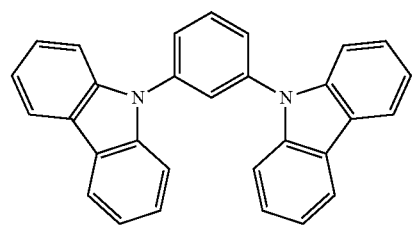

mCP

When the organic light-emitting device is a full color organic light-emitting device, the emission layer may be patterned into a red emission layer, a green emission layer, and a blue emission layer. Alternatively, the emission layer may have a structure in which the red emission layer, the green emission layer, and/or the blue emission layer are layered to emit white light or other various embodiments are possible.

The emission layer may include the condensed cyclic compound represented by Formula 1. The emission layer may further include a dopant. The dopant may include at least one selected from a fluorescent dopant and a phosphorescent dopant.

In some embodiments, the emission layer may include the condensed cyclic compound represented by Formula 1 only, and the condensed cyclic compound may be a TADF emitter.

In some embodiments, the emission layer may include the condensed cyclic compound represented by Formula 1, the condensed cyclic compound may be a TADF emitter, and the emission layer may further include any host which is not the condensed cyclic compound represented by Formula 1.

For example, a host in the emission layer may include the condensed cyclic compound represented by Formula 1.

The dopant in the emission layer may include a fluorescent dopant which emits light according to a fluorescent emission mechanism or a phosphorescent dopant which emits light according to a phosphorescent emission mechanism.

According to an embodiment, the dopant in the emission layer may be a phosphorescent dopant, and the phosphorescent dopant may include an organometallic compound represented by Formula 81:

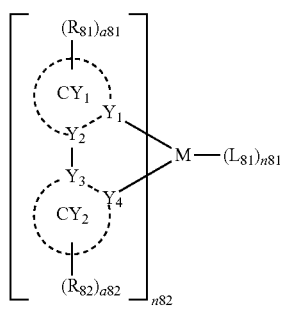

Formula 81 wherein, in Formula 81,

M may be selected from iridium (Ir), platinum (Pt), osmium (Os), titanium (Ti), zirconium (Zr), hafnium (Hf), europium (Eu), terbium (Tb), and thulium (Tm), $Y_1$ to $Y_4$ may be each independently carbon (C) or nitrogen (N), $Y_1$ and $Y_2$ are linked via a single bond or a double bond, and $Y_3$ and $Y_4$ are linked via a single bond or a double bond, $CY_1$ and $CY_2$ may be each independently selected from a benzene ring, a naphthalene ring, a fluorene ring, a spirofluorene ring, an indene ring, a pyrrole ring, a thiophene ring, a furan ring, an imidazole ring, a pyrazole ring, a thiazole ring, an isothiazole ring, an oxazole ring, an isoxazole ring, a pyridine ring, a pyrazine ring, a pyrimidine ring, a pyridazine ring, a quinoline ring, an isoquinoline ring, a benzoquinoline ring, a quinoxaline ring, a quinazoline ring, a carbazole ring, a benzoimidazole ring, a benzofuran ring, a benzothiophene ring, an isobenzothiophene ring, a benzoxazole ring, an isobenzoxazole ring, a triazole ring, a tetrazole ring, an oxadiazole ring, a triazine ring, a dibenzofuran ring, or a dibenzothiophene ring, and $CY_1$ and $CY_2$ are optionally further linked to each other through an organic linking group, $R_{81}$ and $R_{82}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), a81 and a82 may be each independently an integer selected from 1 to 5, n81 may be an integer selected from 0 to 4, n82 may be 1, 2, or 3, $L_{81}$ may be a monovalent organic ligand, a divalent organic ligand, or a trivalent organic ligand, and $Q_1$ to $Q_7$ may have the same definitions as $Q_1$ to $Q_3$ in —Si($Q_1$)($Q_2$)($Q_3$) in Formula 1.

$R_{81}$ and $R_{82}$ may be understood by referring to the description provided herein in connection with $R_{11}$.

The phosphorescent dopant may include at least one selected from Compounds PD1 to PD78, and FIr$_6$, but embodiments are not limited thereto:

PD1

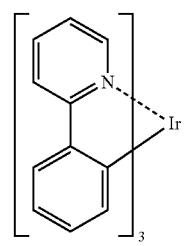

PD2

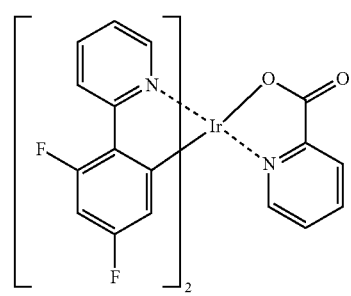

PD3

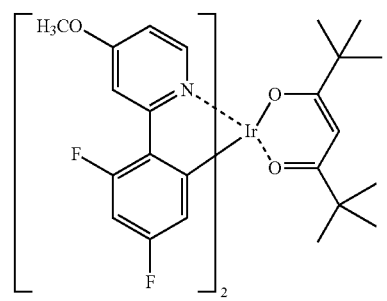

-continued
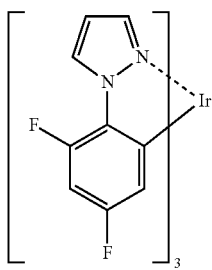
PD4
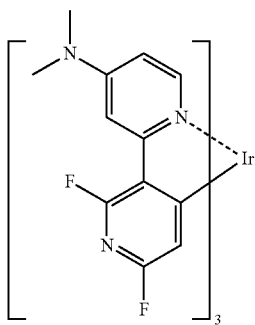
PD5
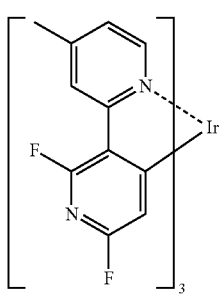
PD6
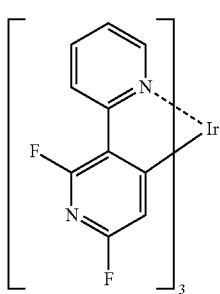
PD7
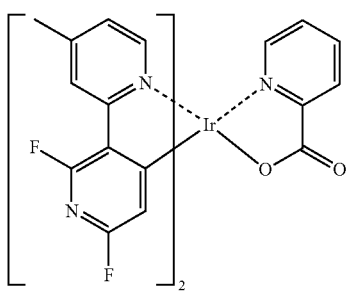
PD8
-continued
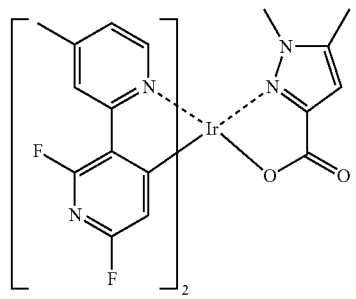
PD9
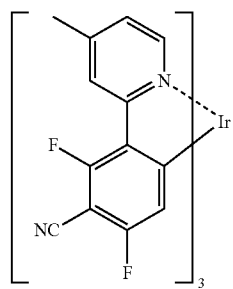
PD10
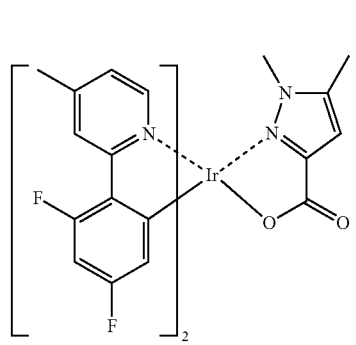
PD11
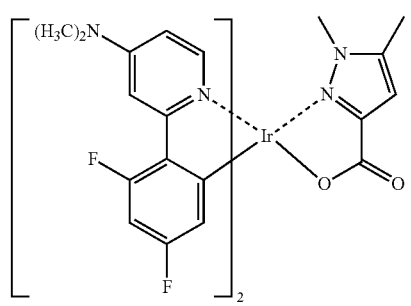
PD12
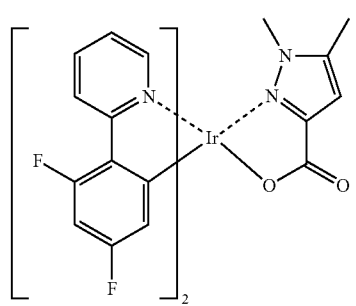
PD13

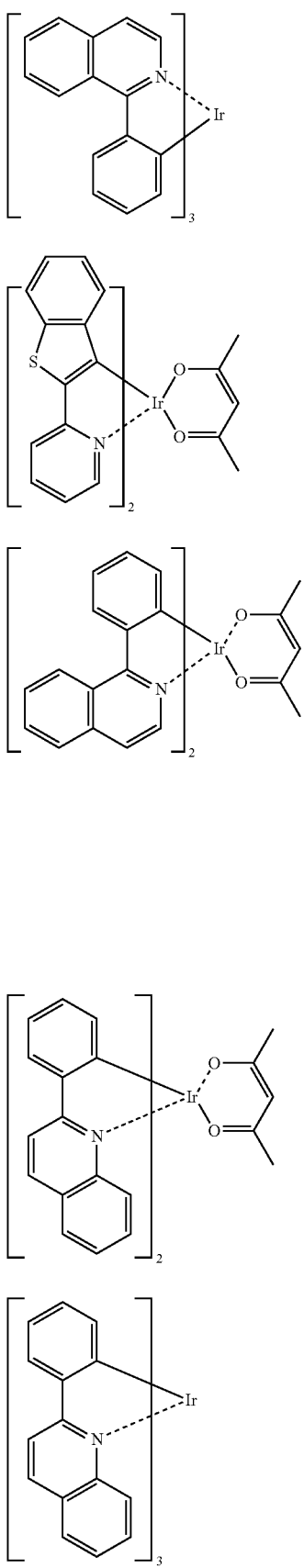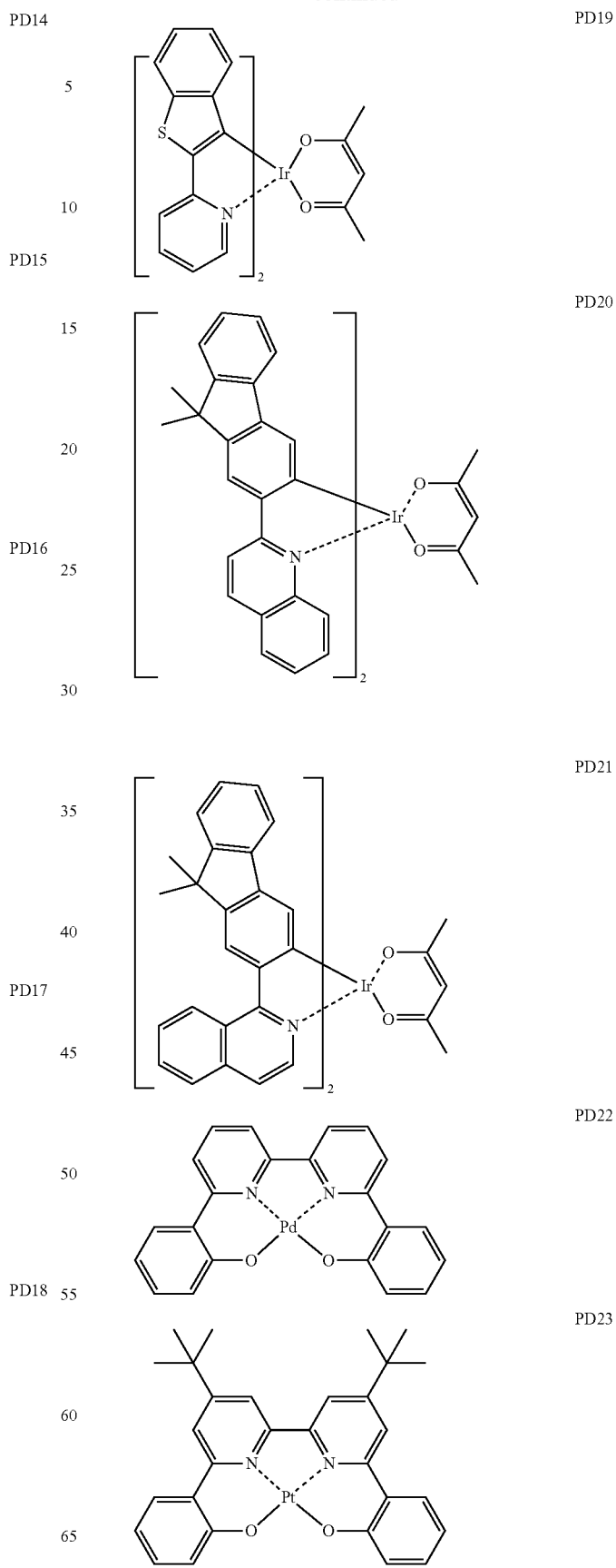

PD24
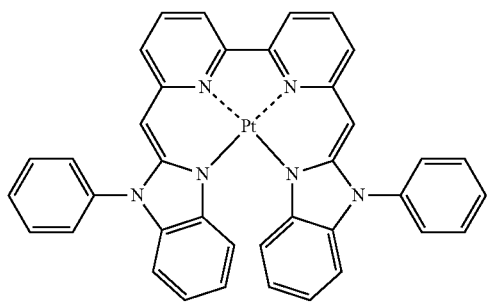
PD25
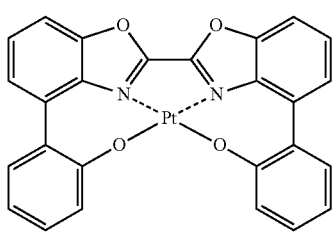
PD26
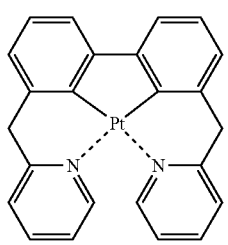
PD27
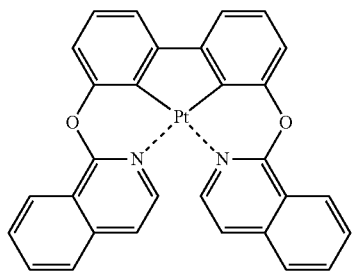
PD28
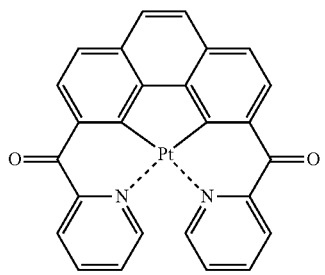
PD29
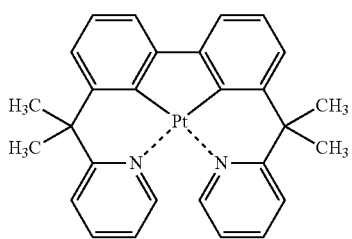
PD30
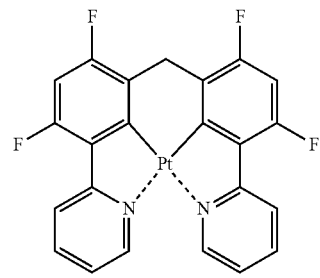
PD31
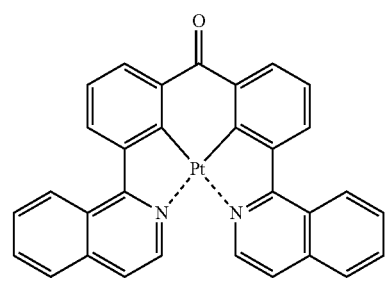
PD32
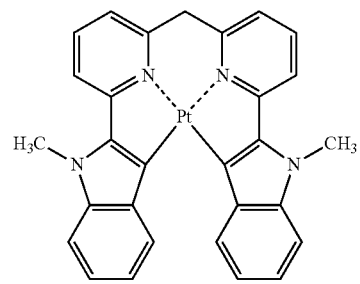
PD33
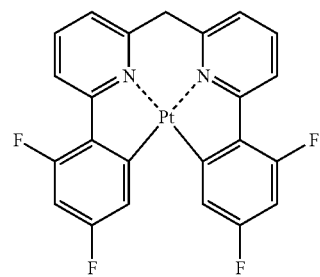
PD34
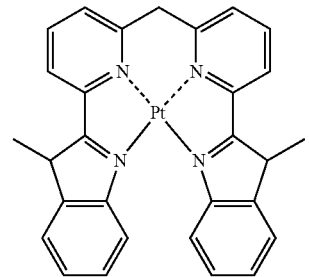

-continued
PD35
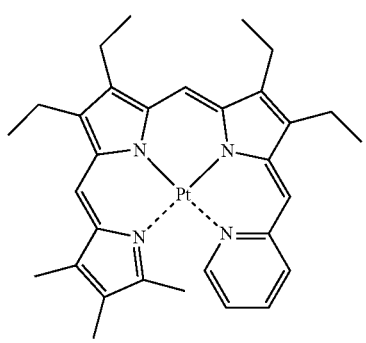
PD36
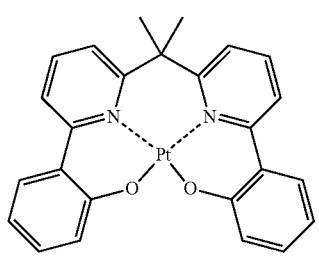
PD37
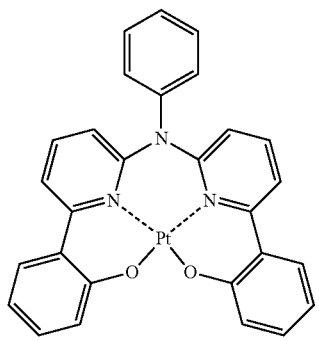
PD38
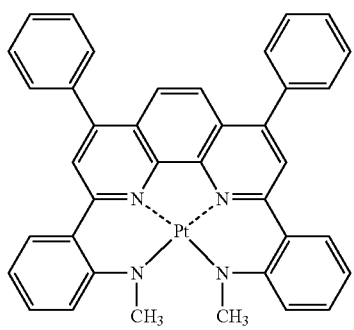
PD39
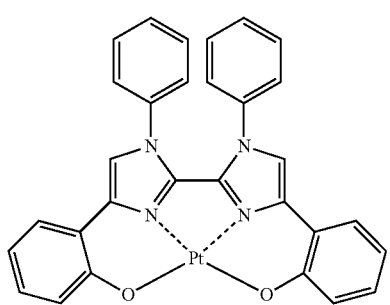
PD40
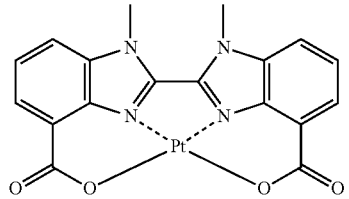
PD41
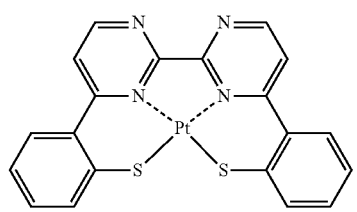
PD42
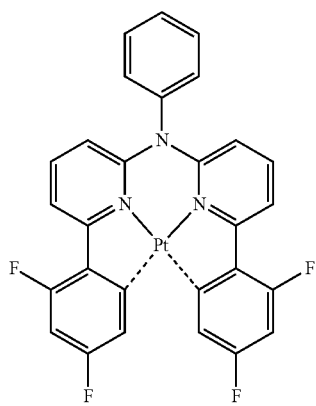
PD43
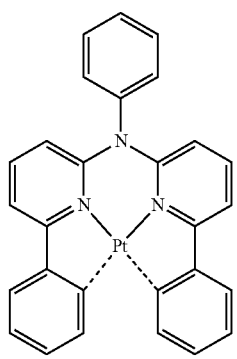
PD44
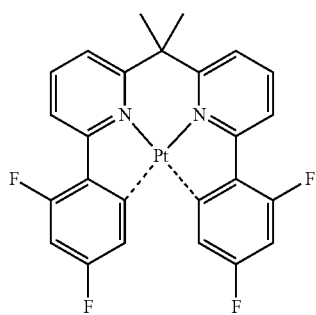

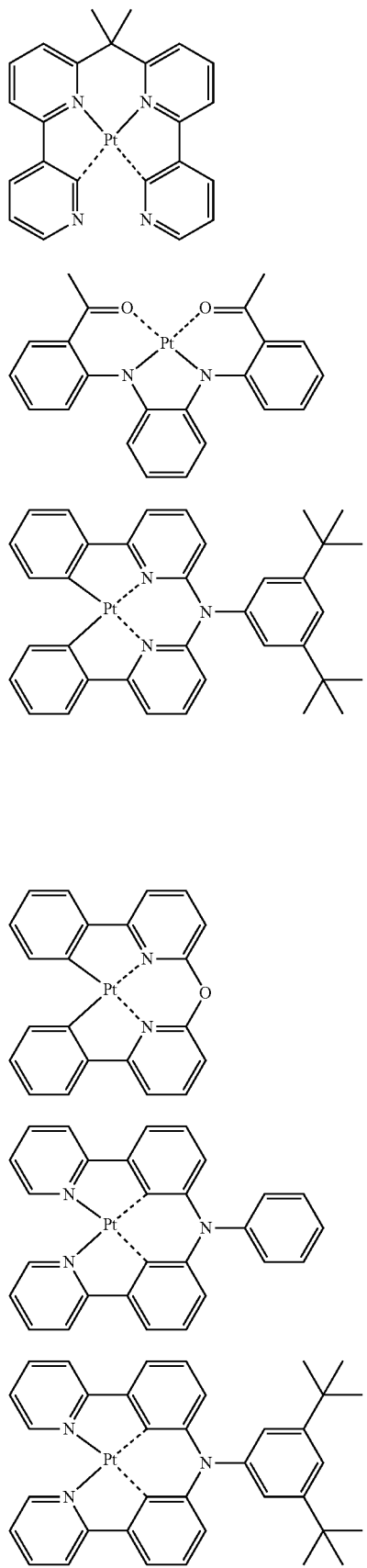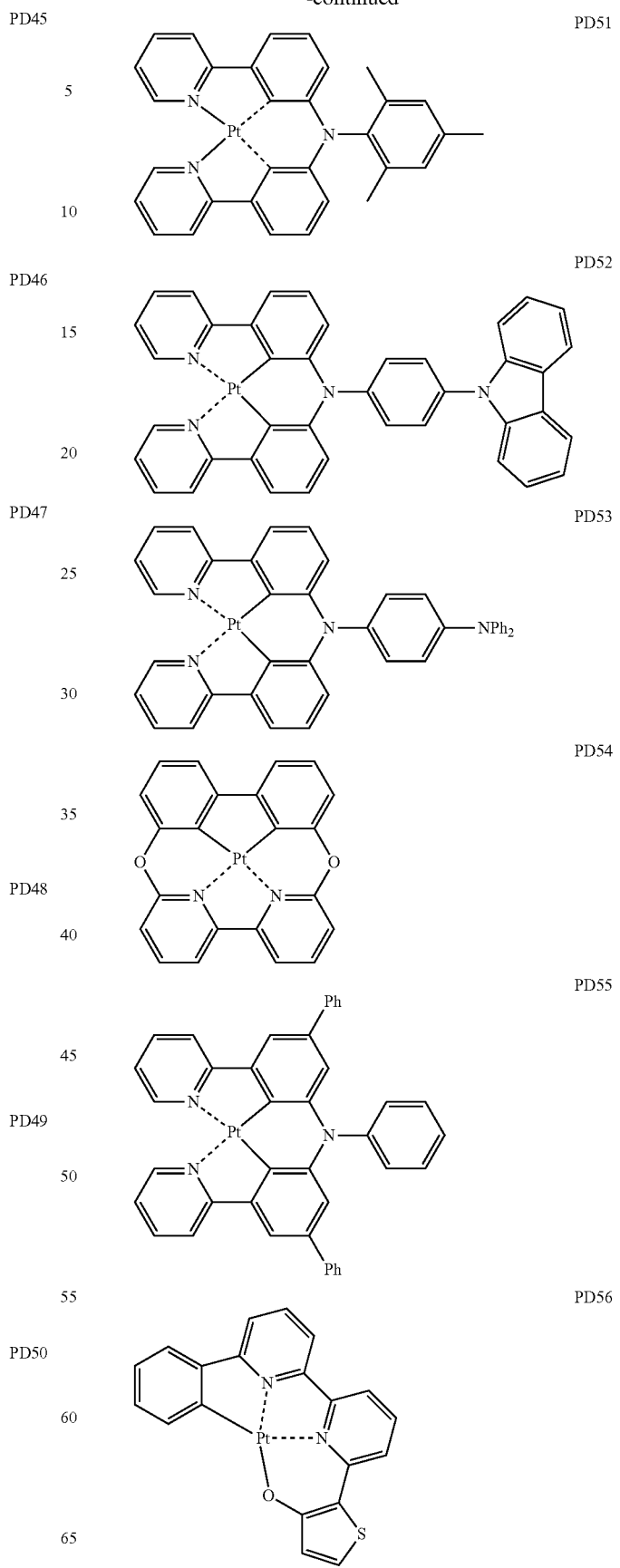

-continued
PD57 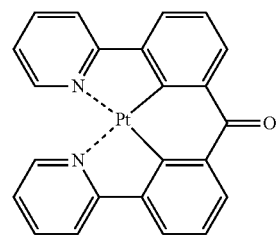
PD58 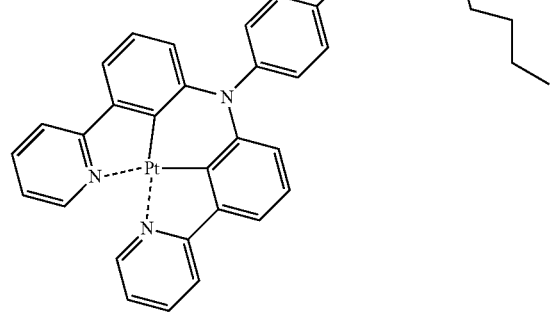
PD59 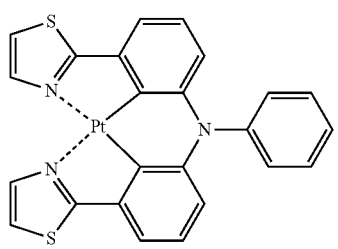
PD60 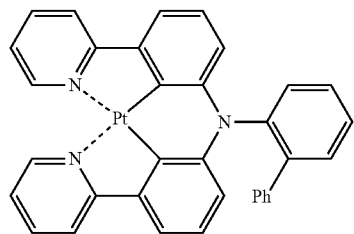
PD61 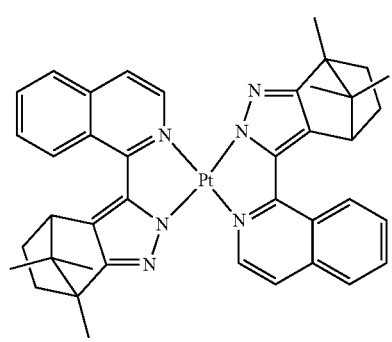
-continued
PD62 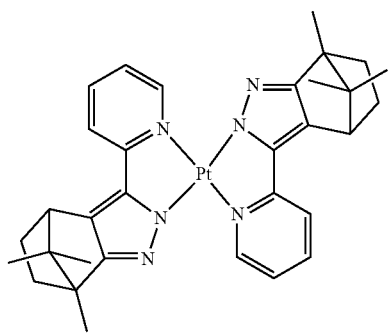
PD63 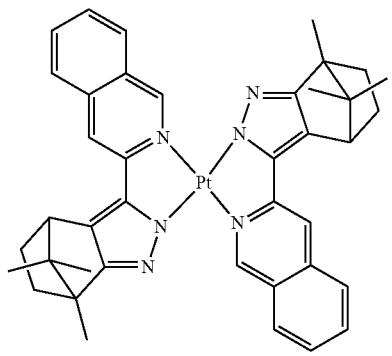
PD64 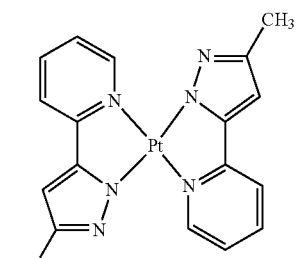
PD65 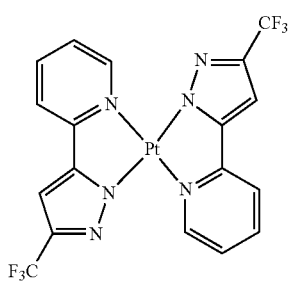
PD66 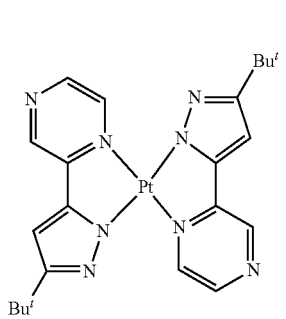

PD67 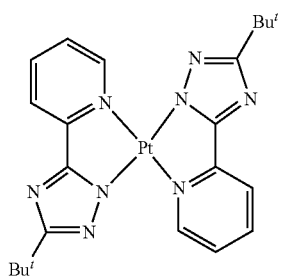
PD68 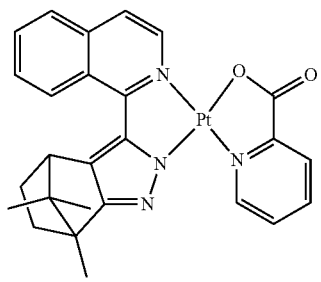
PD69 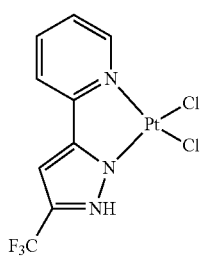
PD70 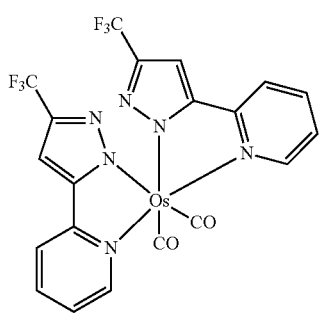
PD71 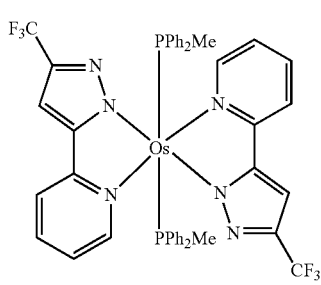
PD72 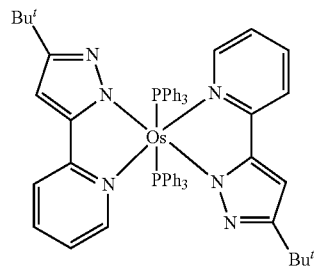
PD73 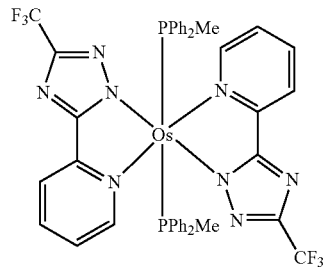
PD74 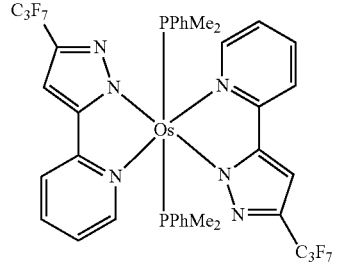
PD75 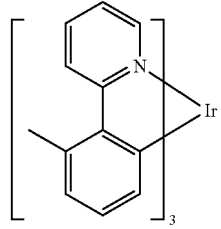
PD76 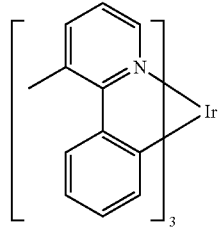
PD77 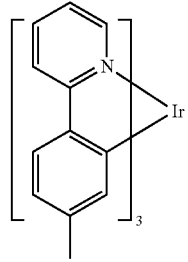

-continued

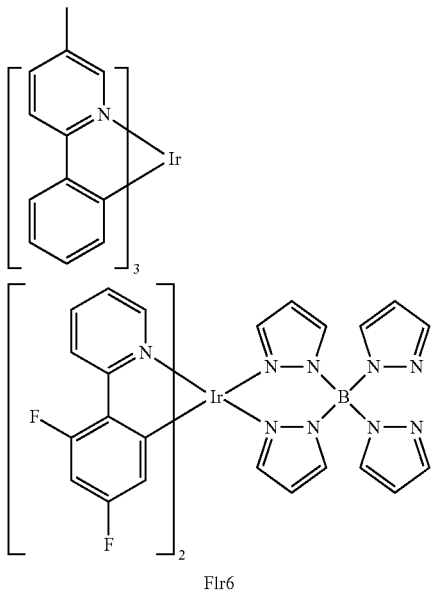

Flr6

PD78

In some embodiments, the phosphorescent dopant may include PtOEP:

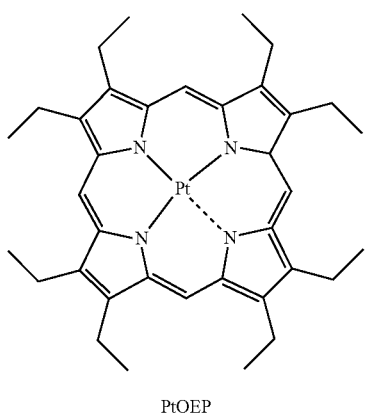

PtOEP

When the emission layer includes a host and a dopant, an amount of the dopant may be in a range of about 0.01 part to about 20 parts by weight based on 100 parts by weight of the host, but embodiments are not limited thereto.

A thickness of the emission layer may be in a range of about 100 Å to about 1,000 Å, for example, about 200 Å to about 600 Å. When the thickness of the emission layer is within this range, light-emission characteristics may be excellent without a substantial increase in driving voltage.

Then, an electron transport region may be disposed on the emission layer.

The electron transport region may include at least one selected from a hole blocking layer, an electron transport layer, and an electron injection layer, but embodiments not limited thereto.

For example, the electron transport region may have a structure of a hole blocking layer/an electron transport layer/an electron injection layer or an electron transport layer/an electron injection layer, but embodiments are not limited thereto. The electron transport layer may have a single layer structure or a multi-layer structure including two or more different materials.

The conditions for forming a hole blocking layer, an electron transport layer, and an electron injection layer may be inferred based on the conditions for forming the hole injection layer.

When the electron transport region includes a hole blocking layer, the hole blocking layer may include, for example, at least one selected from BCP and Bphen, but embodiments are not limited thereto.

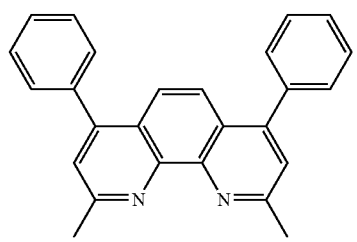

BCP

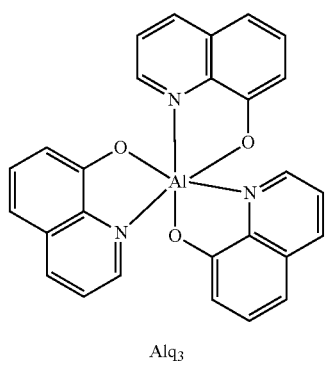

Bphen

A thickness of the hole blocking layer may be in a range of about 20 Å to about 1,000 Å, for example, about 30 Å to about 300 Å. When the thickness of the hole blocking layer is within these ranges, the hole blocking layer may have improved hole blocking ability without a substantial increase in driving voltage.

The electron transport layer may further include at least one selected from BCP, BPhen, $Alq_3$, BAlq, TAZ, and NTAZ.

$Alq_3$

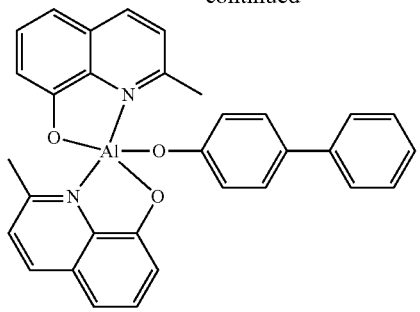

BAlq

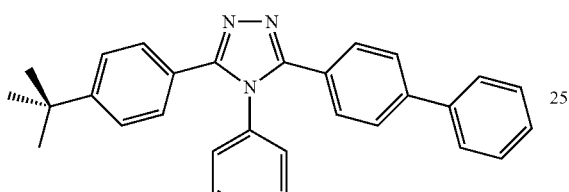

TAZ

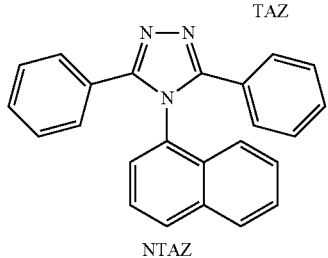

NTAZ

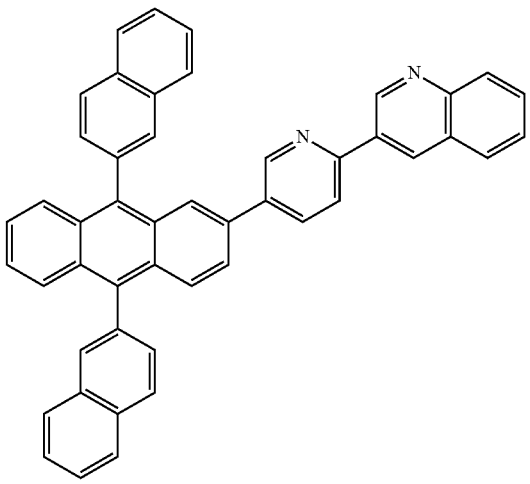

ET2

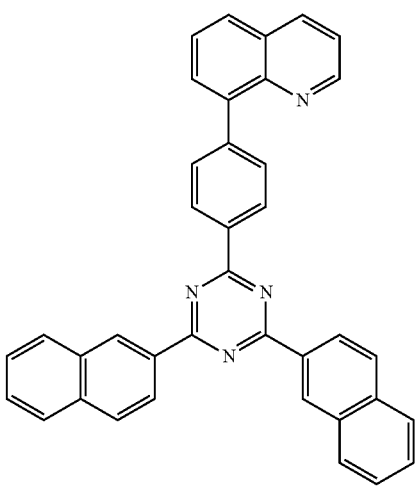

ET3

In some embodiments, the electron transport layer may include at least one selected from Compounds ET1, ET2, and ET3, but embodiments are not limited thereto.

ET1

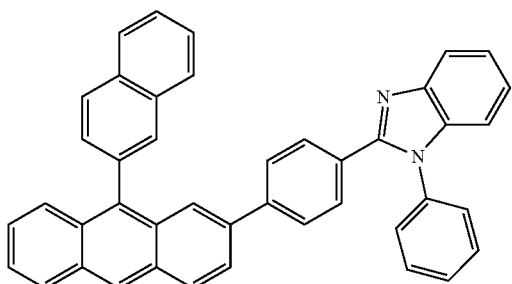

A thickness of the electron transport layer may be in a range of about 100 Å to about 1,000 Å, for example, about 150 Å to about 500 Å. While not wishing to be bound by a theory, it is understood that when the thickness of the electron transport layer is within the range described above, the electron transport layer may have satisfactory electron transport characteristics without a substantial increase in driving voltage.

The electron transport layer may further include a metal-containing material in addition to the materials described above.

The metal-containing material may include a Li complex. The Li complex may include, for example, Compound ET-D1 (lithium quinolate, LiQ) or ET-D2.

ET-D1

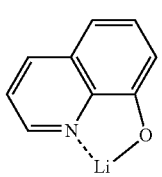

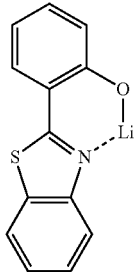

ET-D2

The electron transport region may include an electron injection layer that allows electrons to be easily provided from the second electrode 19.

The electron injection layer may include at least one selected from, LiF, NaCl, CsF, Li$_2$O, and BaO.

A thickness of the electron injection layer may be in a range of about 1 Å to about 100 Å, for example, about 3 Å to about 90 Å. While not wishing to be bound by a theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A second electrode material may be selected from a metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as second electrode material. To manufacture a top emission-type light-emitting device, a transmissive electrode formed using ITO or IZO may be used as the second electrode 19.

Hereinbefore, the organic light-emitting device has been described with reference to FIG. 1, but embodiments are not limited thereto.

A $C_1$-$C_{60}$ alkyl group as used herein refers to a linear or branched aliphatic saturated hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —O$A_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by placing at least one carbon-carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group as used herein refers to a hydrocarbon group formed by placing at least one carbon-carbon triple bond in the middle or at the terminal of the $C_2$-$C_{60}$ alkyl group. Detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent monocyclic saturated hydrocarbon group including 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as a $C_3$-$C_{10}$ cycloalkyl group.

A $C_1$-$C_{10}$ heterocycloalkyl group as used herein refers to a monovalent saturated monocyclic group including at least one heteroatom selected from N, O, P, Si and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as a $C_1$-$C_{10}$ heterocycloalkyl group.

A $C_3$-$C_{10}$ cycloalkenyl group as used herein refers to a monovalent monocyclic group that has 3 to 10 carbon atoms and at least one carbon-carbon double bond in the ring thereof, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group including at least one heteroatom selected from N, O, P, Si and S as a ring-forming atom, 1 to 10 carbon atoms, and at least one double bond in its ring. Detailed examples of the $C_2$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as a $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a heterocyclic aromatic system that has at least one heteroatom selected from N, O, P, Si and S as a ring-forming atom, and 1 to 60 carbon atoms. A $C_1$-$C_{60}$ heteroarylene group as used herein refers to a divalent group having a heterocyclic aromatic system that has at least one heteroatom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —O$A_{102}$ (wherein $A_{102}$ is the $C_6$-$C_{60}$ aryl group), and a $C_6$-$C_{60}$ arylthio group as used herein indicates —S$A_{103}$ (wherein $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as ring-forming atoms, wherein the molecular structure as a whole is non-aromatic in the entire molecular structure. Detailed examples of the non-aromatic condensed polycyclic group include a fluorenyl group. A divalent non-aromatic condensed polycyclic group as used herein refers to a divalent group having the same structure as the monovalent non-aromatic condensed polycyclic group.

A monovalent non-aromatic condensed hetero-polycyclic group as used herein refers to a monovalent group that has a plurality of rings condensed with each other, has a heteroatom selected from N, O P, Si and S, other than carbon atoms (for example, the number of carbon atoms may be in a range of 1 to 60), as ring-forming atoms, wherein the molecular structure as a whole is non-aromatic in the entire molecular structure. The monovalent non-aromatic condensed heteropolycyclic group includes a carbazolyl group. A divalent non-aromatic condensed hetero-polycyclic group as used herein refers to a divalent group having the same structure as the monovalent non-aromatic condensed heteropolycyclic group.

At least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group (where, a carbazolyl group is excepted from the monovalent non-aromatic condensed heteropolycyclic group) and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ may be each independently selected from a hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group (where, a carbazolyl group is excepted from the monovalent non-aromatic condensed heteropolycyclic group).

When a group containing a specified number of carbon atoms is substituted with any of the substituents listed above, the number of carbon atoms in the resulting "substituted" group may be the number of atoms contained in the original (base) group plus the number of carbon atoms (if any) contained in the substituent. For example, the "substituted $C_1$-$C_{30}$ alkyl" may refer to a $C_1$-$C_{30}$ alkyl group substituted with $C_{6-60}$ aryl group, in which the total number of carbon atoms may be $C_7$-$C_{90}$.

The "biphenyl group" used therein refers to "a phenyl group substituted with a phenyl group".

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLE

Synthesis Example 1: Synthesis of Compound 13

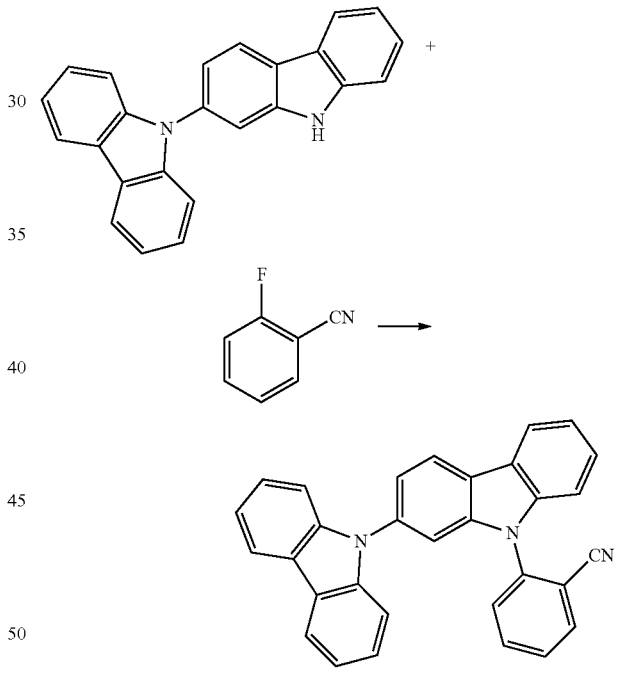

18 grams (g) (54.15 millimoles (mmol)) of 9H-2,9'-bicarbazole, 5.88 milliliters (mL) (54.15 mmol) of 2-fluorobenzonitrile, and 2.16 g (54.15 mmol) of 60% sodium hydride were added to 200 mL of DMF in a round bottom flask, and the mixture was heated under reflux for 12 hours. Once the reaction was completed, the reaction product was cooled to room temperature. 600 mL of methanol was added dropwise and the product crystallized. The solid was filtered, and washed with water and methanol. The resultant solid was dried in a vacuum oven to obtain Compound 13 (17 g, the yield of 72%).

MS (m/z, [M]+): 433.2

Synthesis Example 2: Synthesis of Compound 109

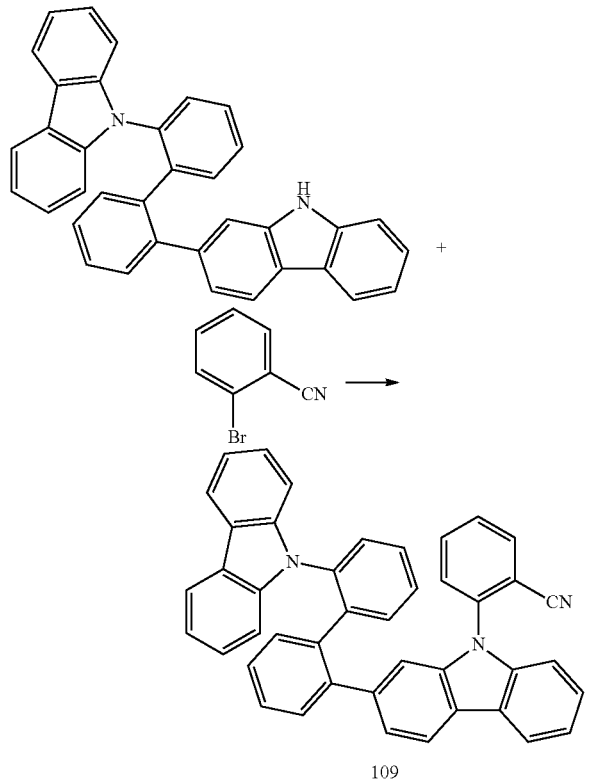

109

10 g (20.64 mmol) of 2-(2'-(9H-carbazol-9-yl)-[1,1'-biphenyl]-2-yl)-9H-carbazole, 11.26 g (61.91 mmol) of 2-bromobenzonitrile, 0.39 g (6.19 mmol) of copper, and 8.55 g (61.91 mmol) of potassium carbonate were added to 200 mL of DMF in a round bottom flask, and the mixture was heated under reflux for 48 hours. Once the reaction was completed, the reaction product was cooled to room temperature, and the solvent was removed therefrom. The resultant was dissolved in hot toluene and filtered through silica. Methylene chloride (MC) and ethyl acetate (EA) were added to the filtrate for crystallization, and the resultant was filtered. The resultant solid was dried in a vacuum oven to obtain Compound 109 (8.34 g, the yield of 69%).

MS (m/z, [M]+): 585.2

Synthesis Example 3: Synthesis of Compound 169

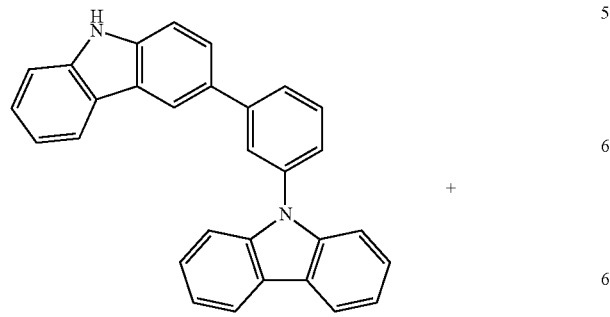

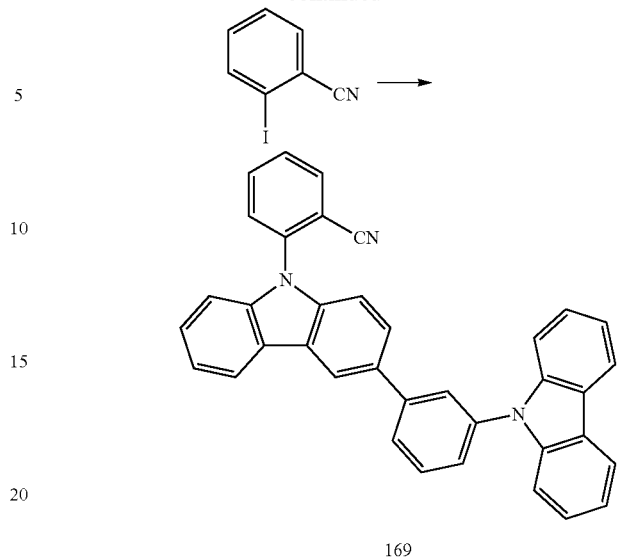

169

10 g (24.48 mmol) of 3-(3-(9H-carbazol-9-yl)phenyl)-9H-carbazole, 16.82 g (73.44 mmol) of 2-iodobenzonitrile, 0.47 g (7.34 mmol) of copper, and 10.15 g (73.44 mmol) of potassium carbonate were added to 200 mL of DMF in a round bottom flask, and the mixture was heated under reflux for 48 hours. Once the reaction was completed, the reaction product was cooled to room temperature. 600 mL of methanol was added dropwise and the product crystallized. The solid was filtered, and washed with water and methanol. The resultant solid was dried in a vacuum oven to obtain Compound 169 (10.7 g, the yield of 86%).

MS (m/z, [M]+): 509.3

Synthesis Example 4: Synthesis of Compound 223

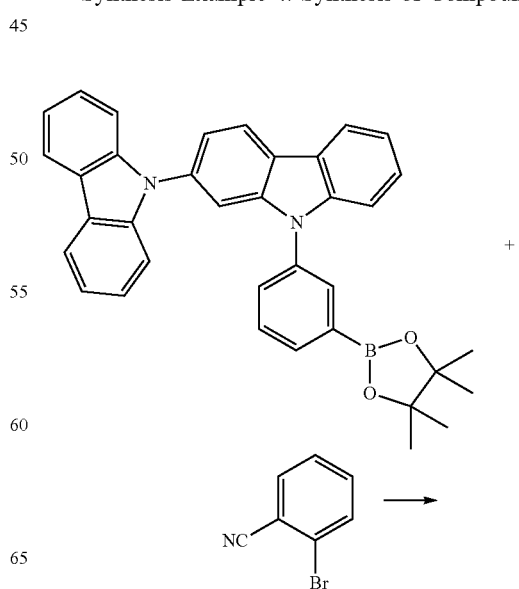

-continued

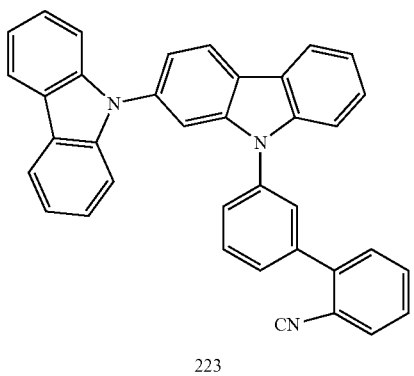

223

26.426 g (49.45 mmol) of 9-(3-(4,4,5,5-tetramethyl-1,3,2-dioxaborolan-2-yl)phenyl)-9H-2,9'-bicarbazole, 7.5 g (41.2 mmol) of 2-bromobenzonitrile, 1.9 g (1.65 mmol) of tetrakis(triphenylphosphine)palladium [Pd(PPh$_3$)$_4$], and 17.085 g (123.61 mmol) of potassium carbonate were added to 200 mL of THF and 100 mL of distilled water in a round bottom flask, and the mixture was heated under reflux for 12 hours. Once the reaction was completed, the reaction product was cooled to room temperature, and THF layer was separated from distilled water. The THF layer separated therefrom was added dropwise to 600 mL of methanol and the product crystallized. Then, the solid was filtered, and washed with water and methanol. The resultant solid was dried in a vacuum oven to obtain Compound 223 (17.85 g, the yield of 85%).

MS (m/z, [M]+): 509.4

Synthesis Example 5: Synthesis of Compound 325

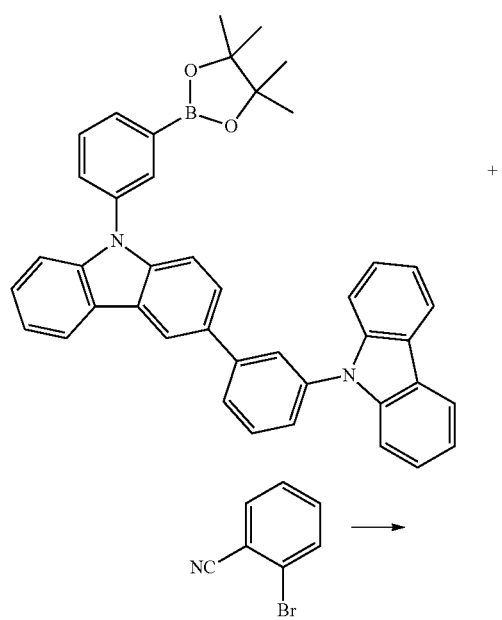

-continued

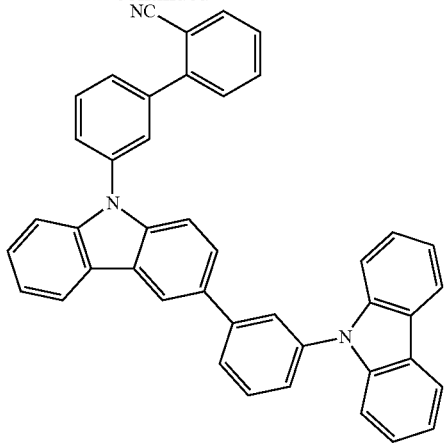

325

28.176 g (46.15 mmol) of 3-(3-(9H-carbazol-9-yl)phenyl)-9-(3-(4,4,5,5-tetramethyl-1,3,2-dioxaborolan-2-yl)phenyl)-9H-carbazole, 7 g (38.46 mmol) of 2-bromobenzonitrile, 1.7 g (1.54 mmol) of tetrakis(triphenylphosphine)palladium [Pd(PPh$_3$)$_4$], and 15.946 g (115.37 mmol) of potassium carbonate were added to 200 mL of THF and 100 mL of distilled water in a round bottom flask, and the mixture was heated under reflux for 12 hours. Once the reaction was completed, the reaction product was cooled to room temperature, and THF was separated from distilled water. The THF separated therefrom was added dropwise to 600 mL of methanol and the product crystallized. The solid was filtered, and washed with water and methanol. The resultant solid was dried in a vacuum oven to obtain Compound 325 (16.89 g, the yield of 75%).

MS (m/z, [M]+): 585.5

Evaluation Example 1: Evaluation on HOMO and LUMO Energy Levels

HOMO and LUMO energy levels of Compounds 13, 109, 169, 223, and 325 were evaluated according to the method indicated in Table 2, and results thereof are shown in Table 3.

TABLE 2

| | |
|---|---|
| HOMO energy level evaluation method | A potential (V)-current (A) graph of each compound was obtained by using cyclic voltammetry (CV) (electrolyte: 0.1 molar (M) Bu$_4$NClO$_4$/solvent: CH$_2$Cl$_2$/electrode: 3 electrode system (working electrode: GC, reference electrode: Ag/AgCl, auxiliary electrode: Pt)). Then, from reduction onset of the graph, a HOMO energy level of the compound was calculated. |
| LUMO energy level evaluation method | Each compound was diluted at a concentration of 1 × 10$^{-5}$M in CHCl$_3$, and an UV absorption spectrum thereof was measured at room temperature by using Shimadzu UV-350 Spectrometer. A LUMO energy level thereof was calculated by using an optical band gap (Eg) from an edge of the absorption spectrum. |

TABLE 3

| Compound No. | HOMO (eV) (found) | LUMO (eV) (found) |
|---|---|---|
| 13 | −5.63 | −2.16 |
| 109 | −5.64 | −2.12 |

TABLE 3-continued

| Compound No. | HOMO (eV) (found) | LUMO (eV) (found) |
|---|---|---|
| 169 | −5.67 | −2.14 |
| 223 | −5.61 | −2.08 |
| 325 | −5.65 | −2.13 |

From Table 3, it is confirmed that Compounds 13, 109, 169, 223, and 325 have electric characteristics that are suitable for use as a material for forming an organic light-emitting device.

Evaluation Example 2: Thermal Characteristics Evaluation

Each of Compounds 13, 109, 169, 223, 325, and A was subjected to thermal analysis ($N_2$ atmosphere, temperature range: room temperature to 800° C. (10° C./min)-TGA, room temperature to 400° C.-DSC, Pan Type: Pt Pan in disposable Al Pan (TGA), disposable Al pan (DSC)) using thermogravimetric analysis (TGA) and differential scanning calorimetry (DSC), and the obtained results are shown in Table 4 below. As shown in Table 4, it was confirmed that Compounds 13, 109, 169, 223, and 325 had excellent thermal stability than that of Compound A.

TABLE 4

| Compound No. | Tg (° C.) |
|---|---|
| 13 | 104 |
| 109 | 125 |
| 169 | 121 |
| 223 | 109 |
| 325 | 117 |
| Compound A | 72 |

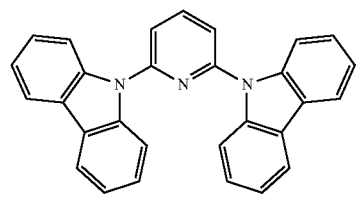

Compound A

Example 1

A glass substrate with a 1,500 Angstrom (Å)-thick ITO (Indium tin oxide) electrode (first electrode, anode) formed thereon was washed with distilled water and ultrasonic waves. When the washing with distilled water was completed, sonification washing was performed using a solvent, such as isopropyl alcohol, acetone, or methanol. The result was dried and then transferred to a plasma washer, and the resultant substrate was washed with oxygen plasma for 5 minutes and transferred to a vacuum depositor.

Compound HT3 and Compound HP-1 were co-deposited on the ITO electrode on the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 150 Å, thereby completing the manufacture of a hole transport region.

Compound 13 (host) and FIr6 (dopant, 10 percent by weight (wt %)) were co-deposited on the hole transport region to form an emission layer having a thickness of 300 Å.

BCP was vacuum deposited on the emission layer to form a hole blocking layer having a thickness of 100 Å, Compound ET3 and Liq were vacuum deposited on the hole blocking layer to form an electron transport layer having a thickness of 250 Å. Then, Liq was deposited on the electron transport layer to form an electron injection layer having a thickness of 5 Å, and Al second electrode (cathode) having a thickness of 1,000 Å was formed on the electron injection layer, thereby completing the manufacture of an organic light-emitting device.

Examples 2 to 5 and Comparative Example 1

Organic light-emitting devices were manufactured in the same manner as in Example 1, except that the compounds shown in Table 5 were used, as a host, instead of Compound 13 in the formation of the emission layer.

Evaluation Example 3: Evaluation on Characteristics of Organic Light-Emitting Devices The driving voltage, current density, luminous efficiency, power efficiency, quantum efficiency, and lifespan of the organic light-emitting devices of Examples 1 to 5 and Comparative Example 1 were measured by using a current-voltage meter (Keithley 2400) and a luminance meter (Minolta Cs-1000A), and results thereof are shown in Table 5. $T_{95}$ (at 500 candelas per square meter ($cd/m^2$)) in Table 5 indicates an amount of time that lapsed when the luminance is decreased from 100% of the initial luminance to 95% of the initial luminance.

TABLE 5

| | Host | Driving voltage (V) | Luminous Efficiency (cd/A) | Power Efficiency (lm/W) | Quantum Efficiency (%) | $T_{95}$ (hr) |
|---|---|---|---|---|---|---|
| Example 1 | 13 | 4.2 | 33.25 | 24.89 | 17.8 | 1.54 |
| Example 2 | 109 | 4.94 | 20.44 | 13.00 | 10.8 | 1.00 |
| Example 3 | 169 | 4.91 | 36.33 | 23.25 | 19.9 | 3.94 |
| Example 4 | 223 | 3.99 | 34.90 | 27.48 | 19 | 1.93 |
| Example 5 | 325 | 4.32 | 30.94 | 22.53 | 17 | 2.45 |
| Comparative Example 1 | Compound A | 6.85 | 15.27 | 7.03 | 8.9 | 0.54 |

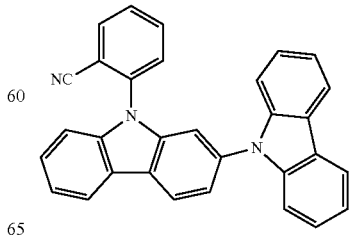

13

TABLE 5-continued

| Host | Driving voltage (V) | Luminous Efficiency (cd/A) | Power Efficiency (lm/W) | Quantum Efficiency (%) | $T_{95}$ (hr) |
|---|---|---|---|---|---|

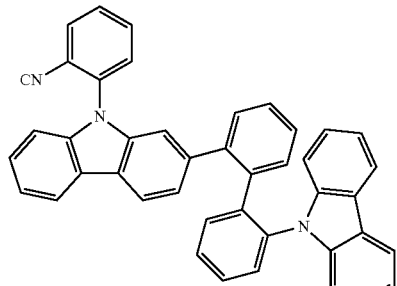

109

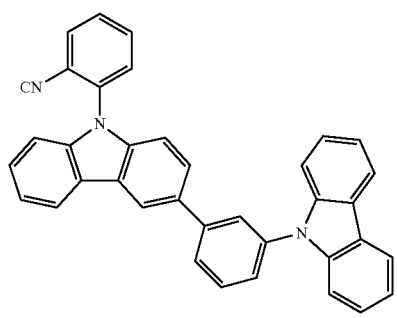

169

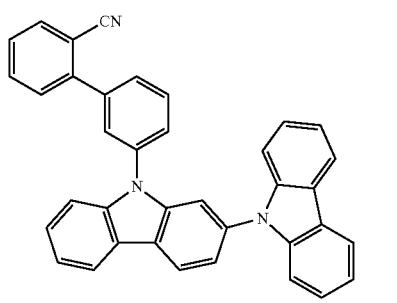

223

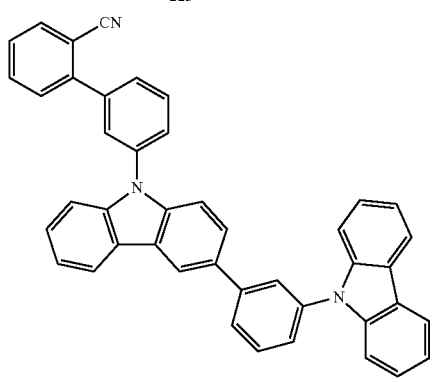

325

TABLE 5-continued

| Host | Driving voltage (V) | Luminous Efficiency (cd/A) | Power Efficiency (lm/W) | Quantum Efficiency (%) | $T_{95}$ (hr) |
|---|---|---|---|---|---|

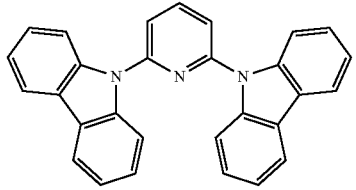

Compound A

Referring to Table 5, it was confirmed that the organic light-emitting devices of Examples 1 to 5 have a lower driving voltage, a higher luminous efficiency, a higher power efficiency, a higher quantum efficiency, and a longer lifespan than the organic light-emitting device of Comparative Example 1.

As described above, according to the one or more of the above embodiments of the present inventive concept, a condensed cyclic compound has excellent electric characteristics and thermal stability, and thus an organic light-emitting device including the condensed cyclic compound may have low driving voltage, high luminous efficiency, high power efficiency, high quantum efficiency, and long lifespan characteristics.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the present disclosure as defined by the following claims.

What is claimed is:

1. A condensed cyclic compound represented by Formula 1:

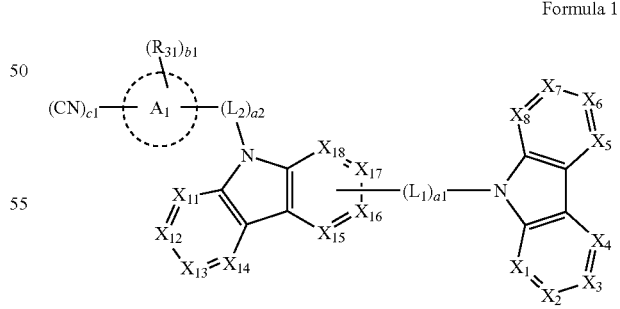

Formula 1 wherein, in Formula 1,
$X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N, $C(R_{15})$, or a carbon atom connected to *-$(L_1)_{a1}$-*', $X_{16}$ is N, $C(R_{16})$, or a carbon atom connected to *-(L$_1$)$_{a1}$-*', X$_{17}$ is N, C(R$_{17}$), or a carbon atom connected to *-(L$_1$)$_{a1}$-*', and X$_{18}$ is N, C(R$_{18}$), or a carbon atom connected to *-(L$_1$)$_{a1}$-*', wherein one of X$_{15}$ to X$_{18}$ is connected to *-(L$_1$)$_{a1}$-*', ring A$_1$ is selected from a C$_5$-C$_{60}$ carbocyclic group and a C$_3$-C$_{60}$ heterocyclic group comprising at least one heteroatom selected from O, S, and Si, L$_1$ is selected from a phenylene group, a pyridinylene group, a pyrimidinylene group, a pyrazinylene group, a pyridazinylene group, a triazinylene group, a fluorenylene group, a dibenzofuranylene group, and a dibenzothiophenylene group; and a phenylene group, a pyridinylene group, a pyrimidinylene group, a pyrazinylene group, a pyridazinylene group, a triazinylene group, a fluorenylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a C$_1$-C$_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si(Q$_{11}$)(Q$_{12}$)(Q$_{13}$), L$_2$ is selected from a phenylene group, a fluorenylene group, a dibenzofuranylene group, and a dibenzothiophenylene group; and a phenylene group, a fluorenylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{10}$ alkyl group, a C$_1$-C$_{10}$ alkoxy group, a phenyl group, a naphthyl group, a fluorenyl group, a dibenzofuranyl group, a dibenzothiophenyl group, and —Si(Q$_{11}$)(Q$_{12}$)(Q$_{13}$), a1 and a2 are each independently an integer selected from 0 to 5, wherein when a1 is 2 or greater, two or more groups L$_1$ are identical to or different from each other, and when a2 is 2 or greater, two or more groups L$_2$ are identical to or different from each other, R$_1$ to R$_8$ are each independently selected from a hydrogen, a deuterium, —F, —Cl, —Br, —I, a hydroxyl group, a cyano group (—CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a Substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, and —Si(Q$_1$)(Q$_2$)(Q$_3$), R$_{11}$ to R$_{15}$ are each independently selected from a hydrogen, a deuterium, —F, —Cl, —Br, —I, a hydroxyl group, a cyano group (—CN), a nitro group, an amino group, an amindino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and —Si(Q$_1$)(Q$_2$)(Q$_3$), R$_{31}$ is selected from a hydrogen, a deuterium, —F, —Cl, —Br, —I, a hydroxyl group, a cyano group (—CN), a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_2$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, and —Si(Q$_1$)(Q$_2$)(Q$_3$), b1 is an integer selected from 0 to 4, c1 is an integer selected from 1 to 4, at least one substituent of the substituted C$_1$-C$_{60}$ alkyl group, substituted C$_2$-C$_{60}$ alkenyl group, substituted C$_2$-C$_{60}$ alkynyl group, substituted C$_1$-C$_{60}$ alkoxy group, substituted C$_3$-C$_{10}$ cycloalkyl group, substituted C$_1$-C$_{10}$ heterocycloalkyl group, substituted C$_3$-C$_{10}$ cycloalkenyl group, substituted C$_2$-C$_{10}$ heterocycloalkenyl group, substituted C$_6$-C$_{60}$ aryl group, substituted C$_6$-C$_{60}$ aryloxy group, substituted C$_6$-C$_{60}$ arylthio group, substituted C$_1$-C$_{60}$ heteroaryl group, substituted monovalent non-aromatic condensed polycyclic group, and substituted monovalent non-aromatic condensed heteropolycyclic group is selected from a deuterium, —F, —Cl, —Br, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{21}$)($Q_{22}$)($Q_{23}$), wherein $Q_1$ to $Q_3$, $Q_{11}$ to $Q_{13}$, and $Q_{21}$ to $Q_{23}$ are each independently selected from a hydrogen, a deuterium, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group in *-($L_1$)$_{a1}$-*', * and *' are each a binding site to a neighboring atom.

2. The condensed cyclic compound of claim 1, wherein ring $A_1$ is selected from a cyclopentane ring, a cyclohexane ring, a cyclopentene ring, a cyclohexene ring, a cycloheptene ring, a benzene ring, a pentalene ring, an indene ring, a naphthene ring, an azulene ring, a heptalene ring, an indacene ring, an acenaphthene ring, a fluorene ring, a spirobifluorene ring, a phenalene ring, a phenanthrene ring, an anthracene ring, a fluoranthene ring, a triphenylene ring, a pyrene ring, a chrysene ring, a naphthacene ring, a picene ring, a perylene ring, a pentaphene ring, a hexacene ring, a furane ring, a thiophene ring, a benzofurane ring, a benzothiophene ring, a dibenzofurane ring, and a dibenzothiophene ring.

3. The condensed cyclic compound of claim 1, wherein ring $A_1$ is selected from a benzene ring, a dibenzofurane ring, and a dibenzothiophene ring.

4. The condensed cyclic compound of claim 1, wherein $L_1$ is selected from groups represented by Formulae 3-1 to 3-56, and $L_2$ is selected from groups represented by Formulae 3-1, 3-15, 3-28, and 3-41 to 3-56:

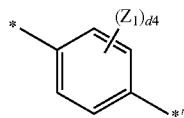

Formula 3-1

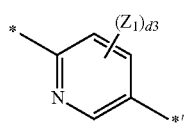

Formula 3-2

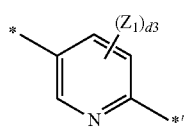

Formula 3-3

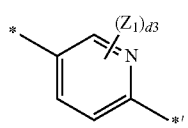

Formula 3-4

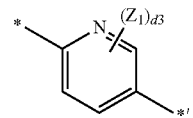

Formula 3-5

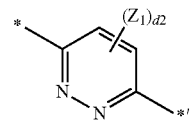

Formula 3-6

Formula 3-7

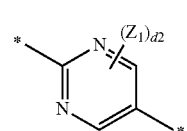

Formula 3-8

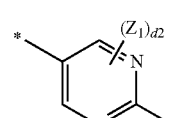

Formula 3-9

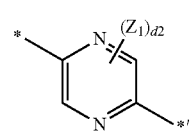

Formula 3-10

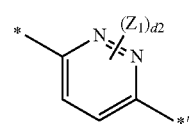

Formula 3-11

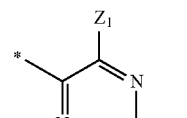

Formula 3-12

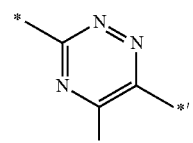

Formula 3-13

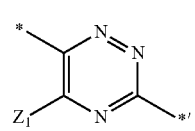

Formula 3-14

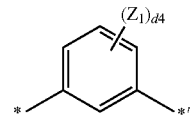

Formula 3-15

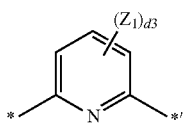
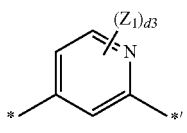
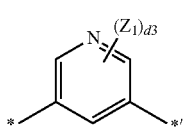
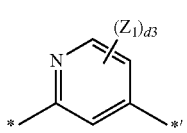
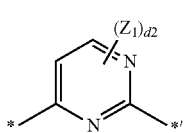
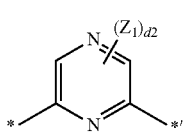
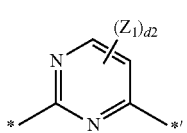
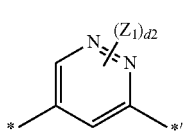
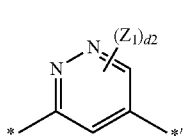
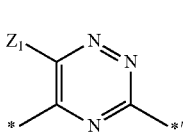
Formula 3-16
Formula 3-17
Formula 3-18
Formula 3-19
Formula 3-20
Formula 3-21
Formula 3-22
Formula 3-23
Formula 3-24
Formula 3-25
Formula 3-26
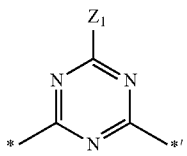
Formula 3-27
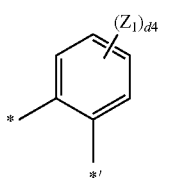
Formula 3-28
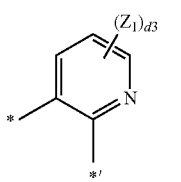
Formula 3-29
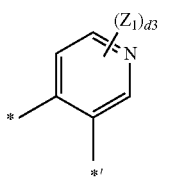
Formula 3-30
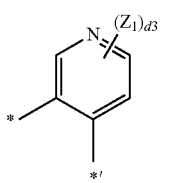
Formula 3-31
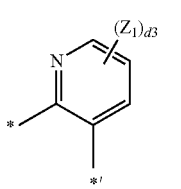
Formula 3-32
Formula 3-33
Formula 3-34
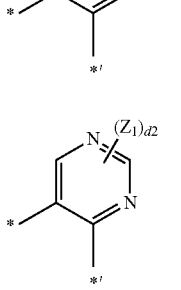

Formula 3-35
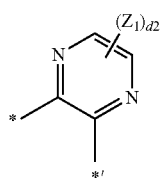
Formula 3-36
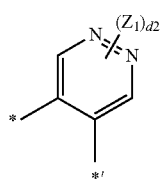
Formula 3-37
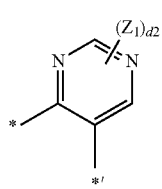
Formula 3-38
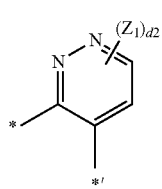
Formula 3-39
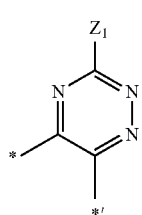
Formula 3-40
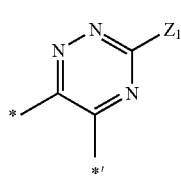
Formula 3-41
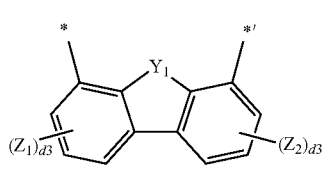
Formula 3-42
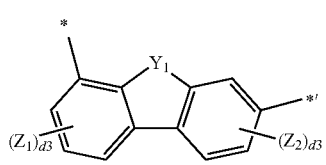
Formula 3-43
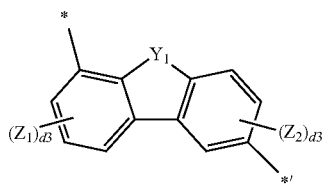
Formula 3-44
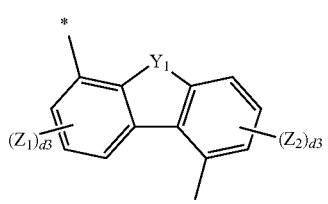
Formula 3-45
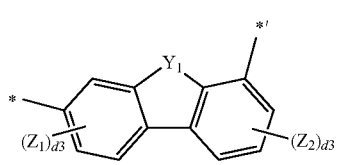
Formula 3-46
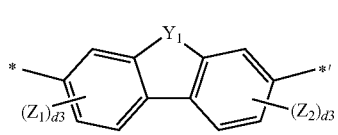
Formula 3-47
Formula 3-48
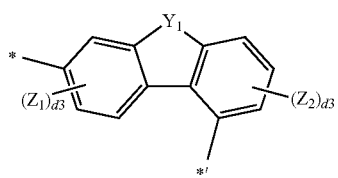
Formula 3-49
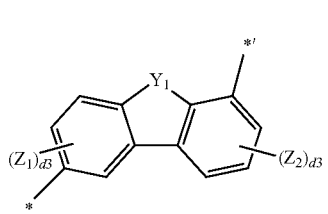
Formula 3-50
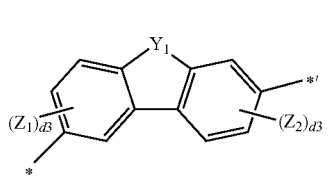
Formula 3-51
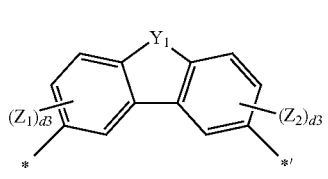

-continued

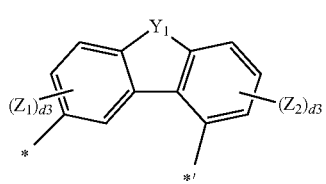
Formula 3-52

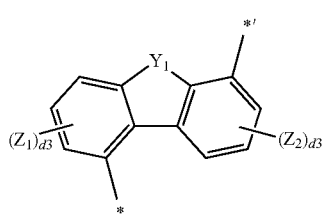
Formula 3-53

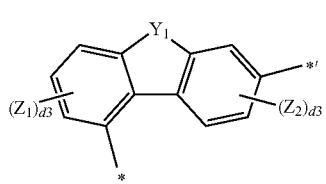
Formula 3-54

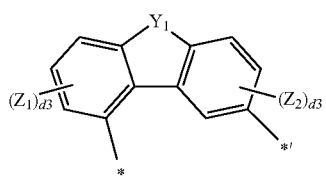
Formula 3-55

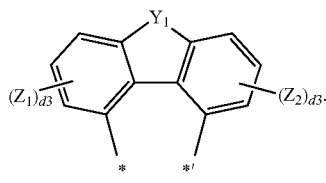
Formula 3-56 wherein, in Formulae 3-1 to 3-56, $Y_1$ is selected from O, S, and $C(Z_3)(Z_4)$, $Z_1$ to $Z_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si$(Q_{11})(Q_{12})(Q_{13})$, wherein $Q_{11}$ to $Q_{13}$ are each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, d4 is an integer selected from 0 to 4,
d3 is an integer selected from 0 to 3,
d2 is an integer selected from 0 to 2, and
and *' are each a binding site to a neighboring atom.

5. The condensed cyclic compound of claim 4, wherein
   i) a1 is 0; or
   ii) when a1 is not 0, at least one of groups $L_1$ is selected from groups represented by Formulae 3-15 to 3-56.

6. The condensed cyclic compound of claim 4, wherein
   $L_1$ is selected from groups represented by Formulae 3-15, 3-28, 3-41, and 3-51,
   $L_2$ is selected from groups represented by Formulae 3-1, 3-15, 3-28, 3-41, and 3-51, and
   a1 and a2 are each independently 0, 1, or 2.

7. The condensed cyclic compound of claim 1, wherein a group represented by *-$(L_1)_{a1}$-*' is selected from groups represented by Formulae 4-1 to 4-39:

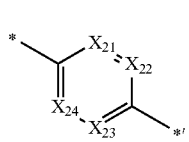
Formula 4-1

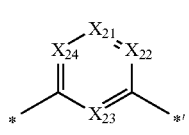
Formula 4-2

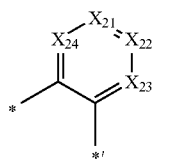
Formula 4-3

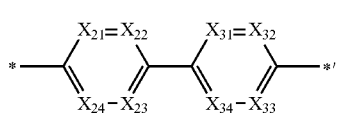
Formula 4-4

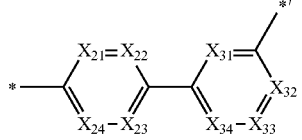
Formula 4-5

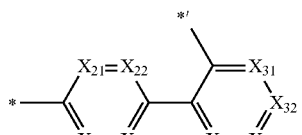
Formula 4-6

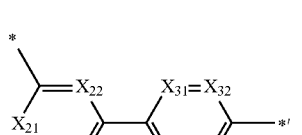
Formula 4-7

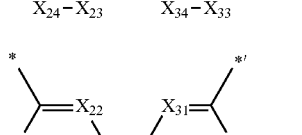
Formula 4-8

Formula 4-9
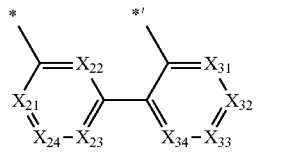
Formula 4-10
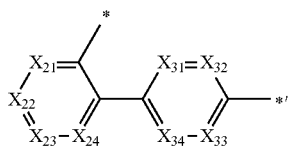
Formula 4-11
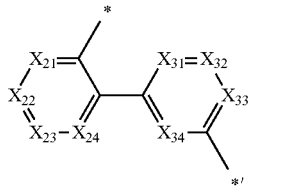
Formula 4-12
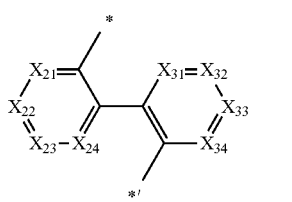
Formula 4-13
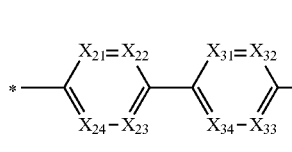
Formula 4-14
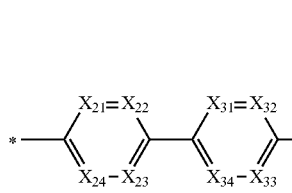
Formula 4-15
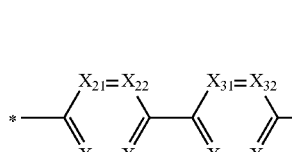
Formula 4-16
Formula 4-17
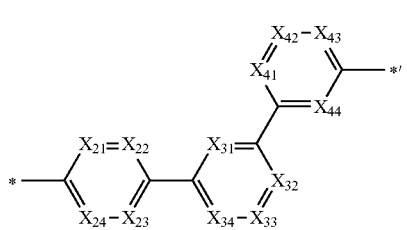
Formula 4-18
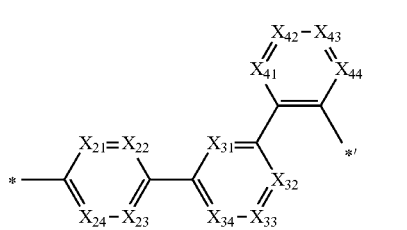
Formula 4-19
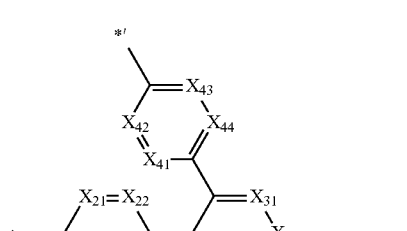
Formula 4-20
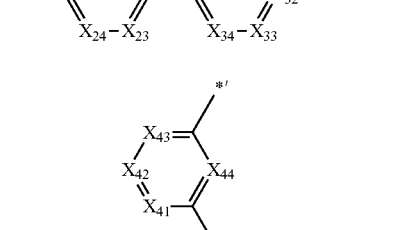
Formula 4-21
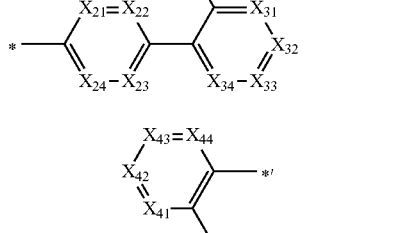
Formula 4-22
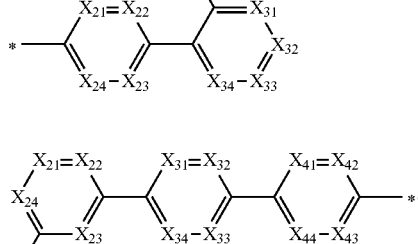
Formula 4-23
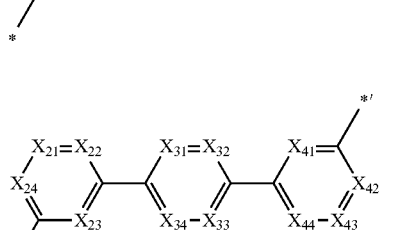

Formula 4-24
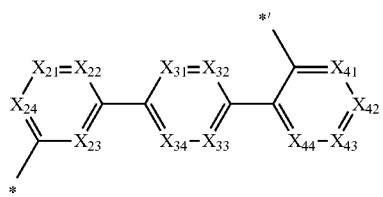
Formula 4-25
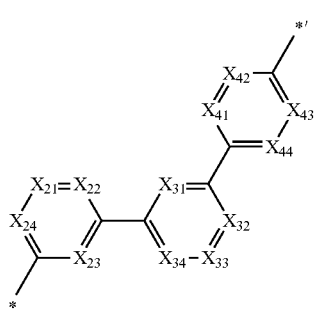
Formula 4-26
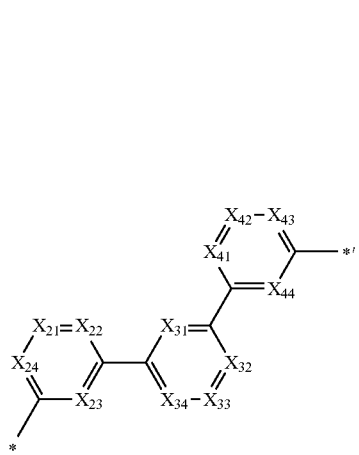
Formula 4-27
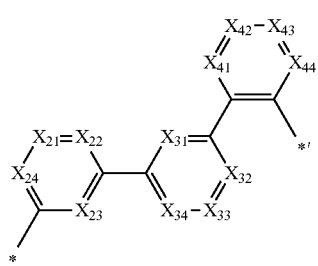
Formula 4-28
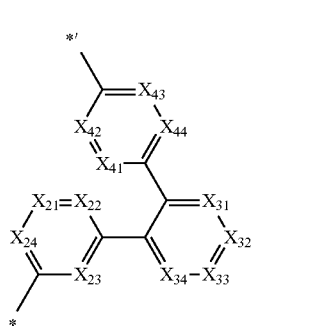
Formula 4-29
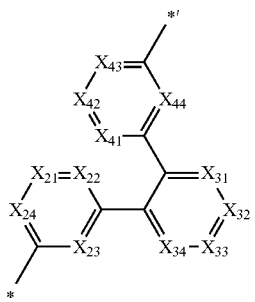
Formula 4-30
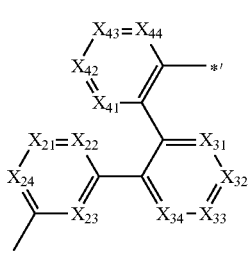
Formula 4-31
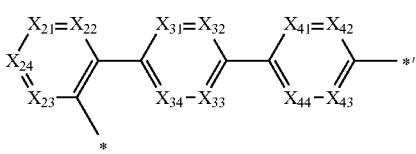
Formula 4-32
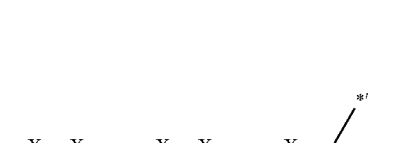
Formula 4-33
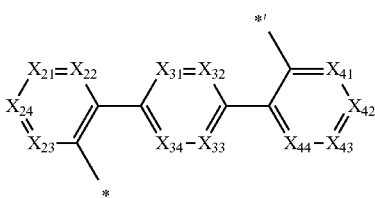
Formula 4-34
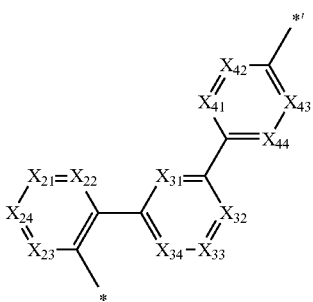

-continued

Formula 4-35

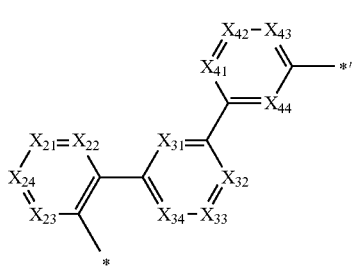

Formula 4-36

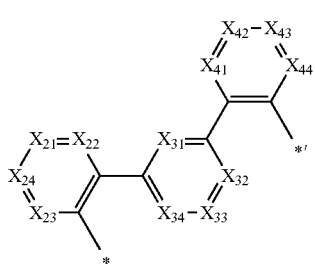

Formula 4-37

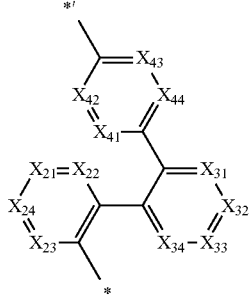

Formula 4-38

Formula 4-39

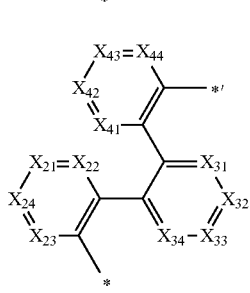

wherein, in Formulae 4-1 to 4-39, $X_{21}$ is N or $C(Z_{21})$, $X_{22}$ is N or $C(Z_{22})$, $X_{23}$ is N or $C(Z_{23})$, $X_{24}$ is N or $C(Z_{24})$, $X_{31}$ is N or $C(Z_{31})$, $X_{32}$ is N or $C(Z_{32})$, $X_{33}$ is N or $C(Z_{33})$, $X_{34}$ is N or $C(Z_{34})$, $X_{41}$ is N or $C(Z_{41})$, $X_{42}$ is N or $C(Z_{42})$, $X_{43}$ is N or $C(Z_{43})$, and $X_{44}$ is N or $C(Z_{44})$, provided that at least one of $X_{21}$ to $X_{24}$ is not N, provided that at least one of $X_{31}$ to $X_{34}$ is not N, and provided that at least one of $X_{41}$ to $X_{44}$ is not N, $Z_{21}$ to $Z_{24}$, $Z_{31}$ to $Z_{34}$, and $Z_{41}$ to $Z_{44}$ are each independently selected from a hydrogen, a deuterium, a cyano group, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si$(Q_{11})(Q_{12})(Q_{13})$, wherein $Q_{11}$ to $Q_{13}$ are each independently a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, and

* and *' are each a binding site to a neighboring atom.

8. The condensed cyclic compound of claim 1, wherein $R_1$ to $R_8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{10}$ alkoxy group;

a $C_1$-$C_{10}$ alkoxy group substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group;

a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si$(Q_{21})(Q_{22})(Q_{23})$; and —Si$(Q_1)(Q_2)(Q_3)$, wherein $Q_1$ to $Q_3$ and $Q_{21}$ to $Q_{23}$ are each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, and $R_{11}$ to $R_{18}$, and $R_{31}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group;

a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si($Q_{21}$)($Q_{22}$)($Q_{23}$); and —Si($Q_1$)($Q_2$)($Q_3$), wherein $Q_1$ to $Q_3$ and $Q_{21}$ to $Q_{23}$ are each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group.

9. The condensed cyclic compound of claim 1, wherein $R_1$ to $R_8$ are each independently selected from a hydrogen, a deuterium, —F, a cyano group, and a $C_1$-$C_{10}$ alkoxy group:

a $C_1$-$C_{10}$ alkoxy group substituted with at least one selected from a deuterium —F, and a cyano group;

a phenyl group, a pyridinyl group, a pyrimidinyl group, a triazinyl group, a dibenzofuranyl group, and a dibenzothiophenyl group;

a phenyl group, a pyridinyl group, a pyrimidinyl group, a triazinyl group, a dibenzofuranyl group, and a dibenzothiophenyl group, each substituted with at least one selected from a deuterium, —F, a cyano group, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, a dibenzothiophenyl group, and —Si($Q_{21}$)($Q_{22}$)($Q_{23}$) g; and —Si($Q_1$)($Q_2$)($Q_3$), $R_{11}$ to $R_{18}$, and $R_{31}$ are each independently selected from a hydrogen, a deuterium, —F, a cyano group, a $C_1$-$C_{10}$ alkyl group, and a $C_1$-$C_{10}$ alkoxy group, a $C_1$-$C_{10}$ alkyl group and a $C_1$-$C_{10}$ alkoxy group, each substituted with at least one selected from a deuterium, —F, and a cyano group;

a phenyl group, a pyridinyl group, a pyrimidinyl group, a triazinyl group, a dibenzofuranyl group, and a dibenzothiophenyl group;

a phenyl group, a pyridinyl group, a pyrimidinyl group, a triazinyl group, a dibenzofuranyl group, and a dibenzothiophenyl group, each substituted with at least one selected from a deuterium, —F, a cyano group, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, a dibenzothiophenyl group, and —Si($Q_{21}$)($Q_{22}$)($Q_{23}$); and —Si($Q_1$)($Q_2$)($Q_3$), $Q_1$ to $Q_3$ and $Q_{21}$ to $Q_{23}$ are each independently a hydrogen, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, and a dibenzothiophenyl group.

10. The condensed cyclic compound of claim 1, wherein at least one of $X_3$, $X_6$, $X_{13}$, and $X_{16}$ is C(CN).

11. The condensed cyclic compound of claim 1, wherein a group represented by

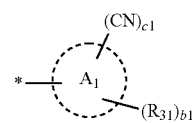

is selected from groups represented by Formulae 5-1 to 5-60:

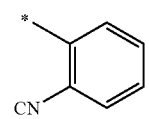

Formula 5-1

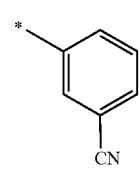

Formula 5-2

Formula 5-3

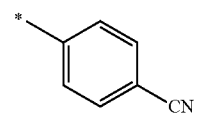

Formula 5-4

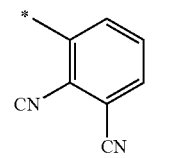

Formula 5-5

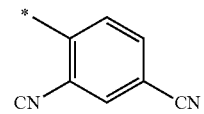

Formula 5-6

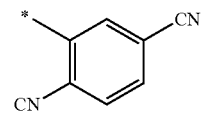

-continued
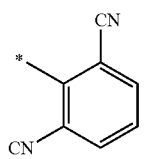 Formula 5-7
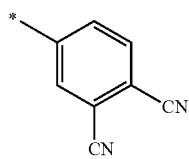 Formula 5-8
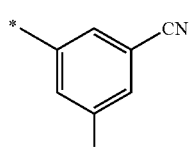 Formula 5-9
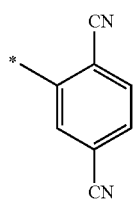 Formula 5-10
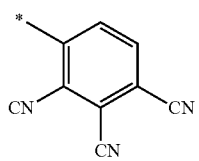 Formula 5-11
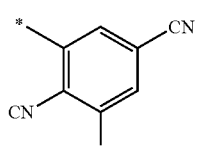 Formula 5-12
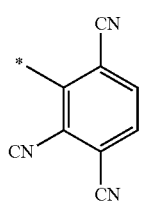 Formula 5-13
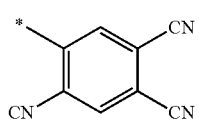 Formula 5-14
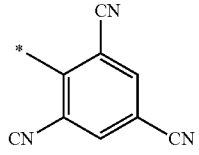 Formula 5-15
-continued
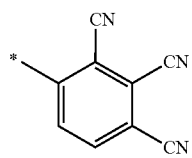 Formula 5-16
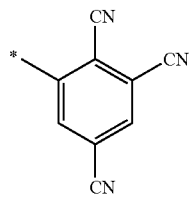 Formula 5-17
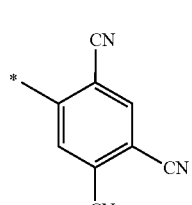 Formula 5-18
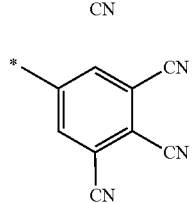 Formula 5-19
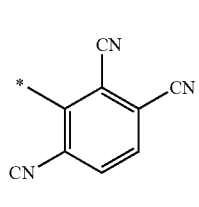 Formula 5-20
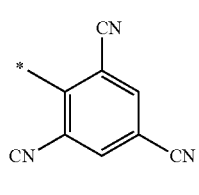 Formula 5-21
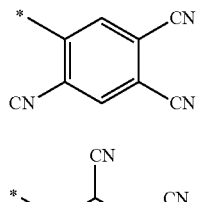 Formula 5-22
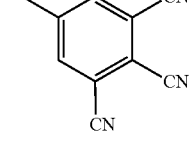 Formula 5-23
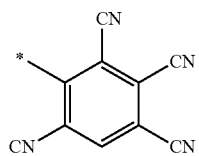 Formula 5-24

-continued
Formula 5-25
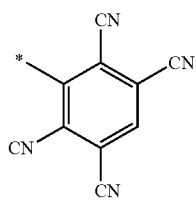
Formula 5-26
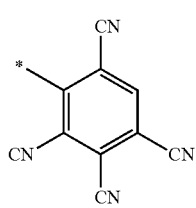
Formula 5-27
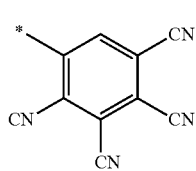
Formula 5-28
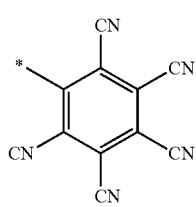
Formula 5-29
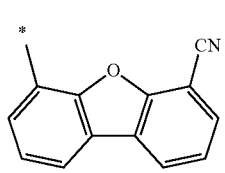
Formula 5-30
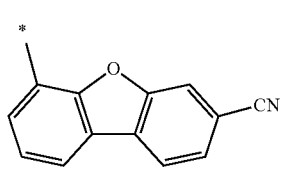
Formula 5-31
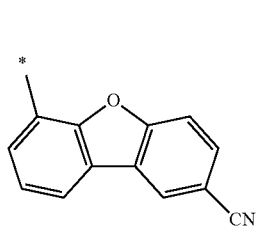
Formula 5-32
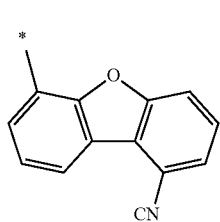
-continued
Formula 5-33
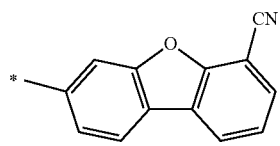
Formula 5-34
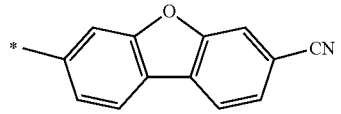
Formula 5-35
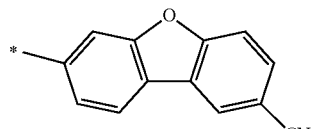
Formula 5-36
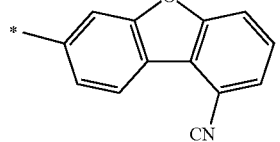
Formula 5-37
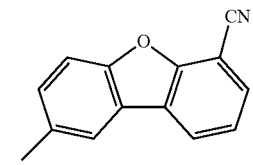
Formula 5-38
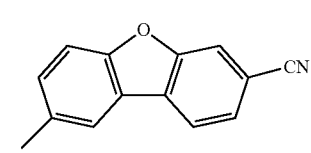
Formula 5-39
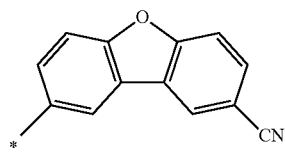
Formula 5-40
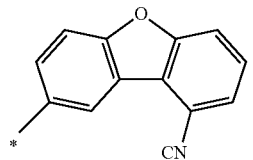
Formula 5-41
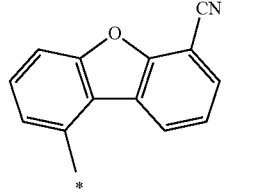

-continued
Formula 5-42
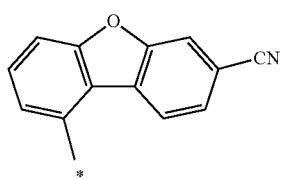
Formula 5-43
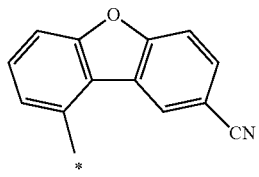
Formula 5-44
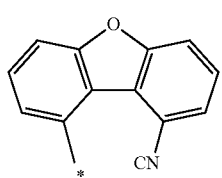
Formula 5-45
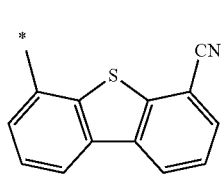
Formula 5-46
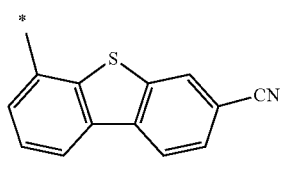
Formula 5-47
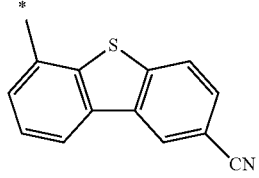
Formula 5-48
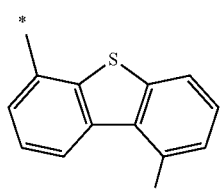
Formula 5-49
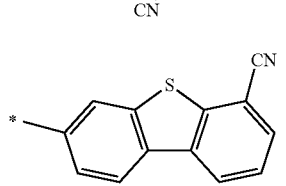
Formula 5-50
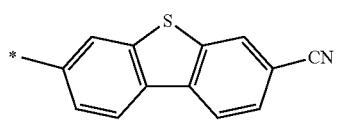
-continued
Formula 5-51
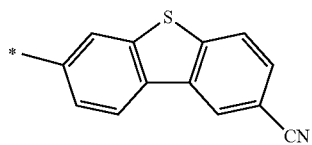
Formula 5-52
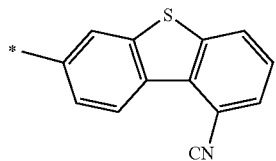
Formula 5-53
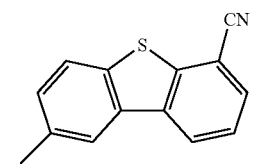
Formula 5-54
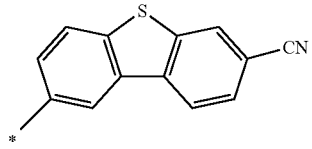
Formula 5-55
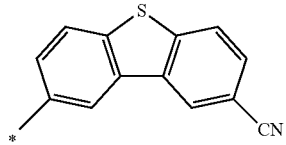
Formula 5-56
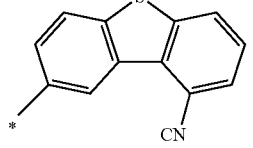
Formula 5-57
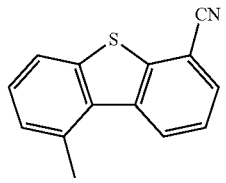
Formula 5-58
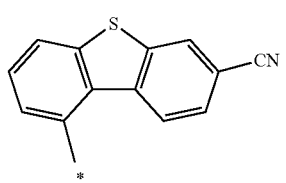
Formula 5-59
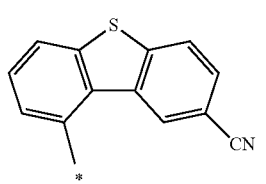

Formula 5-60

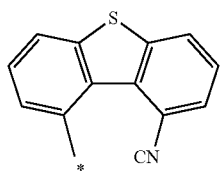

wherein, in Formulae 5-1 to 5-60, * is a binding site to a neighboring atom.

12. The condensed cyclic compound of claim 1, represented by one of Formulae 1A to 1D:

Formula 1A

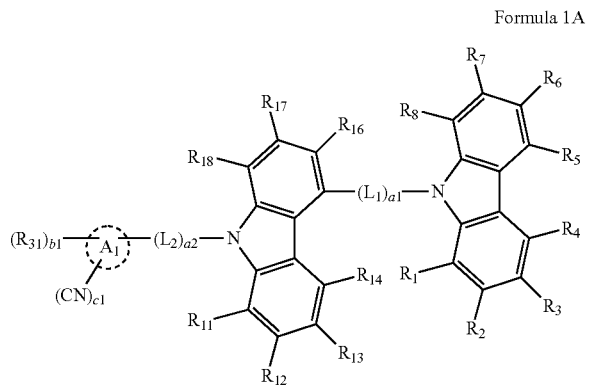

Formula 1B

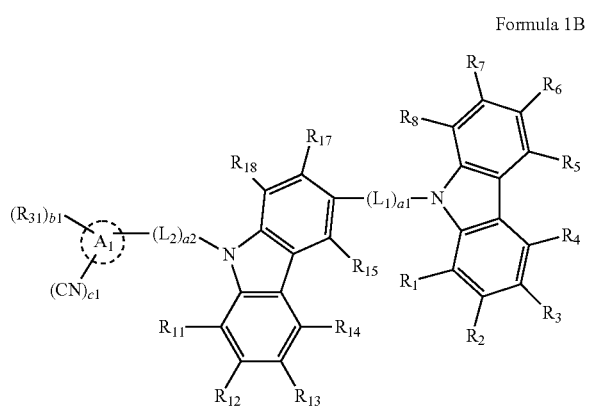

Formula 1C

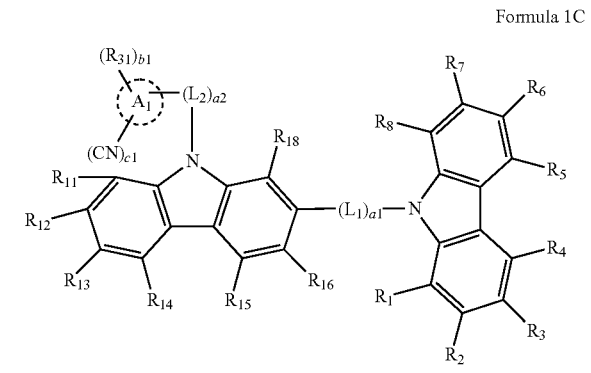

Formula 1D

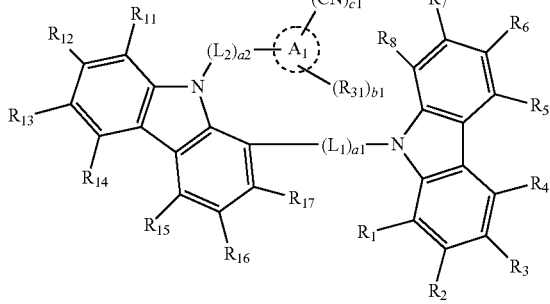

wherein, in Formulae 1A to 1D,
ring $A_1$ is independently selected from a benzene ring, a dibenzofurane ring, and a dibenzothiophene ring,
$L_1$ is selected from groups represented by Formulae 3-15, 3-28, 3-41, and 3-51,
$L_2$ is selected from groups represented by Formulae 3-1, 3-15, 3-28, 3-41, and 3-51,
a1 and a2 are each independently selected from 0, 1, and 2,
$R_1$ to $R_8$ are each independently selected from
a hydrogen, a deuterium, —F, a cyano group, and a $C_1$-$C_{10}$ alkoxy group;
a $C_1$-$C_{10}$ alkoxy group substituted with at least one selected from a deuterium, —F, and a cyano group;
a phenyl group, a pyridinyl group, a pyrimidinyl group, a triazinyl group, a dibenzofuranyl group, and a dibenzothiophenyl group;
a phenyl group, a pyridinyl group, a pyrimidinyl group, a triazinyl group, a dibenzofuranyl group, and a dibenzothiophenyl group, each substituted with at least one selected from a deuterium, —F, a cyano group, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, a dibenzothiophenyl group, and —Si($Q_{21}$)($Q_{22}$)($Q_{23}$); and
—Si($Q_1$)($Q_2$)($Q_3$),
wherein $Q_1$ to $Q_3$ and $Q_{21}$ to $Q_{23}$ are each independently selected from a hydrogen, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, and a dibenzothiophenyl group,
$R_{11}$ to $R_{18}$, and $R_{31}$ are each independently selected from
a hydrogen, a deuterium, —F, a cyano group, a $C_1$-$C_{10}$ alkyl group, and a $C_1$-$C_{10}$ alkoxy group;
a $C_1$-$C_{10}$ alkyl group and a $C_1$-$C_{10}$ alkoxy group, each substituted with at least one selected from a deuterium, —F, and a cyano group;
a phenyl group, a pyridinyl group, a pyrimidinyl group, a triazinyl group, a dibenzofuranyl group, and a dibenzothiophenyl group;
a phenyl group, a pyridinyl group, a pyrimidinyl group, a triazinyl group, a dibenzofuranyl group, and a dibenzothiophenyl group, each substituted with at least one selected from a deuterium, —F, a cyano group, a $C_1$-$C_{10}$ alkyl group, a $C_1$-$C_{10}$ alkoxy group, a phenyl group, a pyridinyl group, a pyrimidinyl group, a triazinyl group, a dibenzofuranyl group, a dibenzothiophenyl group, and —Si($Q_{21}$)($Q_{22}$)($Q_{23}$); and
—Si($Q_1$)($Q_2$)($Q_3$),
wherein $Q_1$ to $Q_3$ and $Q_{21}$ to $Q_{23}$ are each independently selected from a hydrogen, a $C_1$-$C_{10}$ alkyl group, a C₁-C₁₀ alkoxy group, a phenyl group, a pyridinyl group, a pyrimidinyl group, a triazinyl group, a dibenzofuranyl group, and a dibenzothiophenyl group, b1 is 0 or 1, and c1 is 1 or 2:

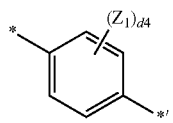
Formula 3-1

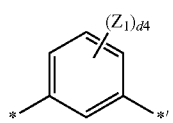
Formula 3-15

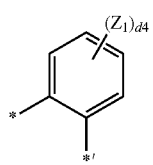
Formula 3-28

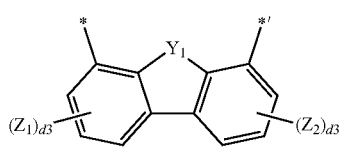
Formula 3-41

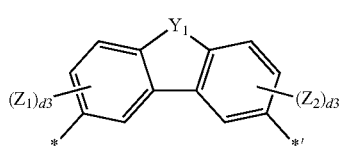
Formula 3-51 wherein, in Formulae 3-41 and 3-51, $Y_1$ is selected from O, S, and $C(Z_3)(Z_4)$, wherein, in Formulae 3-1, 3-15, 3-28, 3-41, and 3-51, $Z_1$ to $Z_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, a dibenzothiophenyl group, and —Si($Q_{11}$)($Q_{12}$)($Q_{13}$), wherein $Q_{11}$ to $Q_{13}$ are each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, a fluorenyl group, a dibenzofuranyl group, and a dibenzothiophenyl group, d4 is an integer selected from 0 to 4, d3 is an integer selected from 0 to 3, and

* and *' are each a binding site to a neighboring atom.

13. The condensed cyclic compound of claim 12, wherein a group represented by

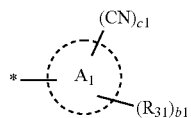

is selected from groups represented by Formulae 5-1 to 5-3, 5-31, 5-39, 5-47, and 5-55:

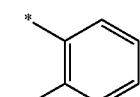
Formula 5-1

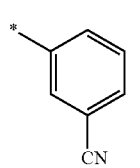
Formula 5-2

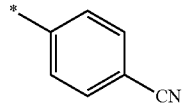
Formula 5-3

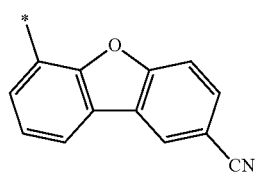
Formula 5-31

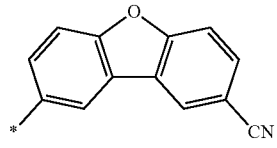
Formula 5-39

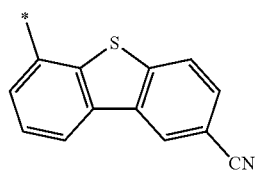
Formula 5-47

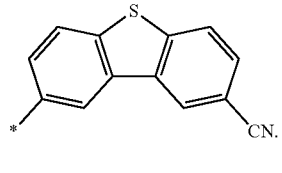
Formula 5-55

14. The condensed cyclic compound of claim 1, represented by one of Compounds 1 to 336:

-continued
| | |
|---|---|
| 1 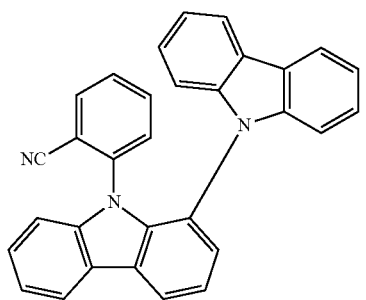 | 6 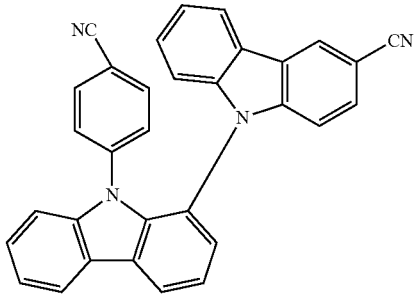 |
| 2 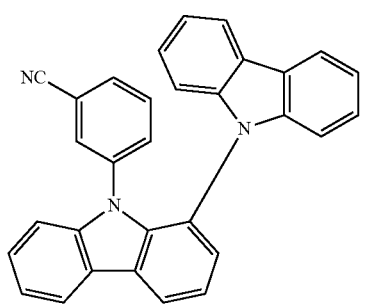 | 7 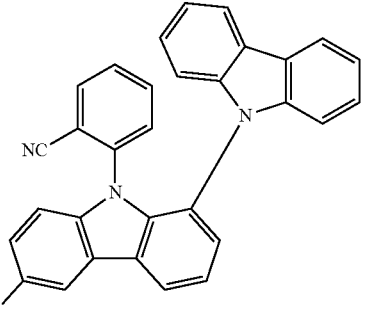 |
| 3 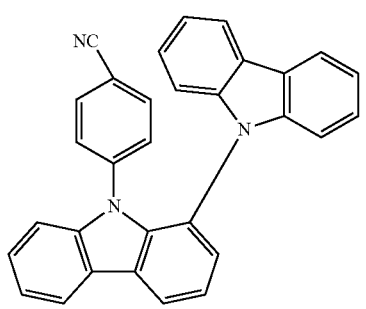 | 8 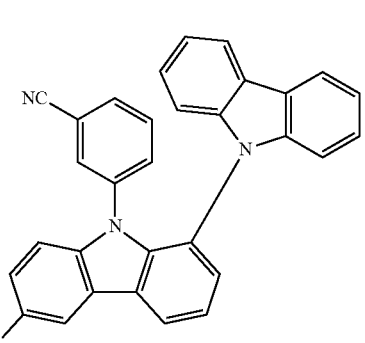 |
| 4 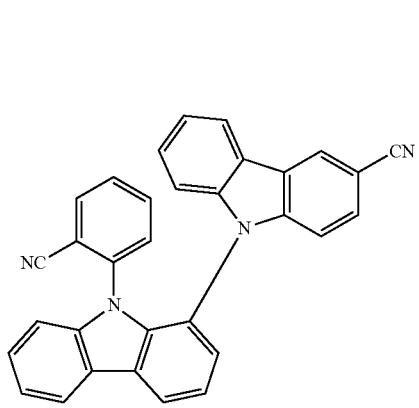 | 9 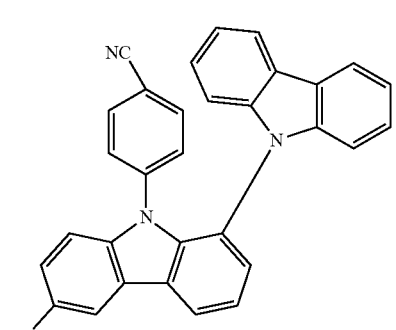 |
| 5 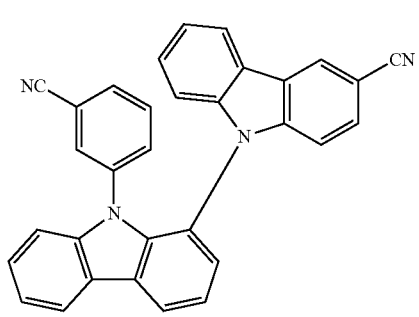 | 10 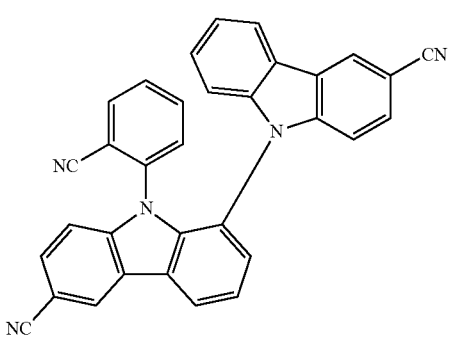 |

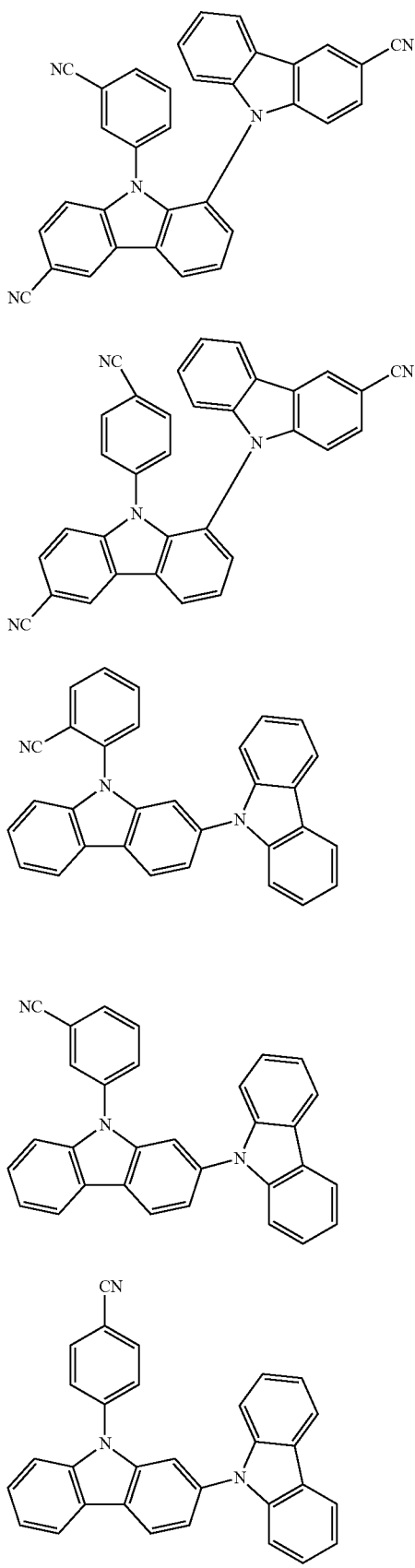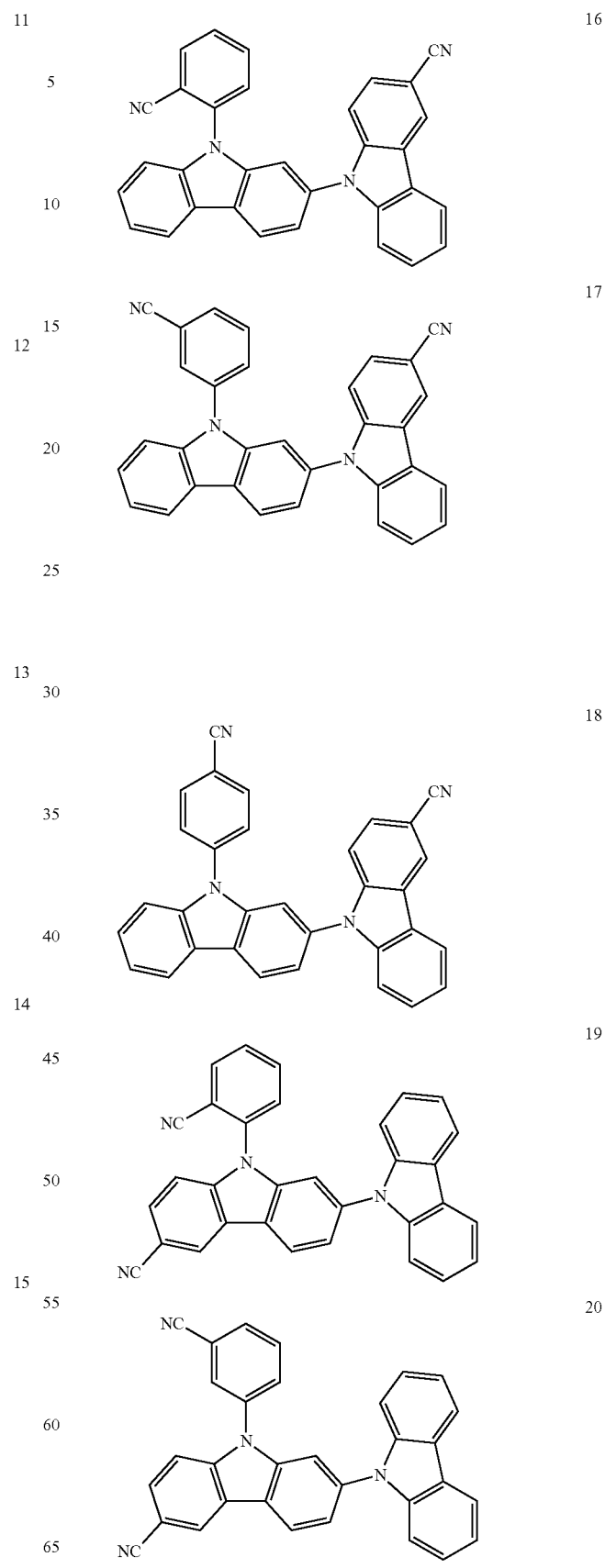

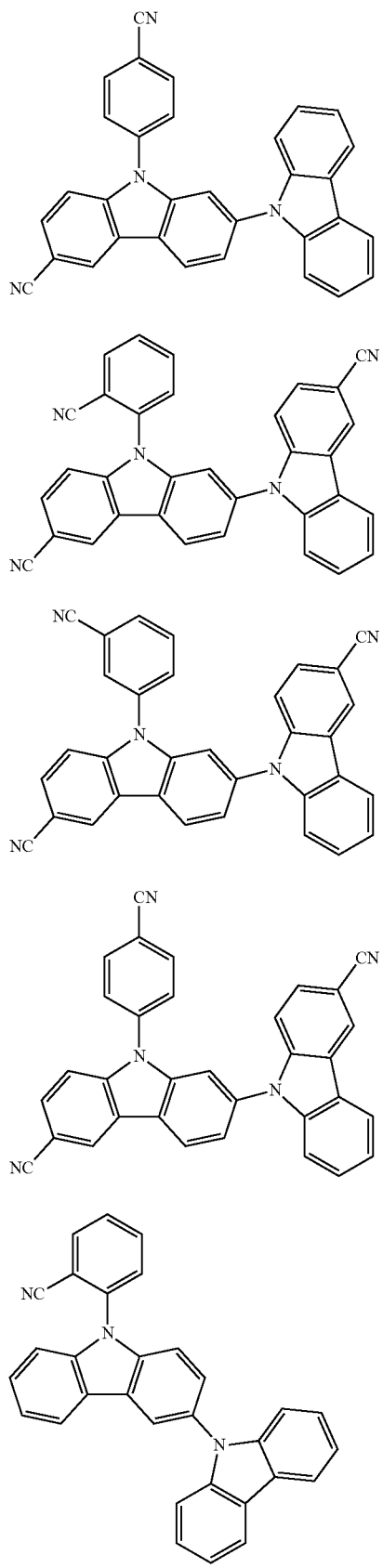
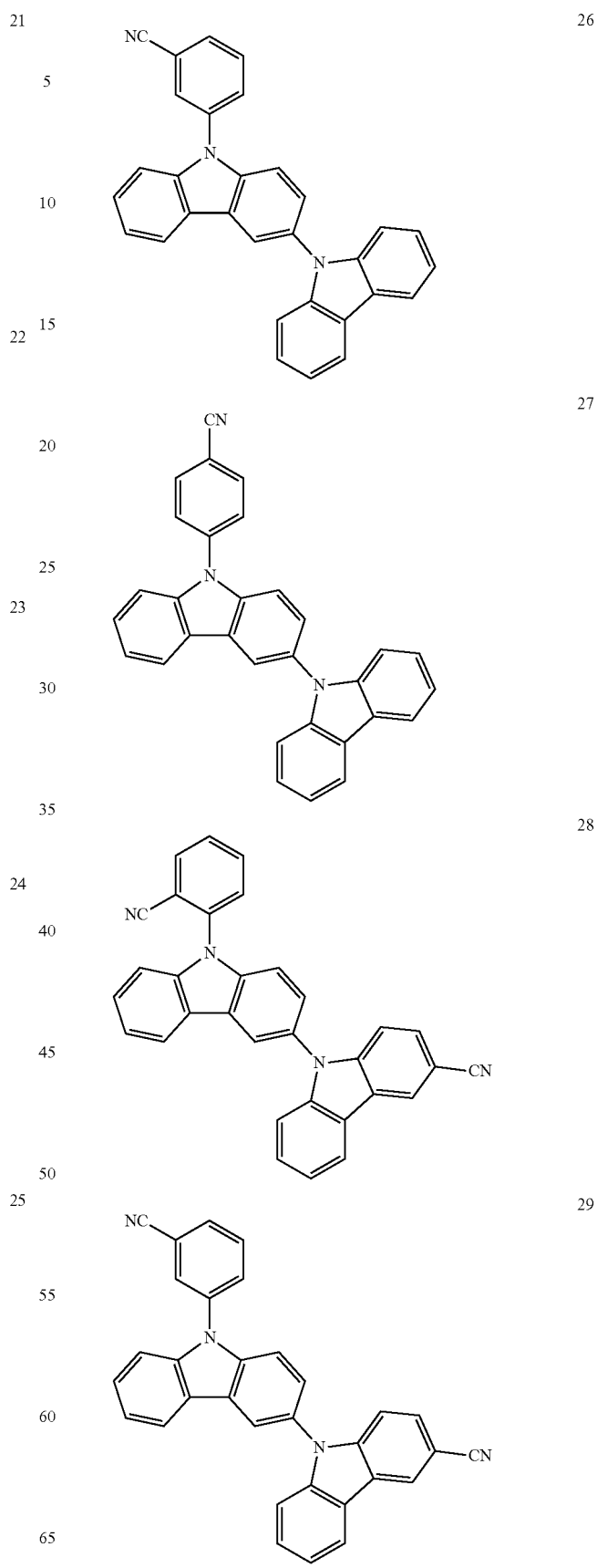

30 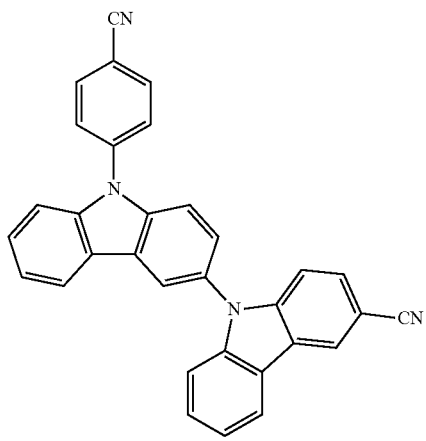
31 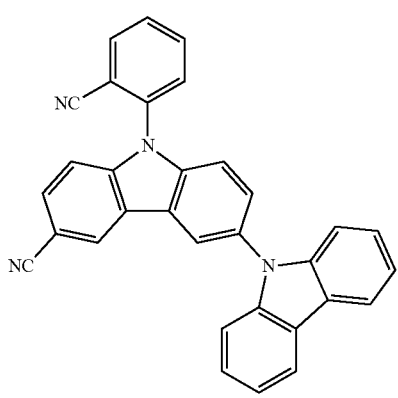
32 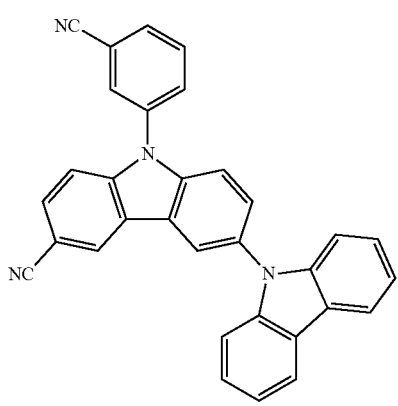
33 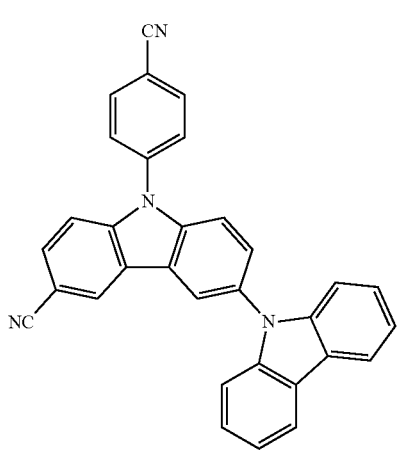
34 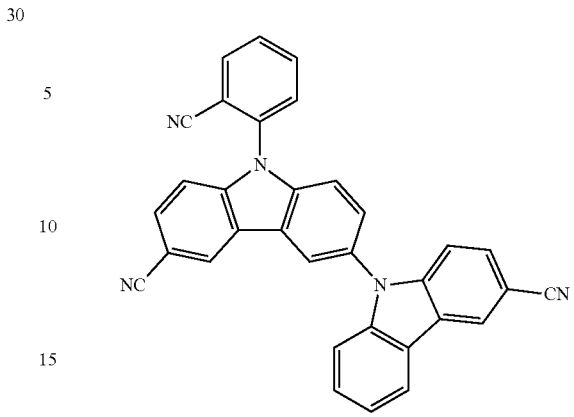
35 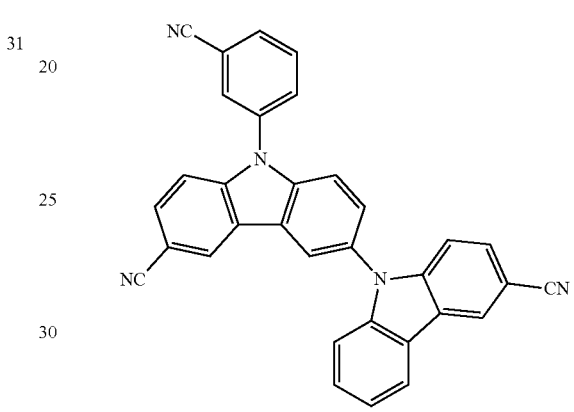
36 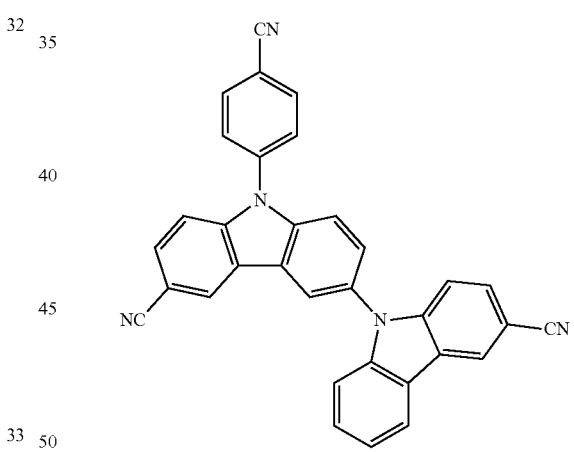
37 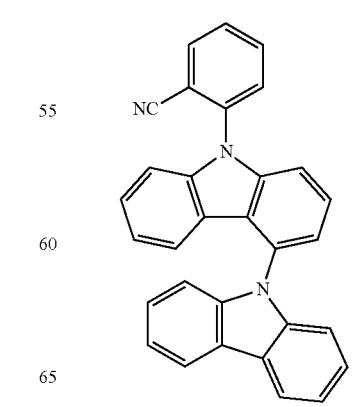

38
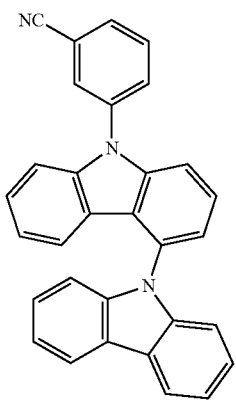
39
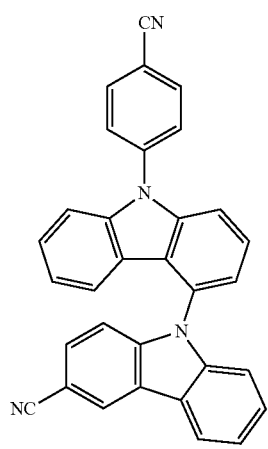
40
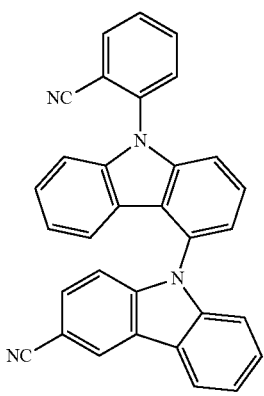
41
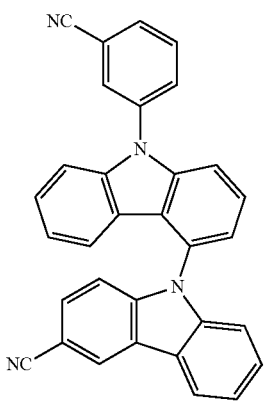
42
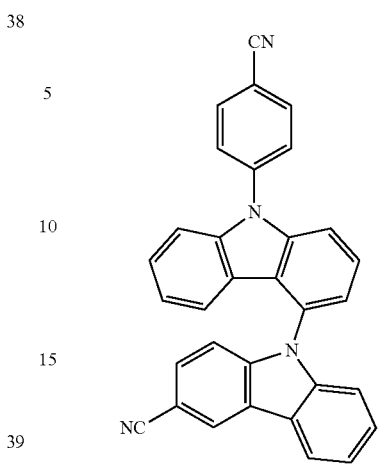
43
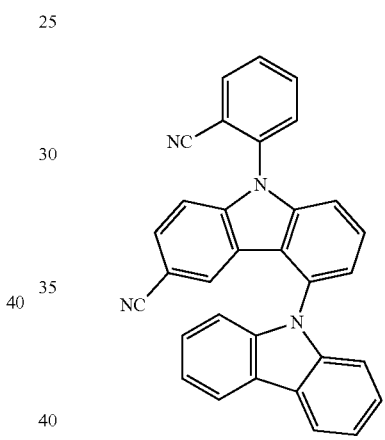
44
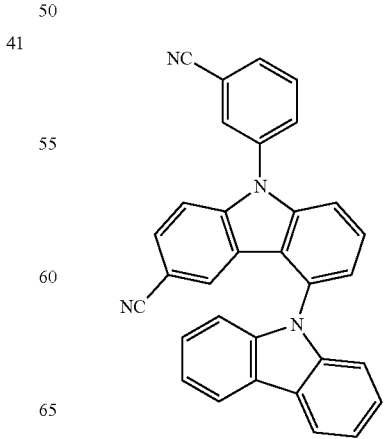

45
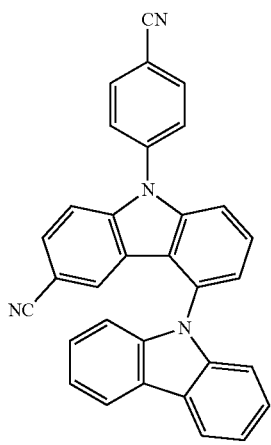
46
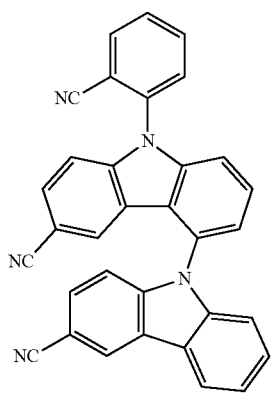
47
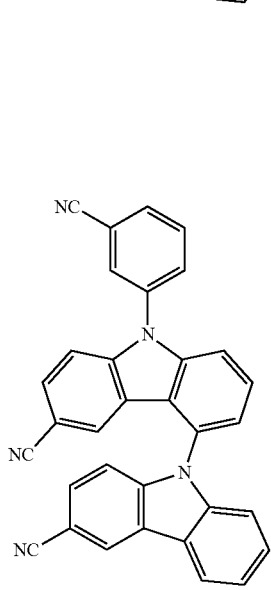
48
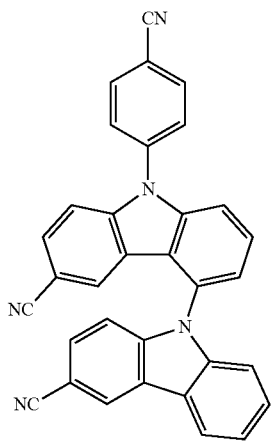
49
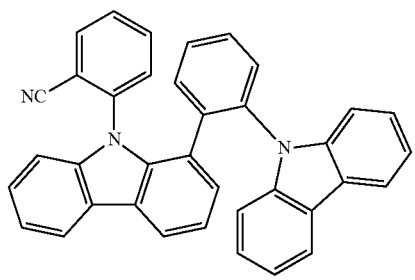
50
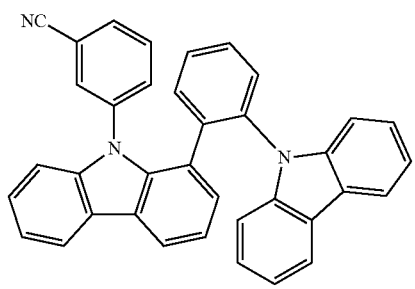
51
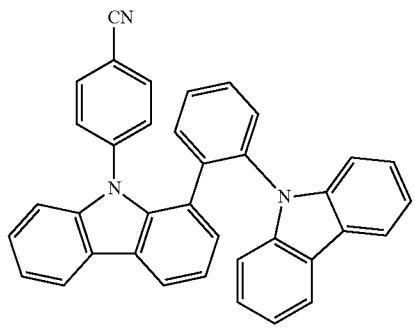
52
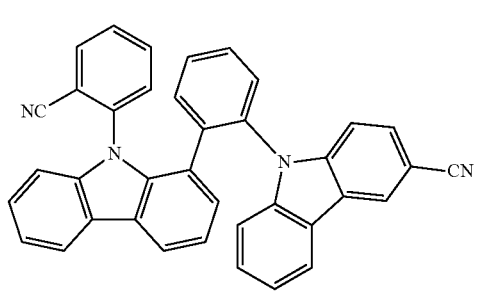

211
-continued
53
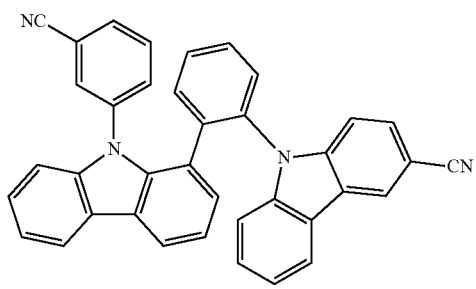
54
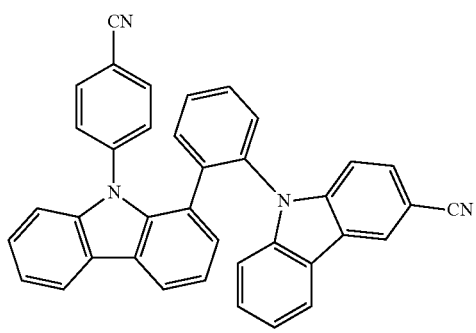
55
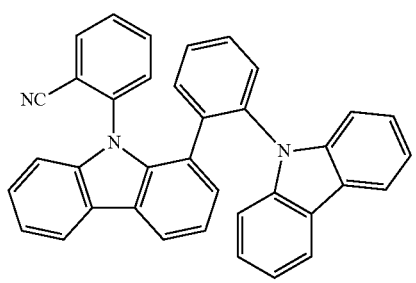
56
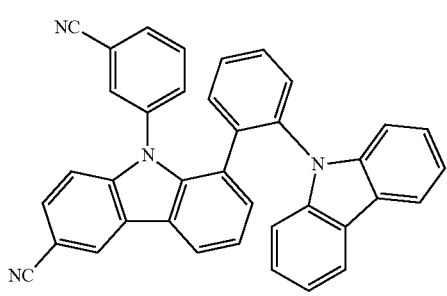
57
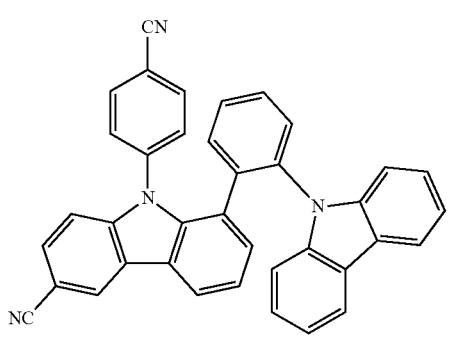
212
-continued
58
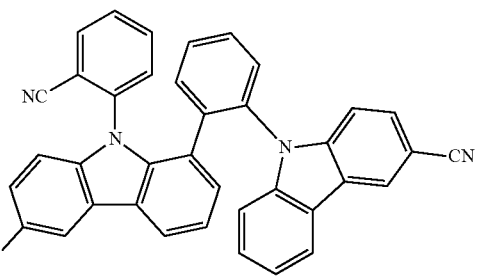
59
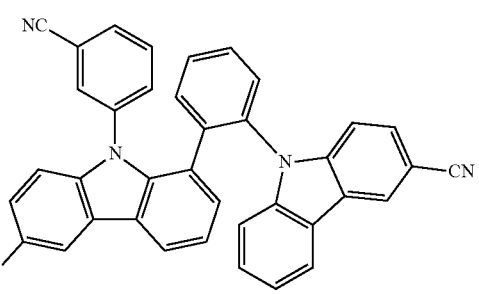
60
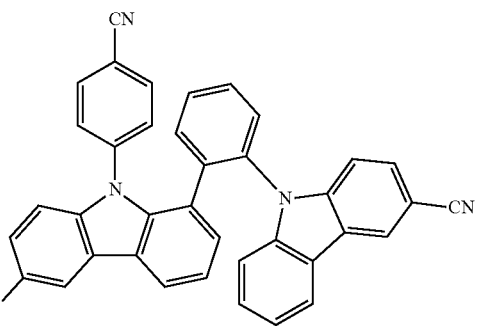
61
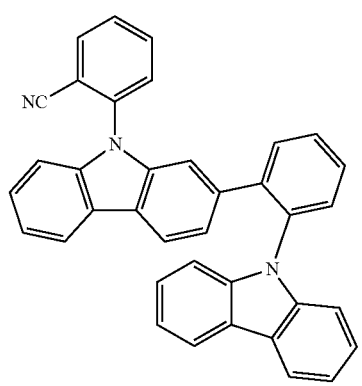

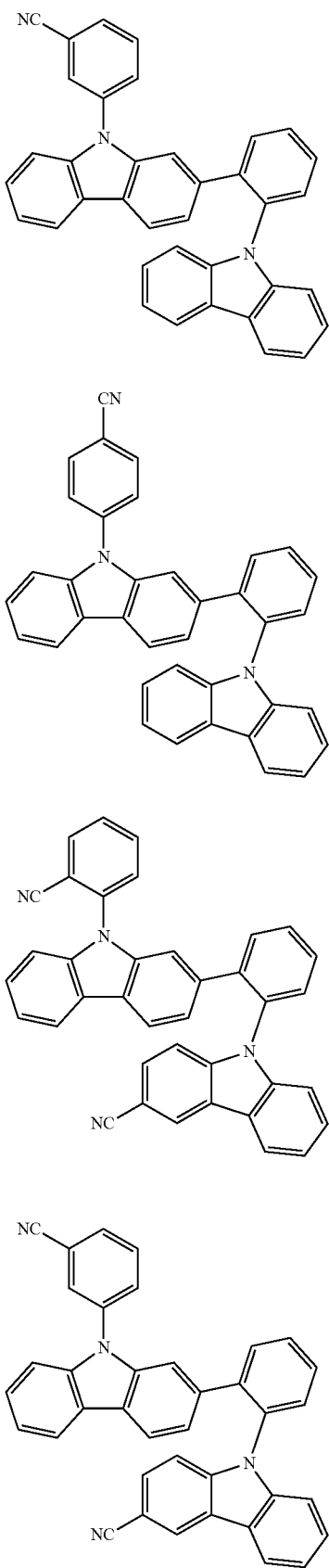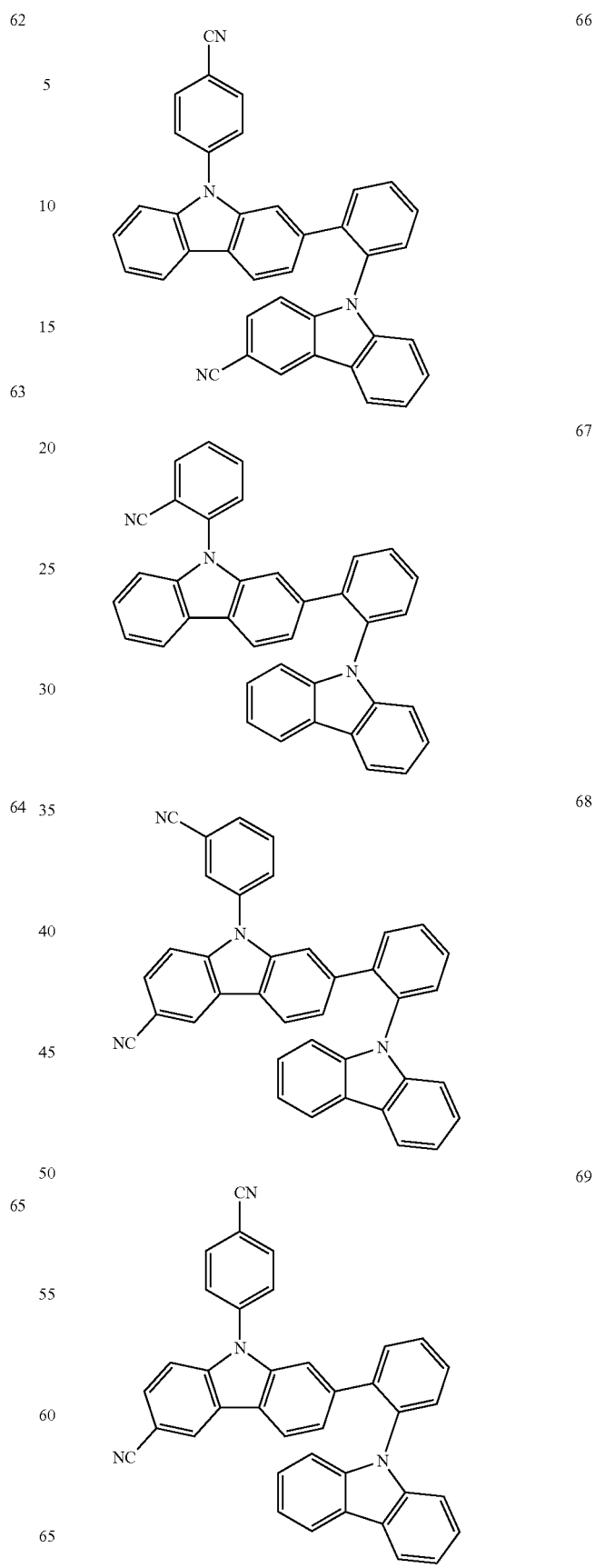

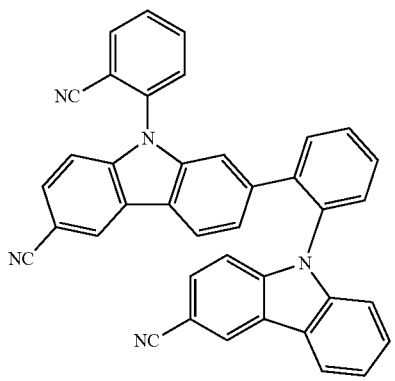
70
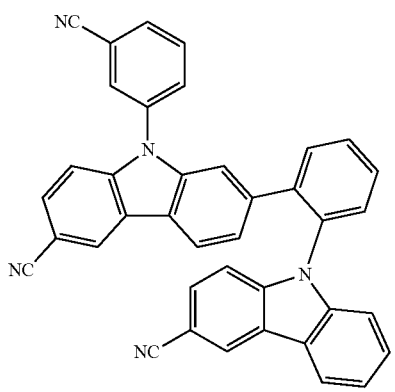
71
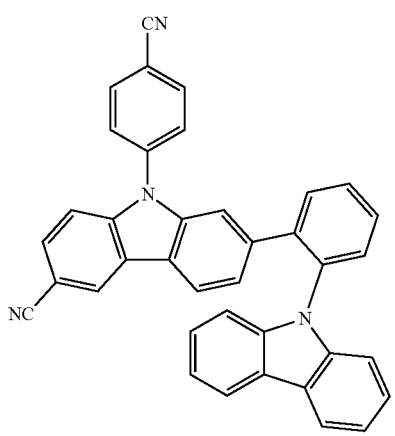
72
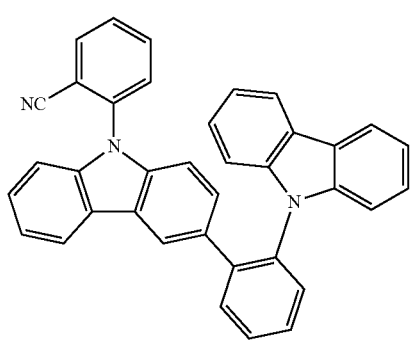
73
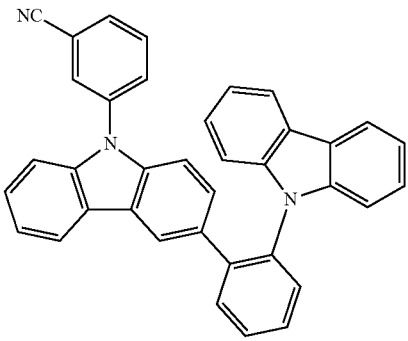
74
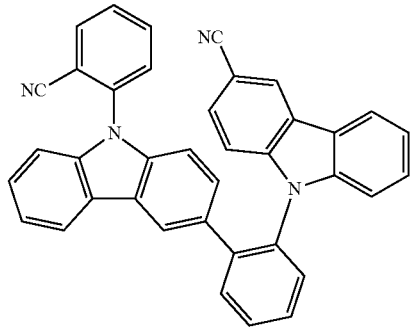
76
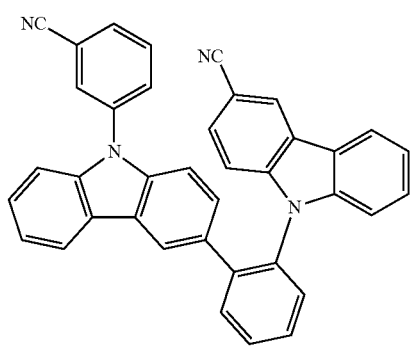
77

-continued
78
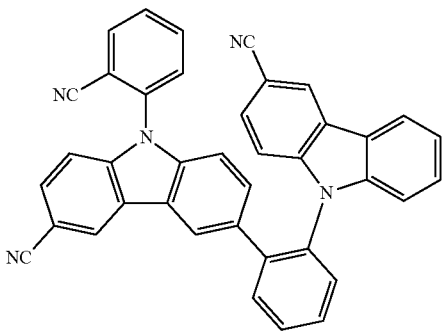
79
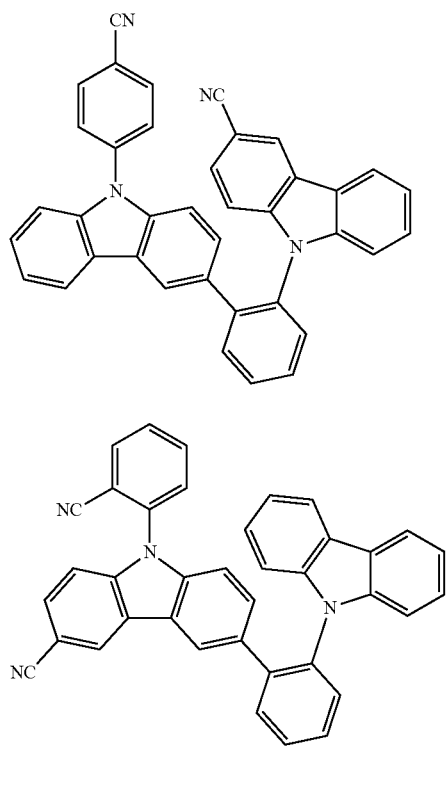
80
81
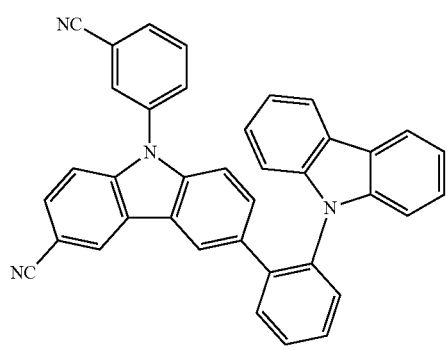
-continued
82
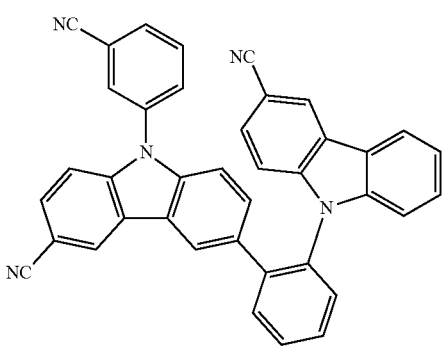
83
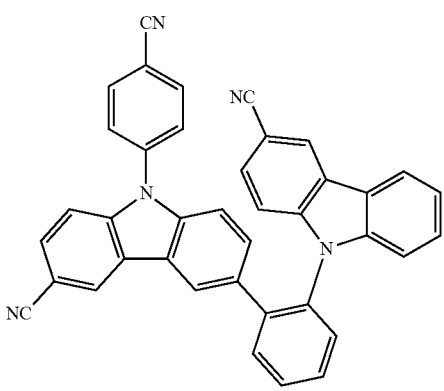
84
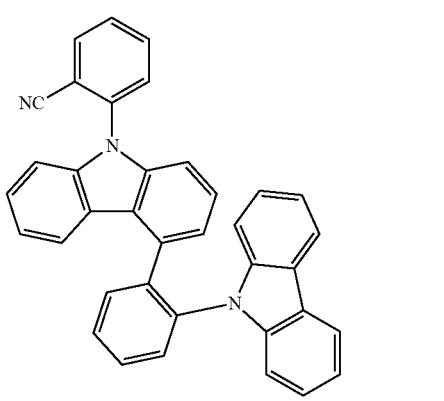
85
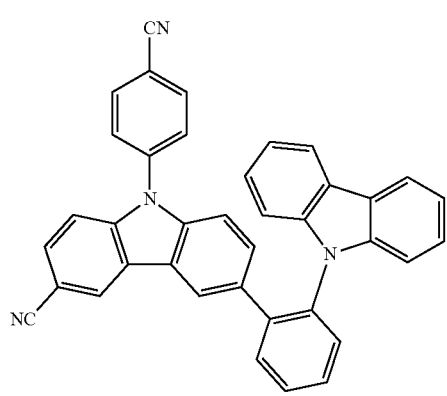

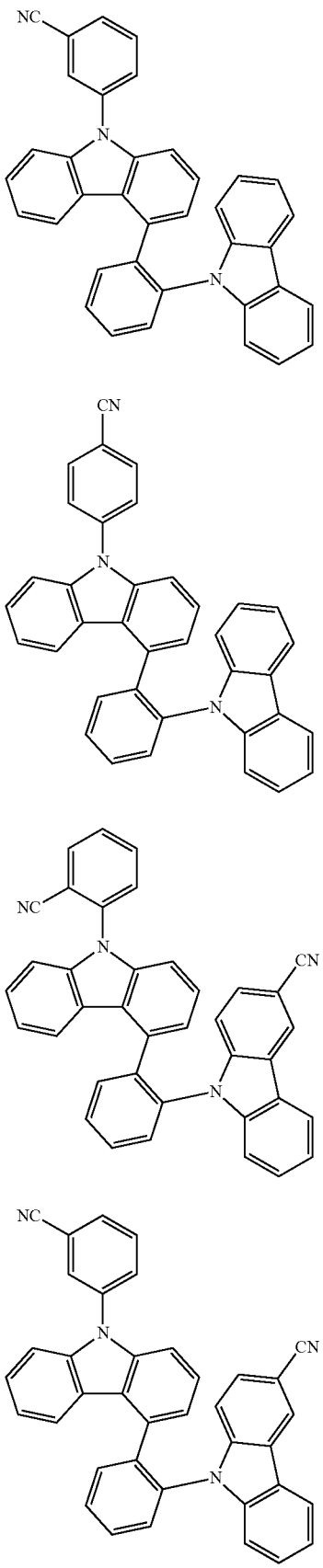
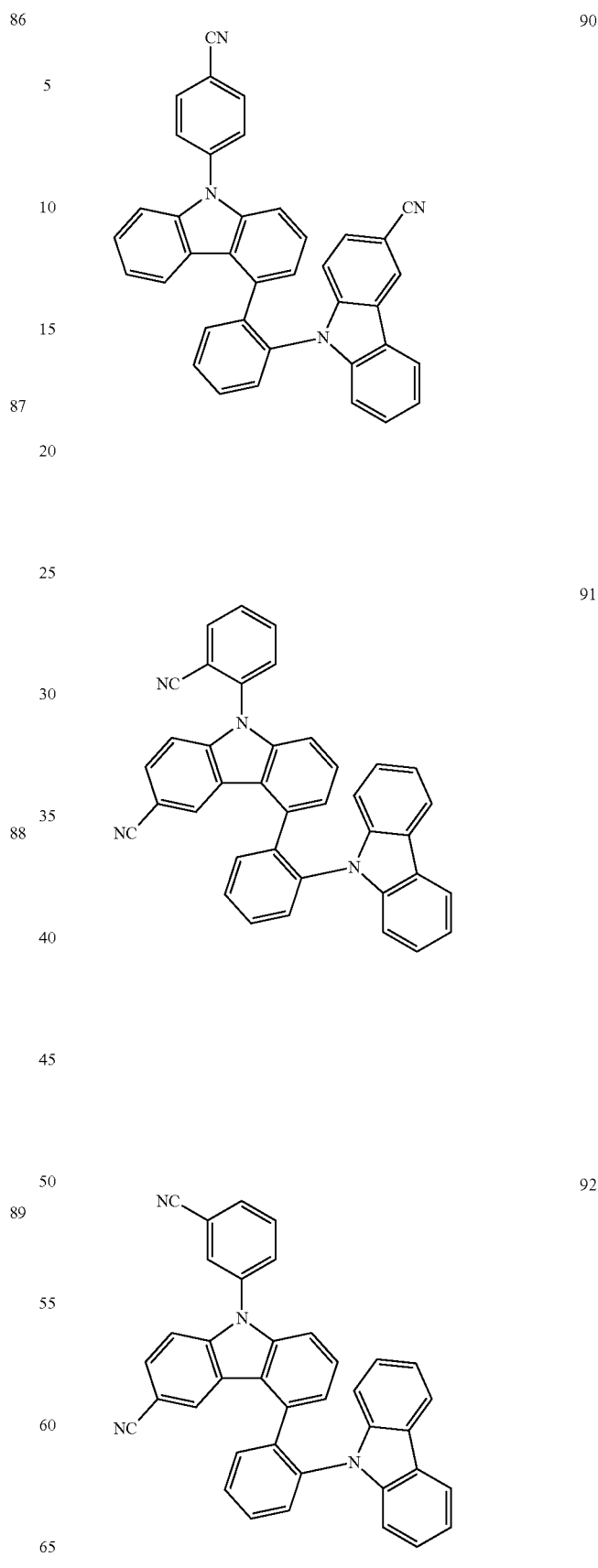

93
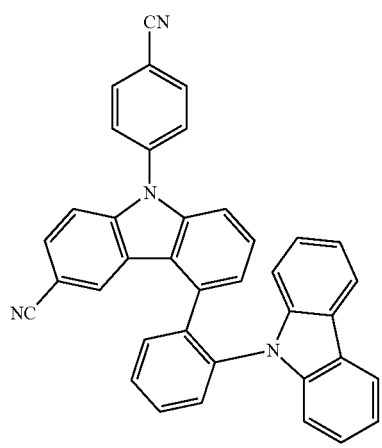
94
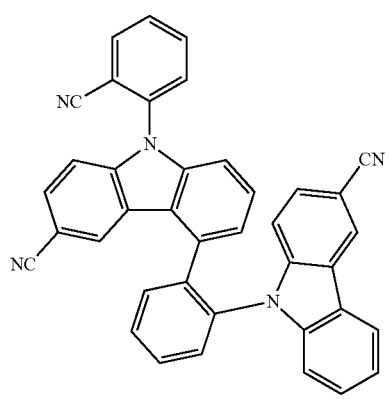
95
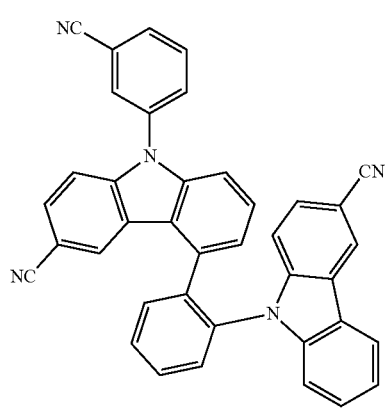
96
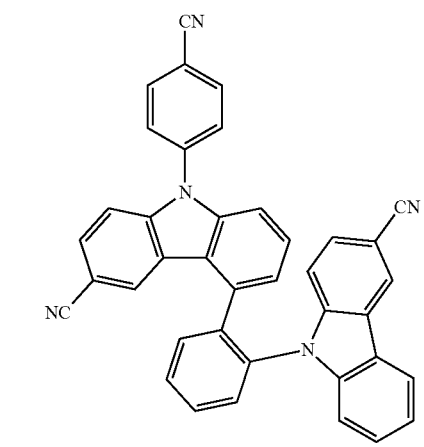
97
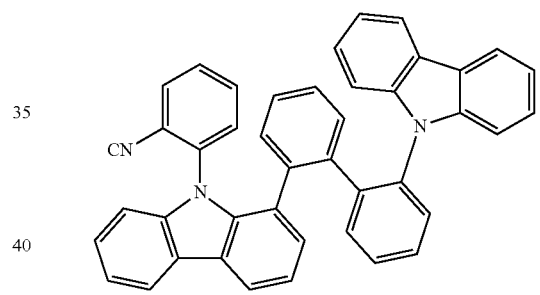
98
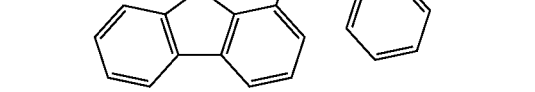
99
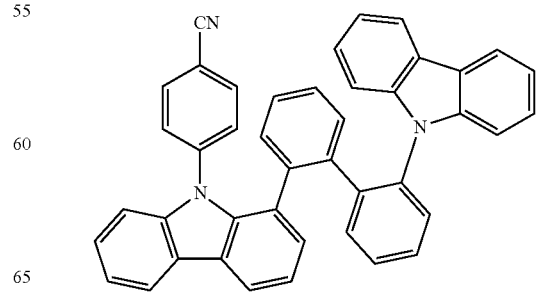

-continued
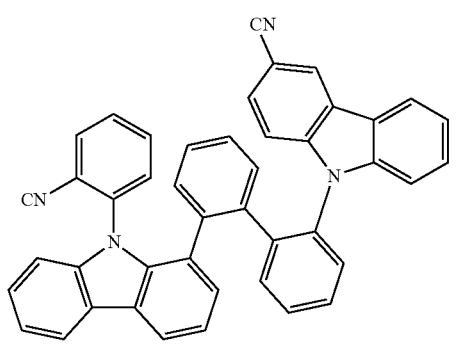
100
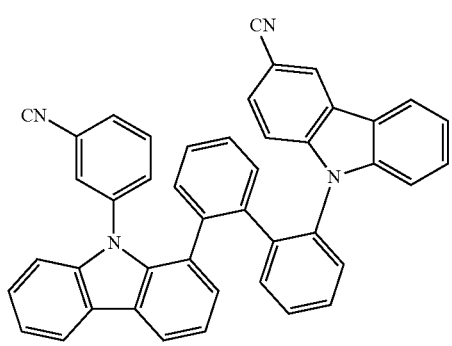
101
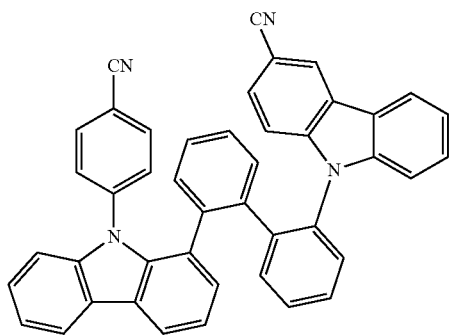
102
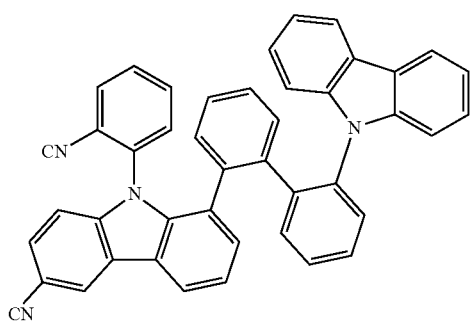
103
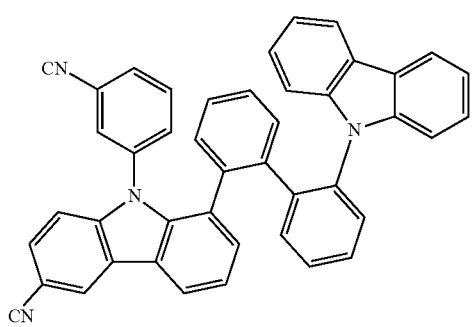
104
-continued
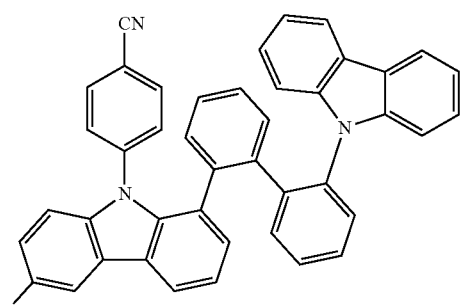
105
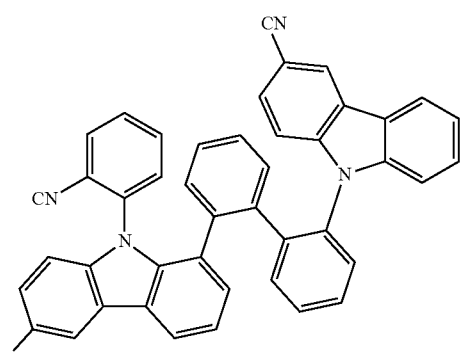
106
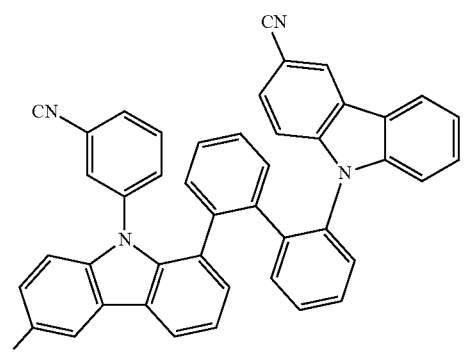
107
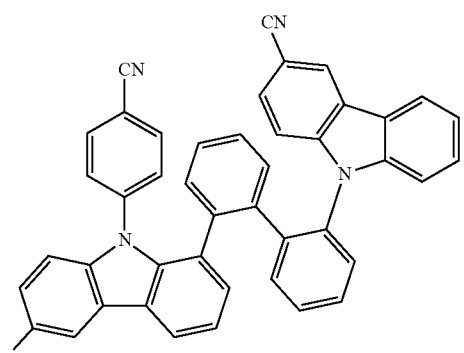
108

109
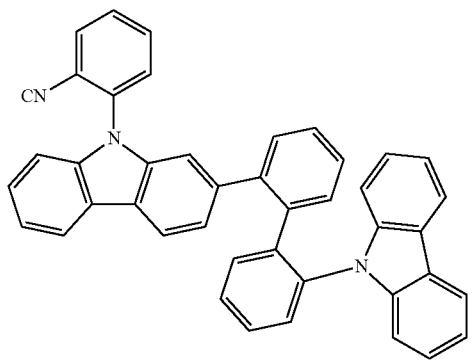
110
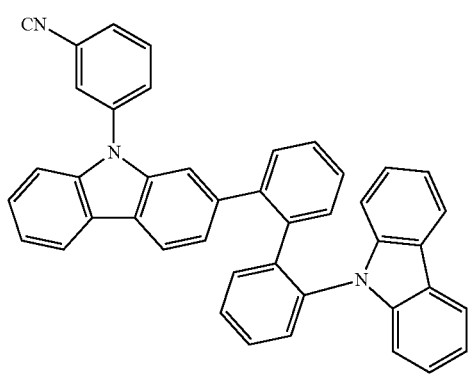
111
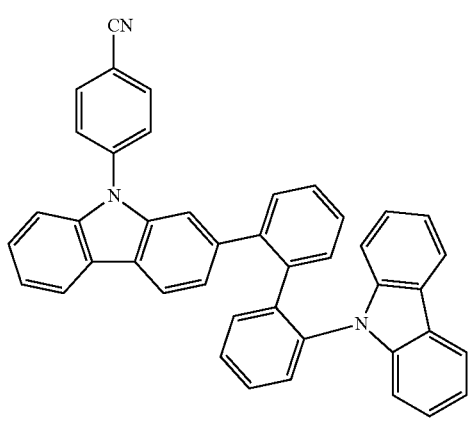
112
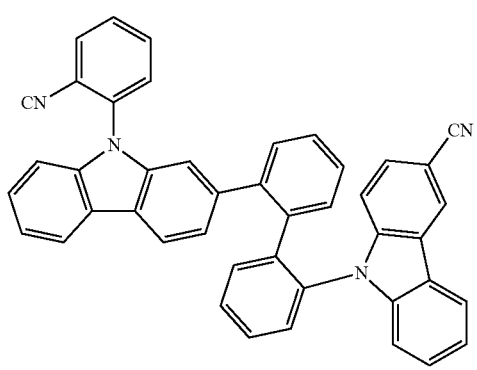
113
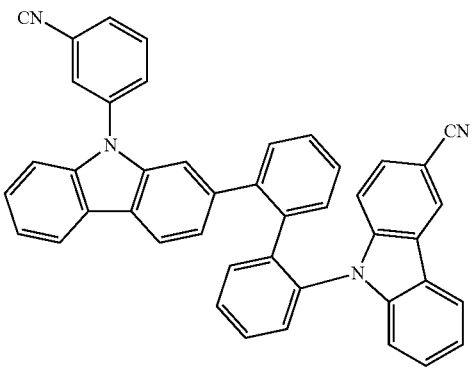
114
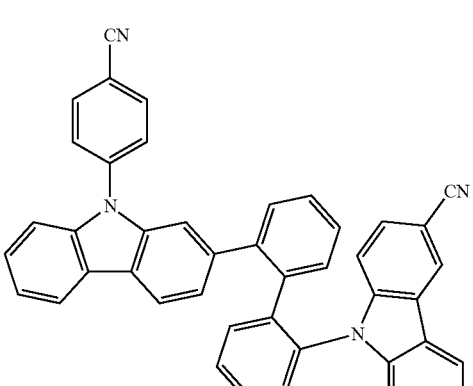
115
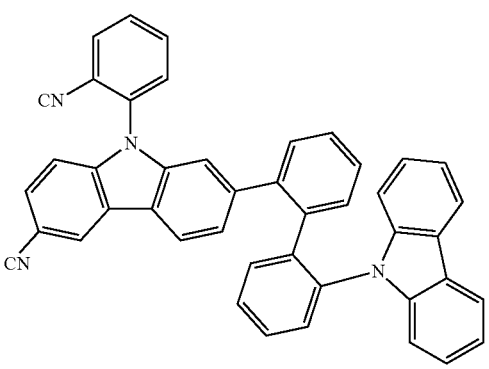
116
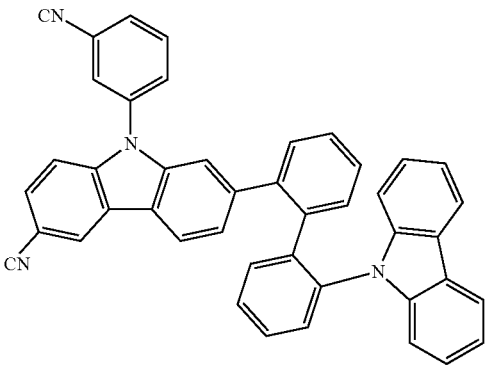

117
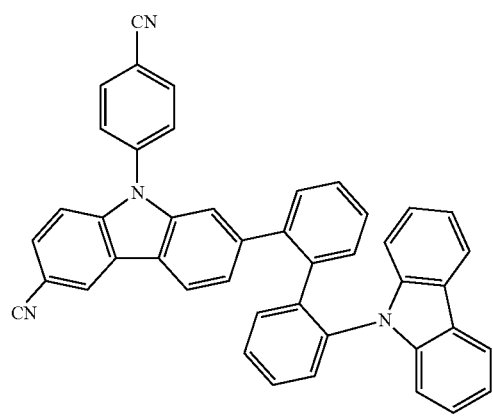
118
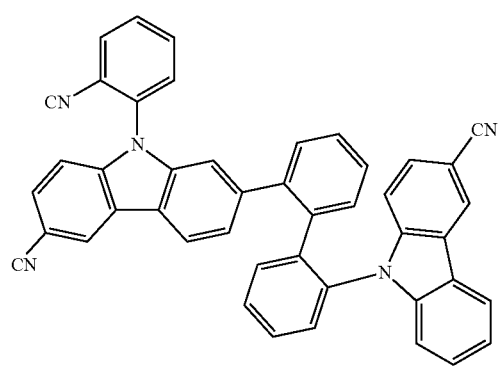
119
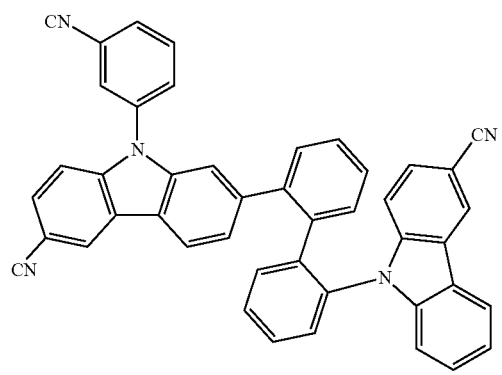
120
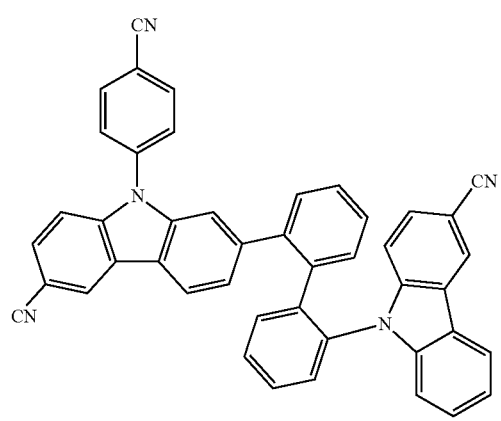
121
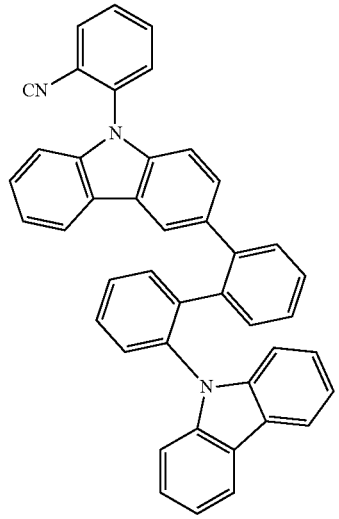
122
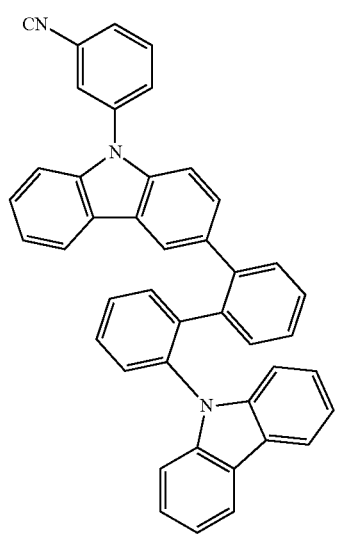
123
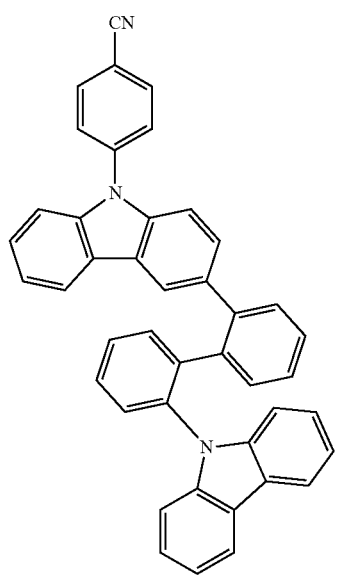

124
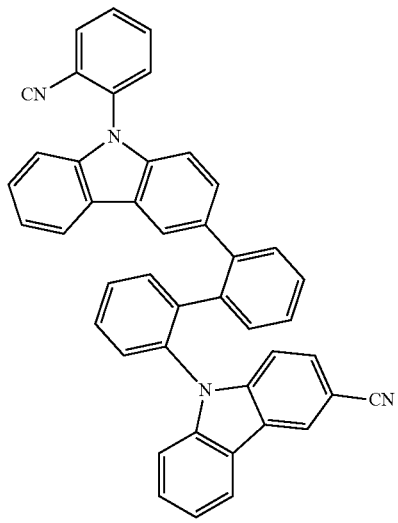
125
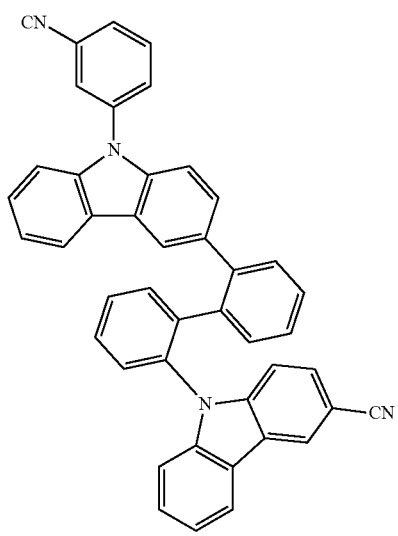
126
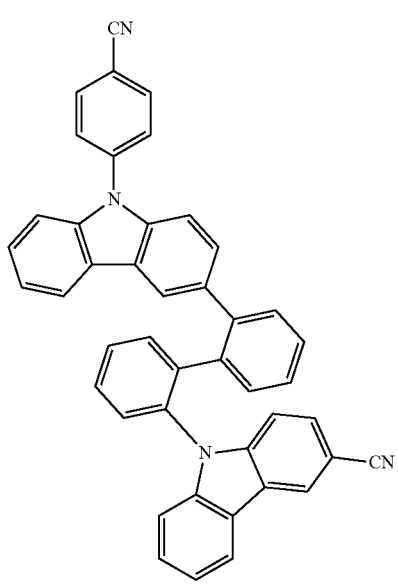
127
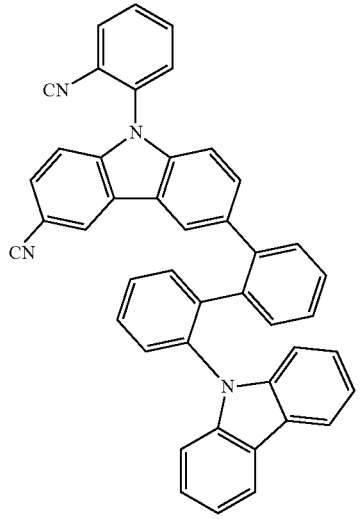
128
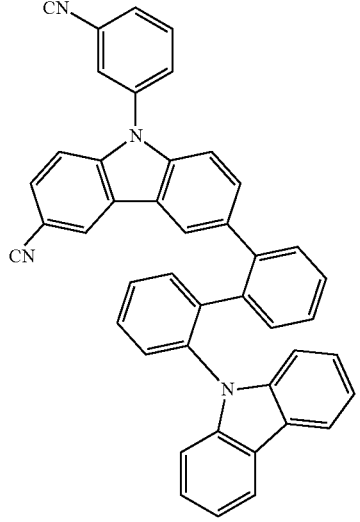
129
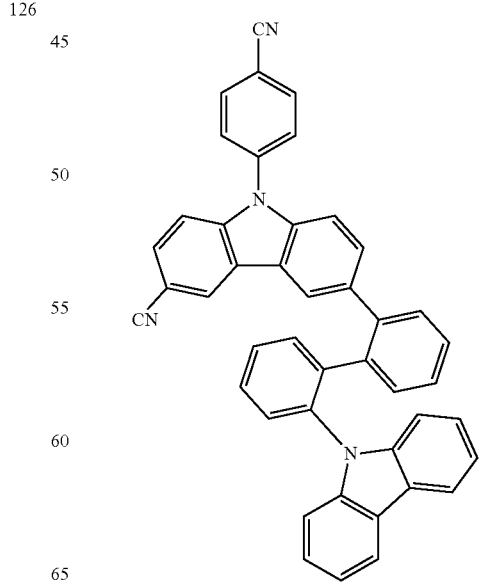

231
-continued
130
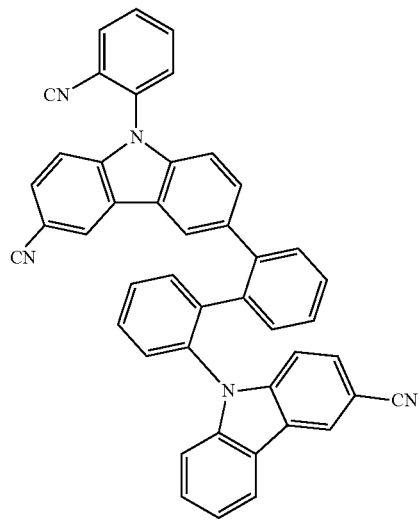
131
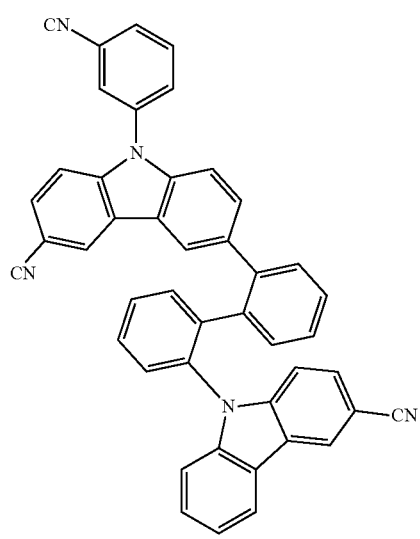
132
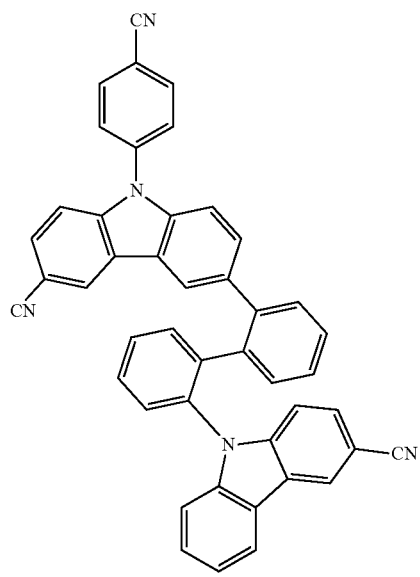
232
-continued
133
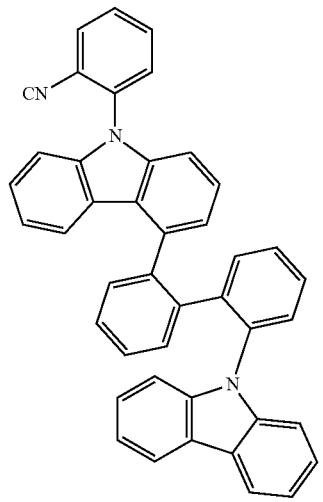
134
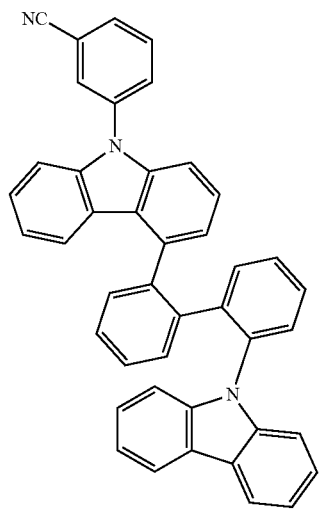
135
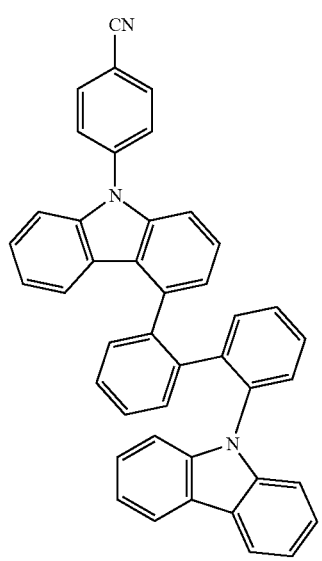

136
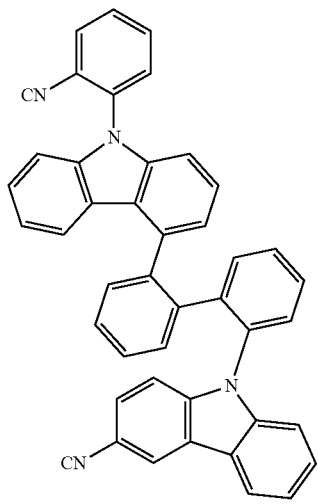
137
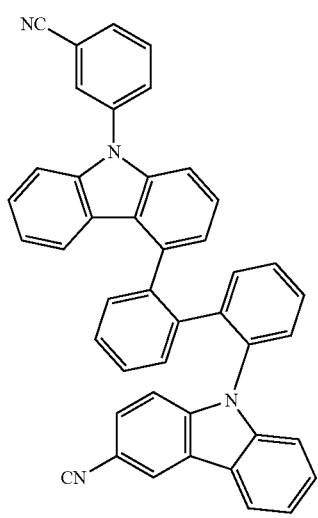
138
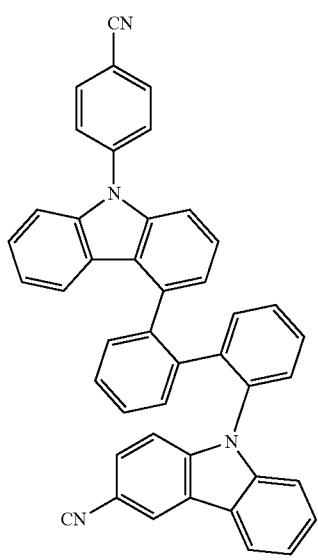
139
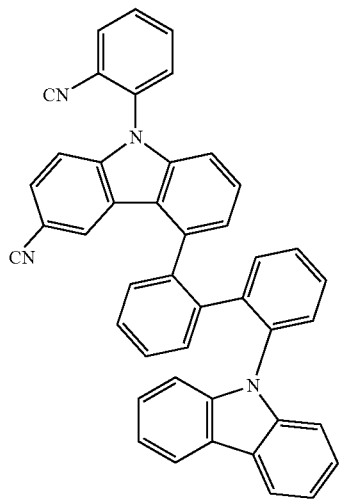
140
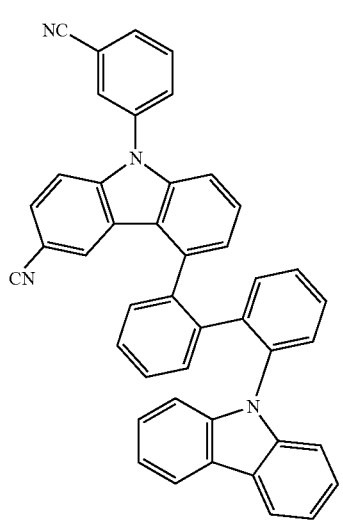
141
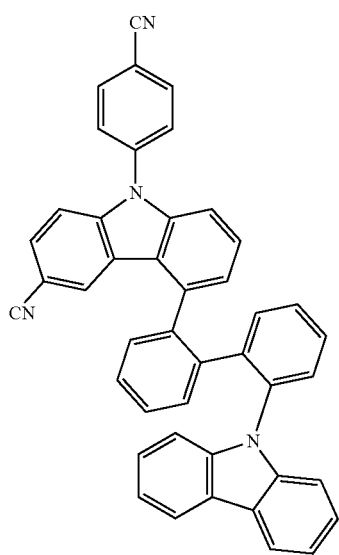

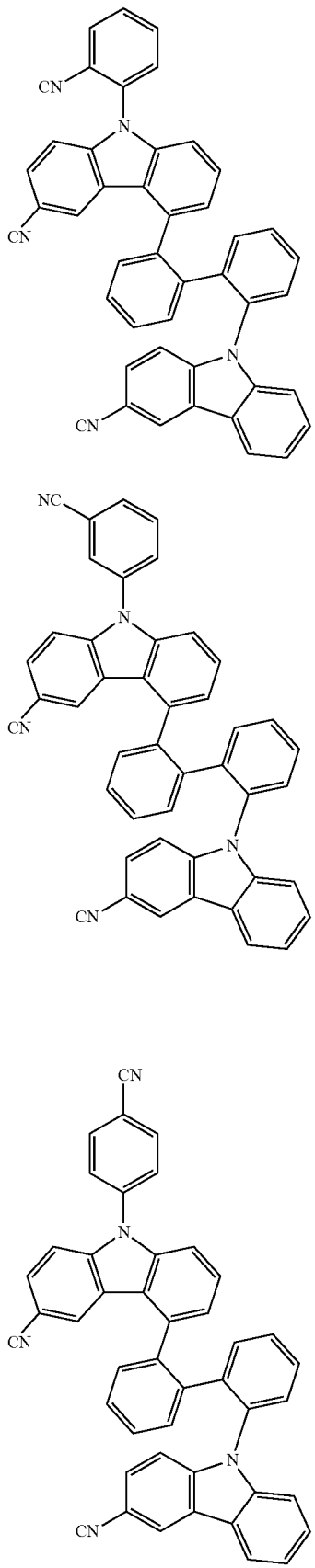
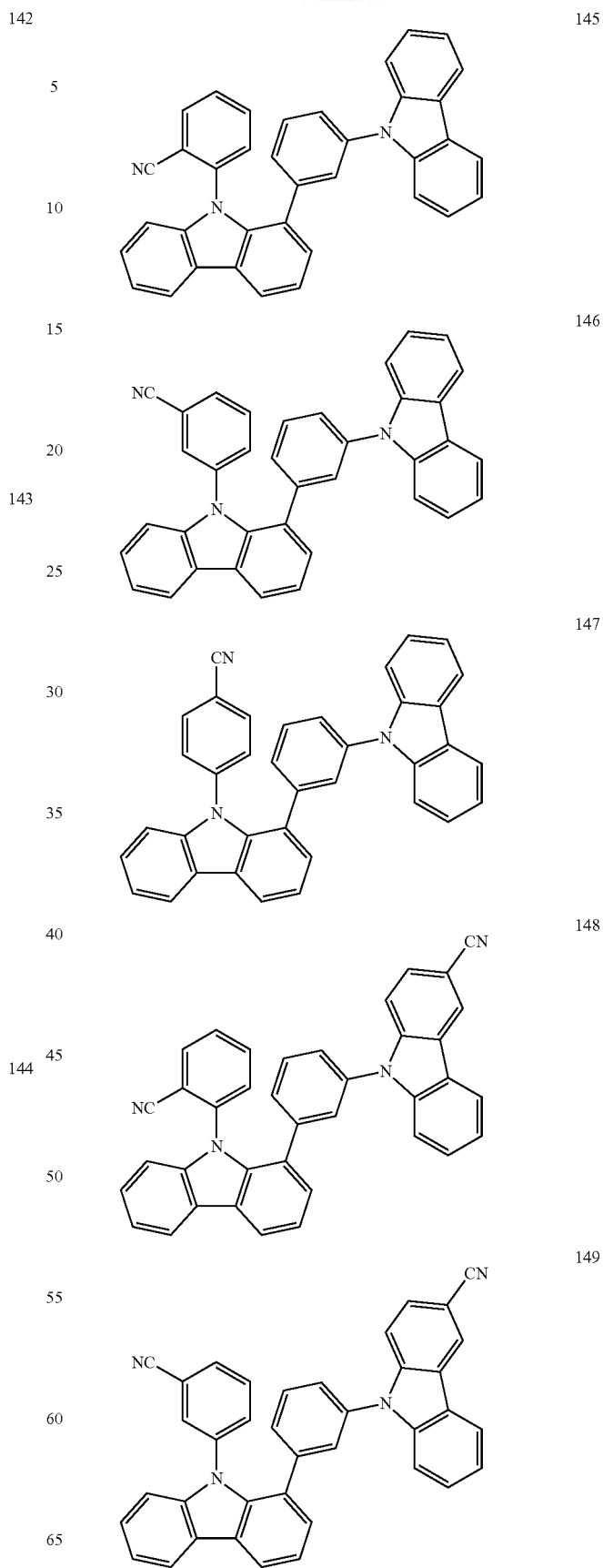

150
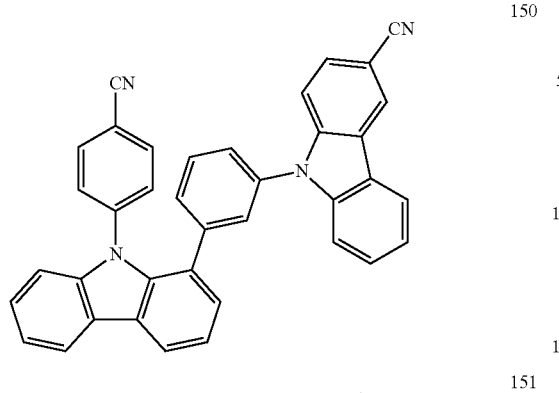
151
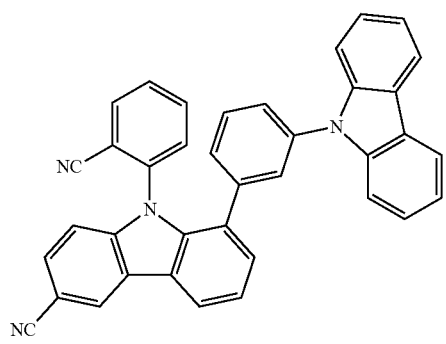
152
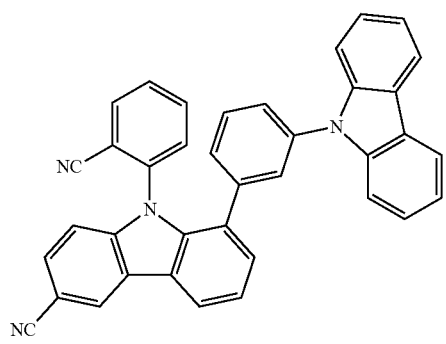
153
154
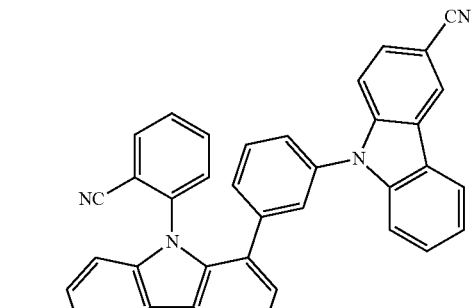
155
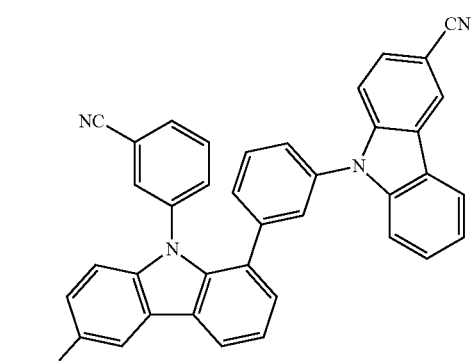
156
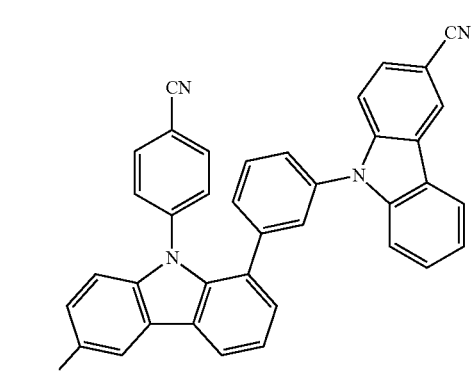
157
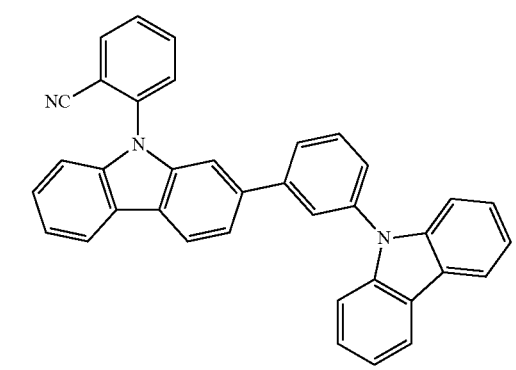

-continued
158
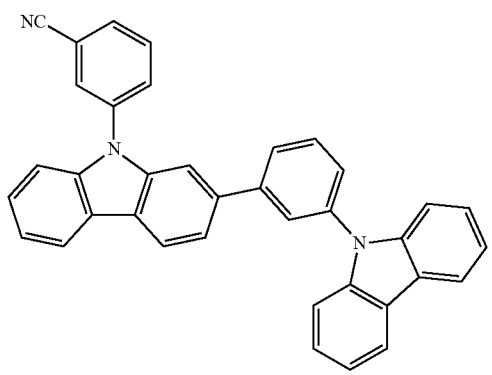
159
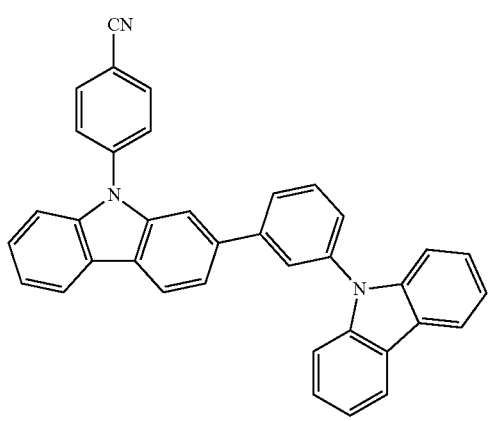
160
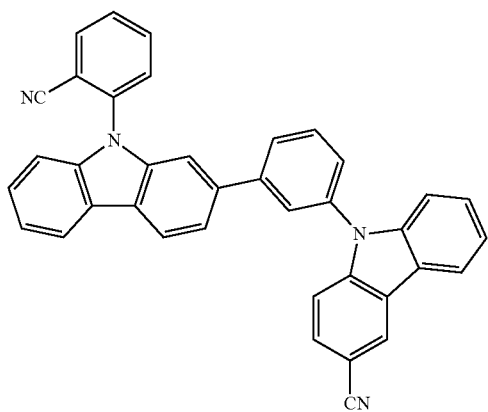
161
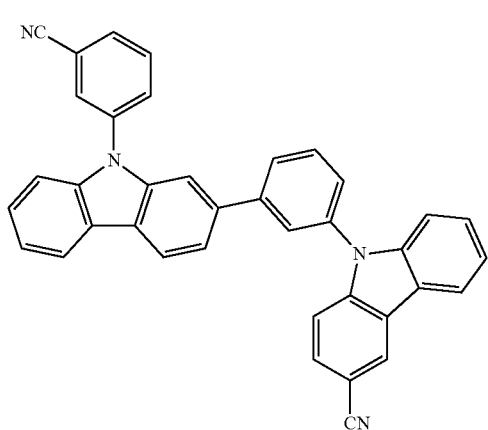
-continued
162
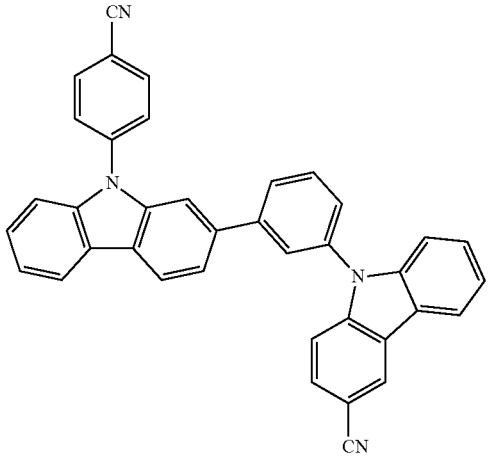
163
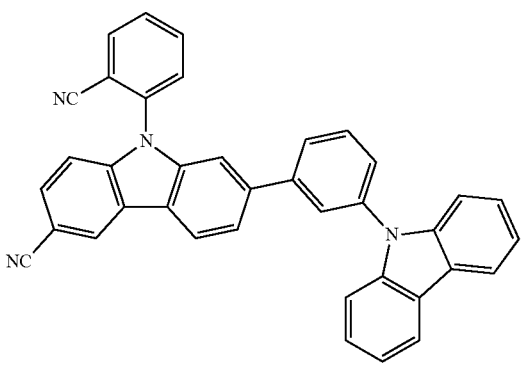
164
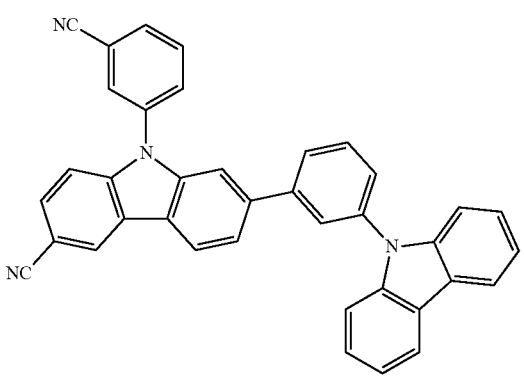
165
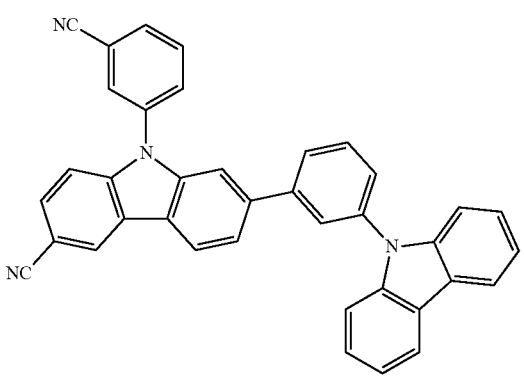

241 242
-continued
166
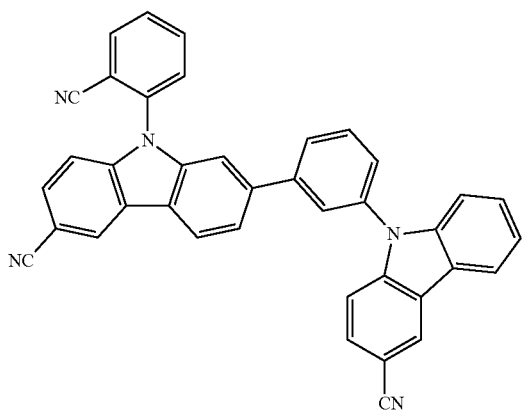
167
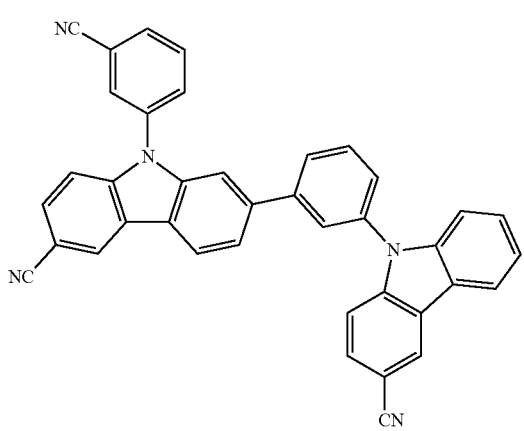
168
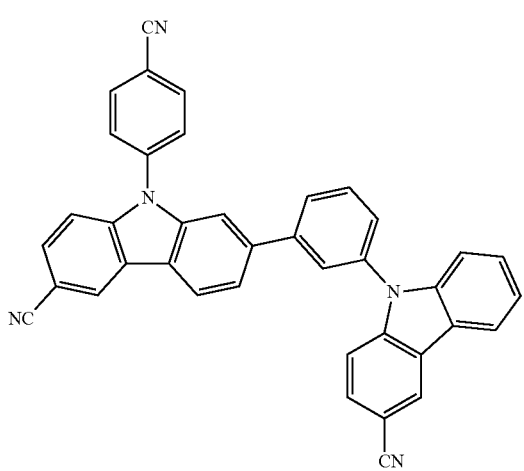
169
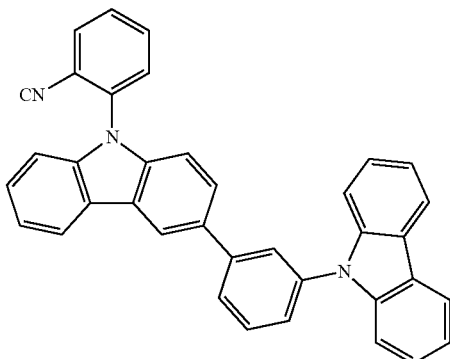
170
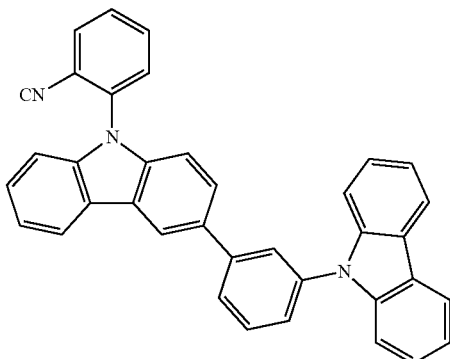
171
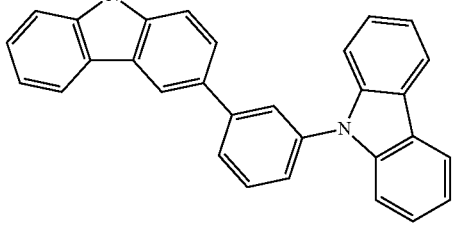
172
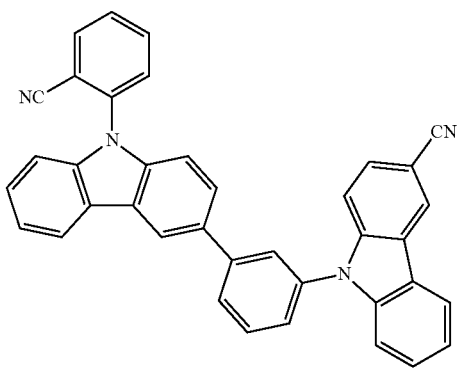

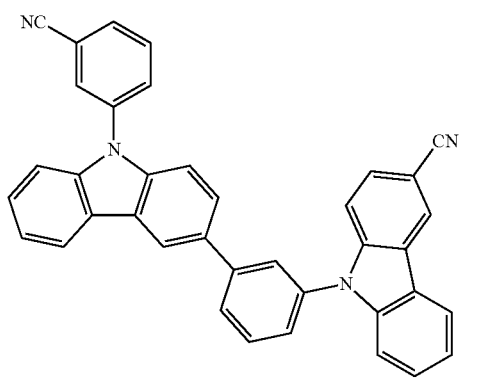
173
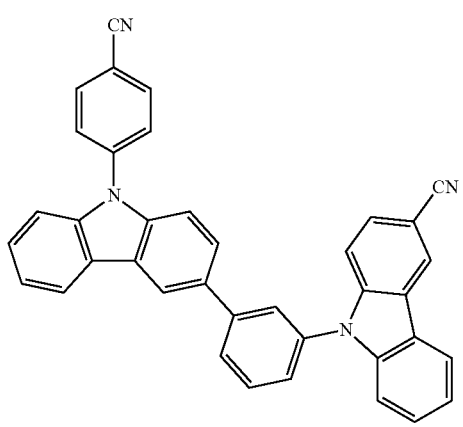
174
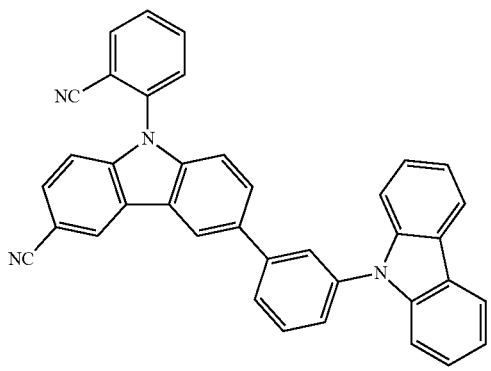
175
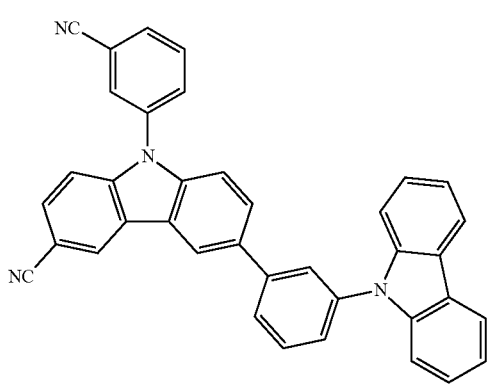
176
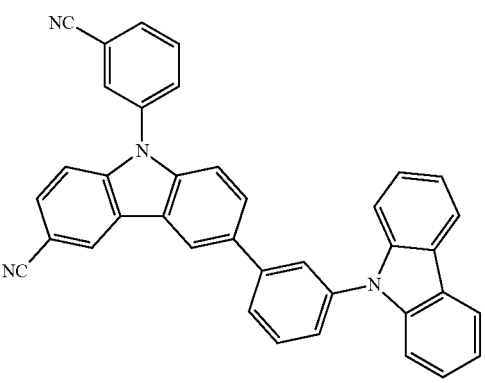
176
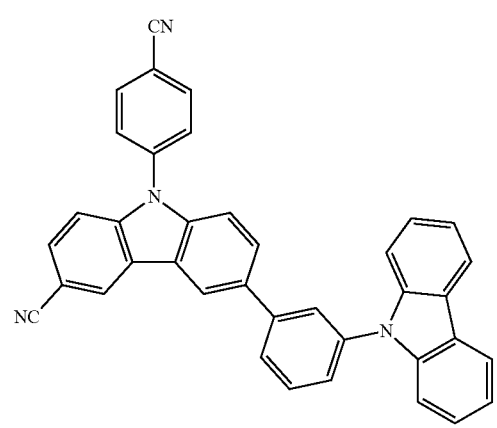
177
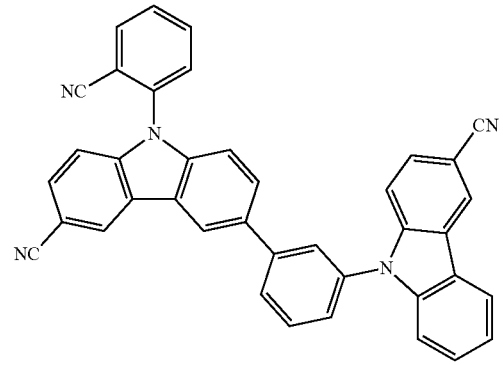
178
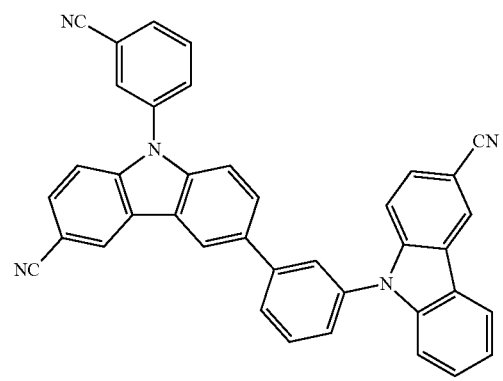
179

-continued
180
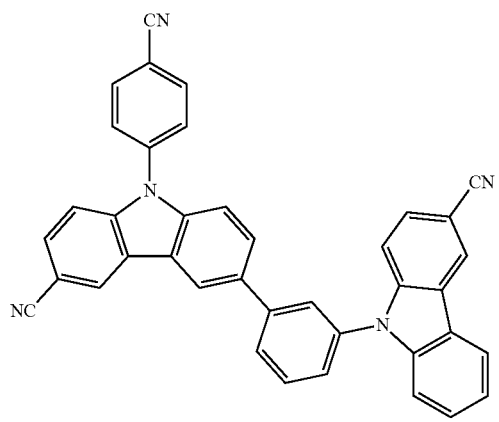
181
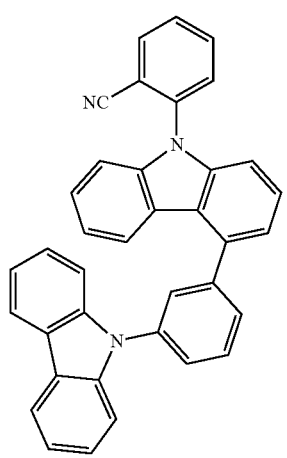
182
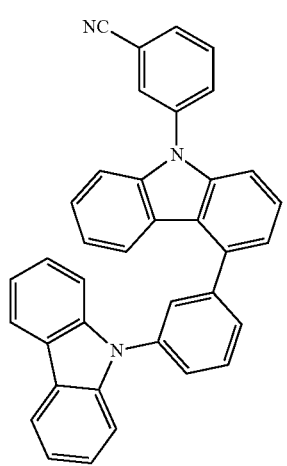
-continued
183
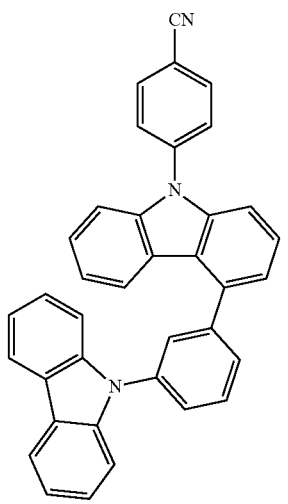
184
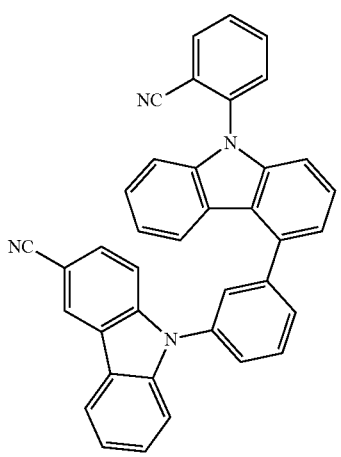
185
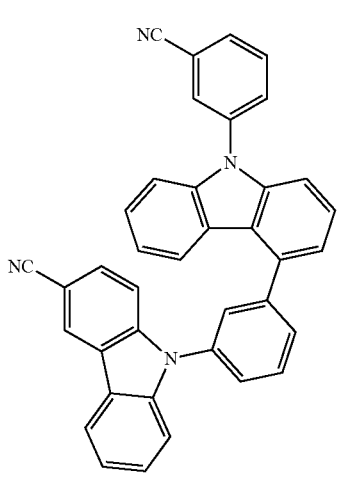

186
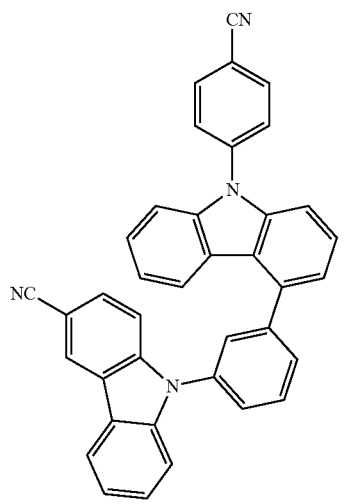
187
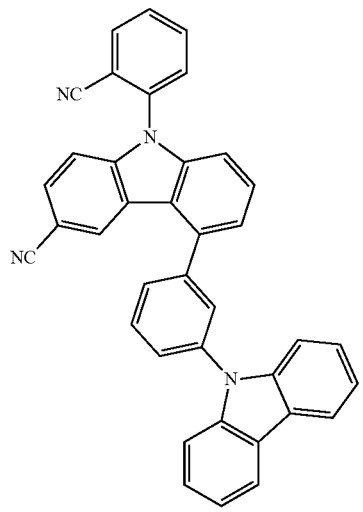
188
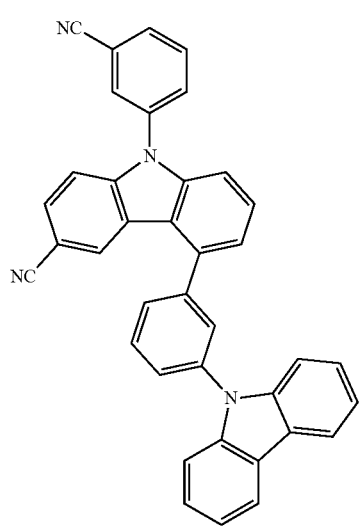
189
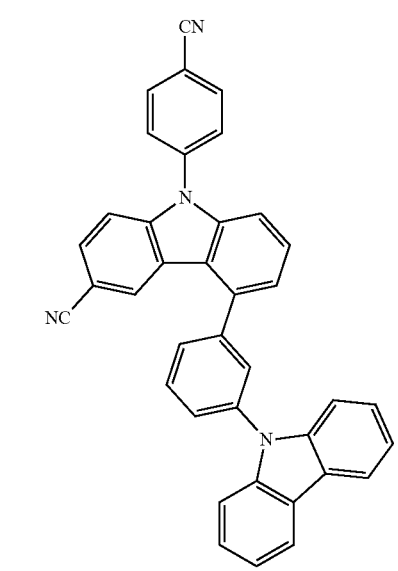
190
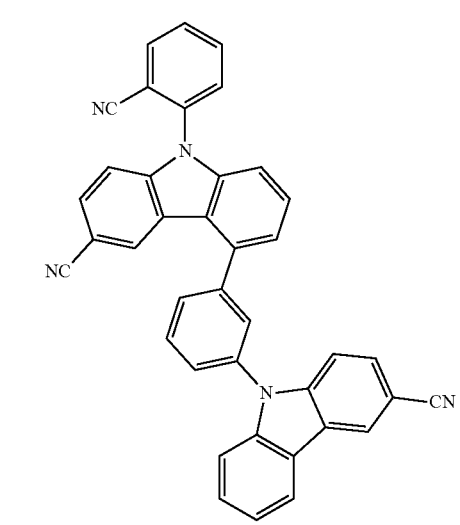
191
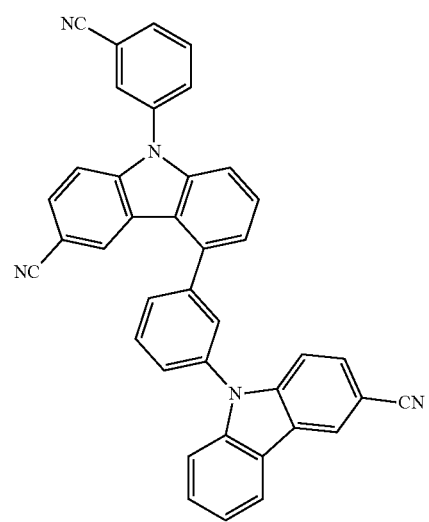

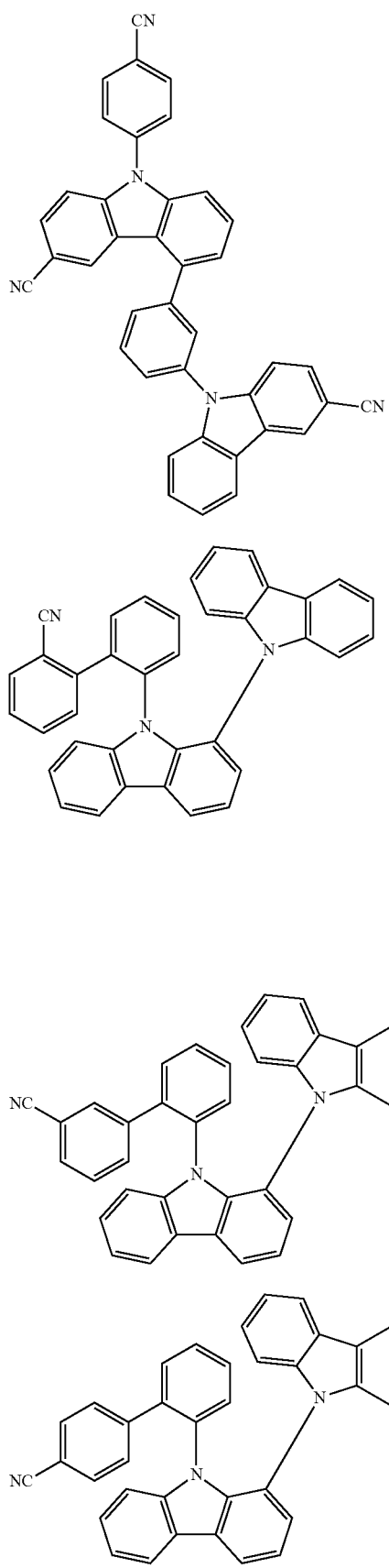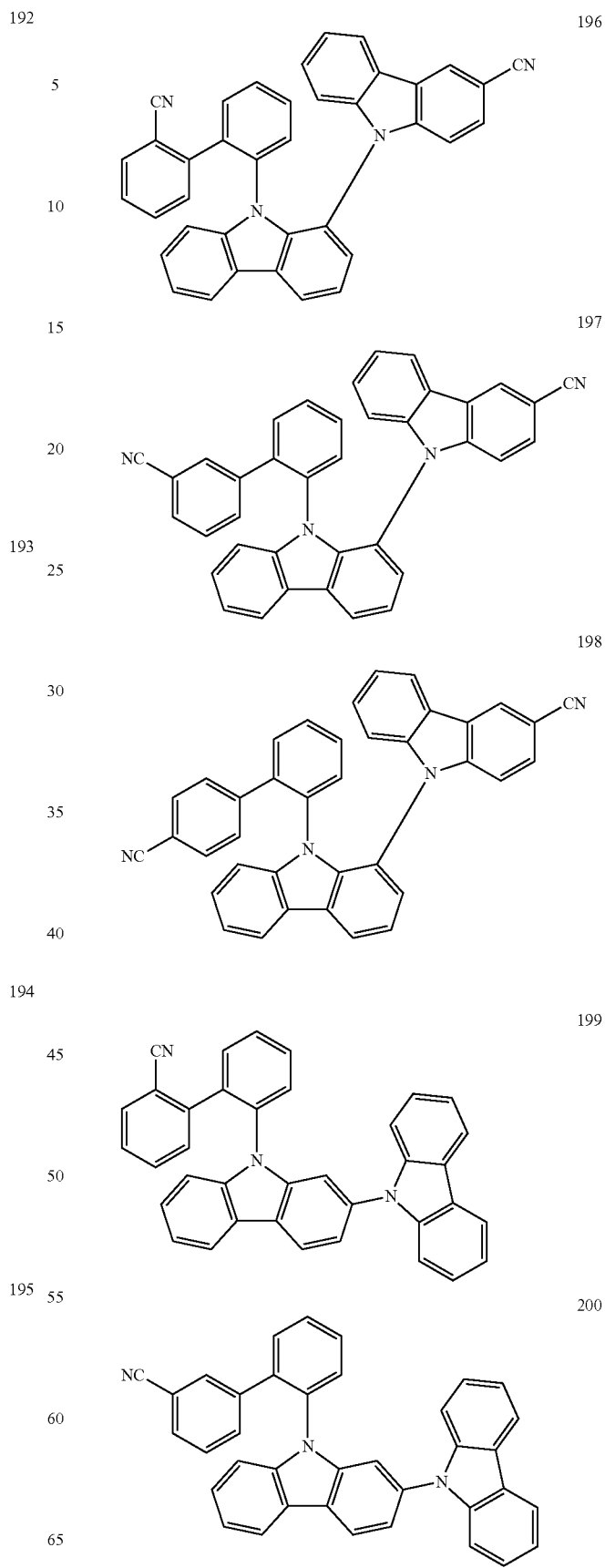

201
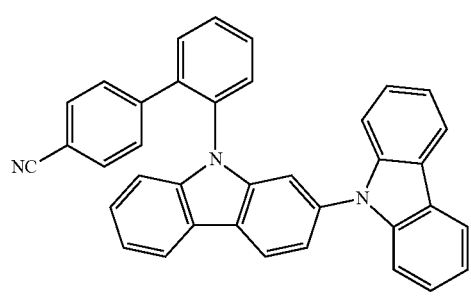
202
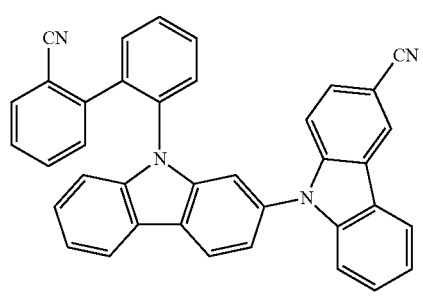
203
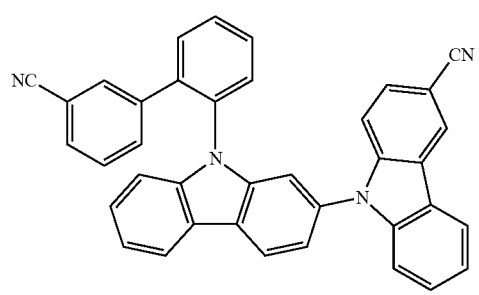
204
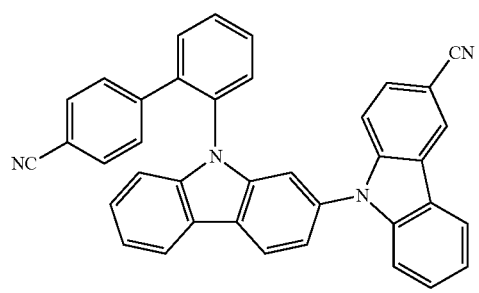
205
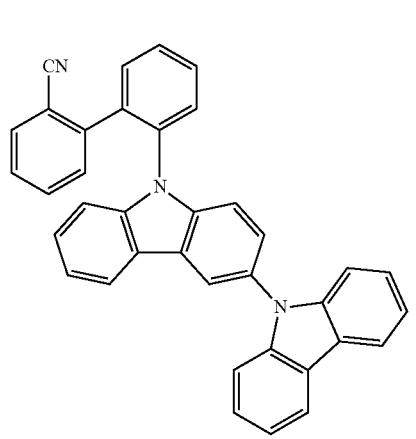
206
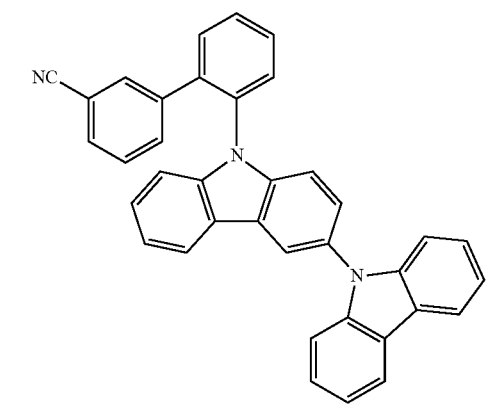
207
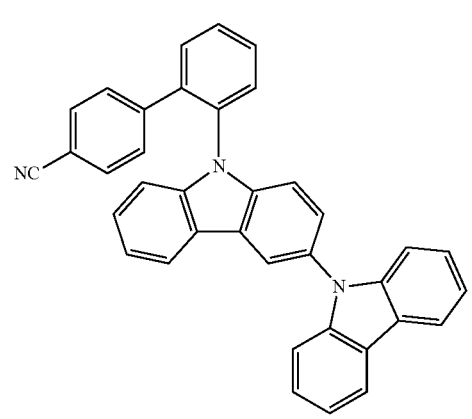
208
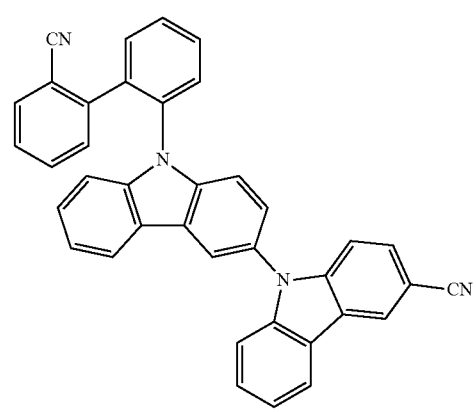
209
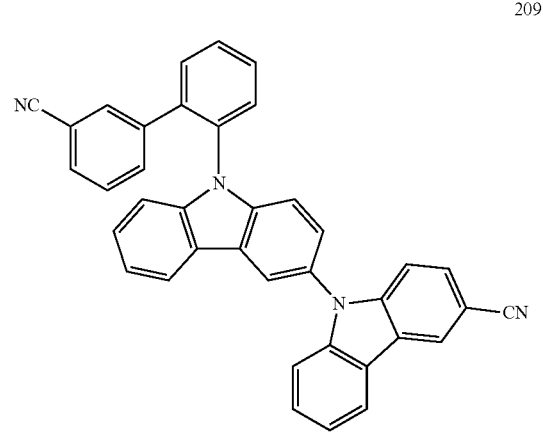

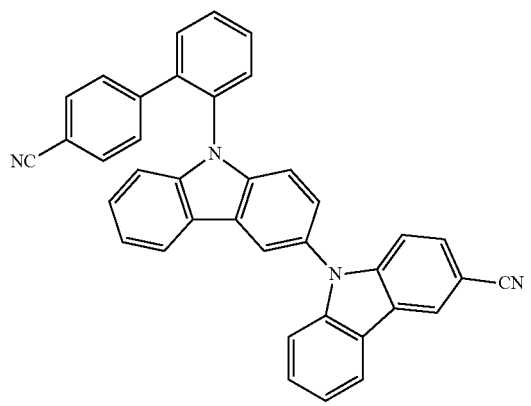
210
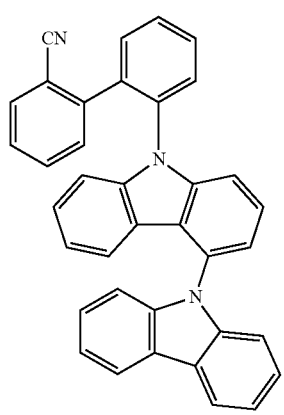
211
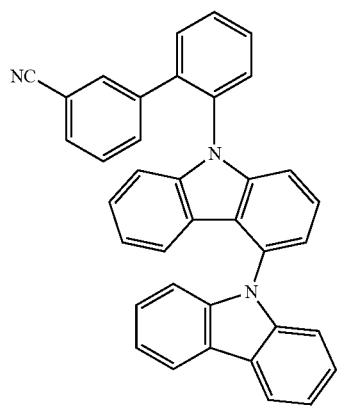
212
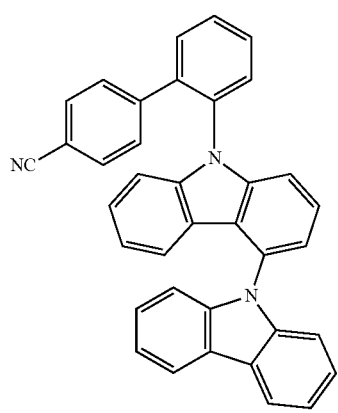
213
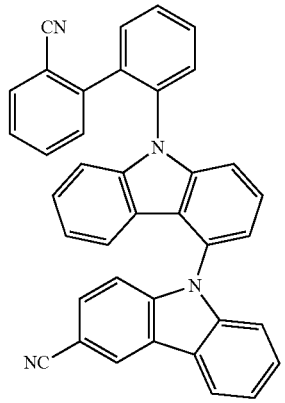
214
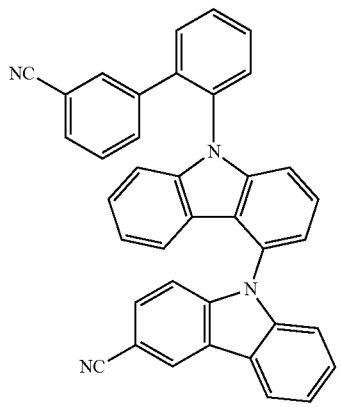
215
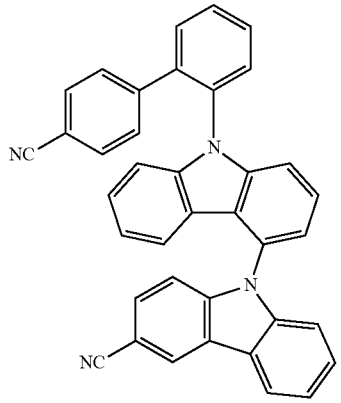
216
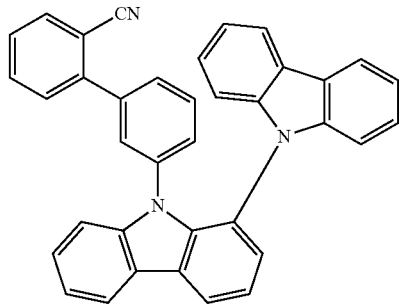
217

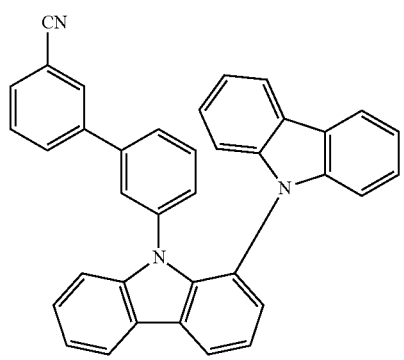
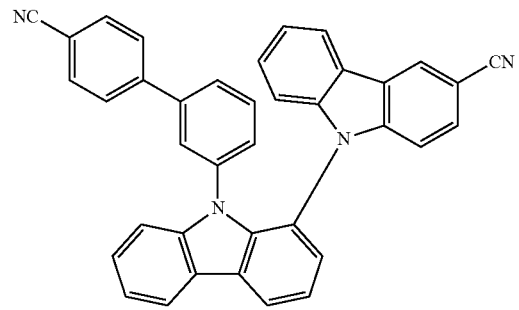

226
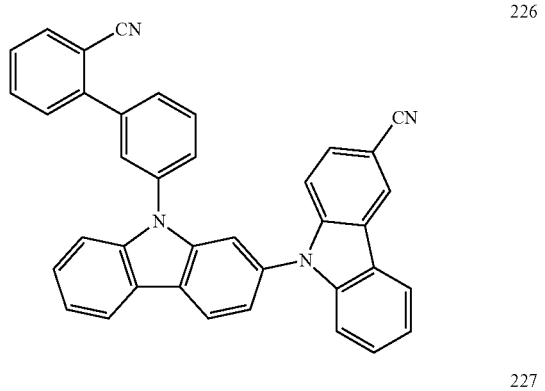
227
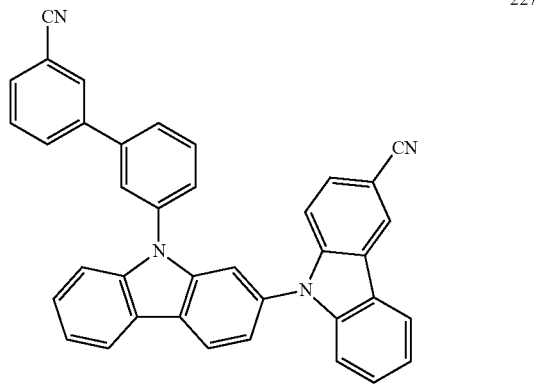
228
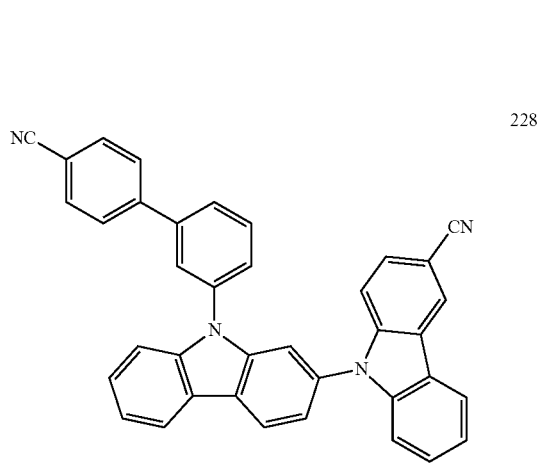
229
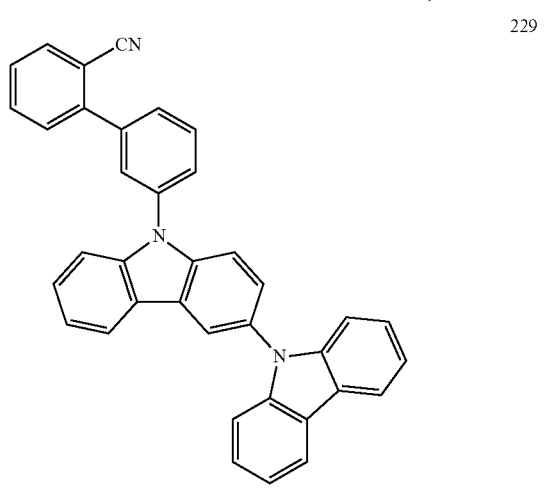
230
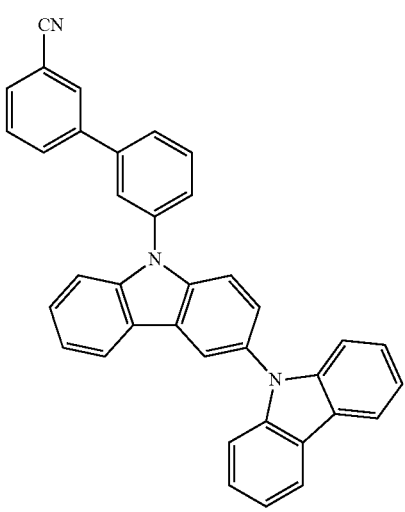
231
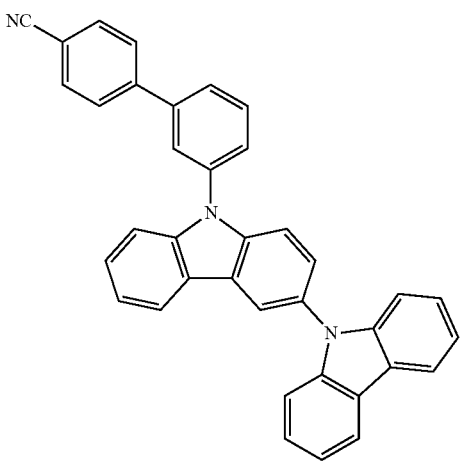
232
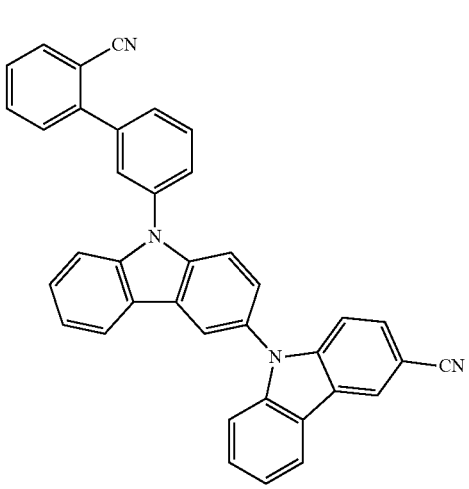

233
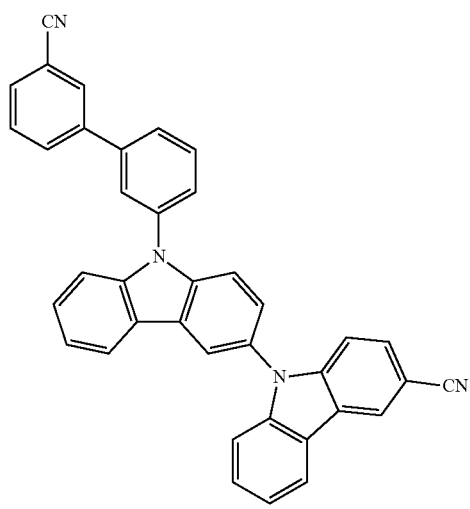
234
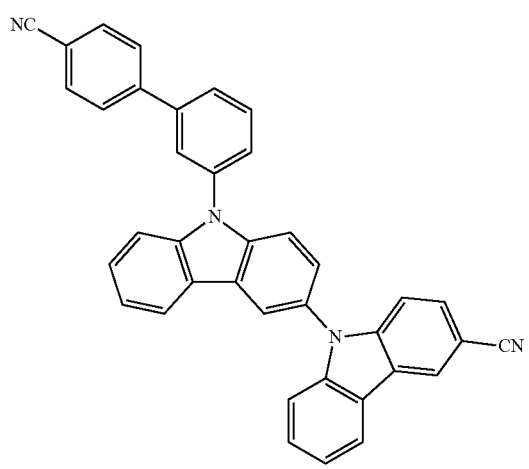
235
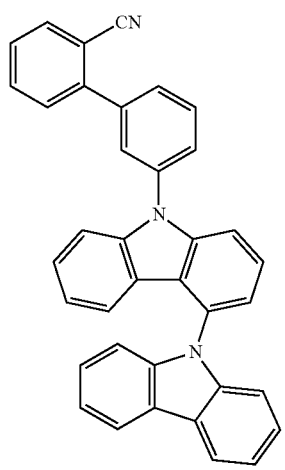
236
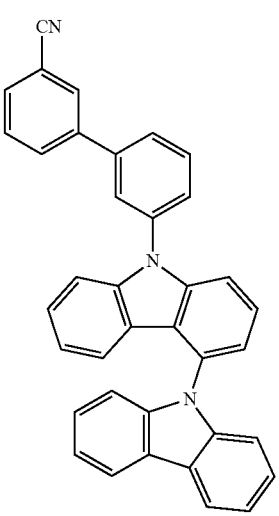
237
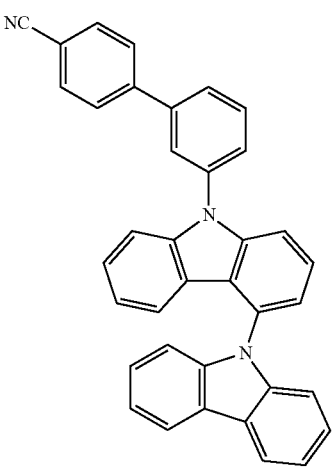
238
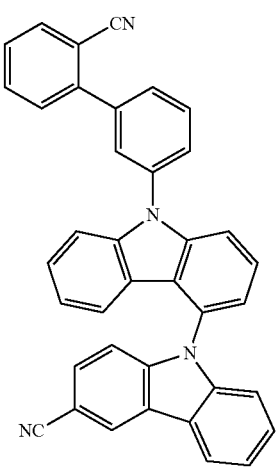

239
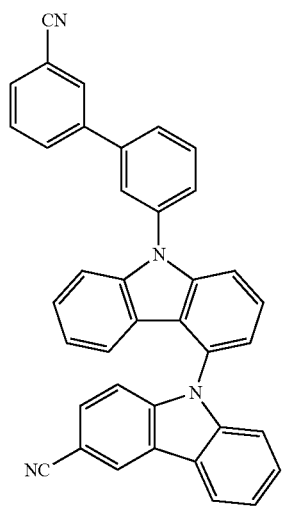
240
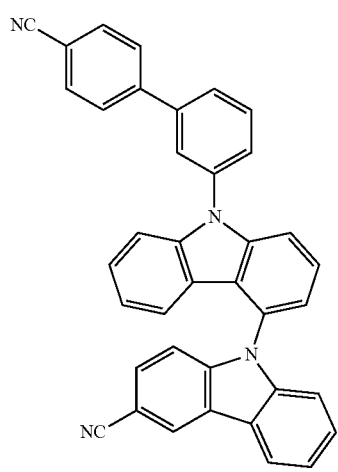
241
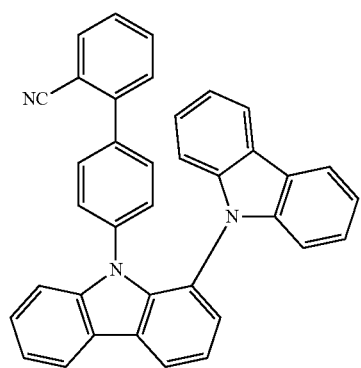
242
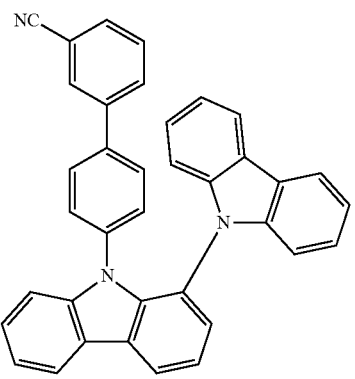
243
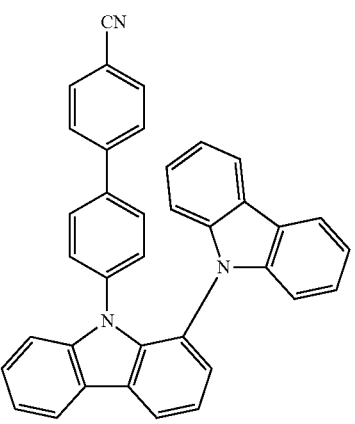
244
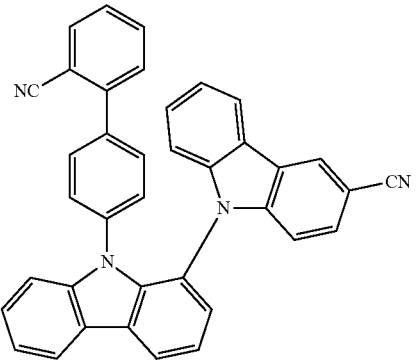
245
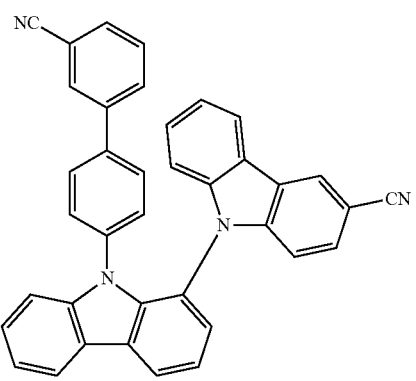

246
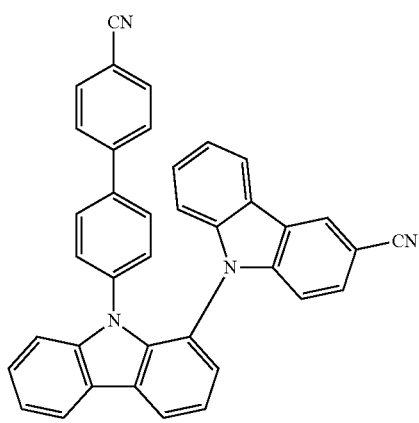
249
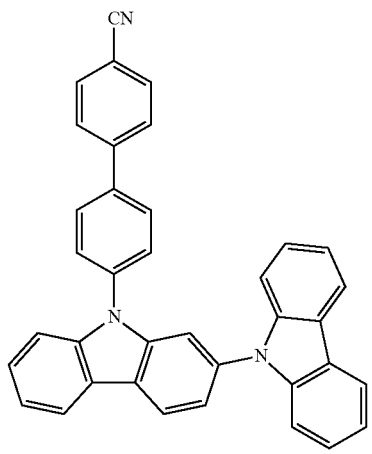
247
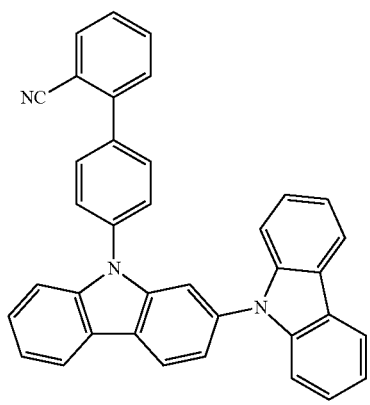
250
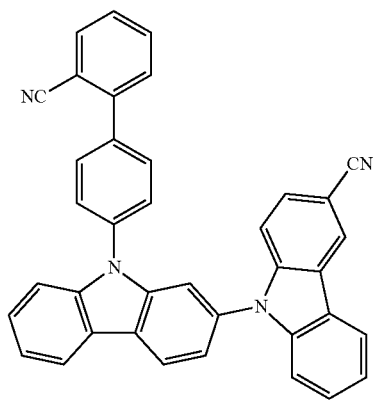
248
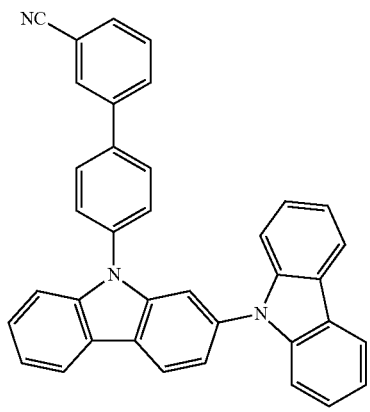
251
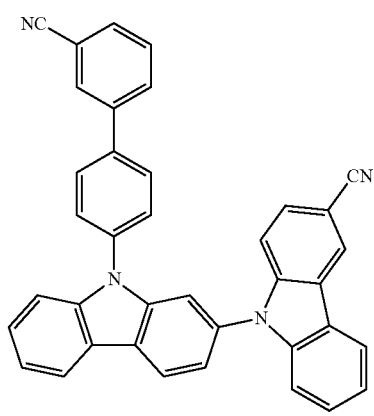

-continued
252
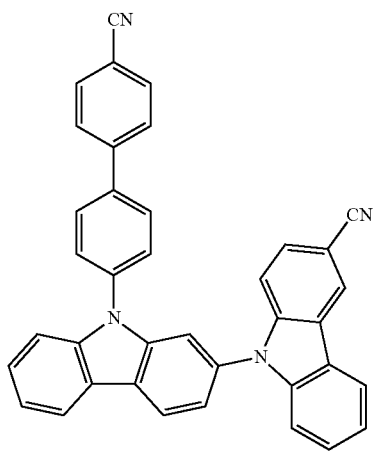
253
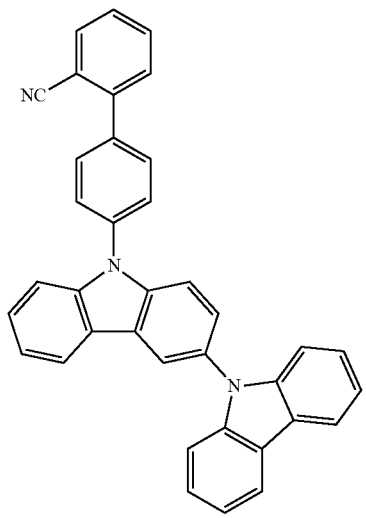
254
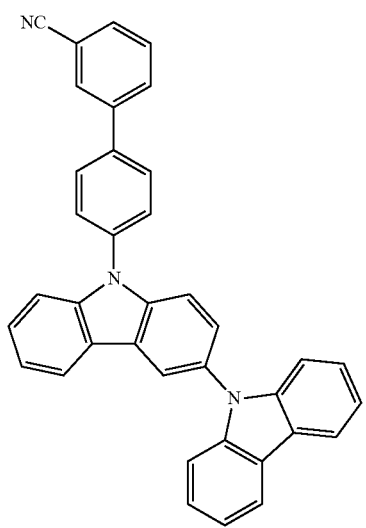
-continued
255
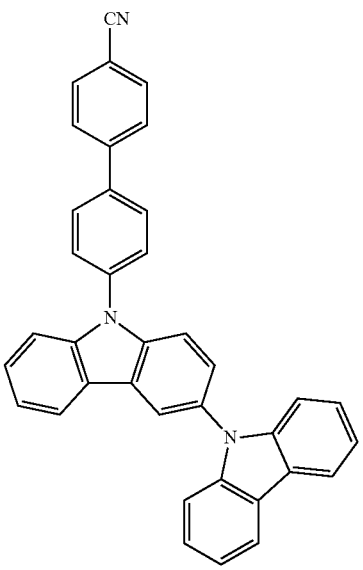
256
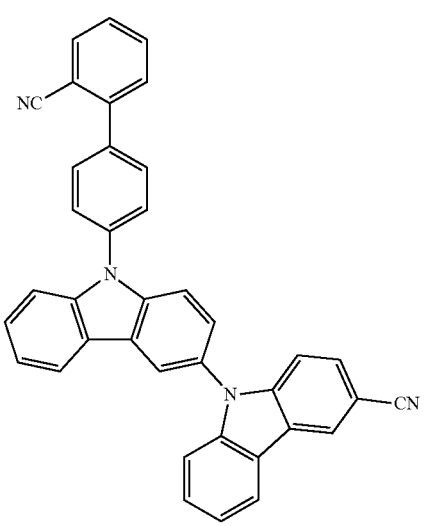
257
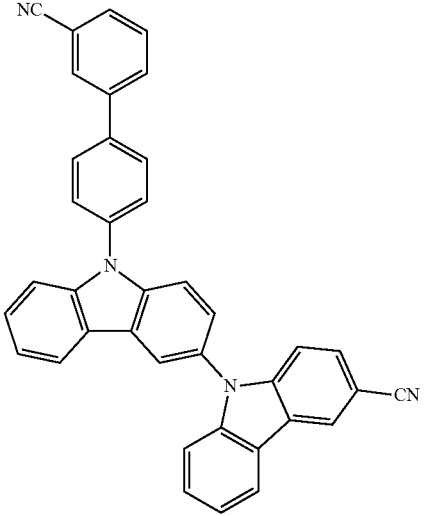

-continued
258
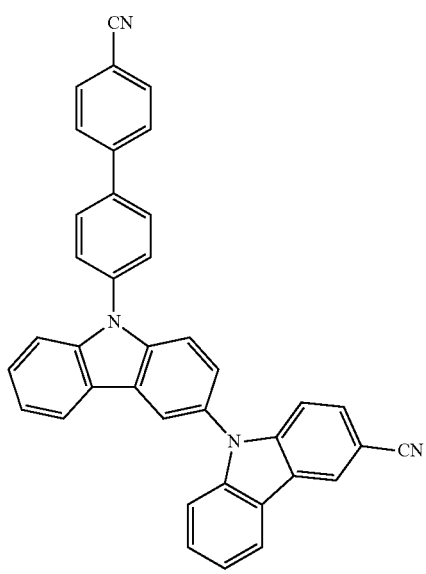
259
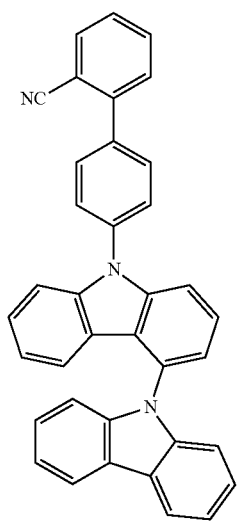
260
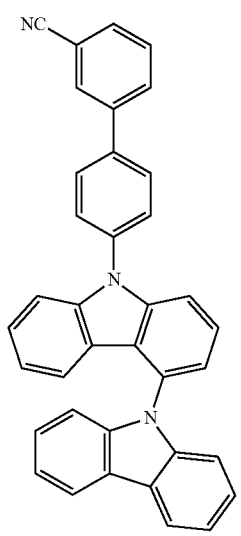
-continued
261
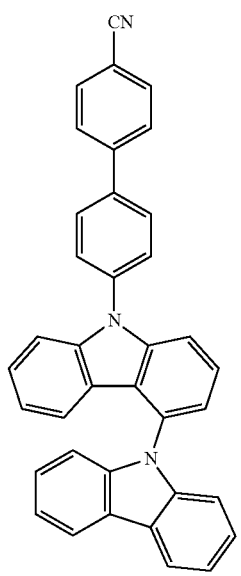
262
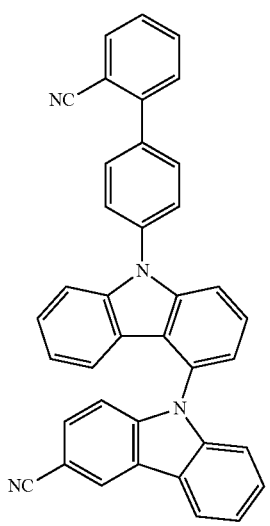
263
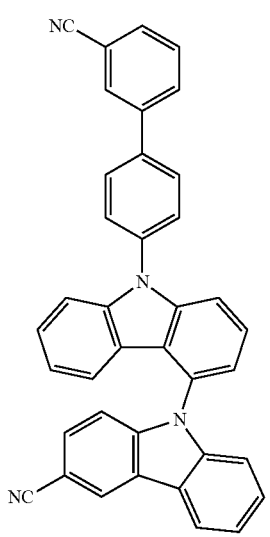

-continued
264
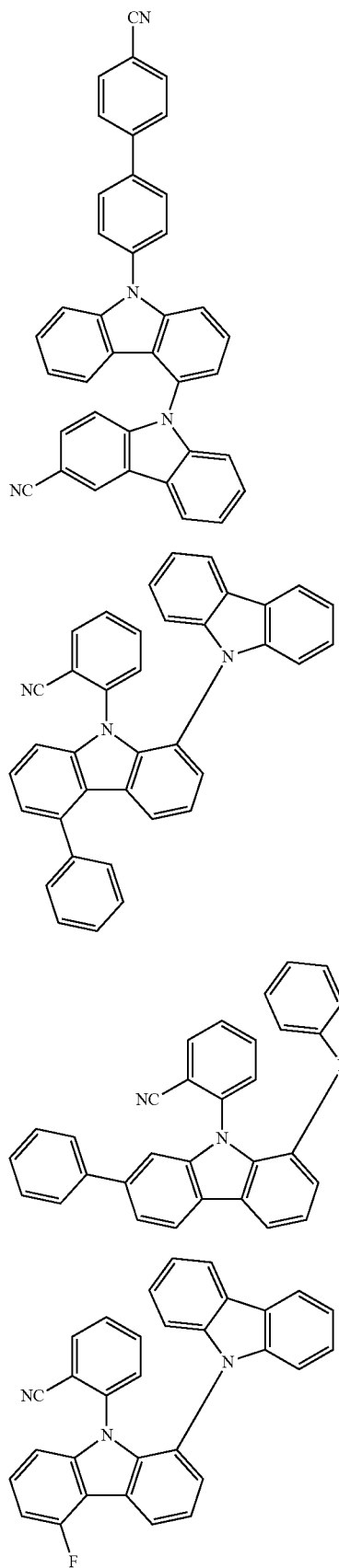
265
266
267
-continued
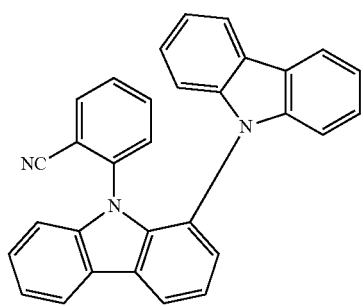
268
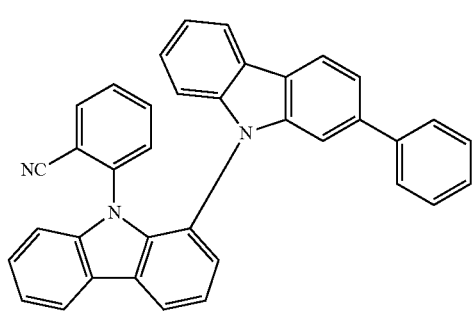
269
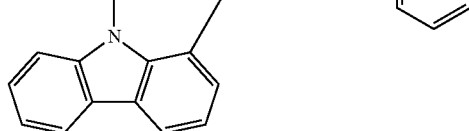
270
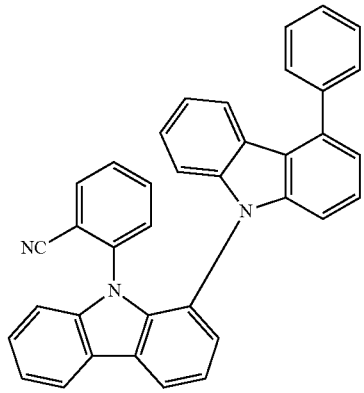
271
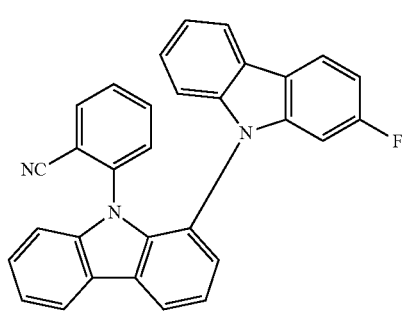
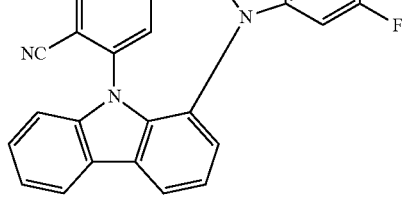
272
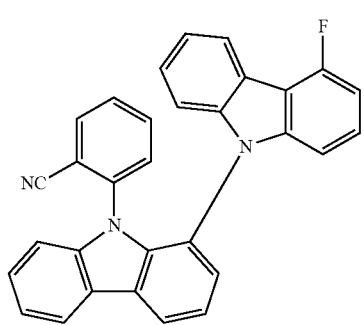

273 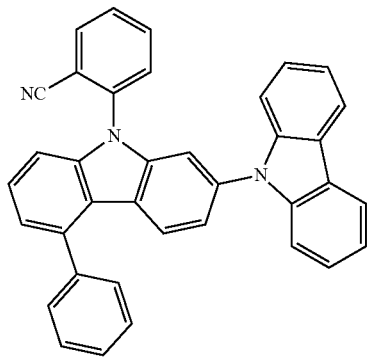
274 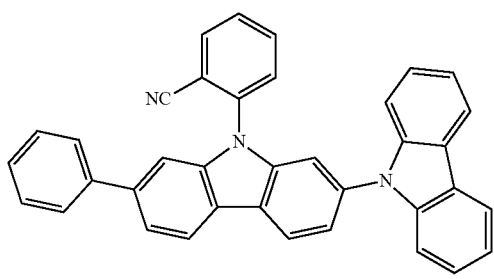
275 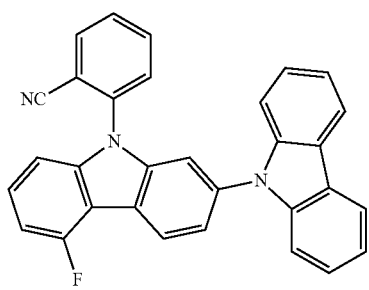
276 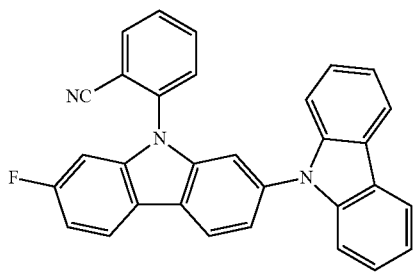
277 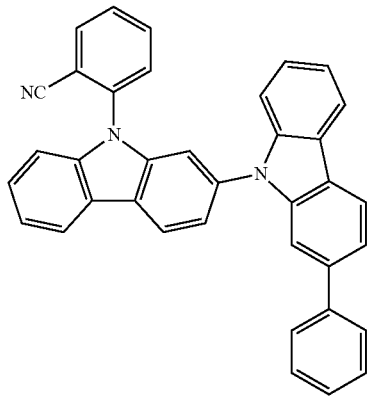
278 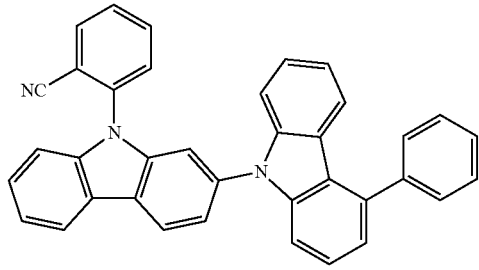
279 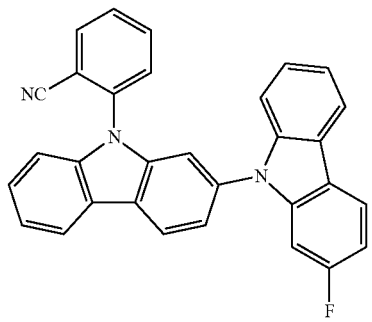
280 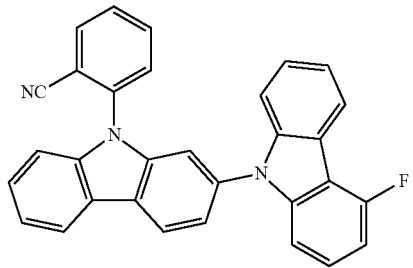
281 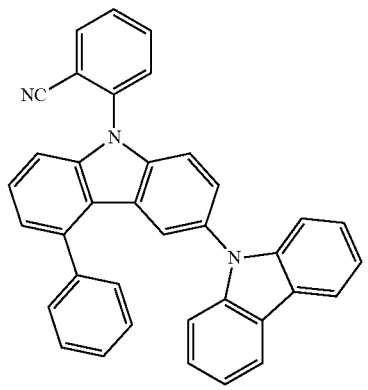

-continued
282
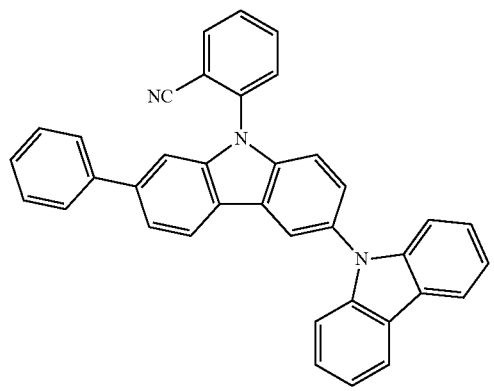
283
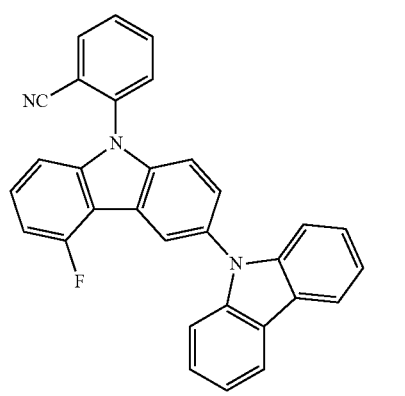
284
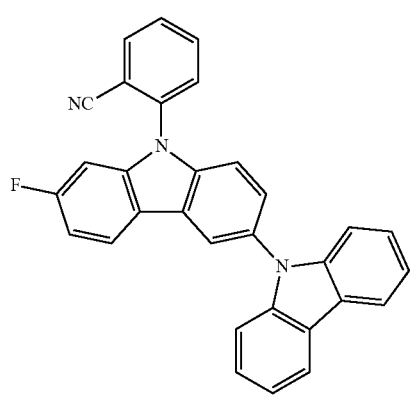
285
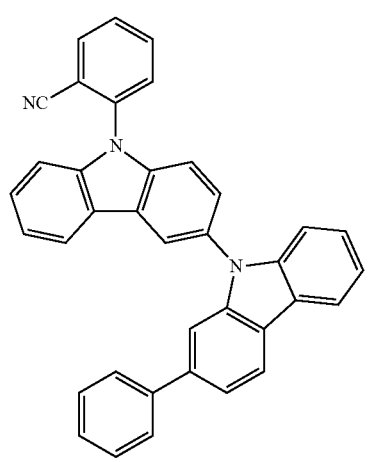
-continued
286
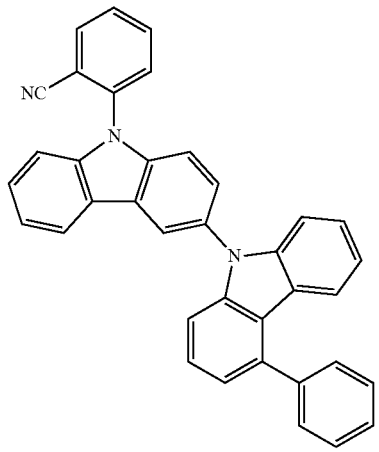
287
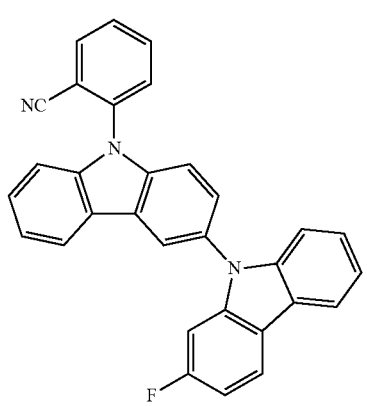
288
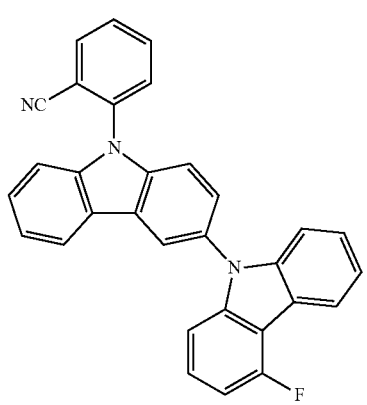

275
-continued
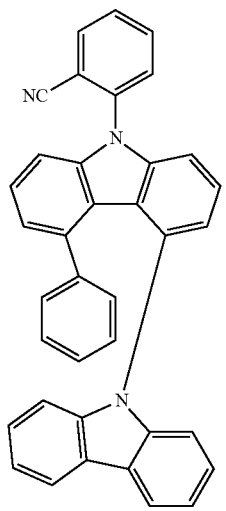
289
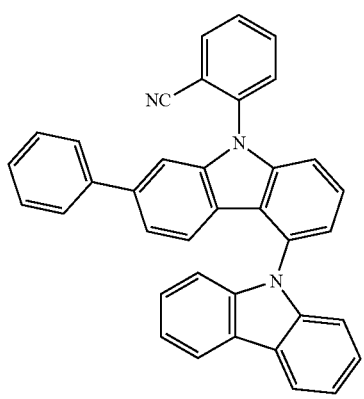
290
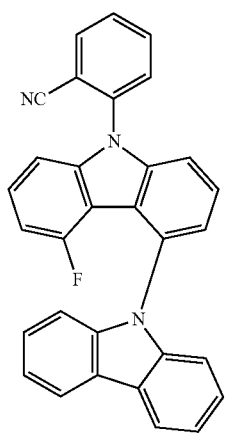
291
276
-continued
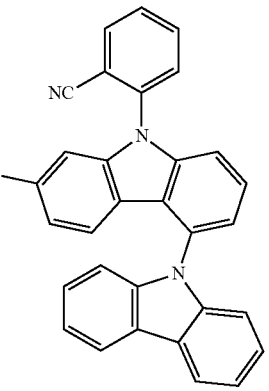
292
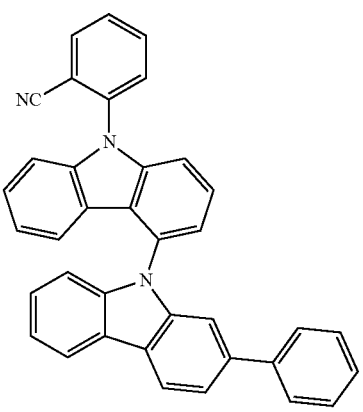
293
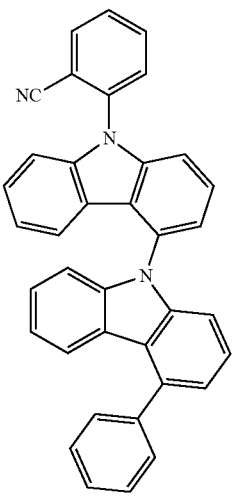
294

277
-continued
295
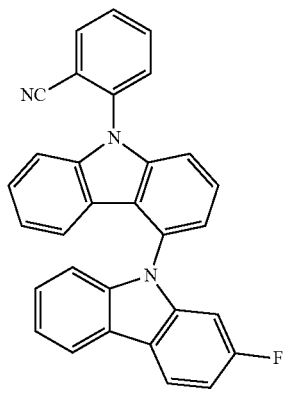
296
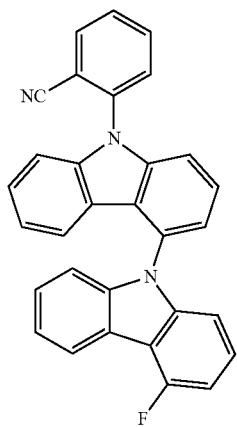
297
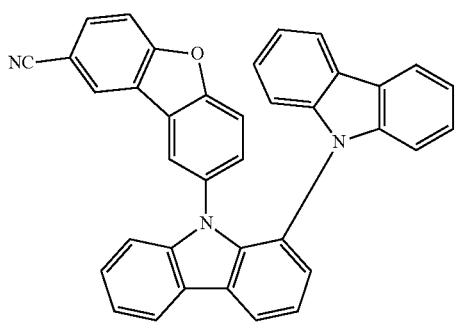
298
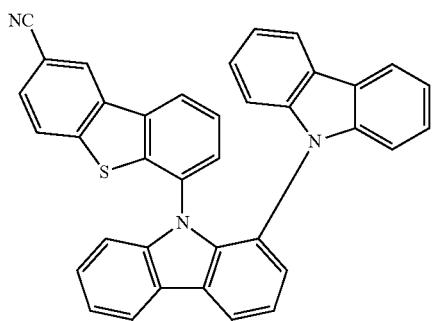
278
-continued
299
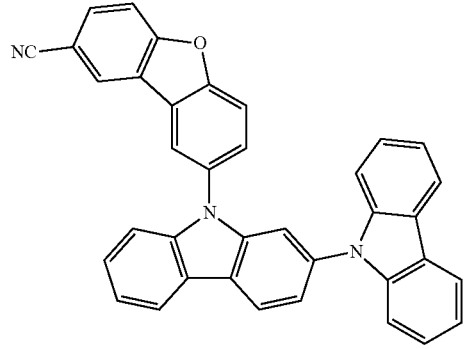
300
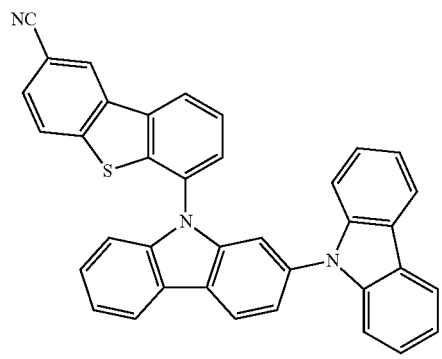
301
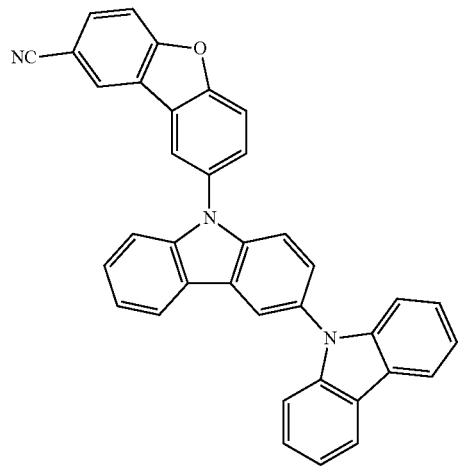
302
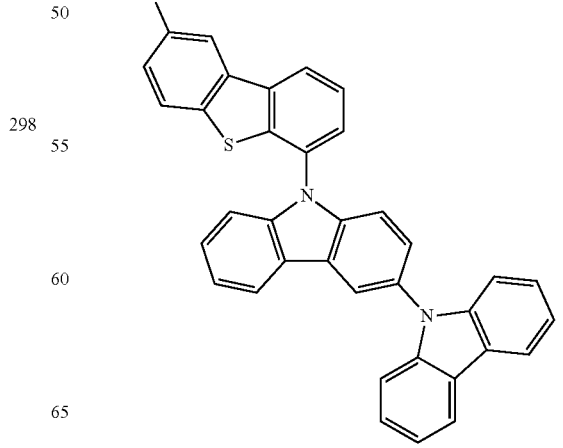

279
-continued
303
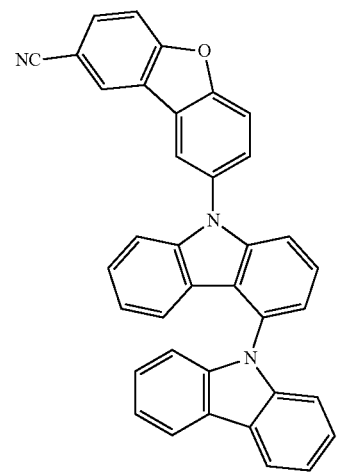
304
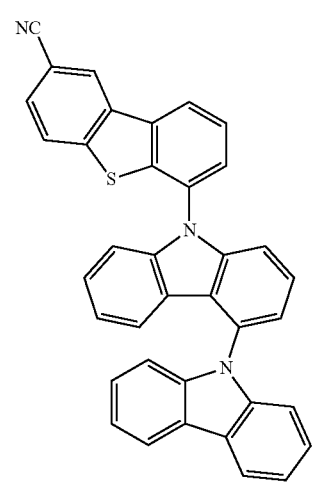
305
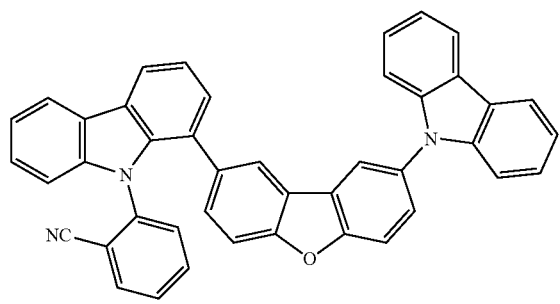
306
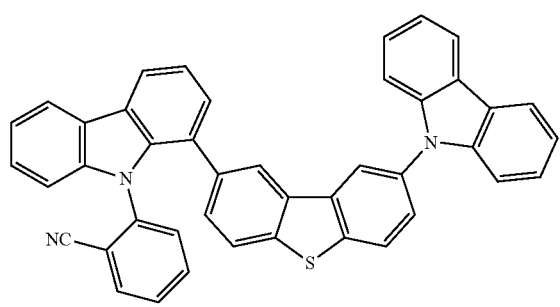
280
-continued
307
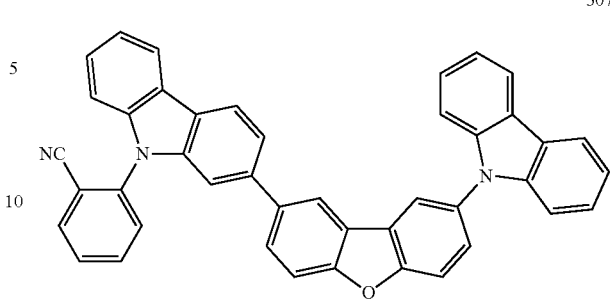
308
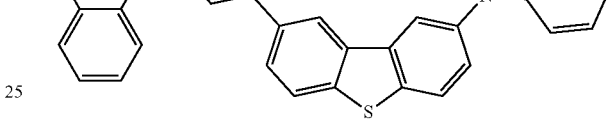
309
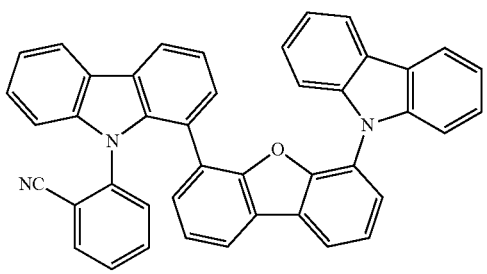
310
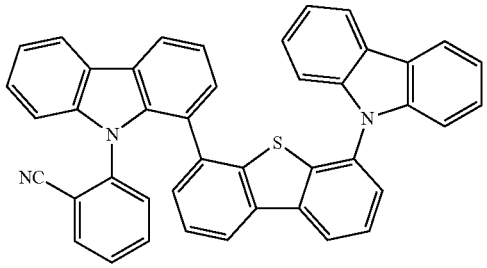
311
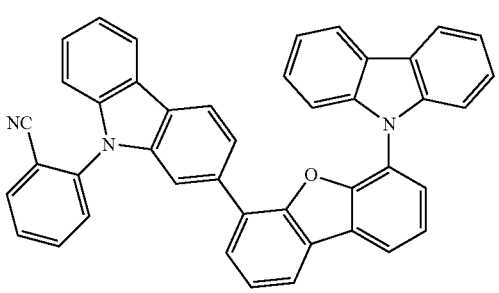

312
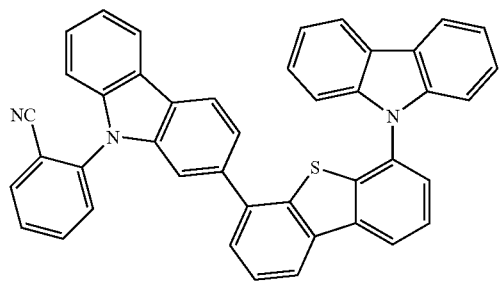
313
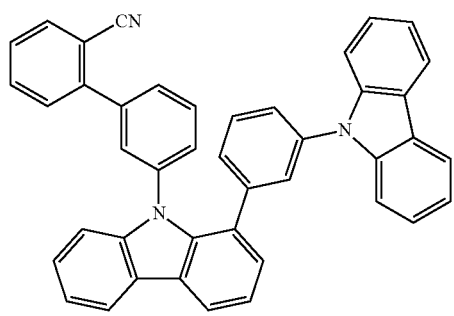
314
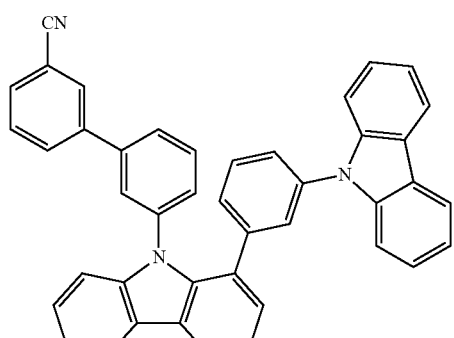
315
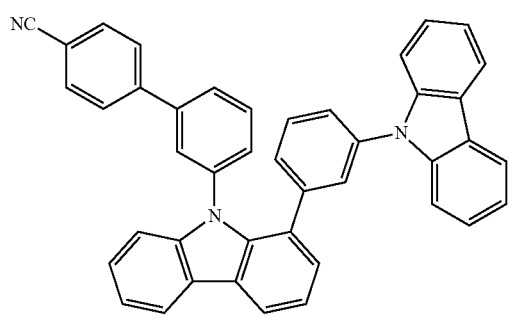
316
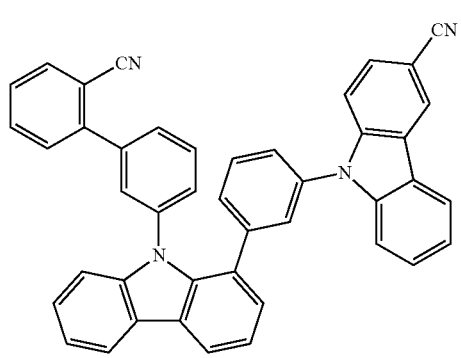
317
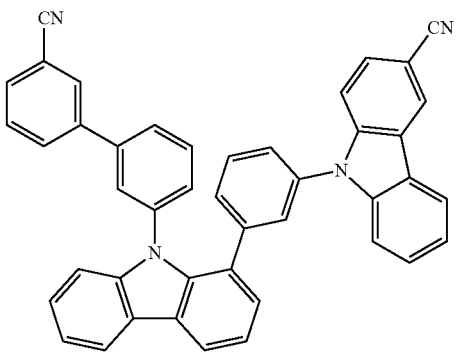
318
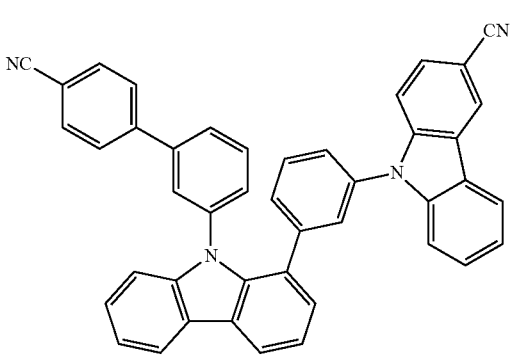
319
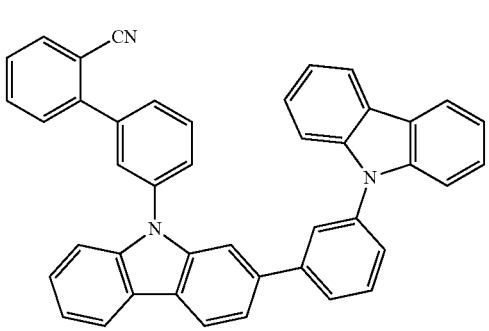
320
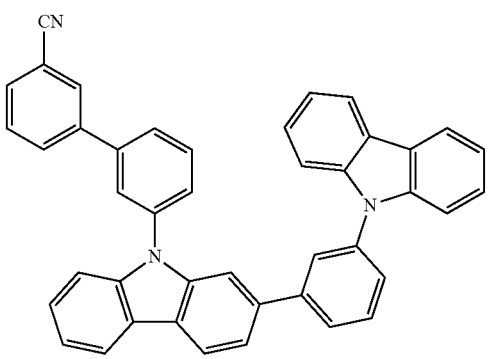

321
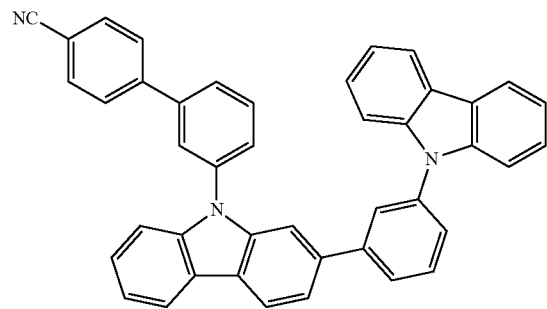
322
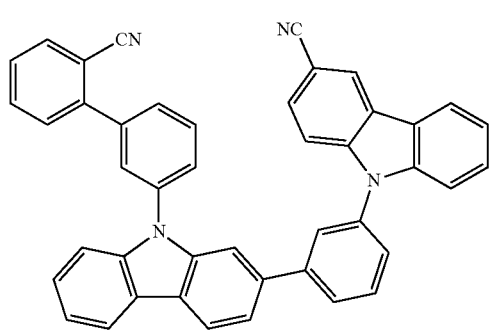
323
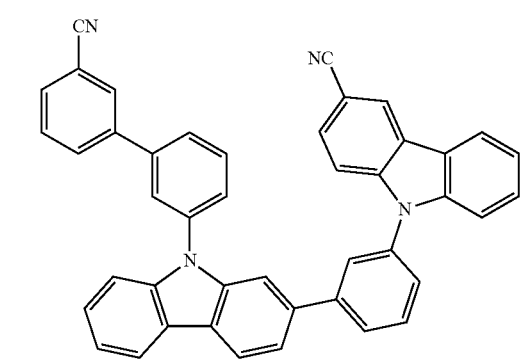
324
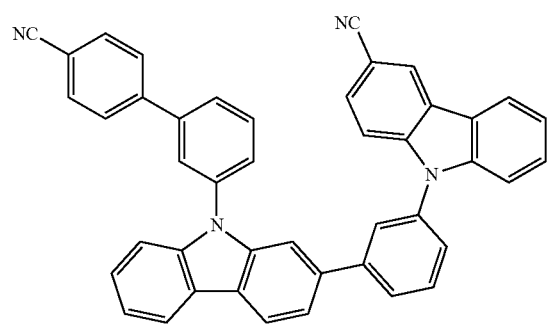
325
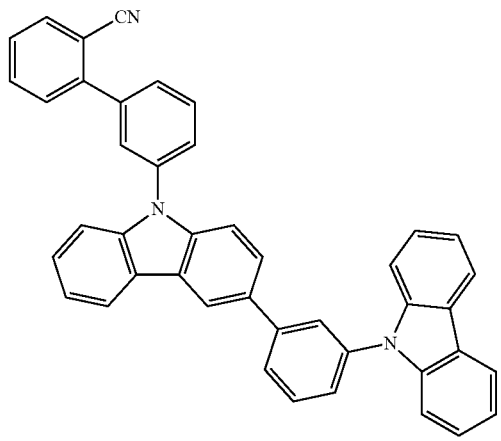
326
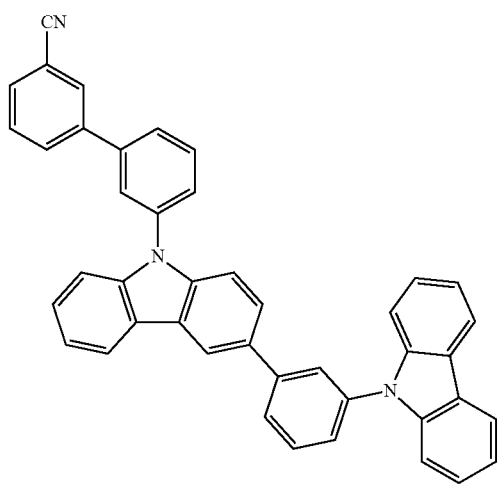
327
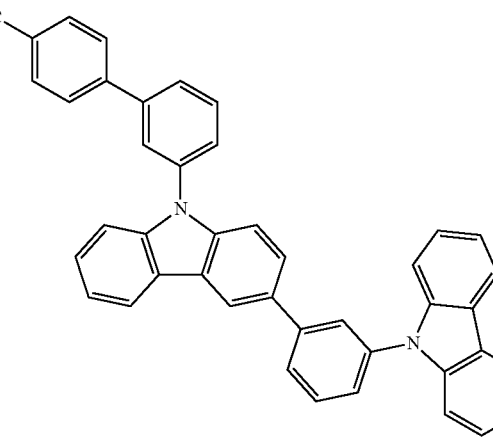

285
-continued
328
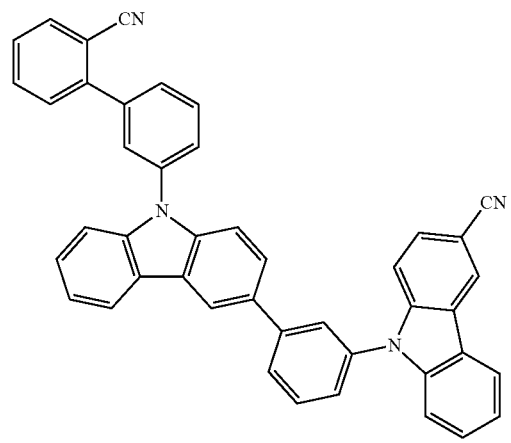
329
331
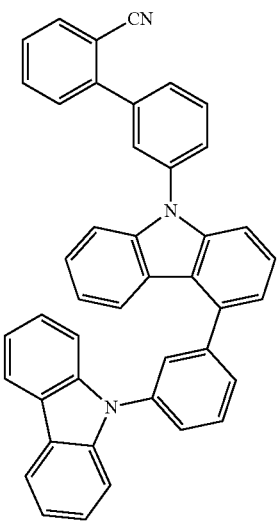
332
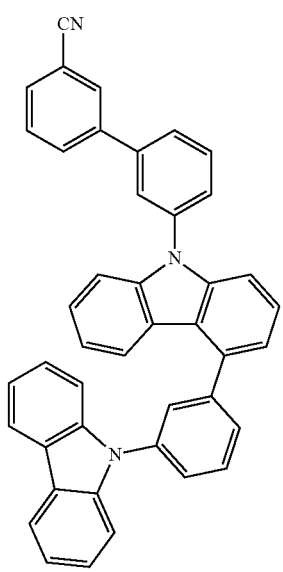
286
-continued
330
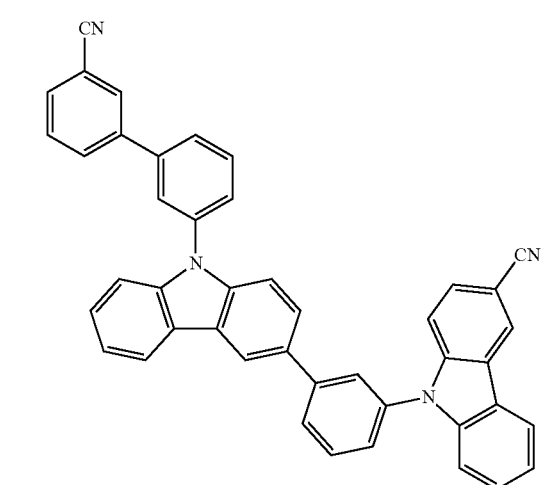
333
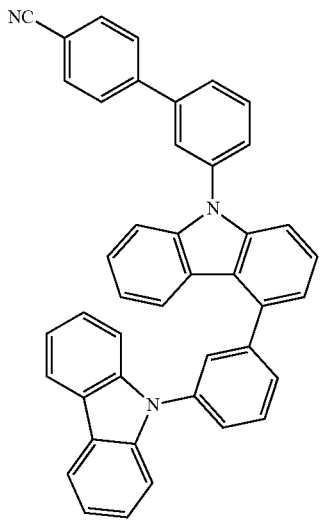

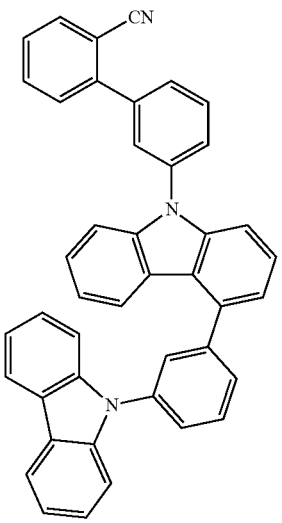

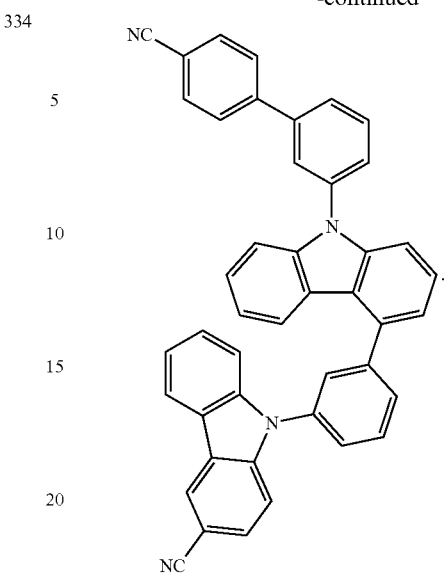

15. An organic light-emitting device comprising:
a first electrode;
a second electrode; and
an organic layer disposed between the first electrode and the second electrode,
wherein the organic layer comprises an emission layer and at least one condensed cyclic compound represented by Formula 1 of claim 1.

16. The organic light-emitting device of claim 15, wherein the first electrode is an anode,
the second electrode is a cathode,
the organic layer comprises a hole transport region disposed between the first electrode and the emission layer and an electron transport region disposed between the emission layer and the second electrode,
wherein the hole transport region comprises at least one selected from a hole injection layer, a hole transport layer, and an electron blocking layer, and
wherein the electron transport region comprises at least one selected from a hole blocking layer, an electron transport layer, and an electron injection layer.

17. The organic light-emitting device of claim 15, wherein the emission layer comprises the at least one condensed cyclic compound represented by Formula 1.

18. The organic light-emitting device of claim 15, wherein the emission layer comprises the at least one condensed cyclic compound represented by Formula 1, wherein the emission layer further comprises a phosphorescent dopant, and wherein an amount of the at least one condensed cyclic compound is larger than an amount of the phosphorescent dopant.

19. The organic light-emitting device of claim 17, wherein the emission layer emits blue light.

20. The organic light-emitting device of claim 15, wherein the emission layer comprises the condensed cyclic compound represented by Formula 1, and wherein the condensed cyclic compound represented by Formula 1 is a thermally activated delayed fluorescence emitter.

* * * * *